US012163953B2

(12) United States Patent
Whitten et al.

(10) Patent No.: US 12,163,953 B2
(45) Date of Patent: Dec. 10, 2024

(54) P-PHENYLENE ETHYNYLENE COMPOUNDS AS BIOACTIVE AND DETECTION AGENTS

(71) Applicant: STC.UNM, Albuquerque, NM (US)

(72) Inventors: David G. Whitten, Albuquerque, NM (US); Harry Craig Pappas, Albuquerque, NM (US); Eric H. Hill, Donostia (ES); Yue Zhang, Albuquerque, NM (US); Eva Yung Hua Chi, Albuquerque, NM (US); Arjun Thapa, Oklahoma City, OK (US); Ying Wang, Albuquerque, NM (US); Patrick L Donabedian, Albuquerque, NM (US); Kiran Bhaskar, Albuquerque, NM (US)

(73) Assignee: STC.UNM, Albuquerque, NM (US)

( * ) Notice: Subject to any disclaimer, the term of this patent is extended or adjusted under 35 U.S.C. 154(b) by 1316 days.

(21) Appl. No.: 16/707,501

(22) Filed: Dec. 9, 2019

(65) Prior Publication Data
US 2020/0158720 A1 May 21, 2020

Related U.S. Application Data

(62) Division of application No. 15/125,896, filed as application No. PCT/US2015/020546 on Mar. 13, 2015, now Pat. No. 10,533,991.

(60) Provisional application No. 62/012,780, filed on Jun. 16, 2014, provisional application No. 61/955,522, filed on Mar. 19, 2014, provisional application No. 61/954,923, filed on Mar. 18, 2014, provisional application No. 61/953,311, filed on Mar. 14, 2014.

(51) Int. Cl.
*C12N 1/20* (2006.01)
*C07K 14/65* (2006.01)
*C08G 61/02* (2006.01)
*C12Q 1/44* (2006.01)
*C12Q 1/46* (2006.01)
*G01N 33/52* (2006.01)

(52) U.S. Cl.
CPC ............ *G01N 33/52* (2013.01); *C07K 14/65* (2013.01); *C08G 61/02* (2013.01); *C12N 1/20* (2013.01); *C12Q 1/44* (2013.01); *C12Q 1/46* (2013.01); *C08G 2261/312* (2013.01); *C08G 2261/3328* (2013.01); *C08G 2261/3422* (2013.01); *C08G 2261/94* (2013.01); *G01N 2333/916* (2013.01); *G01N 2333/918* (2013.01); *G01N 2800/2828* (2013.01)

(58) Field of Classification Search
CPC .............. G01N 33/52; G01N 2333/916; G01N 2333/918; G01N 2800/2828; C07K 14/65; C08G 61/02; C08G 2261/312; C08G 2261/3328; C08G 2261/3422; C08G 2261/94; C12N 1/20; C12Q 1/44; C12Q 1/46
See application file for complete search history.

(56) References Cited

U.S. PATENT DOCUMENTS

| | | | |
|---|---|---|---|
| 4,251,386 A | 2/1981 | Saeki et al. | |
| 5,449,809 A | 9/1995 | Wingert et al. | |
| 5,489,400 A | 2/1996 | Liu et al. | |
| 6,743,640 B2 | 6/2004 | Whitten et al. | |
| 6,841,669 B2 | 1/2005 | Cipriani et al. | |
| 7,122,383 B2 | 10/2006 | Jones et al. | |
| 7,514,267 B1 * | 4/2009 | Lopez .................. | G01N 33/554 435/7.1 |
| 8,455,265 B2 | 6/2013 | Whitten et al. | |
| 8,598,053 B2 | 12/2013 | Whitten et al. | |
| 8,618,009 B2 | 12/2013 | Schanze et al. | |
| 8,753,570 B2 | 6/2014 | Whitten et al. | |
| 9,005,540 B2 | 4/2015 | Schanze et al. | |
| 9,125,415 B2 | 9/2015 | Schanze et al. | |
| 9,527,806 B2 | 12/2016 | Whitten et al. | |
| 9,549,549 B2 | 1/2017 | Whitten et al. | |

(Continued)

FOREIGN PATENT DOCUMENTS

| | | |
|---|---|---|
| CA | 2973982 C | 4/2018 |
| JP | 3198365 B2 | 8/2001 |

(Continued)

OTHER PUBLICATIONS

Tan (C. Tan et. al., Photophysics, aggregation and amplified quenching of a water-soluble poly(phenylene ethynylene), Chem. Commun., 2002, 446-447).*
PubChem. Substance Record for SID 76464254, Retrieved from the Internet. <URL: https://pubchem.ncbi.nlm.nih.gov/substance/76464254#section=Top>, (Jun. 12, 2009), 5 pgs.
"U.S. Appl. No. 12/529,390, Examiner Interview Summary mailed Jan. 31, 2012", 3 pgs.
"U.S. Appl. No. 12/529,390, Examiner Interview Summary mailed Nov. 13, 2012", 3 pgs.

(Continued)

*Primary Examiner* — Kumar R Bhushan
(74) *Attorney, Agent, or Firm* — Schwegman Lundberg & Woessner, P.A.

(57) ABSTRACT

Various embodiments relate to p-phenylene ethynylene compounds as bioactive and detection agents. In various embodiments, the present invention provides a method of inducing germination of microbial spores including contacting the microbial spores with a p-phenylene ethynylene compound. In various embodiments, the present invention provides a method for detecting an enzyme, a method of protein analysis, or a method of detecting a chemical agent, including introducing a p-phenylene ethylylene compound to a composition including an enzyme substrate, and analyzing the fluorescence of the p-phenylene ethynylene compound. Various embodiments provide sensors that include a p-phenylene ethynylene compound and an enzyme substrate.

19 Claims, 28 Drawing Sheets

(56) References Cited

U.S. PATENT DOCUMENTS

| | | |
|---|---|---|
| 9,750,250 B2 | 9/2017 | Whitten et al. |
| 9,968,698 B2 | 5/2018 | Whitten et al. |
| 10,058,099 B2 | 8/2018 | Whitten et al. |
| 10,092,000 B2 | 10/2018 | Whitten et al. |
| 10,533,991 B2 | 1/2020 | Whitten et al. |
| 10,772,851 B2 | 9/2020 | Neumann et al. |
| 2002/0177828 A1 | 11/2002 | Batich et al. |
| 2003/0134959 A1 | 7/2003 | Hancock et al. |
| 2003/0168756 A1 | 9/2003 | Balkus, Jr. et al. |
| 2003/0178607 A1 | 9/2003 | Swager et al. |
| 2004/0241768 A1 | 12/2004 | Whitten et al. |
| 2005/0059168 A1 | 3/2005 | Bazan et al. |
| 2005/0148254 A1 | 7/2005 | Lu et al. |
| 2006/0120923 A1 | 6/2006 | Swager et al. |
| 2006/0175193 A1 | 8/2006 | Inganas et al. |
| 2007/0065049 A1 | 3/2007 | Alldredge-howard et al. |
| 2007/0215841 A1 | 9/2007 | Ford et al. |
| 2008/0085566 A1* | 4/2008 | Swager .................. C09K 11/06 428/407 |
| 2008/0090021 A1 | 4/2008 | Long et al. |
| 2010/0035948 A1 | 2/2010 | Kumar et al. |
| 2010/0285081 A1 | 11/2010 | Chen et al. |
| 2011/0076648 A1 | 3/2011 | Lindheim et al. |
| 2011/0159605 A1 | 6/2011 | Whitten et al. |
| 2011/0223058 A1 | 9/2011 | Whitten et al. |
| 2011/0293470 A1 | 12/2011 | Schanze et al. |
| 2012/0271023 A1 | 10/2012 | Whitten et al. |
| 2013/0210828 A1 | 8/2013 | Whitten et al. |
| 2013/0273800 A1 | 10/2013 | Whitten et al. |
| 2013/0330386 A1 | 12/2013 | Whitten et al. |
| 2014/0086795 A1 | 3/2014 | Schanze et al. |
| 2014/0242148 A1 | 8/2014 | Whitten et al. |
| 2014/0341776 A1 | 11/2014 | Schanze et al. |
| 2015/0115362 A1 | 4/2015 | Su et al. |
| 2015/0125396 A1* | 5/2015 | Feuerstein ......... G01N 33/6896 424/9.6 |
| 2015/0132184 A1 | 5/2015 | Whitten et al. |
| 2016/0222150 A1 | 8/2016 | Whitten et al. |
| 2017/0023554 A1 | 1/2017 | Whitten et al. |
| 2017/0057970 A1 | 3/2017 | Whitten et al. |
| 2017/0164614 A1 | 6/2017 | Whitten et al. |
| 2018/0020663 A1 | 1/2018 | Whitten et al. |
| 2018/0221309 A1 | 8/2018 | Neumann et al. |

FOREIGN PATENT DOCUMENTS

| | | | |
|---|---|---|---|
| WO | WO-2005065323 A2 | 7/2005 | |
| WO | WO-2008143731 A2 | 11/2008 | |
| WO | WO-2009158606 A2 | 12/2009 | |
| WO | WO-2009158606 A9 | 12/2009 | |
| WO | WO-2010044743 A1 | 4/2010 | |
| WO | WO-2010054304 A2 | 5/2010 | |
| WO | WO-2011044580 A2 | 4/2011 | |
| WO | WO-2011044580 A3 | 4/2011 | |
| WO | WO-2012009472 A2 | 1/2012 | |
| WO | WO-2012009484 A2 | 1/2012 | |
| WO | WO-2012079085 A2 | 6/2012 | |
| WO | WO-2013020096 A2 | 2/2013 | |
| WO | WO-2013020096 A3 | 2/2013 | |
| WO | WO-2013055417 A2 | 4/2013 | |
| WO | WO-2013055417 A3 | 4/2013 | |
| WO | WO-2015138965 A1 | 9/2015 | |
| WO | WO-2016115362 A1 | 7/2016 | |

OTHER PUBLICATIONS

"U.S. Appl. No. 12/529,390, Non Final Office Action mailed Jul. 18, 2012", 7 pgs.

"U.S. Appl. No. 12/529,390, Non-Final Office Action mailed Nov. 1, 2011", 11 pgs.

"U.S. Appl. No. 12/529,390, Notice of Allowance mailed Feb. 5, 2013", 10 pgs.

"U.S. Appl. No. 12/529,390, Preliminary Amendment mailed Sep. 1, 2009", 13 pgs.

"U.S. Appl. No. 12/529,390, Response filed May 1, 2012 to Non Final Office Action mailed Nov. 1, 2011", 19 pgs.

"U.S. Appl. No. 12/529,390, Response filed Dec. 18, 2012 to Non Final Office Action mailed Jul. 18, 2012", 16 pgs.

"U.S. Appl. No. 13/001,478 , Response filed Dec. 19, 2013 to Non Final Office Action mailed Oct. 3, 2013", 10 pgs.

"U.S. Appl. No. 13/001,478, Non Final Office Action mailed Oct. 3, 2013", 6 pgs.

"U.S. Appl. No. 13/001,478, Notice of Allowance mailed Jan. 31, 2014", 7 pgs.

"U.S. Appl. No. 13/001,478, Preliminary Amendment filed Dec. 27, 2010", 1 pg.

"U.S. Appl. No. 13/001,478, Response filed Jul. 11, 2013 to Restriction Requirement mailed Jun. 13, 2013", 9 pgs.

"U.S. Appl. No. 13/001,478, Restriction Requirement mailed Jun. 13, 2013", 7 pgs.

"U.S. Appl. No. 13/128,571, Response filed Nov. 19, 2012 to Restriction Requirement mailed Oct. 17, 2012", 6 pgs.

"U.S. Appl. No. 13/128,571, Non Final Office Action mailed Feb. 13, 2013", 10 pgs.

"U.S. Appl. No. 13/128,571, Notice of Allowance mailed Aug. 28, 2013", 9 pgs.

"U.S. Appl. No. 13/128,571, Preliminary Amendment filed May 10, 2011", 5 pgs.

"U.S. Appl. No. 13/128,571, Preliminary Amendment filed May 31, 2011", 3 pgs.

"U.S. Appl. No. 13/128,571, Response filed May 13, 2013 to Non Final Office Action mailed Feb. 13, 2013", 12 pgs.

"U.S. Appl. No. 13/128,571, Restriction Requirement mailed Oct. 17, 2012", 6 pgs.

"U.S. Appl. No. 13/503,067 , Response filed Mar. 11, 2013 to Non Final Office Action mailed Oct. 10, 2012", 11 pgs.

"U.S. Appl. No. 13/503,067 , Response filed Jul. 11, 2013 to Final Office Action mailed Jun. 6, 2013", 7 pgs.

"U.S. Appl. No. 13/503,067, Final Office Action mailed Jun. 6, 2013", 11 pgs.

"U.S. Appl. No. 13/503,067, Non Final Office Action mailed Oct. 10, 2012", 11 pgs.

"U.S. Appl. No. 13/503,067, Notice of Allowance mailed Aug. 2, 2013", 10 pgs.

"U.S. Appl. No. 13/809,572, Amendment 312 filed Oct. 21, 2016", 5 pgs.

"U.S. Appl. No. 13/809,572, Final Office Action mailed Feb. 18, 2016", 20 pgs.

"U.S. Appl. No. 13/809,572, Non Final Office Action mailed Sep. 24, 2015", 17 pgs.

"U.S. Appl. No. 13/809,572, Notice of Allowance mailed Aug. 10, 2016", 8 pgs.

"U.S. Appl. No. 13/809,572, Preliminary Amendment filed Jan. 10, 2013", 9 pgs.

"U.S. Appl. No. 13/809,572, Response filed Dec. 16, 2015 to Non-Final Office Action mailed Sep. 24, 2015", 11 pgs.

"U.S. Appl. No. 13/809,572, Response filed Apr. 22, 2016 to Final Office Action mailed Apr. 18, 2016", 9 pgs.

"U.S. Appl. No. 13/809,573, 312 Amendment filed Jul. 30, 2018", 3 pgs.

"U.S. Appl. No. 13/809,573, Corrected Notice of Allowability mailed Sep. 7, 2018", 4 pgs.

"U.S. Appl. No. 13/809,573, Final Office Action mailed Dec. 15, 2016", 15 pgs.

"U.S. Appl. No. 13/809,573, Non Final Office Action mailed Jan. 22, 2016", 13 pgs.

"U.S. Appl. No. 13/809,573, Non Final Office Action mailed Aug. 25, 2016", 13 pgs.

"U.S. Appl. No. 13/809,573, Non Final Office Action mailed Oct. 11, 2017", 12 pgs.

"U.S. Appl. No. 13/809,573, Notice of Allowance mailed May 17, 2018", 7 pgs.

"U.S. Appl. No. 13/809,573, Preliminary Amendment filed Jan. 10, 2013", 9 pgs.

(56) References Cited

OTHER PUBLICATIONS

"U.S. Appl. No. 13/809,573, PTO Response to Rule 312 Communication mailed Aug. 3, 2018", 2 pgs.
"U.S. Appl. No. 13/809,573, Response filed Jan. 10, 2018 to Non-Final Office Action mailed Oct. 11, 2017", 13 pgs.
"U.S. Appl. No. 13/809,573, Response filed Apr. 17, 2017 to Final Office Acton mailed Dec. 15, 2016", 17 pgs.
"U.S. Appl. No. 13/809,573, Response filed Sep. 24, 2015 to Restriction Requirement mailed Jul. 24, 2015", 9 pgs.
"U.S. Appl. No. 13/809,573, Response filed Apr. 22, 2016 to Non-Final Office Action mailed Jan. 22, 2016", 13 pgs.
"U.S. Appl. No. 13/809,573, Response filed Sep. 22, 2016 to Non-Final Office Actino mailed Aug. 25, 2016", 18 pgs.
"U.S. Appl. No. 13/809,573, Restriction Requirement mailed Jul. 24, 2015", 7 pgs.
"U.S. Appl. No. 13/993,026 Response filed Sep. 8, 2015 to Final Office Action mailed Jun. 8, 2015", 10 pgs.
"U.S. Appl. No. 13/993,026, Advisory Action mailed Sep. 17, 2015", 7 pgs.
"U.S. Appl. No. 13/993,026, Final Office Action mailed Jun. 8, 2015", 15 pgs.
"U.S. Appl. No. 13/993,026, Non Final Office Action mailed Jan. 27, 2015", 9 pgs.
"U.S. Appl. No. 13/993,026, Preliminary Amendment filed Jun. 10, 2013", 7 pgs.
"U.S. Appl. No. 13/993,026, Response filed Apr. 9, 2015 to Non Final Office Action mailed Jan. 27, 2015", Response to Non Final Office Action, 11 pgs.
"U.S. Appl. No. 14/092,409, Notice of Allowance mailed Dec. 10, 2014", 10 pgs.
"U.S. Appl. No. 14/092,409, Preliminary Amendment filed Nov. 25, 2014", 4 pgs.
"U.S. Appl. No. 14/092,409, Preliminary Amendment filed Dec. 3, 2013", 4 pgs.
"U.S. Appl. No. 14/127,465, Non Final Office Action mailed Jan. 21, 2015", 4 pgs.
"U.S. Appl. No. 14/127,465, Notice of Allowance mailed Apr. 30, 2015", 7 pgs.
"U.S. Appl. No. 14/127,465, Preliminary Amendment filed Dec. 18, 2013", 8 pgs.
"U.S. Appl. No. 14/127,465, Response filed Apr. 20, 2015 to Non Final Office Action mailed Jan. 21, 2015", 9 pgs.
"U.S. Appl. No. 14/233,130, 312 Amendment mailed Nov. 11, 2016", 3 pgs.
"U.S. Appl. No. 14/233,130, Final Office Action mailed Jun. 29, 2016", 16 pgs.
"U.S. Appl. No. 14/233,130, Notice of Allowance mailed Sep. 12, 2016", 13 pgs.
"U.S. Appl. No. 14/233,130, Preliminary Amendment filed Jan. 15, 2014", 11 pgs.
"U.S. Appl. No. 14/233,130, PTO Response to Rule 312 Communication mailed Dec. 8, 2016", 2 pgs.
"U.S. Appl. No. 14/233,130, Response filed Dec. 10, 2015 to Restriction Requirement mailed Oct. 22, 2015", 12 pgs.
"U.S. Appl. No. 14/233,130, Response filed Aug. 12, 2016 to Final Office Action mailed Jun. 29, 2016", 13 pgs.
"U.S. Appl. No. 14/533,612, Advisory Action mailed Nov. 24, 2017", 5 pgs.
"U.S. Appl. No. 14/533,612, Final Office Action mailed Jul. 13, 2017", 11 pgs.
"U.S. Appl. No. 14/533,612, Non Final Office Action mailed Jan. 20, 2017", 11 pgs.
"U.S. Appl. No. 14/533,612, Notice of Allowance mailed Jan. 8, 2018", 8 pgs.
"U.S. Appl. No. 14/533,612, Response filed Oct. 11, 2016 to Restriction Requirement mailed Aug. 25, 2016", 8 pgs.
"U.S. Appl. No. 14/533,612, Response filed Oct. 12, 2017 to Final Office Action mailed Jul. 13, 2017", 15 pgs.
"U.S. Appl. No. 14/533,612, Response filed Dec. 12, 2017 to Final Office Action mailed Jul. 13, 2017", 16 pgs.
"U.S. Appl. No. 14/533,612, Response filed Apr. 20, 2017 to Non-Final Office Action mailed Jan. 20, 2017", 11 pgs.
"U.S. Appl. No. 14/533,612, Restriction Requirement mailed Aug. 25, 2016", 8 pgs.
"U.S. Appl. No. 15/018,179, Non Final Office Action mailed Dec. 13, 2016", 12 pgs.
"U.S. Appl. No. 15/018,179, Notice of Allowance mailed May 3, 2017", 9 pgs.
"U.S. Appl. No. 15/018,179, Response filed Sep. 9, 2016 to Restriction Requirement mailed Jul. 13, 2016", 15 pgs.
"U.S. Appl. No. 15/018,179, Response filed Mar. 10, 2017 to Non-Final Office Action mailed Dec. 13, 2016", 13 pgs.
"U.S. Appl. No. 15/018,179, Restriction Requirement mailed Jul. 13, 2016", 10 pgs.
"U.S. Appl. No. 15/125,896, 312 Amendment filed Nov. 7, 2019", 3 pgs.
"U.S. Appl. No. 15/125,896, Final Office Action mailed Feb. 11, 2019", 9 pgs.
"U.S. Appl. No. 15/125,896, Non-Final mailed Sep. 11, 2018", 17 pgs.
"U.S. Appl. No. 15/125,896, Notice of Allowance mailed Aug. 12, 2019", 12 pgs.
"U.S. Appl. No. 15/125,896, Preliminary Amendment mailed Sep. 13, 2016", 11 pgs.
"U.S. Appl. No. 15/125,896, PTO Response to Rule 312 Communication mailed Nov. 19, 2019", 2 pgs.
"U.S. Appl. No. 15/125,896, Response filed Dec. 6, 2018 to Non0Final Office Action mailed Sep. 11, 2018", 16 pgs.
"U.S. Appl. No. 15/125,896, Response filed May 23, 2018 to Restriction Requirement mailed Mar. 27, 2018", 12 pgs.
"U.S. Appl. No. 15/125,896, Restriction Requirement mailed Mar. 27, 2018", 6 pgs.
"U.S. Appl. No. 15/348,756, Examiner Interview Summary mailed Jun. 28, 2018", 2 pgs.
"U.S. Appl. No. 15/348,756, Final Office Action mailed Nov. 8, 2017", 25 pgs.
"U.S. Appl. No. 15/348,756, Non Final Office Action mailed Mar. 9, 2018", 29 pgs.
"U.S. Appl. No. 15/348,756, Non Final Office Action mailed Jun. 23, 2017", 26 pgs.
"U.S. Appl. No. 15/348,756, Notice of Allowability mailed Sep. 20, 2018", 5 pgs.
"U.S. Appl. No. 15/348,756, Notice of Allowance mailed Aug. 24, 2018", 11 pgs.
"U.S. Appl. No. 15/348,756, Preliminary Amendment filed Nov. 18, 2016 to", 7 pgs.
"U.S. Appl. No. 15/348,756, PTO Response to Rule 312 Communication mailed Oct. 3, 2018", 2 pgs.
"U.S. Appl. No. 15/348,756, Response filed Jan. 18, 2018 to Final Office Action mailed Nov. 8, 2017", 10 pgs.
"U.S. Appl. No. 15/348,756, Response filed May 31, 2018 to Non-Final Office Action mailed Mar. 9, 2018", 12 pgs.
"U.S. Appl. No. 15/348,756, Response filed Sep. 25, 2017 to Non-Final Office Action mailed Jun. 23, 2017", 10 pgs.
"U.S. Appl. No. 15/368,148, Non Final Office Action mailed Jul. 6, 2017", 16 pgs.
"U.S. Appl. No. 15/368,148, Notice of Allowance mailed Jan. 30, 2018", 16 pgs.
"U.S. Appl. No. 15/368,148, Preliminary Amendment filed Dec. 2, 2016", 10 pgs.
"U.S. Appl. No. 15/368,148, Response filed Jun. 12, 2017 to Restriction Requirement mailed Apr. 12, 2017", 10 pgs.
"U.S. Appl. No. 15/368,148, Response filed Nov. 6, 2017 to Non-Final Office Action mailed Jul. 6, 2017", 17 pgs.
"U.S. Appl. No. 15/368,148, Restriction Requirement mailed Apr. 12, 2017", 11 pgs.
"U.S. Appl. No. 15/886,469, Final Office Action mailed Oct. 25, 2019", 17 pgs.
"U.S. Appl. No. 15/886,469, Non Final Office Action mailed Feb. 28, 2019", 30 pgs.
"U.S. Appl. No. 15/886,469, Notice of Allowance mailed May 6, 2020", 14 pgs.

(56) References Cited

OTHER PUBLICATIONS

"U.S. Appl. No. 15/886,469, Response filed Dec. 18, 2019 to Final Office Action mailed Oct. 25, 2019", 14 pgs.
"U.S. Appl. No. 15/886,469, Response filed Jul. 20, 2018 to Restriction Requirement mailed May 25, 2018", 13 pgs.
"U.S. Appl. No. 15/886,469, Response filed Jul. 29, 2019 to Non-Final Office Action mailed Feb. 28, 2019", 15 pgs.
"U.S. Appl. No. 15/886,469, Restriction Requirement mailed May 25, 2018", 12 pgs.
"U.S. Appl. No. 14/233,130, Non Final Office Action mailed Jan. 14, 2016", 14 pgs.
"U.S. Appl. No. 14/233,130, Response filed Apr. 1, 2016 to Non-Final Office Action mailed Jan. 14, 2016", 14 pgs.
"U.S. Appl. No. 14/233,130, Restriction Requirement mailed Oct. 22, 2015", 11 pgs.
"European Application Serial No. 09771137.8, Office Action mailed Feb. 9, 2011", 1 pg.
"European Application Serial No. 09771137.8, Office Action mailed Feb. 14, 2011", 2 pgs.
"European Application Serial No. 09771137.8, Office Action mailed Mar. 3, 2011", 1 pg.
"European Application Serial No. 09771137.8, Office Action mailed Mar. 16, 2011", 1 pg.
"European Application Serial No. 09771137.8, Response filed Feb. 18, 2011 to Office Action mailed Feb. 9, 2011", 6 pgs.
"European Application Serial No. 09771137.8, Search Report mailed Nov. 4, 2013", 6 pgs.
"European Application Serial No. 16737889.2, Extended European Search Report mailed Mar. 21, 2018", 7 pgs.
"International Application Serial No. PCT/US2008/002756, International Preliminary Report on Patentability mailed Sep. 1, 2009", 6 pgs.
"International Application Serial No. PCT/US2008/002756, International Search Report mailed Feb. 2025, 09", 2 pgs.
"International Application Serial No. PCT/US2008/002756, Written Opinion mailed Feb. 25, 2009", 5 pgs.
"International Application Serial No. PCT/US2009/048838, International Preliminary Report on Patentability mailed Jan. 5, 2011", 7 pgs.
"International Application Serial No. PCT/US2009/048838, International Search Report mailed Apr. 30, 2010", 4 pgs.
"International Application Serial No. PCT/US2009/048838, Written Opinion mailed Apr. 30, 2010", 6 pgs.
"International Application Serial No. PCT/US2009/063715, International Preliminary Report on Patentability mailed May 10, 2011", 6 pgs.
"International Application Serial No. PCT/US2009/063715, International Search Report mailed May 27, 2010", 4 pgs.
"International Application Serial No. PCT/US2009/063715, Written Opinion mailed May 27, 2010", 5 pgs.
"International Application Serial No. PCT/US2010/052332, International Preliminary Report on Patentability mailed Apr. 11, 2012", 7 pgs.
"International Application Serial No. PCT/US2010/052332, International Search Report mailed Jun. 24, 2011", 4 pgs.
"International Application Serial No. PCT/US2010/052332, Written Opinion mailed Jun. 24, 2011", 6 pgs.
"International Application Serial No. PCT/US2011/043908, International Preliminary Report on Patentability mailed Jan. 15, 2013", 7 pgs.
"International Application Serial No. PCT/US2011/043908, International Search Report and Written Opinion mailed Apr. 6, 2012", 11 pgs.
"International Application Serial No. PCT/US2011/043922, International Preliminary Report on Patentability mailed Jan. 15, 2013", 4 pgs.
"International Application Serial No. PCT/US2011/043922, International Search Report mailed Mar. 19, 2012", 3 pgs.
"International Application Serial No. PCT/US2011/043922, Written Opinion mailed Mar. 19, 2012", 3 pgs.
"International Application Serial No. PCT/US2011/064460, International Preliminary Report on Patentability mailed Jun. 20, 2013", 7 pgs.
"International Application Serial No. PCT/US2011/064460, International Search Report mailed Jun. 19, 2012", 6 pgs.
"International Application Serial No. PCT/US2011/064460, Written Opinion mailed Jun. 19, 2012", 5 pgs.
"International Application Serial No. PCT/US2012/045598, International Preliminary Report on Patentability mailed Jan. 23, 2014", 6 pgs.
"International Application Serial No. PCT/US2012/045598, International Search Report mailed May 27, 2013", 3 pgs.
"International Application Serial No. PCT/US2012/045598, Written Opinion mailed May 27, 2013", 4 pgs.
"International Application Serial No. PCT/US2012/049613, International Preliminary Report on Patentability mailed Feb. 13, 2014", 9 pgs.
"International Application Serial No. PCT/US2012/049613, International Search Report mailed Feb. 26, 2013", 3 pgs.
"International Application Serial No. PCT/US2012/049613, Written Opinion mailed Feb. 26, 2013", 7 pgs.
"International Application Serial No. PCT/US2015/020546, International Preliminary Report on Patentability mailed Sep. 22, 2016", 7 pgs.
"International Application Serial No. PCT/US2015/020546, International Search Report mailed Aug. 10, 2015", 4 pgs.
"International Application Serial No. PCT/US2015/020546, Invitation to Pay Additional Fees and Partial Search Report mailed May 20, 2015", 2 pgs.
"International Application Serial No. PCT/US2015/020546, Written Opinion mailed Aug. 10, 2015", 5 pgs.
"International Application Serial No. PCT/US2016/013431, International Preliminary Report on Patentability mailed Jul. 27, 2017", 9 pgs.
"International Application Serial No. PCT/US2016/013431, International Search Report mailed Apr. 25, 2016", 3 pgs.
"International Application Serial No. PCT/US2016/013431, Written Opinion mailed Apr. 25, 2016", 7 pgs.
"Japanese Application Serial No. 2017-554255, Office Action mailed Jan. 9, 2018", with machine translation, 5 pgs.
"Japanese Application Serial No. 2017-554255, Office Action mailed Apr. 17, 2018", w/English translation, 11 pgs.
"Japanese Application Serial No. 2017-554255, Response filed Apr. 3, 2018 to Office Action mailed Jan. 9, 2018", (w/ English Claims), 17 pgs.
"Korean Application Serial No. 10-2017-7022348, Notice of Preliminary Rejection mailed May 16, 2018", with English translation of claims, 4 pgs.
"Korean Application Serial No. 10-2017-7022348, Response filed Jul. 12, 2018 to Notice of Preliminary Rejection mailed May 16, 2018", with English translation of claims, 9 pgs.
Addinall, Stephen, et al., "Temperature Shift Experiments with an ftsZ84(Ts) Strain Reveal Rapid Dynamics of FtsZ Localization and Indicate that the Z Ring Is Required throughout Septation and Cannot Reoccupy Division Sites Once Constriction Has Initiated", J. of Bacteriology, vol. 179, No. 13, (1997), 4277-4284.
Ambade, A. V, et al., "Fluorescent Polyelectrolytes as Protein Sensors", In: Polym. Int., 2007, vol. 56, (2007), 474-481.
Anderson, David E, et al., "Assembly Dynamics of FtsZ Rings in Bacillus subtilis and *Escherichia coli* and Effects of FtsZ-Regulating Proteins", Journal of Bacteriology, 186(17)., (2004), 5775-5781.
Antoci, Jr., Valentin, et al., "Vancomycin covalently bonded to titanium alloy prevents bacterial colonization", Journal of Orthopaedic Research, 25(7), (2007), 858-866.
Arnt, Lachelle, et al., "Cationic Facially Amphiphilic Poly(phenylene ethynylene)s Studied at the Air-Water Interface", Langmuir, 19(6), (2004), 2404-2408.
Arnt, Lachelle, et al., "New Poly(phenyleneethynylene)s with Cationic, Facially Amphiphilic Structures", Journal of the American Chemical Society, 124(26), (2002), 7664-7665.

(56) References Cited

OTHER PUBLICATIONS

Arnt, Lachelle, et al., "Nonhemolytic Abiogenic Polymers as Antimicrobial Peptide Mimics", J. Polym. Sci., Part A: Polym. Chem., 42(15), (2004), 3860-3864.

Bartlett, Grant R., "Phosphorus Assay in Column Chromatography", The Journal of Biological Chemistry, 234(3), (1959), 466-468.

Beaujuge, Pierre M., et al., "Spectral Engineering in pie-Conjugated Polymers with Intramolecular Donor-Acceptor Interactions", Accounts of Chemical Research, 43(11), (Nov. 2010), 1396-1407.

Beckloff, Nicholas, et al., "Activity of an Antimicrobial Peptide Mimetic against Planktonic and Biofilm Cultures of Oral Pathogens", Antimicrobial Agents and Chemotherapy, 51, (2007), 4125-4132.

Boeneman, Kelly, et al., "*Escherichia coli* DnaA forms helical structures along the longitudinal cell axis distinct from MreB fillaments", Molecular Microbiology, 72(3)., (2009), 645-657.

Bruns, R., et al., "Chapter 3—R&D in material protection: New biocides", In: Directory of Microbicides for the Protection of Materials—A Handbook, Paulus, W., Editor, (2005), 25-46.

Buffet-Bataillon, Sylvie, et al., "Emergence of resistance to antibacterial agents: the role of quaternary ammonium compounds—a critical review", International Journal of Antimicrobial Agents, 39(5)., (2012), 381-389.

Burton, Paul, et al., "Two Pathways of Division Inhibition in UV-Irradiated *E. coli*", Mol Gen Genet., 190(1)., (1983), 128-132.

Cabiscol, Elisa, et al., "Oxidative stress in bacteria and protein damage by reactive oxygen species", International Microbiology, 3., (2000), 3-8.

Capuano, Ben, et al., "The Synthesis and Preliminary Pharmacological Evaluation of a Series of Substituted 4'-Phenoxypropyl Analogues of the Atypical Antipsychotic Clozapine", Aust. J. Chem., 63, (2010), 116-124.

Ceri, H., et al., "The Calgary Biofilm Device: New Technology for Rapid Determination of Antibiotic Susceptibilities of Bacterial Biofilms", Journal of Clinical Microbiology, 37(6), (1999), 1771-1776.

Chamchod, Farida, et al., "Modeling methicillin-resistant *Staphylococcus aureus* in hospitals: Transmission dynamics, antibiotic usage and its history", Theor Biol Med Model. , 9, 25., (2012), 1-14.

Chemburu, et al., "Conjugated Polyelectrolyte Supported Bead Based Assays for Phospholipase A2 Activity", (2008), 14492-14499.

Chemburu, Sireesha, et al., "Light-Induced Biocidal Action of Conjugated Polyelectrolytes Supported on Colloids", Langmuir, 24, (2008), 11053-11062.

Choi, W. S., et al., "Synthesis of Two Types of Nanoparticles in Polyelectrolyte Capsule Nanoreactors and Their Dual Functionality", J. Am. Chem. Soc., 127, (2005), 16136-16142.

Clark, A. P. Z., et al., "An Amphiphilic Poly(phenylene ethynylene) as the Structure-Directing Agent for Periodic Nanoscale Silica Composite Materials", Nano Letters, 5, (2005), 1647-1652.

Cooper, B S, et al., "Methicillin-resistant *Staphylococcus aureus* in hospitals and the community: Stealth dynamics and control catastrophes", Proc. Nat. Acad. Sci., 2004, 101(27), (2004), 10223-10228.

Corbitt, Thomas, et al., "Antimicrobial Non-Woven Fibrous Materials", U.S. Appl. No. 61/528,603, filed Aug. 29, 2011, 17 pgs.

Corbitt, Thomas S., et al., "Conjugated Polyelectrolyte Capsules: Light-Activated Antimicrobial Micro Roach Motels", ACS Appl. Mater. Interfaces, 1(1), (2009), 48-52.

Corbitt, Thomas S., et al., "Light and dark biocidal activity of cationic poly(arylene ethynylene) conjugated polyelectrolytes", Photochem. Photobiol. Sci., 8, (2009), 998-1005.

Costerton, J. William, et al., "Mechanism of Electrical Enhancement of Efficacy of Antibiotics in Killing Biofilm Bacteria", Antimicrobial Agents and Chemotherapy, 38(12), (1994), 2803-2809.

Cramton, Sarah, et al., "The Intercellular Adhesion (ica) Locus Is Present in *Staphylococcus aureus* and Is Required for Biofilm Formation", Infection and Immunity, 67(10)., (1999), 5427-5433.

Dascier, Dimitri, et al., "Efficacy of End-Only-Functionalized Oligo(arylene-ethynylene)s in Killing Bacterial Biofilms", Langmuir, 28(31), (2012), 11286-11290.

De Geest, B. G., et al., "Release mechanisms for polyelectrolyte capsules", Chem. Soc. Rev., 36, (2007), 636-649.

Ding, Liping, et al., "Insight into the Mechanism of Antimicrobial Poly(phenylene ethynylene) Polyelectrolytes: Interactions with Phosphatidylglycerol Lipid Membranes", Langmuir, 25(24), (2009), 13742-13751.

Donlan, Rodney M., et al., "Microbial Life on Surfaces", Emerging Infectious Diseases, 8(9), (2002), 881-890.

Eun, Ye-Jin, et al., "Fabrication of Microbial Biofilm Arrays by Geometric Control of Cell Adhesion", Langmuir, 25(8), (2009), 4643-4654.

Evans, D, et al., "Critical Micelle Concentrations for Alkyltrimethylammonium Bromides in Water from 25 to 160° C.", J. Solution Chem., 13(2)., (1984), 87-101.

Fan, Qu-Li, et al., "Water-Soluble Cationic Poly(p-phenyleneethynylene)s (PPEs): Effects of Acidity and Ionic Strength on Optical Behavior.", Macromolecules. vol. 38, (2005), 2927-2936.

Fang, Zhen, et al., "Low-Bandgap Donor-Acceptor Conjugated Polymer Sensitizers for Dye-Sensitized Solar Cells", Journal of the American Chemical Society, 133(9), (2011), 3063-3069.

Ferreira, Isabel C.F.R, et al., "Screening of antimicrobial activity of diarylamines in the 2,3,5-trimethylbenzo[b]thiophene series a structure-activity evaluation study", Bioorganic & Medicinal Chemistry Letters, 14(23), (2004), 5831-5833.

Flemming, Hans-Curt, et al., "The biofilm matrix", Nat Rev Microbiol., 8(9)., (2010), 623-633.

Galaev, Igor Y., "'Smart' polymers in biotechnology and medicine", Russian Chemical Reviews, 64(5), (1995), 471-489.

Gao, Yuan, et al., "Recent Advances in Antimicrobial tTeatment of Textiles", Textile Research Journal, 78(1), (2008), 60-72.

Gaylord, Brent, et al., "DNA Hybridization Detection with Water-Soluble Conjugated Polymers and Chromophore-Labeled Single-Stranded DNA", Journal of the American Chemical Society, vol. 125, No. 4, (Jan. 29, 2003), 896-900.

George, Wayne N., et al., "Amplified fluorescence quenching in high ionic strength media.", Soft Matter. vol. 3, (2007), 1381-1387.

Gilbert, P, et al., "Biofilms in vitro and in vivo: do singular mechanism imply cross-resistance?", J Appl Microbiol.,92 Suppl., (2002), 98S-110S.

Goehring, Nathan, et al., "Diverse Paths to Midcell: Assembly of the Bacterial Cell Division Machinery", Current Biology, 15., (2005), R514-R526.

Gorwitz, R, et al., "More Challenges in the Prevention and Management of Community-Associated, Methicillin-Resistant *Staphylococcus aureus* Skin Disease", Ann. Intern. Med., 148 (4)., (2008), 310-312.

Guan, Bin, et al., "Different Functionalization of the Internal and External Surfaces in Mesoporous Materials for Biosensing Applications Using "Click" Chemistry", Langmuir, 27(1), (2010), 328-334.

Harrison, Joe J., et al., "Microtiter susceptibility testing of microbes growing on peg lids: a miniaturized biofilm model for high-throughput screening", Nature Protocols, 5(7), (2010), 1236-1254.

Hill, Eric, et al., "Cationic oligo-p-phenylene ethynylenes form complexes with surfactants for long-term light-activated biocidal applications", Photochem. Photobiol. Sci., 13., (2014), 247-253.

Hill, Eric, et al., "Molecular Dynamics Simulation Study of the Interaction of Cationic Biocides with Lipid Bilayers: Aggregation Effects and Bilayer Damage", Langmuir 28, (2012), 14849-14854.

Hill, Eric, et al., "Photochemistry of "End-Only" Oligo-p-phenylene Ethynylenes: Complexation with Sodium Dodecyl Sulfate Reduces Solvent Accessibility", Langmuir, 29(31), (2013), 9712-9720.

Hill, Eric H, et al., "The influence of structured interfacial water on the photoluminescence of carboxyester-terminated oligo-p-phenylene ethynylenes", Journal of Physical Organic Chemistry, 27:252-257, (2014), 7 pgs.

Hoffman, Allan S., "Bioconjugates of Intelligent Polymers and Recognition Proteins for Use in Diagnostics and Affinity Separations", Clinical Chemistry, 46:9, (2000), 1478-1486.

(56) References Cited

OTHER PUBLICATIONS

Hortholary, Cedric, et al., "An Approach to Long and Unsubstituted Molecular Wires: Synthesis of Redox-Active, Cationic Phenylethynyl Oligomers Designed for Self-Assembled Monolayers", J. Org. Chem., 68(6), (2003), 2167-2174.

Huisgen, Rolf, "Centenary Lecture—1,3-Dipolar Cycloadditions", Proceedings of the Chemical Society of London, (Oct. 1961), 357-369.

Ibraeva, Zhanar E., et al., "Solution Properties and Complexation of Polyampholytes based on N,N-Dimethyldiallyl-ammonium Chloride and Maleic Acid or Alkyl (Aryl) Derivatives of Malemic Acids", Macromol. Chem. Phys., 205, (2004), 2464-2472.

Ingersol, Laura, "Antifungal Activity of Cationic Conjugated Polyelectrolytes and Oligomers against Candida albicans", Thesis for Master's in Science, Biomedical Science. University of New Mexico, <https://digitalrepository.unm.edu/biom_etds/82>, (2014), 113 pgs.

Ista, Linnea K., et al., "Conjugated-Polyelectrolyte-Grafted Cotton Fibers Act as "Micro Flypaper" for the Removal and Destruction of Bacteria", ACS Applied Materials & Interfaces, 3(8), (2011), 2932-2937.

Ji, E., "Conjugated polyelectrolytes: Synthesis, photophysical studies and applications to sensors and biocidal activity", Ph.D. dissertation, Univ. of Florida, 2009, (2009), 167 pgs.

Ji, E., et al., "pH-Dependent Optical Properties of a Poly(phenylene ethynylene) Conjugated Polyampholyte", In: Langmuir, vol. 27, (Dec. 28, 2010), 1565-1568.

Ji, Eunkyung, et al., "Antibacterial Activity of Conjugated Polyelectrolytes with Variable Chain Lengths", Langmuir, 27, (2011), 10763-10769.

Ji, Eunkyung, et al., "Light and Dark-Activated Biocidal Activity of Conjugated Polyelectrolytes", ACS Applied Materials & Interfaces, 3(8), (2011), 2820-2829.

Jiang, Hui, et al., "Conjugated Polyelectrolytes: Synthesis, Photophysics, and Applications", Angew. Chem. Int. Ed., 48(24), (2009), 4300-4316.

Jiang, Hui, et al., "Effects of Polymer Aggregation and Quencher Size on Amplified Fluorescence Quenching of Conjugated Polyelectrolytes", Langmuir, 23(18), (2007), 9381-9486.

Jones, Tineke, "Response of Escherichia coli to Environmental Stress", Stress Response of Foodborne Microorganisms. NovaScience Publishers., (2012), 293-330.

Kenawy, El-Refaie, et al., "The Chemistry and Applications of Antimicrobial Polymers: A State-of-the-Art Review", Biomacromolecules, 8(5), (2007), 1359-1384.

Kilger, Robert, et al., "Bidirectional energy transfer between the triplet T1 state of photofrin and singlet oxygen in deuterium oxide", Chemical Physics Letter 343, (2001), 543-548.

Kim, Chae Kyu, et al., "Complexation of Anionic Conjugated Polyelectrolyte with Cationic Surfactant", Macromolecular Research, vol. 13 No. 5, (2005), 460-462.

Kim, Sook Kyung, et al., "Chemosensors for Pyrophosphate", Accounts of Chemical Research 42, (2009), 23-31.

Klevens, R M, et al., "Estimating Health Care-Associated Infections and Deaths in U.S. Hospitals", Public Health Rep., 2007, 122(2)., (2002), 160-166.

Kolb, Hartmuth C., et al., "Click Chemistry: Diverse Chemical Function from a Few Good Reactions", Angew. Chem. Int. Ed., 40, (2001), 2004-2021.

Kotz, Joachim, "Inter- and intramolecular interactions in polyelectrolyte complex formation with polyampholytes", Macromolecular Chemistry and Physics, 194(2), (1993), 397-410.

Kruse, T, et al., "Dysfunctional MreB inhibits chromosome segregation in Escherichia coli", EMBO J., 22(19)., (2003), 5283-5292.

Leach, Michelle K., et al., "Electrospinning Fundamentals: Optimizing Solution and Apparatus Parameters", Journal of Visualized Experiments, 47, (2011), 4 pgs.

Lee, H., et al., "Shell Cross-Linked Hyaluronic Acid/Polylysine Layer-by-Layer Polyelectrolyte Microcapsules Prepared by Removal of Reducible Hyaluronic Acid Microgel Cores", Biomacromolecules, 8, (2007), 3705-3711.

Lee, Wen-Fu, et al., "Synthesis and solubility of the poly(sulfobetaine)s and the corresponding cationic polymers: 2. Aqueous solution properties of poly[ N,N'-dimethyl-(acrylamido propyl) ammonium propane sulfonate]", Polymer, 36(2), (1995), 357-364.

Leid, Jeff, et al., "Human Leukocytes Adhere to Penetrate, and Respond to Staphylococcus aureus Biofilms", Infection and Immunity, 70(11)., (2002), 6339-6345.

Lin, Ching-Yao, et al., "Design and Characterization of Novel Porphyrins with Oligo(phenylethylnyl) Links of Varied Length for Dye-Sensitized Solar Cells: Synthesis and Optical, Electrochemical, and Photovoltaic Investigation", J. Phys. Chem. C., 113(2), (2009), 755-764.

Lindig, Barbara, et al., "Determination of the Lifetime of Singlet Oxygen in D2O Using 9, IO-Anthracenedipropionic Acid, a Water-Soluble Probe", J. Am. Chem. Soc., 102 (17)., (1980), 5590-5593.

Lindsay, D., et al., "Bacterial biofilms within the clinical setting: what healthcare professionals should know", Journal of Hospital Infection, 64, (2006), 313-325.

Liu, Yan, et al., "Conjugated Polyelectrolyte-Based Real-Time Fluorescence Assay for Alkaline Phosphatase with Pyrophosphate as Substrate", Anal. Chem. 80, (2008), 8605-8612.

Liu, Yan, et al., "Conjugated polyelectrolytes as fluorescent sensors", Journal of Photochemistry and Photobiology C: Photochemistry Reviews, 10(4), (2009), 173-190.

Lock, Rowena, et al., "Cell-division inhibitors: new insights for Future anibiotics", Nature Reviews Drug Discovery, 7., (2008), 324-338.

Lowe, Andrew B., et al., "Synthesis and Solution Properties of Zwitterionic Polymers", Chem. Rev., 102, (2002), 4177-4189.

Lu, L., et al., "Biocidal Activity of a Light-Absorbing Fluorescent Conjugated Polyelectrolyte", Langmuir, 21, (2005), 10154-10159.

Lu, Timothy K., et al., "Dispersing biofilms with engineered enzymatic bacteriophage", Proc. Natl. Acad. Sci. USA, 104(27), (2007), 11197-11202.

Maciag-Dorszynska, Monika, et al., "Mutations in central carbon metabolism genes suppress defects in nucleoid position and cell division of replication mutants in Escherichia coli", Gene 503., (2012), 31-35.

Magrex-Debar, Elisabeth, et al., "Evaluation of biohazards in dehydrated biofilms", International Journal of Food Microbiology 55., (2000), 239-243.

Mah, Thien-Fah, et al., "Mechanisms of biofilm resistance to antimicrobial agents", Trends in Microbiology vol. 9 No. 1., (2001), 34-39.

Maisch, Tim, et al., "The role of singlet oxygen and oxygen concentration in photodynamic inactivation of bacteria", The National Academy of Sciences of the USA. PNAS vol. 104, No. 17, (2007), 7223-7228.

Malik, Zvi, et al., "New Trends in Photobiology (Invited Review) Bactericidal Effects of Photoactivated Porphyrins—An Alternative Approach to Antimicrobial Drugs", Journal of Photochemistry and Photobiology B: Biology, 5(3-4)., (1990), 281-293.

Mann, Ethan, et al., "Modulation of eDNA Release and Degradation Affects Staphylococcus aureus Biofilm Maturation", PLOS One, 4(6)., (2009), e5822.

McCormick, C. L., "Polyampholytes (Overview)", In: Polymeric Materials Encyclopedia, vol. 7, CRC Press, Boca Raton, FL, (1996), 5462-5476.

McNeill, Karol, et al., "Acid tolerance response of bioélm cells of Streptococcus mutans", FEMS Microbiology Letters, 221., (2003), 25-30.

McQuade, D. Tyler, et al., "Signal Amplification of a Turn-On Sensor: Harvesting the Light Captured by a Conjugated Polymer", J. Am. Chem. Soc., 122, (2000), 12389-12390.

Miranda, Oscar R, et al., "Array-Based Sensing of Proteins Using Conjugated Polymers", JACS 129:9856-9857, (2007), 2 pgs.

Narendiran, "Electrospun Ultrathin Nylon Fibers for Protective Applications", Journal of Applied Polymer Science, vol. 116, (Jan. 7, 2010), 2181-2187.

(56) References Cited

OTHER PUBLICATIONS

Neuhaus, Francis, et al., "A Continuum of Anionic Charge: Structures and Functions of D-Alanyl-Teichoic Acids in Gram-Positive Bacteria", Microbiology and Molecular Biology Reviews, 67(4)., (2003), 686-723.
Nickerson, Emma, et al., "*Staphylococcus aureus* disease and drug resistance in resource-limited countries in south and east Asia", Lancet Infect. Dis., 9., (2009), 130-135.
Nikaido, Hiroshi, "Outer Membrane", *Escherichia coli* and *Salmonella*: cellular and molecular biology. 2nd ed. Washington, D.C: American Society for Microbiology., (1996), 29-47.
Notestein, Justin M., et al., "Covalent Grafting of m-Phenylene-Ethynylene Oligomers to Oxide Surfaces", Chem. Mater., 22, (2010), 5319-5327.
Ogawa, Katsu, et al., "Conjugated Polyelectrolyte-Grafted Silica Microspheres", Langmuir, 23(8), (2007), 4541-4548.
Olson, Merle E., et al., "Biofilm bacteria: formation and comparative susceptibility to antibiotics", Canadian Journal of Veterinary Research-Revue Canadienne De Recherche Veterinaire, 66, (2002), 86-92.
Pappas, et al., "Anti-fungal Properties of Cationic Phenylene Ethynylenes and their impact on ß-glucan exposure", Antimicrobial Agents and Chemotherapy, vol. 60, No. 8, (2016), 4519-4529 pgs.
Parthasarathy, Anand, "Conjugated Polyelectrolytes with Imidazolium Solubilizing Groups Properties and Application to Photodynamic Inactivation of Bacteria", ACS Applied Materials & Interfaces vol. 7, No. 51, (2015), 28027-28034.
Pasquier, Nicolas, et al., "From Multifunctionalized poly(ethylene Imine)s toward Antimicrobial Coatings", Biomacromolecules, 8, (2007), 2874-2882.
Patel, Dinesh G., et al., "It Takes More Than an Imine: The Role of the Central Atom on the Electron-Accepting Abilitty of Benzotriazole and Benzothiadiazole Oligomers", Journal of the American Chemical Society, 134(5), (2012), 2599-2612.
Pinto, Mauricio, et al., "Amplified fluorescence quenching and biosensor application of a poly (para-phenylene) cationic polyelectrolyte", Res. Chem. Intermed. 33, (2007), 79-90.
Pinto, Mauricio R., et al., "Amplified fluorescence sensing of protease activity with conjugated polyelectrolytes", Proc. Natl. Acad. Sci. USA, 101(20), (2004), 7505-7510.
Pinto, Mauricio R., et al., "Conjugated Polyelectrolytes: Synthesis and Applications", Synthesis, 9, (2002), 1293-1309.
Potera, Carol, "C. Microbiology—Forging a Link Between Biofilms and Disease", Science, 283(5409), (1999), 1837-1939.
Reddinger, Jerry L., et al., "Molecular Engineering of p-Conjugated Polymers", Radical Polymerisation Polyelectrolytes, Series: Advances in Polymer Science, vol. 145, (1999), 57-122.
Rice, Kelly, et al., "The cidA murein hydrolase regulator contributes to DNA release and biofilm development in *Staphylococcus aureus*", Proc. Nat. Acad. Sci., 104(19)., (2007), 8113-8118.
Rico, Ana Isabel, et al., "Role of *Escherichia coli* FtsN protein in the assembly and stability of the cell division ring", Molecular Microbiology, 76(3)., (2010), 760-771.
Rolinson, George, "Forty years of ß-lactam research", Journal of Antimicrobial Chemotherapy, 41., (1998), 589-603.
Romberg, Laura, et al., "Assembly Dynamics of the Bacterial Cell Division Protein FTSZ: Poised at the Edge of Stability", Annual Review of Microbiology, 57., (2003), 125-154.
Ron, Eliora, et al., "Growth Rate of *Escherichia coli* at Elevated Temperature: Lomitation by Methionine", Journal of Bacteriology, 107(1)., (1971,), 391-396.
Schanze, K. S, et al., "Functional Polyelectrolytes", In: Langmuir, 2009, vol. 25, (2009), 13698-13702.
Schild, H. G., "Poly(N-Isopropylacrylamide): Experiment, Theory and Application", Prog. Polym. Sci., 17, (1992), 163-249.
Schlüter, A. D., "The Tenth Anniversary of Suzuki Polycondensation (SPC)", Journal of Polymer Science Part A: Polymer Chemistry, 39(10), (2001), 1533-1556.

Senthilkumar, Sadasivam, et al., "Photophysical properties of coumarin-30 dye in aprotio and protic solvents of varying polarities", Photochemistry and Photobiology, 80, (2004), 104-111.
Shi, Songqing, et al., "Synthesis and Characterization of a Water-Soluble Poly(p-phenylenevinylene) Derivative", Macromolecules, 23(8), (1990), 2119-2124.
Stewart, Philip, et al., "Antibiotic resistance of bacteria in biofilms", Lancet, 358., (2001), 135-138.
Stewart, Philip S., et al., "Physiological heterogeneity in biofilms", Nature Reviews Microbiology, 6, (Mar. 2008), 199-210.
Storz, Gisela, et al., "Oxidative stress", Current Opinion in Microbiology, 2., (1999), 188-194.
Stricker, Jesse, et al., "Rapid assembly dynamics of the *Escherichia coli* FtsZ-ring demonstrated by fluorescence recovery after photobleaching", Proc. Nat. Acad. Sci., 99(5)., (2002), 3171-3175.
Tacconelli, Evelina, et al., "Does antibiotic exposure increase the risk of methicillin-resistant *Staphylococcusaureus* (MRSA) isolation? A systematic review and meta-analysis", J. Antimicrob. Chemother. ,61(1)., (2008), 26-38.
Tan, et al., "Hyper-Efficient Quenching of a Conjugated Polyelectrolyte By Dye-Doped Silica Nanoparticles: Better Quenching In The Nonaggregated State", Langmuir Letter 26(3), (Nov. 19, 2009), 1528-1532.
Tan, et al., "Thermodynamics of Sodium Dodecyl Sulfate Partitioning into Lipid Membranes", Biophysics Journal vol. 83, (2002), 1547-1556 pgs.
Tan, C, et al., "Photophysics, aggregation and amplified quenching of a water-soluble poly (phenylene ethynylene)", Chem. Commun., (2002), 446-447.
Tan, C., et al., "Solvent-induced Self-Assembly of a Meta-Linked Conjugated Polyelectrolyte. Helix Formation. Guest Intercalation, and Amplified Quenching", Adv. Mater., vol. 16, No. 14, (2004), 1208-1212.
Tan, Chunyan, et al., "Amplified Quenching of a Conjugated Polyelectrolyte by Cyanine Dyes", J. Am. Chem. Soc., 126, (2004), 13685-13694.
Tang, Yanli, et al., "Light-induced antibacterial activity of symmetrical and asymmetrical oligophenylene ethynylenes", Langmuir, 27(8), (2011), 4956-4962.
Tang, Yanli, et al., "Synthesis, Self-Assembly, and Photophysical Behavior of Oligo Phenylene Ethynylenes: From Molecular to Supramolecular Properties", Langmuir, 25(1), (2009), 21-25.
Tang, Yanli, et al., "Synthesis, Self-Assembly, and Photophysical Properties of Cationic Oligo(p-phenyleneethynylene)s", Langmuir, 27(8), (2011), 4945-4955.
Teitzel, Gail, "Heavy Metal Resistance of Bio?lm and Planktonic Pseudomonas aeruginosa", Applied and Environmental Microbiology, 69(4)., (2003), 2313-2320.
Tew, G. N, et al., "", Biochimica et Biophysica Acta 2006, (2006), 1387-1392.
Thomas, III, Samuel W., et al., "Chemical Sensors Based on Amplifying Fluorescent Conjugated Polymers", Chem. Rev., 107, (2007), 1339-1386.
Tiller, J. C., et al., "Designing surfaces that kill bacteria on contact", Proc. Natl. Acad. Sci. USA, 98(11), (May 22, 2001), 5981-5985.
Tong, W., et al., "Single Polyelectrolyte Microcapsules Fabricated By Glutaraldehyde-Mediated Covalent Layer-By-Layer Assembly", Macromol. Rapid Commun., 27, (2006), 2078-2083.
Trauble, Hermann, et al., "The Structure of *Escherichia coli* Membranes Studied by Fluorescence Measurement of Lipid Phase Transitions", Biophys. Acta, 307., (1973), 491-512.
Turro, J, et al., "Luminescent Probes for Detergent Solutions. A Simple Procedure for Determination of the Mean Aggregation Number of Micelles", J. Am. Chem. Soc., 100., (1978), 5951-5952.
Valle, Jaione, et al., "Broad-spectrum biofilm inhibition by a secreted bacterial polysaccharide", Proc. Natl. Acad. Sci. USA, 103(33), (2006), 12558-12563.
Vollmer, Waldemar, et al., "Peptidoglycan structure and architecture", FEMS Microbiol. Rev. 32(2)., (2008), 149-167.
Wallow, Thomas I., et al., "In Aqua Synthesis of Water-Soluble Poly(p-phenylene) Derivatives", J. Am. Chem. Soc., 113, (1991), 7411-7412.

(56) References Cited

OTHER PUBLICATIONS

Wang, et al., "Antimicrobial activity of cationic conjugated polyelectrolytes and oligomers against *Saccharomyces cerevisiae* vegetative cells and Ascospores", ACS Applied Materials and Interfaces, (2013), 4555-4561 pgs.

Wang, Deli, et al., "Biosensors from conjugated polyelectrolyte complexes", Proc. Natl. Acad. Sci. USA, 96, (1999), 12287.

Wang, Deli, et al., "Photoluminescence Quenching of Conjugated Macromolecules by Bipyridinium Derivatives in Aqueous Media: Charge Dependence", Langmuir, 17, (2001), 1262-1266.

Wang, Ying, et al., "Direct Visualization of Bactericidal Action of Cationic Conjugated Polyelectrolytes and Oligomers", Langmuir, 28, (2012), 65-70.

Wang, Ying, et al., "Membrane Perturbation Activity of Cationic Phenylene Ethynylene Oligomers and Polymers: Selectivity against Model Bacterial and Mammalian Membranes", Langmuir, 26(15), (Jun. 29, 2010), 12509-12514.

Wang, Ying, et al., "Understanding the Dark and Light-Enhanced Bactericidal Action of Cationic Conjugated Polyelectrolytes and Oligomers", Langmuir, 29(2)., (2013), 781-792.

Wang, Yingsheng, et al., "Photochemical probes of intramolecular electronc and energy transfer", Chemical Physics, 176, (1993), 305-319.

Wang, Z., et al., "Preparation and application of single polyelectrolyte microcapsules possessing tunable autofluorescent properties.", Colloids and Surfaces A: Physicochemical and Engineering Aspects, 329, (2008), 58-66.

Wosnick, Jordan H., et al., "Synthesis and Application of Poly(phenyleneEthynylene)s for Bioconjugation: A Conjugated Polymer-Based Fluorogenic Probe", American Chemical Society, 127, (2005), 3400-3405.

Xu, Shimei, et al., "Effect of the Anionic-Group/Cationic-Group Ratio on the Swelling Behavior and Controlled Release of Agrochemicals of the Amphoteric, Superabsorbent Polymer Poly(acrylic acid-co-diallyldimethylammonium chloride)", Journal of Applied Polymer Science, 102, (2006), 986-991.

Yang, Chaoyong James, et al., "Direct Synthesis of an Oligonucleotide-Poly-(phenylene ethynylene) Conjugate with a Precise One-to-One Molecular Ratio", Angew. Chem. Int. Ed. 44, (2005), 2572-2576.

Zhai, Lei, et al., "A Simple Method to Generate Side-Chain Derivatives of Regioregular Polythiophene via the GRIM Metathesis and Post-polymerization Functionalization", Macromolecules 36, (2003), 61-64.

Zhang, Lian-Hui, et al., "Quorum sensing and signal interference: diverse implications", Molecular Microbiology, 53(6), (2004), 1563-1571.

Zhao, Xiaoyong, et al., "Variable Band Gap Poly(arylene ethynylene) Conjugated Polyelectrolytes", Macromolecules, 39, (2006), 6355-6366.

Zhinjou, Zhou, "Studies of a cyanine-based biosensor and light-induced antibacterial activities of oligophenyleneethynylenes", Dissertation, Chemistry, University of New Mexico, Albuquerque, NM, (Dec. 2010), 165 pgs.

Zhou, Zhijun, et al., ""End-Only" Functionalized Oligo(phenylene ethynylene)s: Synthesis, Photophysical and Biocidal Activity, Journal of Physical Chemistry Letters, 1(21), (2010), 3207-3212.

Zhu, Huiguang, et al., "Synthesis of Size-Controlled Monodisperse Manganese Carbonate Microparticles as Templates for Uniform Polyelectrolyte Microcapsule Formation.", Chern. Mater., 17, (2005), 2323-2328.

\* cited by examiner

P-PHENYLENE ETHYNYLENE COMPOUNDS AS BIOACTIVE AND DETECTION AGENTS

CROSS-REFERENCE TO RELATED APPLICATIONS

This application is a divisional of U.S. patent application Ser. No. 15/125,896, filed on Sep. 13, 2016, which is a U.S. National Stage Filing under 35 U.S.C. § 371 of International Patent Application Serial No. PCT/US2015/020546, filed Mar. 13, 2015, and published on Sep. 17, 2015 as WO2015/138965, which claims the benefit of the priority filing dates of U.S. Provisional Application No. 61/953,311, filed on Mar. 14, 2014. U.S. Provisional Application No. 61/954,923, filed on Mar. 18, 2014, U.S. Provisional Application No. 61/955,522, filed on Mar. 19, 2014, and U.S. Provisional Application No. 62/012,780, filed on Jun. 16, 2014, the disclosures of which are incorporated by reference herein in their entireties.

STATEMENT OF GOVERNMENT SUPPORT

This invention was made with Government support under HDTRA-11-1-0004 awarded by the Defense Threat Reduction Agency (DTRA), under DMR1207362 and CBET-1150855 awarded by the National Science Foundation (NSF), and under R21 NS07708 awarded by the National Institutes of Health (NIH). The U.S. Government has certain rights in this invention.

BACKGROUND

Agents that can kill the viable bacteria, such as antibiotics, can be ineffective to terminate the viability of the bacterial spores, making populations of such bacteria difficult to control. Even if the entire mature population is killed, viable spores are still available for germination to restore a potentially pathogenic bacterial population.

Detecting enzymes, proteins, or chemical agents can be valuable for a wide variety of uses. For example, abnormal formation and deposition of amyloid protein aggregates is associated with a number of neurodegenerative diseases, including, but not limited to, Alzheimer's disease, Parkinson's disease, Huntington's disease, systemic amyloidosis and inherited organ-specific amyloidoses, and transmissible prion diseases such as bovine spongiform encephalopathy, chronic wasting disease, and sheep scrapie. Each of these diseases is characterized by symptoms including cross-β-sheet rich aggregates, formed from characteristic proteins depending upon the specific disease. Understanding, diagnosing, and treating these diseases require tools to locate and track the formation of amyloid aggregates in living organisms, particularly the putative toxic aggregate forms. The primary method for amyloid detection is histopathological staining of tissue sections with fluorescent dyes, of which the commonest currently is Thioflavin T. Existing dyes have limitations; they target primarily mature aggregates and they cannot distinguish between amyloids with differing conformations, particularly oligomeric/pre-fribillar aggregates that are considered the primary toxic species.

SUMMARY OF THE INVENTION

In various embodiments, the present invention provides a method of inducing germination of microbial spores including contacting the microbial spores with a p-phenylene ethynylene compound.

In various embodiments, the present invention provides a method for detecting an enzyme. The method includes (i) introducing an enzyme to a composition including a p-phenylene ethynylene compound and an enzyme substrate. The method also includes (ii) analyzing the change in fluorescence of the p-phenylene ethynylene compound following introduction of the enzyme.

In various embodiments, the present invention provides a method for detecting an enzyme. The method includes (i) introducing an enzyme to a composition including a p-phenylene ethynylene compound and an enzyme substrate; and (ii) analyzing the change in fluorescence of the p-phenylene ethynylene compound following introduction of the enzyme. The p-phenylene ethynylene compound has the structure:

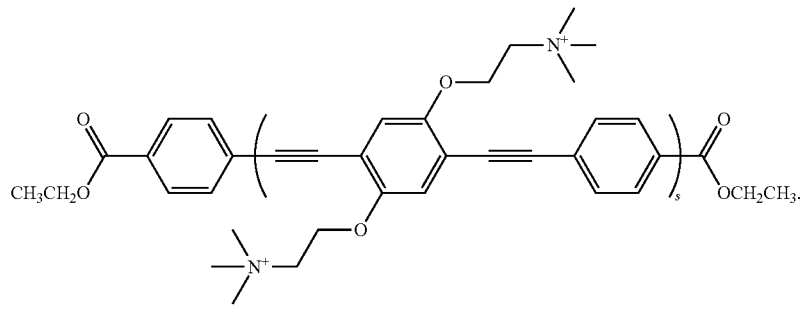

The variable s is about 1 to about 3. The enzyme substrate is 1,2-dilauroyl-sn-glycero-phospho-(1'-rac-glycerol). The enzyme is at least one of phospholipase A1, phospholipase A2, and phospholipase C.

In various embodiments, the present invention provides a method for detecting an enzyme. The method includes (i) introducing an enzyme to a composition including a p-phenylene ethynylene compound and an enzyme substrate. The method also includes (ii) analyzing the change in fluorescence of the p-phenylene ethynylene compound following introduction of the enzyme. The p-phenylene ethynylene compound has the structure:

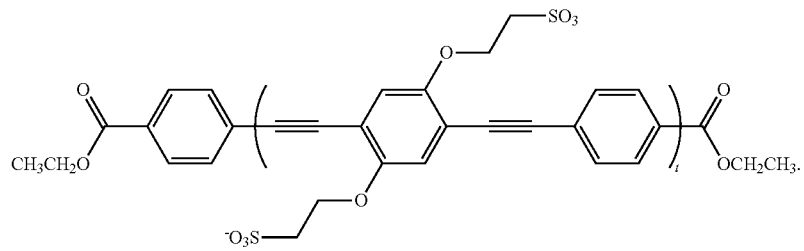

The variable t is about 1 to about 3. The enzyme substrate is lauroyl choline. The enzyme is acetylcholinesterase.

In various embodiments, the present invention provides a sensor. The sensor includes a p-phenylene ethynylene compound and an enzyme substrate.

In various embodiments, the present invention provides a sensor. The sensor includes a cationic p-phenylene ethynylene compound and an anionic enzyme substrate. The p-phenylene ethynylene compound has the structure:

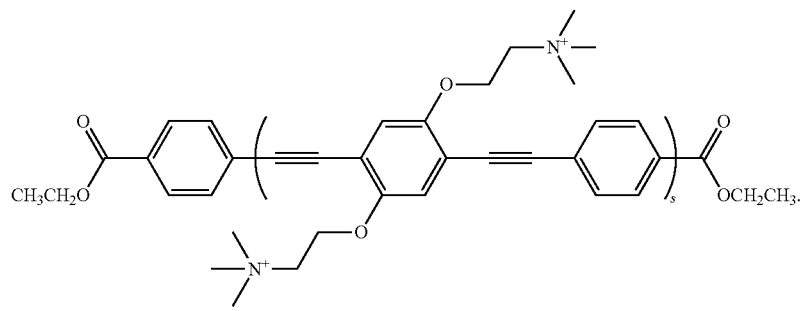

The variable s is about 1 to about 3. The anionic enzyme substrate is 1,2-dilauroyl-sn-glycero-phospho-(1'-rac-glycerol).

In various embodiments, the present invention provides a sensor. The sensor includes a p-phenylene ethynylene compound and an enzyme substrate. The p-phenylene ethynylene compound has the structure:

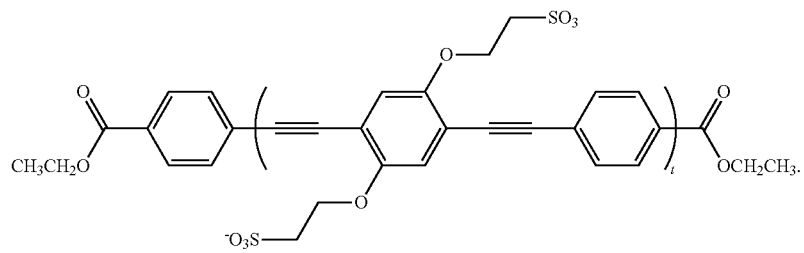

The variable t is about 1 to about 3. The enzyme substrate is lauroyl choline.

In various embodiments, the present invention provides a method for protein analysis. The method includes (i) introducing a p-phenylene ethynylene compound to a biological sample including at least one protein. The method also includes (ii) analyzing the fluorescence of the p-phenylene ethynylene compound in the presence of the biological sample including the at least one protein.

In various embodiments, the present invention provides a method for protein analysis. The method includes (i) analyzing the fluorescence of a p-phenylene ethynylene compound. The method includes (ii) introducing the p-phenylene ethynylene compound to a biological sample including at least one protein. The method includes (iii) analyzing the fluorescence of the p-phenylene ethynylene compound in the presence of the biological sample including the at least one protein. The method also includes (iv) determining the morphology of the at least one protein in the biological sample by analyzing spectral changes between the fluorescence of the p-phenylene ethynylene compound of step (i) and the fluorescence of the p-phenylene ethynylene compound in the presence of the biological sample including the at least one protein of step (iii). The p-phenylene ethynylene compound has the structure:

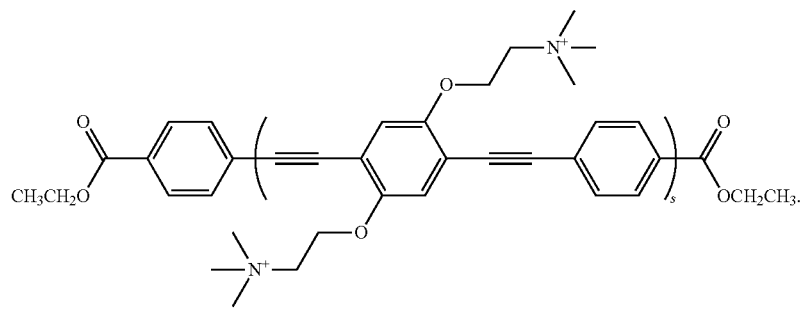

The variable s is 1. The protein is at least one of an amyloid beta protein, Aβ-40, Aβ-42, tau, and α-synuclein, islet amyloid precursor protein, Huntingtin, prion, lysozyme, TDP-43 (transactive response DNA-binding protein 43), FUS (fused in sarcoma), and insulin.

In various embodiments, the present invention provides a method for detecting a chemical agent. The method includes (i) exposing a sensor composition including a complex including a p-phenylene ethynylene compound and an enzyme substrate to a sample. The method includes (ii) introducing an enzyme to the sensor composition of step (i). The method also includes (iii) analyzing the change in fluorescence of the p-phenylene ethynylene compound between the exposing step (i) and the introducing an enzyme step (ii).

In various embodiments, the present invention provides a method for detecting a chemical agent. The method includes (i) exposing a sensor composition including a complex including a p-phenylene ethynylene compound and an enzyme substrate to a sample. The method includes (ii) introducing an enzyme to the sensor composition of step (i). The method also includes (iii) analyzing the change in fluorescence of the p-phenylene ethynylene compound between the exposing step (i) and the introducing an enzyme step (ii). The p-phenylene ethynylene compound has the structure:

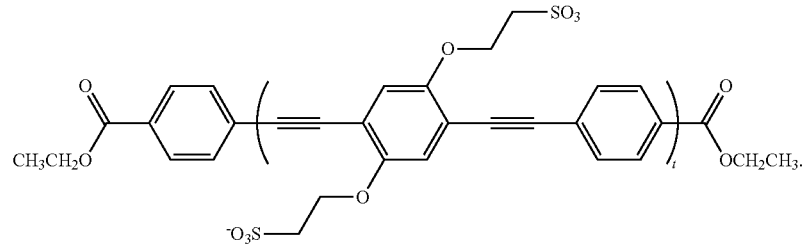

The variable t is about 1 to about 3. The enzyme substrate is lauroyl choline. A change in fluorescence between the exposing step (i) and the introducing an enzyme step (ii) indicates the presence of a chemical agent that does interact with the enzyme.

In various embodiments, the present invention provides a sensor for detecting the presence of a chemical agent. The sensor includes a sensor composition including a complex including a p-phenylene ethynylene compound and an enzyme substrate.

In various embodiments, the present invention provides a sensor for detecting the presence of a chemical agent. The sensor includes a sensor composition including a complex including a p-phenylene ethynylene compound and an enzyme substrate. The p-phenylene ethynylene compound has the structure

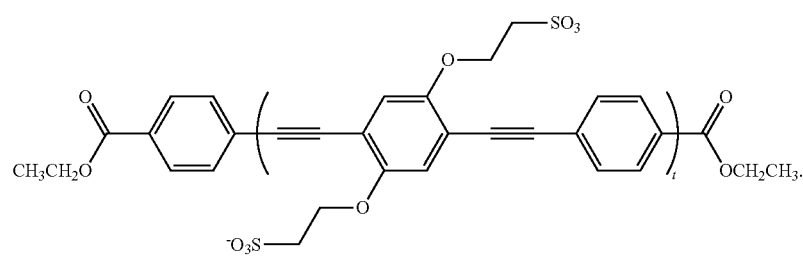

The variable t is about 1 to about 3. The enzyme substrate is lauroyl choline.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1A:
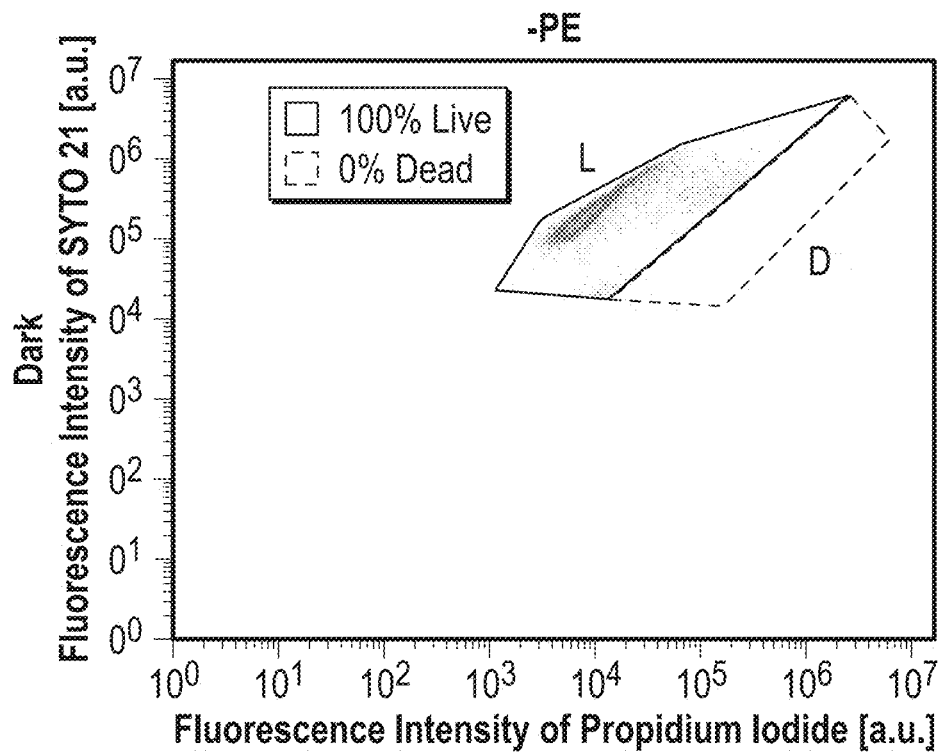
FIGS. 1A-D illustrate flow cytometry-reported fluorescence of stained *B. atrophaeus* vegetative cells following various treatment conditions, in accordance with various embodiments.

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%0% and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. A comma can be used as a delimiter or digit group separator to the left or right of a decimal mark; for example, "0.000.1" is equivalent to "0.0001."

In the methods of manufacturing described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%6, 99.5%, 99.9%, 99.99%, or at least about 99.999% or more, or 100%.

The term "organic group" as used herein refers to any carbon-containing functional group. For example, an oxygen-containing group such as an alkoxy group, aryloxy group, aralkyloxy group, oxo(carbonyl) group, a carboxyl group including a carboxylic acid, carboxylate, and a carboxylate ester; a sulfur-containing group such as an alkyl and aryl sulfide group; and other heteroatom-containing groups. Non-limiting examples of organic groups include OR, OOR, OC(O)N(R)$_2$, CN, CF$_3$. OCF$_3$, R, C(O), methylenedioxy, ethylenedioxy, N(R)$_2$, SR, SOR, SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R. (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R, C(=NOR)R, and substituted or unsubstituted (C$_1$-C$_{100}$)hydrocarbyl, wherein R can be hydrogen (in examples that include other carbon atoms) or a carbon-based moiety, and wherein the carbon-based moiety can be substituted or unsubstituted.

The term "substituted" as used herein in conjunction with a molecule or an organic group as defined herein refers to the state in which one or more hydrogen atoms contained therein are replaced by one or more non-hydrogen atoms. The term "functional group" or "substituent" as used herein refers to a group that can be or is substituted onto a molecule or onto an organic group. Examples of substituents or functional groups include, but are not limited to, a halogen (e.g., F, Cl, Br, and I); an oxygen atom in groups such as hydroxy groups, alkoxy groups, aryloxy groups, aralkyloxy groups, oxo(carbonyl) groups, carboxyl groups including carboxylic acids, carboxylates, and carboxylate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxyamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR, OC(O)N(R)$_2$. CN, NO, NO$_2$, ONO$_2$, azido, CF$_3$, OCF$_3$, R, O (oxo), S (thiono), C(O), S(O), methylenedioxy, ethylenedioxy, N(R)$_2$, SR, SOR SO$_2$R, SO$_2$N(R)$_2$, SO$_3$R, C(O)R, C(O)C(O)R, C(O)CH$_2$C(O)R, C(S)R, C(O)OR, OC(O)R, C(O)N(R)$_2$, OC(O)N(R)$_2$, C(S)N(R)$_2$, (CH$_2$)$_{0-2}$N(R)C(O)R. (CH$_2$)$_{0-2}$N(R)N(R)$_2$, N(R)N(R)C(O)R, N(R)N(R)C(O)OR, N(R)N(R)CON(R)$_2$, N(R)SO$_2$R, N(R)SO$_2$N(R)$_2$, N(R)C(O)OR, N(R)C(O)R, N(R)C(S)R, N(R)C(O)N(R)$_2$, N(R)C(S)N(R)$_2$, N(COR)COR, N(OR)R, C(=NH)N(R)$_2$, C(O)N(OR)R. and C(=NOR)R, wherein R can be hydrogen or a carbon-based moiety for example, R can be hydrogen. (C$_1$-C$_{100}$)hydrocarbyl, alkyl, acyl, cycloalkyl, aryl, aralkl, heterocyclyl, heteroaryl, or heteroarylalkyl; or wherein two R groups bonded to a nitrogen atom or to adjacent nitrogen atoms can together with the nitrogen atom or atoms form a heterocyclyl.

The term "alkyl" as used herein refers to straight chain and branched alkyl groups and cycloalkyl groups having from 1 to 40 carbon atoms, 1 to about 20 carbon atoms, 1 to 12 carbons or, in some embodiments, from 1 to 8 carbon atoms. Examples of straight chain alkyl groups include those with from 1 to 8 carbon atoms such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. As used herein, the term "alkyl" encompasses n-alkyl, isoalkyl, and anteisoalkyl groups as well as other branched chain forms of alkyl. Representative substituted alkyl groups can be substituted one or more times with any of the groups listed herein, for example, amino, hydroxy, cyano, carboxy, nitro, thio, alkoxy, and halogen groups.

The term "alkenyl" as used herein refers to straight and branched chain and cyclic alkyl groups as defined herein, except that at least one double bond exists between two carbon atoms. Thus, alkenyl groups have from 2 to 40 carbon atoms, or 2 to about 20 carbon atoms, or 2 to 12 carbons or, in some embodiments, from 2 to 8 carbon atoms. Examples include, but are not limited to vinyl, —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, cyclohexenyl, cyclopentenyl, cyclohexadienyl, butadienyl, pentadienyl, and hexadienyl among others.

The term "alkynyl" as used herein refers to straight and branched chain alkyl groups, except that at least one triple bond exists between two carbon atoms. Thus, alkynyl groups have from 2 to 40 carbon atoms, 2 to about 20 carbon atoms, or from 2 to 12 carbons or, in some embodiments, from 2 to 8 carbon atoms. Examples include, but are not limited to —C≡CH, —C≡C(CH$_3$), —C≡C(CH$_2$CH$_3$), —CH$_2$C≡CH, —CH$_2$C≡C(CH$_3$), and —CH$_2$C≡C(CH$_2$CH$_3$) among others.

The term "acyl" as used herein refers to a group containing a carbonyl moiety wherein the group is bonded via the carbonyl carbon atom. The carbonyl carbon atom is bonded to a hydrogen forming a "formyl" group or is bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. An acyl group can include 0 to about 12, 0 to about 20, or 0 to about 40 additional carbon atoms bonded to the carbonyl group. An acyl group can include double or triple bonds within the meaning herein. An acryloyl group is an example of an acyl group. An acyl group can also include heteroatoms within the meaning herein. A nicotinoyl group (pyridyl-3-carbonyl) is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "aryl" as used herein refers to cyclic aromatic hydrocarbons that do not contain heteroatoms in the ring. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain about 6 to about 14 carbons in the ring portions of the groups. Aryl groups can be unsubstituted or substituted, as defined herein. Representative substituted aryl groups can be mono-substituted or substituted more than once, such as, but not limited to, 2-, 3⁻, 4-, 5-, or 6-substituted phenyl or 2-8 substituted naphthyl groups, which can be substituted with carbon or non-carbon groups such as those listed herein.

The term "heterocyclyl" as used herein refers to aromatic and non-aromatic ring compounds containing three or more ring members, of which one or more is a heteroatom such as, but not limited to, N, O, and S.

The term "alkoxy" as used herein refers to an oxygen atom connected to an alkyl group, including a cycloalkyl group, as are defined herein. Examples of linear alkoxy groups include but are not limited to methoxy, ethoxy, propoxy, butoxy, pentyloxy, hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like. An alkoxy group can include one to about 12-20 or about 12-40 carbon atoms bonded to the oxygen atom, and can further include double or triple bonds, and can also include heteroatoms. For example, an allyloxy group is an alkoxy group within the meaning herein. A methoxyethoxy group is also an alkoxy group within the meaning herein, as is a methylenedioxy group in a context where two adjacent atoms of a structure are substituted therewith.

The term "amine" as used herein refers to primary, secondary, and tertiary amines having, e.g., the formula $N(group)_3$ wherein each group can independently be H or non-H, such as alkyl, aryl, and the like. Amines include but are not limited to $R-NH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

The term "amino group" as used herein refers to a substituent of the form $-NH_2$, $-NHR$, $-NR_2$, $-NR_3^+$, wherein each R is independently selected, and protonated forms of each, except for $-NR_3^+$, which cannot be protonated. Accordingly, any compound substituted with an amino group can be viewed as an amine. An "amino group" within the meaning herein can be a primary, secondary, tertiary, or quaternary amino group. An "alkylamino" group includes a monoalkylamino, dialkylamino, and trialkylamino group.

The terms "halo," "halogen," or "halide" group, as used herein, by themselves or as part of another substituent, mean, unless otherwise stated, a fluorine, chlorine, bromine, or iodine atom.

The term "hydrocarbon" or "hydrocarbyl" as used herein refers to a molecule or functional group, respectively, that includes carbon and hydrogen atoms. The term can also refer to molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a-C_b)$hydrocarbyl, wherein a and b are integers and mean having any of a to b number of carbon atoms. For example, $(C_1-C_4)$hydrocarbyl means the hydrocarbyl group can be methyl ($C_1$), ethyl ($C_2$), propyl ($C_3$), or butyl ($C_4$). $(C_0-C_b)$hydrocarbyl means in certain embodiments there is no hydrocarbyl group.

The term "solvent" as used herein refers to a liquid that can dissolve a solid, another liquid, or a gas. Non-limiting examples of solvents are silicones, organic compounds, water, alcohols, ionic liquids, and supercritical fluids.

The term "number-average molecular weight" as used herein refers to the ordinary arithmetic mean of the molecular weight of individual molecules in a sample. It is defined as the total weight of all molecules in a sample divided by the total number of molecules in the sample. Experimentally, the number-average molecular weight ($M_n$) is determined by analyzing a sample divided into molecular weight fractions of species I having n, molecules of molecular weight $M_i$ through the formula $M_n = \Sigma M_i n_i / \Sigma n_i$. The number-average molecular weight can be measured by a variety of well-known methods including gel permeation chromatography, spectroscopic end group analysis, and osmometry. If unspecified, molecular weights of polymers given herein are number-average molecular weights.

The term "room temperature" as used herein refers to a temperature of about 15° C. to about 28° C.

As used herein, "degree of polymerization" is the number of repeating units in a polymer.

As used herein, the term "polymer" refers to a molecule having at least one repeating unit and can include copolymers. As used herein, the term "oligomer" refers to a relatively low molecular weight polymer in which the number of repeating units can be, for example, from 1 to 10. The properties of the oligomer can vary with the removal of one or a few of the units.

The term "copolymer" as used herein refers to a polymer that includes at least two different repeating units. A copolymer can include any suitable number of repeating units.

The polymers described herein can terminate in any suitable way. In some embodiments, the polymers can terminate with an end group that is independently chosen from a suitable polymerization initiator, $-H$, $-OH$, a substituted or unsubstituted $(C_1-C_{20})$hydrocarbyl (e.g., $(C_1-C_{10})$alkyl, $(C_6-C_{20})$aryl, or an alkyne) interrupted with 0, 1, 2, or 3 groups independently selected from $-O-$, substituted or unsubstituted $-NH-$, and $-S-$, a poly(substituted or unsubstituted $(C_1-C_{20})$hydrocarbyloxy), a poly(substituted or unsubstituted $(C_1-C_{20})$hydrocarbylamino) and a halogen.

In various embodiments, salts having a positively charged counterion can include any suitable positively charged counterion. For example, the counterion can be ammonium ($NH_4^+$), or an alkali metal such as sodium ($Na^+$), potassium ($K^+$), or lithium ($Li^+$). In some embodiments, the counterion can have a positive charge greater than +1, which can in some embodiments complex to multiple ionized groups, such as $Zn^{2+}$, $A^{3+}$, or alkaline earth metals such as $Ca^{2+}$ or $Mg^{2+}$.

In various embodiments, salts having a negatively charged counterion can include any suitable negatively charged counterion. For example, the counterion can be a halide, such as fluoride, chloride, iodide, or bromide. In other examples, the counterion can be nitrate, hydrogen sulfate, dihydrogen phosphate, bicarbonate, nitrite, perchlorate, iodate, chlorate, bromate, chlorite, hypochlorite, hypobromite, cyanide, amide, cyanate, hydroxide, permanganate. The counterion can be a conjugate base of any carboxylic acid, such as acetate or formate. In some embodiments, a counterion can have a negative charge greater than −1, which can in some embodiments complex to multiple ionized groups, such as oxide, sulfide, nitride, arsenate, phosphate, arsenite, hydrogen phosphate, sulfate, thiosulfate, sulfite, carbonate, chromate, dichromate, peroxide, or oxalate.

The p-phenylene ethynylene compounds described herein can include counterions. For example, a p-phenylene ethynylene compound bearing a $-N^+(CH_3)_3$ can have a negatively charged counterion, such as $Br^-$ or $I^-$, associated with it.

As used herein, the term “3-methylimidazolium” refers to a substituent having the structure

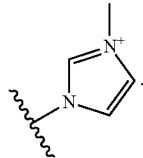 [SMILES: *n1cc[n+](C)c1]

The wavy line indicates the point of attachment to the rest of the molecule.

As used herein, the term “$(C_1\text{-}C_{10})$alkyl-(1,4-substituted 1,4-diazabicyclo[2.2.2]octane-1,4-diium)-” refers to a substituent having the structure

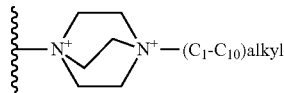

The wavy line indicates the point of attachment to the rest of the molecule.

As used herein, a “cationic p-phenylene ethynylene compound” refers to a p-phenylene ethynylene compound that has a net positive charge.

As used herein, the term “anionic enzyme substrate” refers to an enzyme substrate that has a net negative charge.

As used herein, an “anionic p-phenylene ethynylene compound” refers to a p-phenylene ethynylene compound that has a net negative charge.

As used herein, the term “biological sample” includes, without limitation, cell cultures or extracts thereof, biopsied material obtained from a mammal or extracts thereof; and blood, saliva, urine, feces, semen, tears, or other body fluids or extracts thereof and other biological fluids.

As used herein, the term “microbial spore” can refer to any suitable microbial spore, such as a eukaryotic spore or a bacterial spore.

As used herein, the term “anionic enzyme substrate” can refer to any suitable anionic enzyme substrate that can be used as described herein. The anionic enzyme substrate can be a substrate that is sufficiently hydrophobic but is not so large that it cannot form a complex with an oligomer. The anionic enzyme substrate can be a phospholipid. The anionic enzyme substrate can be a lipopolysaccharide or other hybrid species that can be a component of a membrane. The anionic enzyme substrate can be an anionic peptide or a small protein with a net-negative patch. The anionic enzyme substrate can be DNA. The anionic enzyme substrate can be 1,2-dilauroyl-sn-glycero-phospho-(1'-rac-glycerol) (DLPG).

As used herein, the term “cationic enzyme substrate” can refer to any suitable cationic enzyme substrate that can be used as described herein. The cationic enzyme substrate can be a substrate that is not so large that it cannot form a complex with an oligomer. The cationic enzyme substrate can be a suitable cleavable amphiphilic substrate. The cationic enzyme substrate can be a cationic phospholipid, such as cationic dimyristoyltrimethylammonium propane (DMTAP). The cationic enzyme substrate can be a cationic peptide or a small protein with a net-positive patch. The cationic enzyme substrate can be DNA. The cationic enzyme substrate can be lauroyl choline. The cationic enzyme substrate can be acetylcholine.

As used herein, the term “phenolate” refers to a p-phenolate, e.g., a phenolate attached via the 4-position.

p-Phenylene Ethynylene Compounds for Inducing Germination of Microbial Spores.

In various embodiments, a method for inducing the germination of microbial spores with a p-phenylene ethynylene compound is described herein. The microbial spores can be at least one of a *Bacillus anthracis*, a *Bacillus atrophaeus*, a *Bacillus cereus*, and a *Bacillus subtilis*.

In various embodiments, the p-phenylene ethynylene compound includes a repeating unit which can have the structure:

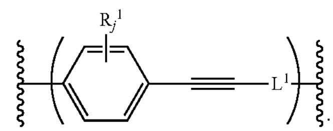

The variable $R^1$ can have the structure:

The variable Z, at each occurrence, can be independently chosen from —$CH_2$—, —O—, —S—, and —NH—. The variable $L^2$ can be independently chosen from a $(C_1\text{-}C_{50})$ hydrocarbylene interrupted by 0, 1, 2, 3, 4, 5, 6, 7, 8, 9, or 10 groups independently chosen from —O—, —S—, and —NH—. The variable $R^2$, at each occurrence, can be independently chosen from —H, $(C_1\text{-}C_5)$alkyl, —$SO_3^-$, —$CO_2^-$, —$H_2PO_4^-$, $HPO_4^{2-}$, $PO_4^{3-}$, phenolate, $(C_1\text{-}C_{10})$alkyl-(1,4-substituted 1,4-diazabicyclo[2.2.2]octane-1,4-diium)-, 3-methylimidazolium and —$N^+(R^A)_3$ wherein at each occurrence $R^A$ is independently $(C_1\text{-}C_5)$alkyl. The variable $L^1$, at each occurrence can be independently chosen from a bond and 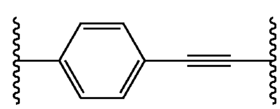 The variable j can be about 0 to about 4.

In various embodiments, the p-phenylene ethynylene compound can include a repeating unit having the structure:

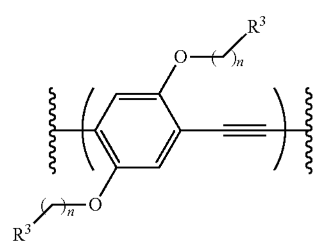

The variable $R^3$, can be independently chosen from —$N^+$(CH$_3$)$_3$,

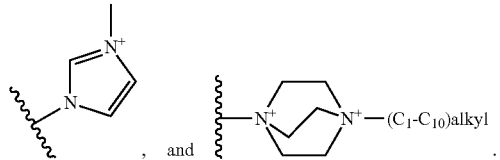

, and

The variable n can be about 2 to about 4.

In various embodiments, the p-phenylene ethynylene compound can have the structure:

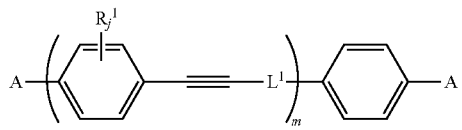

The variable $R^1$ can have the structure:

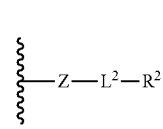

The variable Z, at each occurrence, can be independently chosen from —CH$_2$—, —O—, —S—, and —NH—. The variable $L^2$, at each occurrence, can be independently chosen from a (C$_1$-C$_{50}$)hydrocarbylene interrupted by 0, 1, 2, 3, 4, 5, 6, 7, 8, 9, or 10 groups independently chosen from —O—, —S—, and —NH—. The variable $R^2$, at each occurrence, can be independently chosen from —H, (C$_1$-C$_5$)alkyl, —, (C$_1$-C$_{10}$)alkyl-(1,4-substituted 1,4-diazabicyclo[2.2.2]octane-1,4-diium)-, 3-methylimidazolium and N$^+$(R$^4$)$_3$ wherein at each occurrence R$^4$ is independently (C$_1$-C$_5$)alkyl. The variable j can be about 0 to about 4. The variable $L^1$, at each occurrence, can be chosen from a bond and

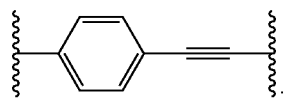

The variable A, at each occurrence, can be independently chosen from —H, substituted or unsubstituted —C(O)O—(C$_1$-C$_{10}$)hydrocarbyl, —C(O)NH—(C$_1$-C$_{10}$)hydrocarbyl, and C(O)OH. The variable m can be about 1 to about 1,000.

In various embodiments, the p-phenylene ethynylene compound can have the structure:

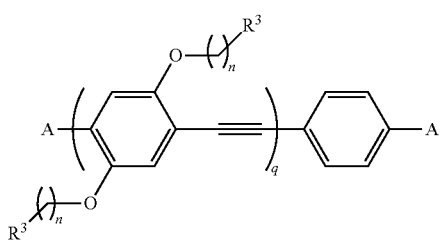

The variable $R^3$, at each occurrence, can be independently chosen from —N$^+$(CH$_3$)$_3$,

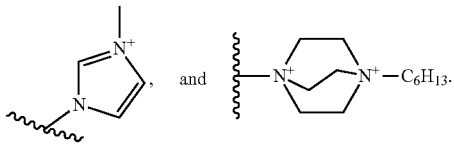

The variable n can be about 2 to about 4. The variable A, at each occurrence can be independently chosen from —H and —C(O)O—(C$_1$-C$_5$)alkyl. In various embodiments, the variable A can be —C(O)OCH$_2$CH$_3$. The variable q can be about 1 to about 50, about 1 to about 40, about 1 to about 30, about 1 to about 20, about 1 to about 10, about 1 to about 5, about 1 to about 3, and about 1, 2, 3, 4, 5, 7, 10, 20, 30, 40, and about 50 or greater.

In various embodiments the p-phenylene ethynylene compound can have the structure:

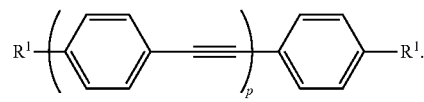

The variable $R^1$, at each occurrence can have the structure:

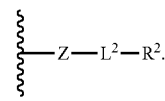

The variable Z, at each occurrence, can be independently chosen from —CH$_2$—, —O—, —S—, and —NH—. The variable $L^2$, at each occurrence, can be a (C$_1$-C$_{50}$)hydrocarbylene interrupted by 0, 1, 2, 3, 4, 5, 6, 7, 8, 9, or 10 groups independently chosen from —O—, —S—, and —NH—. The variable $R^2$, at each occurrence can be independently chosen from N$^+$(R$^4$)$_3$, (C$_1$-C$_{10}$)alkyl-(1,4-substituted 1,4-diazabicyclo[2.2.2]octane-1,4-diium)-, and 3-methylimidazolium. The variable $R^4$, at each occurrence, can be independently (C$_1$-C$_5$)alkyl. The variable p can be about 1 to about 10, about 1 to about 7, about 1 to about 5, about 1 to about 3, or about 1, 2, 3, 4, 5, 6, 7, 8, 9, or about 10 or greater.

In various embodiments, the variable Z, at each occurrence, can be —O—. The variable $L^2$, at each occurrence, can independently be a (C$_1$-C$_5$)alkyl. The variable $R^2$, at each occurrence, can be independently chosen from —N$^+$(CH$^3$)$_3$,

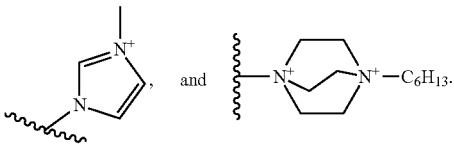

The variable p can be about 1 to about 5, about 1 to about 3, or about 1, 2, 3, 4, or about 5 or greater.

In various embodiments, the p-phenylene ethynylene compound can have the structure:

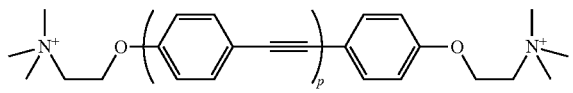

The variable P can be about 1, 2, 3, 4, or about 5 or greater.

Method for Detecting Enzymes

In various embodiments, a method for detecting enzymes is described herein. The method includes (i) introducing an enzyme to a composition including a p-phenylene ethynylene compound and an enzyme substrate; and (ii) analyzing the change in fluorescence of the p-phenylene ethynylene compound following introduction of the enzyme. The introducing step (i) can include introducing the p-phenylene ethynylene compound and the enzyme substrate to a sample which includes an enzyme. Further, the introducing step (i) can include introducing a sample which includes an enzyme to the p-phenylene ethynylene compound and the enzyme substrate. In various embodiments, the p-phenylene ethynylene compound and the enzyme substrate form a complex. In various embodiments, the introduction step (i) and the analyzing step (ii) occur in an aqueous environment.

In various embodiments, the fluorescence of the p-phenylene ethynylene compound can decrease following the introduction of the enzyme. The fluorescence can decrease due to a molecular transformation of the enzyme substrate to an entity or entities that do not complex with the p-phenylene ethynylene compound.

In various embodiments, the the p-phenylene ethynylene compound can be a cationic p-phenylene ethynylene compound. In various embodiments, the cationic p-phenylene ethynylene compound can have the structure:

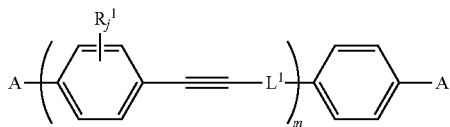

The variable $R^1$ can have the structure:

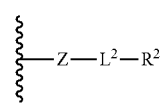

The variable Z, at each occurrence, can be independently chosen from —$CH_2$—, —O—, —S—, and —NH—. The variable $L^2$, at each occurrence, can be independently chosen from $(C_1$-$C_{50})$hydrocarbylene interrupted by 0, 1, 2, 3, 4, 5, 6, 7, 8, 9, or 10 groups independently chosen from —O—, —S—, and —NH—. The variable $R^2$, at each occurrence, can be independently chosen from —H, ($C_1$-$C_5$)alkyl, —$SO_3$, —$CO_2^-$, —$H_2PO_4^-$, $HPO_4^{2-}$, $PO_4^{3-}$, phenolate, —$N^+(R^A)_3$, ($C_1$-$C_{10}$)alkyl-(1,4-substituted 1,4-diazabicyclo[2.2.2]octane-1,4-diium)-, and 3-methylimidazolium. The variable $R^A$, at each occurrence, can be independently ($C_1$-$C_5$)alkyl. Further, at least one $R^2$ can be independently chosen from $N^+(R^A)_3$, ($C_1$-$C_{10}$)alkyl-(1 1,4-substituted 1,4-diazabicyclo[2.2.2]octane-1,4-diium)-, and 3-methylimidazolium, such that the cationic p-phenylene ethynylene compound has a net positive charge. The variable j can be about 0 to about 4, about 1 to about 2, or 0, 1, 2, 3, or 4. The variable $L^1$, at each occurrence, can be independently chosen from a bond and

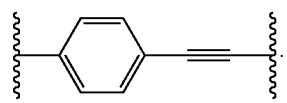

The variable A, at each occurrence, can be independently chosen from —H, substituted or unsubstituted —C(O)O—($C_1$-$C_{10}$)hydrocarbyl, and —C(O)NH—($C_1$-$C_{10}$)hydrocarbyl. The variable m can be about 1 to about 10, about 1 to about 7 about 1 to about 5, about 1 to about 3 or about 1, 2, 3, 4, 5, 6, 7, 8, 9, or about 10 or greater.

In various embodiments, the cationic p-phenylene ethynylene compound can have the structure:

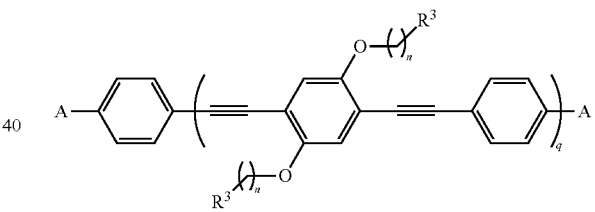

The variable $R^3$, at each occurrence, can be independently chosen from —$N^+(CH_3)_3$,

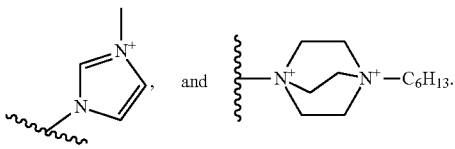

The variable n can be about 2 to about 4, or about 2, 3, or about 4 or greater. The variable A, at each occurrence, is independently chosen from —H and —C(O)O—($C_1$-$C_5$) alkyl. The variable q is about 1 to about 5, about 1 to about 3, or about 1, 2, 3, 4, or about 5 or greater.

In various embodiments, the cationic p-phenylene ethynylene compound can have the structure:

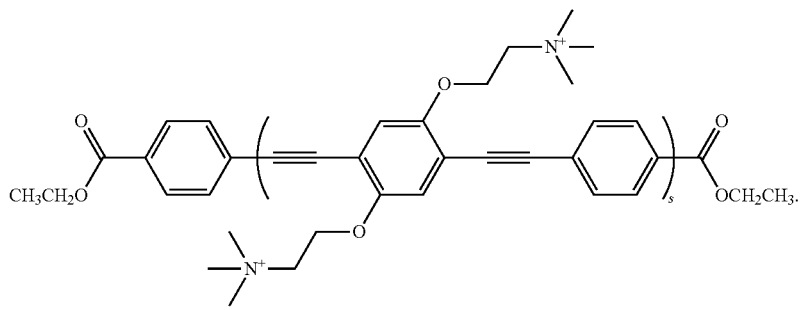

The variable s can be about 1 to about 3, or about 1, 2 or about 3 or greater.

In various embodiments, the enzyme substrate can be an anionic enzyme substrate. For example, the anionic enzyme substrate can be 1,2-dilauroyl-sn-glycero-phospho-(1'-rac-glycerol) (DLPG), having the structure:

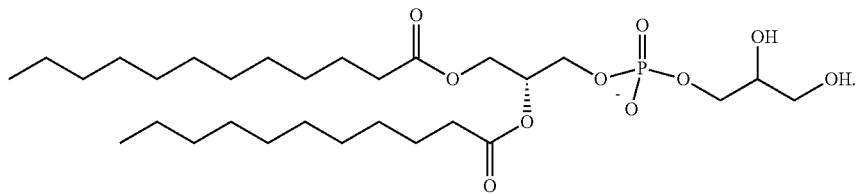 [SMILES: CCCCCCCCCCCC(=O)OC[C@H](COP(=O)(O)OCC(O)CO)OC(=O)CCCCCCCCCC]

In various embodiments, the p-phenylene ethynylene compound is an anionic p-phenylene ethynylene compound. In various embodiments, the anionic p-phenylene ethynylene compound can have the structure:

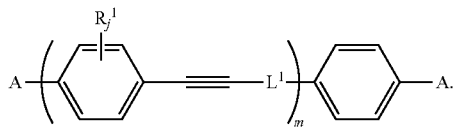

The variable $R^1$ can have the structure:

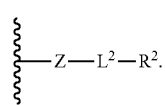

The variable Z, at each occurrence, can be independently chosen from —$CH_2$—, —O—, —S—, and —NH—. The variable $L^2$, at each occurrence, can be independently chosen from ($C_1$-$C_{50}$)hydrocarbylene interrupted by 0, 1, 2, 3, 4, 5, 6, 7, 8, 9, or 10 groups independently chosen from —O—, —S—, and —NH—. The variable $R^2$, at each occurrence, can be independently chosen from —H, ($C_1$-$C_5$)alkyl, —$SO_3^-$, —$CO_2^-$, —$H_2PO_4^-$, $HPO_4^{2-}$, $PO_4^{3-}$, and phenolate. Further, at least one $R^2$ can be an anionic group such as $SO_3^-$, —$CO_2^-$, —$H_2PO_4^-$, $HPO_4^{2-}$, $PO_4^{3-}$, or phenolate, such that the anionic p-phenylene ethynylene compound can have a net negative charge. The variable j can be about 0 to about 4, about 1 to about 2, or 0, 1, 2, 3, or 4. The variable $L^1$, at each occurrence, can be independently chosen from a bond and

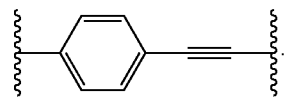

The variable A, at each occurrence, can be independently chosen from —H, substituted or unsubstituted —C(O)O—($C_1$-$C_{10}$)hydrocarbyl, and —C(O)NH—($C_1$-$C_{10}$)hydrocarbyl. The variable m can be about 1 to about 10, about 1 to about 7 about 1 to about 5, about 1 to about 3 or about 1, 2, 3, 4, 5, 6, 7, 8, 9, or about 10 or greater.

In various embodiments, the anionic p-phenylene ethynylene compound can have the structure:

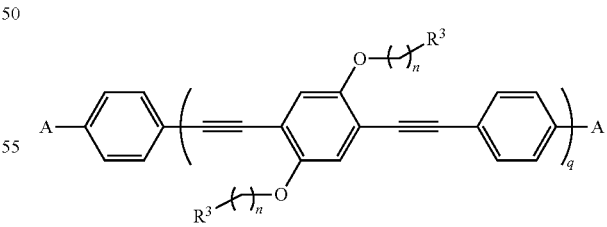

The variable $R^3$, at each occurrence, can be independently chosen from $SO_3^-$, —$CO_2^-$, —$H_2PO_4^-$, $HPO_4^{2-}$, $PO_4^{3-}$, and phenolate. The variable $R^3$ can be —$SO_3^-$. The variable n can be about 2 to about 4, or about 2, 3, or about 4 or greater. The variable A, at each occurrence, is independently chosen from —H and —C(O)O—($C_1$-$C_5$)alkyl. The variable q is about 1 to about 5, about 1 to about 3, or about 1, 2, 3, 4, or about 5 or greater.

In various embodiments, the anionic p-phenylene ethynylene compound can have the structure:

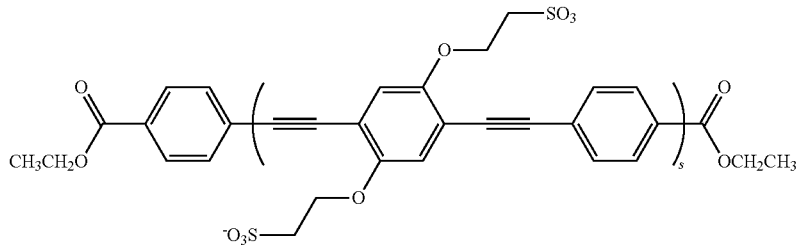

The variable s can be about 1 to about 3 or about 1, 2 or about 3 or greater.

In various embodiments, the enzyme substrate can be a cationic enzyme substrate. The cationic enzyme substrate can be a substituted or unsubstituted $(C_1-C_{25})$hydrocarbyl-$C(O)O$—$(C_1-C_{10})$alkyl-$N^+((C_1-C_5)$alkyl$)_3$. The cationic enzyme substrate can be a substituted or unsubstituted $(C_1-C_{25})$alkyl-$C(O)O$—$(C_1-C_4)$alkyl-$N^+(CH_3)_3$. In various embodiments the cationic enzyme substrate can be chosen from lauroyl choline and acetylcholine. The cationic enzyme substrate can be lauroyl choline.

In various embodiments, the enzyme can be any suitable enzyme. For example, the enzyme can be a protolytic enzyme, a DNA restriction enzyme, a phosphatase, or a kinase. In various embodiments, the enzyme can be chosen from phospholipase A1, phospholipase A2, phospholipase C. and acetyl cholinesterase.

In various embodiments, the method includes (i) introducing an enzyme to a composition including a p-phenylene ethynylene compound and an enzyme substrate; and (ii) analyzing the change in fluorescence of the p-phenylene ethynylene compound following introduction of the enzyme. The p-phenylene ethynylene compound can have the structure:

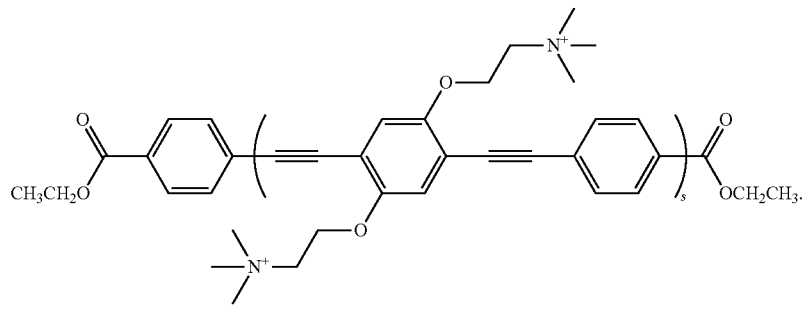

The variable s can be about 1 to about 3, or about 1, 2 or about 3 or greater. The enzyme substrate can be 1,2-dilauroyl-sn-glycero-phospho-(1'-rac-glycerol). In various embodiments, the enzyme can be any suitable enzyme. For example, the enzyme can be a protolytic enzyme, a DNA restriction enzyme, a phosphatase, or a kinase. The enzyme can be at least one of phospholipase A1, phospholipase A2, and phospholipase C.

In various embodiments, the method can include (i) introducing an enzyme to a composition including a p-phenylene ethynylene compound and an enzyme substrate; and (ii) analyzing the change in fluorescence of the p-phenylene ethynylene compound following introduction of the enzyme. The p-phenylene ethynylene compound can have the structure:

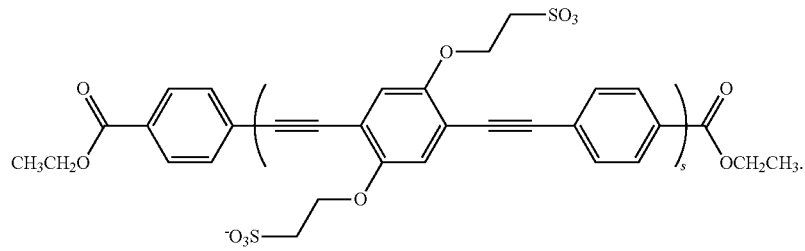

The variable s can be about 1 to about 3, or about 1, 2 or about 3 or greater. The enzyme substrate can be lauroyl choline. The enzyme can be any suitable enzyme. The enzyme can be a phospholipase (e.g., PLA1, PLA2, PLC, PLB). The enzyme can be butyrylcholinesterase. The enzyme can be acetylcholinesterase.

Sensor for Detecting Enzymes

In various embodiments a sensor is described herein. The sensor may be a sensor for the detection of enzymes. The sensor includes a p-phenylene ethynylene compound and an enzyme substrate. In various embodiments, the p-phenylene ethynylene compound can be a charged p-phenylene ethynylene compound and the enzyme substrate can be an oppositely charged enzyme substrate. In various embodiments, the p-phenylene ethynylene compound and the enzyme substrate form a complex.

In various embodiments, the the p-phenylene ethynylene compound can be a cationic p-phenylene ethynylene compound. In various embodiments, the cationic p-phenylene ethynylene compound can have the structure:

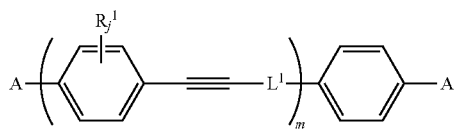

The variable $R^1$ can have the structure:

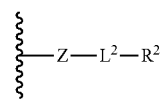

The variable Z, at each occurrence, can be independently chosen from —$CH_2$—, —O—, —S—, and —NH—. The variable $L^2$, at each occurrence, can be independently chosen from ($C_1$-$C_{50}$)hydrocarbylene interrupted by 0, 1, 2, 3, 4, 5, 6, 7, 8, 9, or 10 groups independently chosen from —O—, —S—, and —NH—. The variable $R^2$, at each occurrence, can be independently chosen from —H, ($C_1$-$C_5$)alkyl, —$SO_3^-$, —$CO_2^-$, —$H_2PO_4^-$, $HPO_4^{2-}$, $PO_4^{3-}$, phenolate, —$N^+(R^A)_3$, ($C_1$-$C_{10}$)alkyl-(1,4-substituted 1,4-diazabicyclo[2.2.2]octane-1,4-diium)-, and 3-methylimidazolium. The variable $R^A$, at each occurrence, can be independently ($C_1$-$C_5$)alkyl. Further, at least one $R^2$ can be independently chosen from $N^+(R^A)_3$, ($C_1$-$C_{10}$)alkyl-(1,4-substituted 1,4-diazabicyclo[2.2.2]octane-1,4-diium)-, and 3-methylimidazolium, such that the cationic p-phenylene ethynylene compound has a net positive charge. The variable j can be about 0 to about 4, about 1 to about 2, or 0, 1, 2, 3, or 4. The variable $L^1$, at each occurrence, can be independently chosen from a bond and

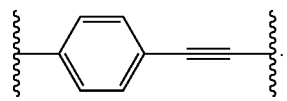 [SMILES: *C#Cc1ccc(*)cc1]

The variable A, at each occurrence, can be independently chosen from —H, substituted or unsubstituted —C(O)O—($C_1$-$C_{10}$)hydrocarbyl, and —C(O)NH—($C_1$-$C_{10}$)hydrocarbyl. The variable m can be about 1 to about 10, about 1 to about 7 about 1 to about 5, about 1 to about 3 or about 1, 2, 3, 4, 5, 6, 7, 8, 9, or about 10 or greater.

In various embodiments, the cationic p-phenylene ethynylene compound can have the structure:

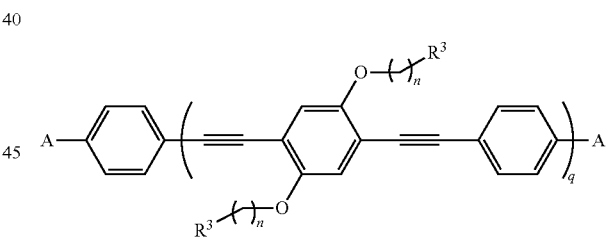

The variable $R^3$, at each occurrence, can be independently chosen from —$N^+(CH_3)_3$,

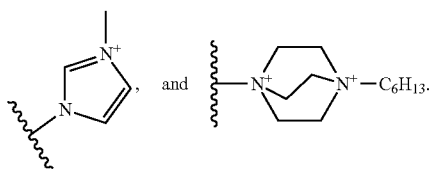

The variable n can be about 2 to about 4, or about 2, 3, or about 4 or greater. The variable A, at each occurrence, can be independently chosen from —H and —C(O)O—($C_1$-$C_5$) alkyl. The variable q can be about 1 to about 5, about 1 to about 3, or about 1, 2, 3, 4, or about 5 or greater.-

In various embodiments, the cationic p-phenylene ethynylene compound can have the structure:

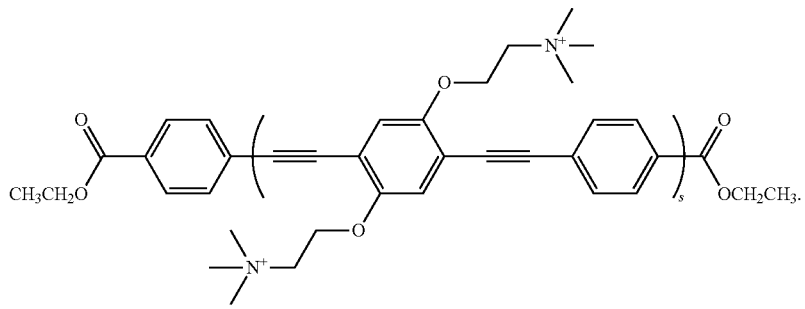

The variable s can be about 1 to about 3, or about 1, 2 or about 3 or greater.

In various embodiments, the enzyme substrate can be an anionic enzyme substrate. For example, the anionic enzyme substrate can be 1,2-dilauroyl-sn-glycero-phospho-(1'-rac-glycerol).

In various embodiments, the p-phenylene ethynylene compound can be an anionic p-phenylene ethynylene compound. In various embodiments, the anionic p-phenylene ethynylene compound can have the structure:

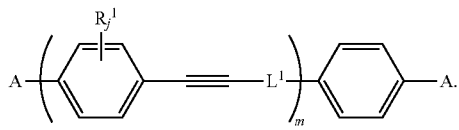

The variable $R^1$ can have the structure:

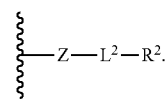

The variable Z, at each occurrence, can be independently chosen from —$CH_2$—, —O—, —S—, and —NH—. The variable $L^2$, at each occurrence, can be independently chosen from ($C_1$-$C_{50}$)hydrocarbylene interrupted by 0, 1, 2, 3, 4, 5, 6, 7, 8, 9, or 10 groups independently chosen from —O—, —S—, and —NH—. The variable $R^2$, at each occurrence, can be independently chosen from —H, ($C_1$-$C_5$)alkyl, —$SO_3^-$, —$CO_2$, —$H_2PO_4^-$, $HPO_4^{2-}$, $PO_4^{3-}$, and phenolate. Further, at least one $R^2$ can be an anionic substituent such as —$SO_3^-$, —CO—, —$H_2PO_4^-$, $HPO_4^{2-}$, $PO_4^{3-}$, or phenolate, such that the anionic p-phenylene ethynylene compound can have a net negative charge. The variable j can be about 0 to about 4, about 1 to about 2, or 0, 1, 2, 3, or 4. The variable $L^1$, at each occurrence, can be independently chosen from a bond and

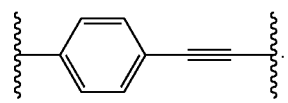

The variable A, at each occurrence, can be independently chosen from —H, substituted or unsubstituted —C(O)O—($C_1$-$C_{10}$)hydrocarbyl, and —C(O)NH—($C_1$-$C_{10}$)hydrocarbyl. The variable m can be about 1 to about 10, about 1 to about 7 about 1 to about 5, about 1 to about 3 or about 1, 2, 3, 4, 5, 6, 7, 8, 9, or about 10 or greater.

In various embodiments, the anionic p-phenylene ethynylene compound can have the structure:

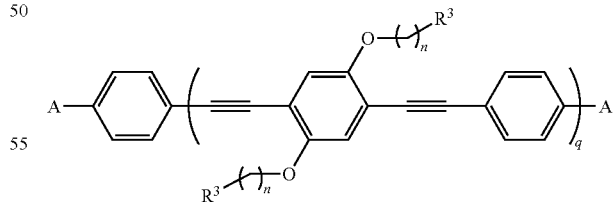

The variable $R^3$, at each occurrence, can be independently chosen from —$SO_3$, —$CO_2^-$, —$H_2PO_4^-$, $HPO_4^{2-}$, $PO_{43}$ and phenolate. The variable $R^3$ can be —$SO_3^-$. The variable n can be about 2 to about 4, or about 2, 3, or about 4 or greater. The variable A, at each occurrence, can be independently chosen from —H and —C(O)O—($C_1$-$C_5$)alkyl. The variable q can be about 1 to about 5, about 1 to about 3, or about 1, 2, 3, 4, or about 5 or greater.

In various embodiments, the anionic p-phenylene ethynylene compound can have the structure:

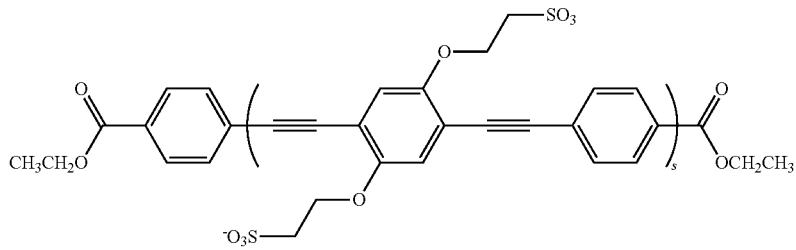

15

The variable s can be about 1 to about 3 or about 1, 2 or about 3 or greater.

In various embodiments, the enzyme substrate can be a cationic enzyme substrate. The cationic enzyme substrate can be a substituted or unsubstituted $(C_1$-$C_{25})$hydrocarbyl-C(O)O—$(C_1$-$C_{10})$alkyl-$N^+$(($C_1$-$C_5$)alkyl)$_3$. The cationic enzyme substrate can be a substituted or unsubstituted $(C_1$-$C_{25})$alkyl-C(O)O—$(C_1$-$C_4$)alkyl-$N^+$($CH_3$)$_3$. In various embodiments the cationic enzyme substrate can be chosen from lauroyl choline and acetylcholine. The cationic enzyme substrate can be lauroyl choline.

In various embodiments the sensor includes a cationic p-phenylene ethynylene compound and an anionic enzyme substrate. The p-phenylene ethynylene compound can have the structure:

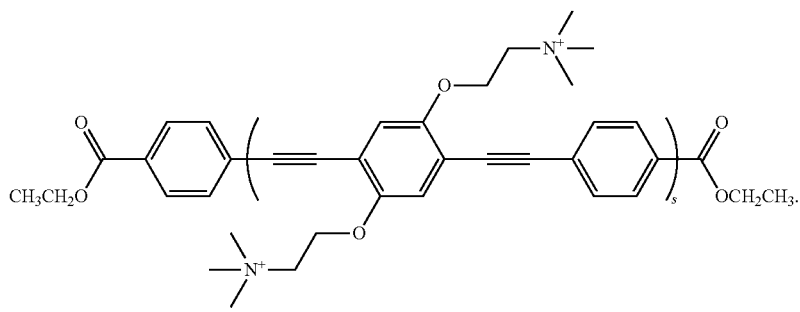

45

The variable s can be about 1 to about 3, or about 1, 2 or about 3 or greater. The anionic enzyme substrate can be 1,2-dilauroyl-sn-glycero-phospho-(1'-rac-glycerol).

In various embodiments the sensor includes a p-phenylene ethynylene compound and an enzyme substrate. The p-phenylene ethynylene compound can have the structure:

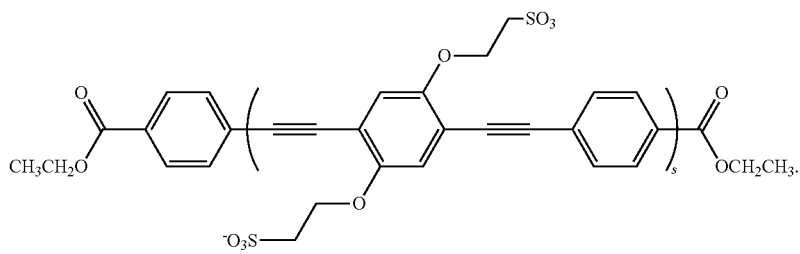

The variable s can be about 1 to about 3, or about 1, 2 or about 3 or greater. The enzyme substrate can be lauroyl choline.

Method of Protein Analysis

In various embodiments, a method for protein analysis is described herein. The method includes (i) introducing a p-phenylene ethynylene compound to a biological sample including at least one protein and (ii) analyzing the fluorescence of the p-phenylene ethynylene compound in the presence of the biological sample including the at least one protein.

It has been unexpectedly discovered that p-phenylene ethynylene compounds can be employed for the selective detection of proteins in biological samples. For example, p-phenylene ethynylene compounds can be used to detect the presence of amyloids in tissue samples. Further, it has been unexpectedly discovered that p-phenylene ethynylene compounds display a distinguishable response to monomeric and fibrillary proteins. For example, p-phenylene ethynylene compounds show display a distinguishable response to monomeric and fibrillary Aβ3-40 amyloid and α-synuclein.

In various embodiments, the fluorescence of the p-phenylene ethynylene compound is analyzed prior to being introduced to the biological sample including the at least one protein. In various embodiments, analyzing the fluorescence of the p-phenylene ethynylene compound in the presence of the biological sample including the at least one protein includes analyzing the spectral changes between the fluorescence of the p-phenylene ethynylene compound of step (i) and the fluorescence of the p-phenylene ethynylene compound in the presence of the biological sample including the at least one protein of step (ii). In various embodiments, the morphology of the protein in the biological sample is determined by analyzing spectral changes between the fluorescence of the p-phenylene ethynylene compound of step (i) and the fluorescence of the p-phenylene ethynylene compound in the presence of the biological sample including the at least one protein of step (ii). In various embodiments, the spectral changes in the fluorescence of the p-phenylene ethynylene compound between step (i) and step (ii) are induced by changes in the conformational freedom of the p-phenylene ethynylene compound between step (i) and step (ii).

In various embodiments, the p-phenylene ethynylene compound can have the structure:

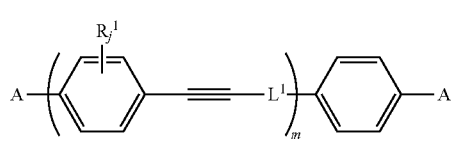

The variable $R^1$ can have the structure:

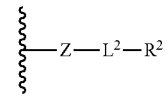

The variable Z, at each occurrence, can be independently chosen from —CH$_2$—, —O—, —S—, and —NH—. The variable $L^2$, at each occurrence, can be independently chosen from (C$_1$-C$_{50}$)hydrocarbylene interrupted by 0, 1, 2, 3, 4, 5, 6, 7, 8, 9, or 10 groups independently chosen from —O—, —S—, and —NH—. The variable $R^2$, at each occurrence, can be independently chosen from —H, (C$_1$-C$_5$)alkyl, —SO$_3^-$, —CO$_2^-$, —H$_2$PO$_4^-$, HPO$_4^{2-}$, PO$_4^{3-}$, phenolate, —N$^+$(R$^A$)$_3$, (C$_1$-C$_{10}$)alkyl-(1,4-substituted 1,4-diazabicyclo[2.2.2]octane-1,4-diium)-, and 3-methylimidazolium. The variable $R^A$, at each occurrence, can be independently (C$_1$-C$_5$)alkyl. The variable j can be about 0 to about 4, about 1 to about 2, or 0, 1, 2, 3, or 4. The variable $L^1$, at each occurrence, can be independently chosen from a bond and

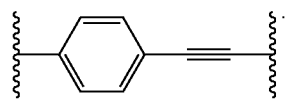 [SMILES: *C#Cc1ccc(*)cc1]

The variable A, at each occurrence, can be independently chosen from —H, substituted or unsubstituted —C(O)O—(C$_1$-C$_{10}$)hydrocarbyl, and —C(O)NH—(C$_1$-C$_{10}$)hydrocarbyl. The variable m can be about 1 to about 10, about 1 to about 7 about 1 to about 5, about 1 to about 3 or about 1, 2, 3, 4, 5, 6, 7, 8, 9, or about 10 or greater.

In various embodiments, the p-phenylene ethynylene compound can have the structure:

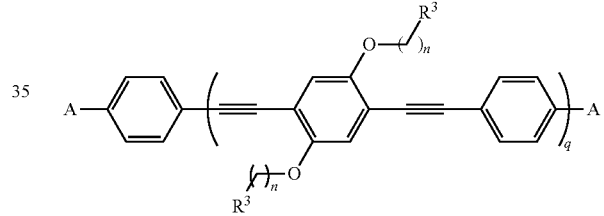

The variable $R^3$, at each occurrence, can be independently chosen from —N$^+$(CH$_3$)$_3$,

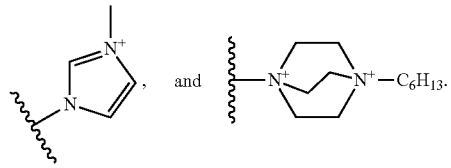

The variable n can be about 2 to about 4, or about 2, 3, or about 4 or greater. The variable A, at each occurrence, can be independently chosen from —H and —C(O)O—(C$_1$-C$_5$) alkyl. The variable q can be about 1 to about 5, about 1 to about 3, or about 1, 2, 3, 4, or about 5 or greater In various embodiments, the p-phenylene ethynylene compound can have the structure:

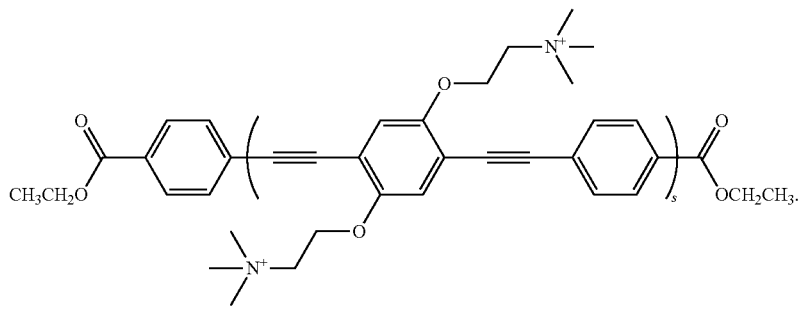

The variable s can be about 1 to about 3, or about 1, 2 or about 3 or greater.

In various embodiments, the protein can be at least one of an amyloid beta protein, Aβ-40, Aβ-42, tau, and α-synuclein, islet amyloid precursor protein, Huntingtin, prion, lysozyme, TDP-43 (transactive response DNA-binding protein 43), FUS (fused in sarcoma), and insulin.

In various embodiments, the method includes (i) analyzing the fluorescence of a p-phenylene ethynylene compound; (ii) introducing the p-phenylene ethynylene compound to a biological sample including at least one protein; (iii) analyzing the fluorescence of the p-phenylene ethynylene compound in the presence of the biological sample including the at least one protein; and (iv) determining the morphology of the at least one protein in the biological sample by analyzing spectral changes between the fluorescence of the p-phenylene ethynylene compound of step (i) and the fluorescence of the p-phenylene ethynylene compound in the presence of the biological sample including the at least one protein of step (iii). The p-phenylene ethynylene compound can have the structure:

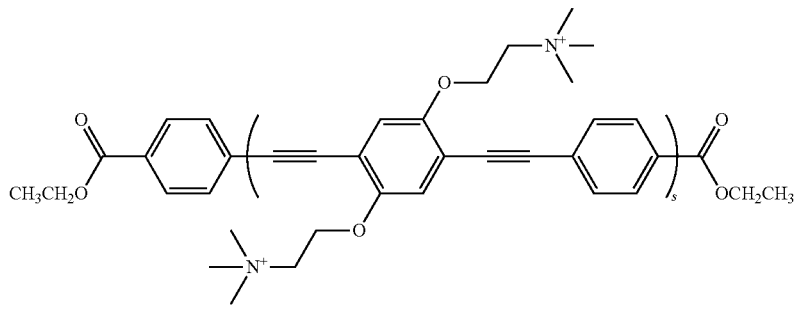

The variable s can be about 1 to about 3, such as about 1. The protein can be at least one of an amyloid beta protein, Aβ-40, Aβ-42, tau, and α-synuclein, islet amyloid precursor protein, Huntingtin, prion, lysozyme, TDP-43 (transactive response DNA-binding protein 43), FUS (fused in sarcoma), and insulin.

Method of Detecting Chemical Agents

In various embodiments, a method for detecting a chemical agent is described herein. The method includes (i) exposing a sensor composition including a complex including a p-phenylene ethynylene compound and an enzyme substrate to a sample; (ii) introducing an enzyme to the sensor composition of step (i); and (iii) analyzing the change in fluorescence of the p-phenylene ethynylene compound between the exposing step (i) and the introducing an enzyme step (ii).

The sample may be, but is not limited to, any solution that has been exposed to a potential chemical agent. Chemical agents include, without limitation, organophosphate nerve agents (e.g. sarin, soman, tabun, VX, and VR) and G-type nerve agents (e.g. diethyl phosphoramidate). The chemical agent can be a pesticide or insecticide, such as an organophosphate pesticide or insecticide, such as malathion (e.g., Diethyl 2-[(dimethoxyphosphorothioyl)sulfanyl]butanedioate)or chlorpyrifos (e.g., O,O-diethyl O-3,5,6-trichloropyridin-2-yl phosphorothioate).

In various embodiments, a change in fluorescence between the exposing step (i) and the introducing an enzyme step (ii) indicates the presence of a chemical agent that does interact with the enzyme. In various embodiments, a minimal change in fluorescence between the exposing step (i) and the introducing an enzyme step (ii) indicates the presence of a chemical agent that does interact with the enzyme.

In various embodiments, the p-phenylene ethynylene compound can be a cationic p-phenylene ethynylene compound. In various embodiments, the cationic p-phenylene ethynylene compound can have the structure:

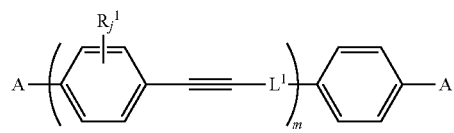

The variable $R^1$ can have the structure:

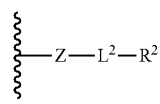

The variable Z, at each occurrence, can be independently chosen from —$CH_2$—, —O—, —S—, and —NH—. The variable $L^2$, at each occurrence, can be independently chosen from ($C_1$-$C_{50}$)hydrocarbylene interrupted by 0, 1, 2, 3, 4, 5, 6, 7, 8, 9, or 10 groups independently chosen from —O—, —S—, and —NH—. The variable $R^2$, at each occurrence, can be independently chosen from —H, ($C_1$-$C_5$)alkyl, —$SO_3^-$, —$CO_2^-$, —$H_2PO_4^-$, $HPO_4^{2-}$, $PO_4^{3-}$, phenolate, —$N^+(R^A)_3$, ($C_1$-$C_{10}$)alkyl-(1,4-substituted 1,4-diazabicyclo[2.2.2]octane-1,4-diium)-, and 3-methylimidazolium. The variable $R^A$, at each occurrence, can be independently ($C_1$-$C_5$)alkyl. Further, at least one $R^2$ can be independently chosen from $N^A(R^A)_3$, ($C_1$-$C_{10}$)alkyl-(1,4-substituted 1,4-diazabicyclo[2.2.2]octane-1,4-diium)-, and 3-methylimidazolium, such that the cationic p-phenylene ethynylene compound has a net positive charge. The variable j can be about 0 to about 4, about 1 to about 2, or 0, 1, 2, 3, or 4. The variable $L^1$, at each occurrence, can be independently chosen from a bond and

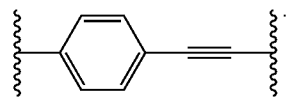

The variable A, at each occurrence, can be independently chosen from —H, substituted or unsubstituted —C(O)O—($C_1$-$C_{10}$)hydrocarbyl, and —C(O)NH—($C_1$-$C_{10}$)hydrocarbyl. The variable m can be about 1 to about 10, about 1 to about 7 about 1 to about 5, about 1 to about 3 or about 1, 2, 3, 4, 5, 6, 7, 8, 9, or about 10 or greater.

In various embodiments, the cationic p-phenylene ethynylene compound can have the structure:

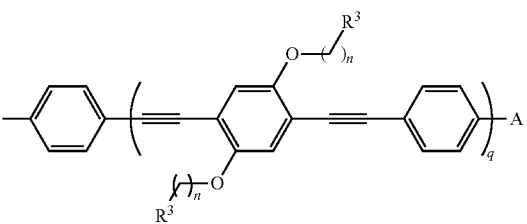

The variable $R^3$, at each occurrence, can be independently chosen from —$N^+(CH_3)_3$,

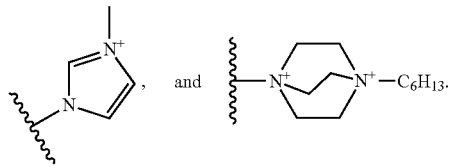

The variable n can be about 2 to about 4, or about 2, 3, or about 4 or greater. The variable A, at each occurrence, can be independently chosen from —H and —C(O)O—($C_1$-$C_5$)alkyl. The variable q can be about 1 to about 5, about 1 to about 3, or about 1, 2, 3, 4, or about 5 or greater.

In various embodiments, the cationic p-phenylene ethynylene compound can have the structure:

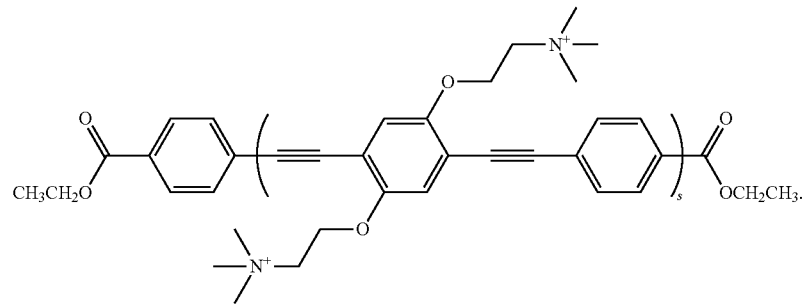

The variable s can be about 1 to about 3, or about 1, 2 or about 3 or greater.

In various embodiments, the enzyme substrate can be an anionic enzyme substrate. For example, the anionic enzyme substrate can be 1,2-dilauroyl-sn-glycero-phospho-(1'-rac-glycerol). In various embodiments, the enzyme can be any suitable enzyme. For example, the enzyme can be a protolytic enzyme, a DNA restriction enzyme, a phosphatase, or a kinase. In various embodiments the enzyme is chosen from phospholipase A1, phospholipase A2 and phospholipase C.

In various embodiments, the p-phenylene ethynylene compound is an anionic p-phenylene ethynylene compound. In various embodiments, the anionic p-phenylene ethynylene compound can have the structure:

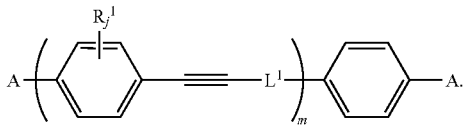

The variable $R^1$ can have the structure:

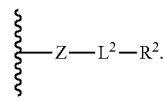

The variable Z, at each occurrence, can be independently chosen from —$CH_2$—, —O—, —S—, and —NH—. The variable $L^2$, at each occurrence, can be independently chosen from ($C_1$-$C_{50}$)hydrocarbylene interrupted by 0, 1, 2, 3, 4, 5, 6, 7, 8, 9, or 10 groups independently chosen from —O—, —S—, and —NH—. The variable $R^2$, at each occurrence, can be independently chosen from —H, ($C_1$-$C_5$)alkyl, —$SO_3^-$, —$CO_2^-$, —$H_2PO_4^-$, $HPO_4^{2-}$, $PO_4^{3-}$, and phenolate. Further, at least one $R^2$ can be an anionic group such as —$SO_3^-$, —$CO_2^-$, —$H_2PO_4^-$, $HPO_4^{2-}$, $PO_4^{3-}$, or phenolate, such that the anionic p-phenylene ethynylene compound can have a net negative charge. The variable j can be about 0 to about 4, about 1 to about 2, or 0, 1, 2, 3, or 4. The variable $L^1$, at each occurrence, can be independently chosen from a bond and

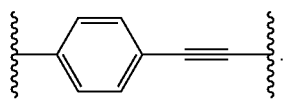

The variable A, at each occurrence, can be independently chosen from —H, substituted or unsubstituted —C(O)O—($C_1$-$C_{10}$)hydrocarbyl, and —C(O)NH—($C_1$-$C_{10}$)hydrocarbyl. The variable m can be about 1 to about 10, about 1 to about 7 about 1 to about 5, about 1 to about 3 or about 1, 2, 3, 4, 5, 6, 7, 8, 9, or about 10 or greater.

In various embodiments, the anionic p-phenylene ethynylene compound can have the structure:

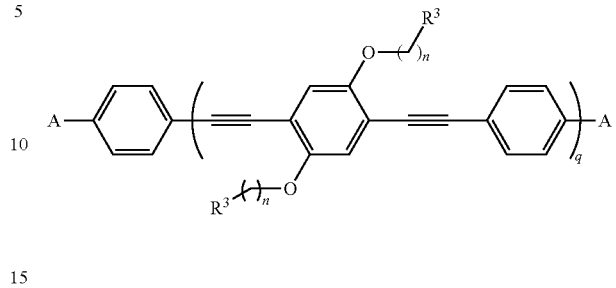

The variable $R^3$, at each occurrence, can independently be chosen from —$SO_3^-$, —$CO_2^-$, —$H_2PO_4^-$, $HPO_4^{2-}$, $PO_4^{3-}$, and phenolate. The variable $R^3$ can be —$SO_3^-$. The variable n can be about 2 to about 4, or about 2, 3, or about 4 or greater. The variable A, at each occurrence, can be independently chosen from —H and —C(O)O—($C_1$-$C_5$)alkyl. The variable q can be about 1 to about 5, about 1 to about 3, or about 1, 2, 3, 4, or about 5 or greater.

In various embodiments, the anionic p-phenylene ethynylene compound can have the structure:

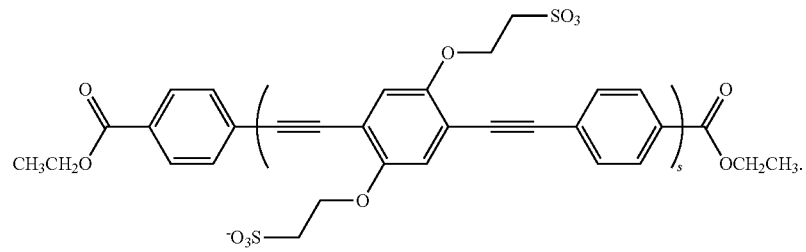

The variable s can be about 1 to about 3 or about 1, 2 or about 3 or greater.

In various embodiments, the enzyme substrate can be a cationic enzyme substrate. The cationic enzyme substrate can be a substituted or unsubstituted ($C_1$-$C_{25}$)hydrocarbyl-C(O)O—($C_1$-$C_{10}$)alkyl-$N^+$(($C_1$-$C_5$)alkyl)$_3$. The cationic enzyme substrate can be a substituted or unsubstituted ($C_1$-$C_{25}$)alkyl-C(O)O—($C_1$-$C_4$)alkyl-$N^+$($CH_3$)$_3$. In various embodiments the cationic enzyme substrate can be chosen from lauroyl choline and acetylcholine. The cationic enzyme substrate can be lauroyl choline.

The enzyme can be any suitable enzyme. The enzyme can be a phospholipase (e.g., PLA1, PLA2, PLC, PLB). The enzyme can be butyrylcholinesterase. In various embodiments, the enzyme can be acetylcholinesterase.

In various embodiments includes (i) exposing a sensor composition including a complex including a p-phenylene ethynylene compound and an enzyme substrate to a sample; (ii) introducing an enzyme to the sensor composition of step (i); and (iii) analyzing the change in fluorescence of the p-phenylene ethynylene compound between the exposing step (i) and the introducing an enzyme step (ii). The p-phenylene ethynylene compound can have the structure:

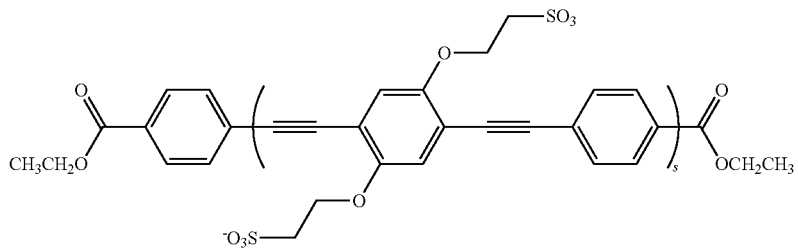

The variable s can be 1. The enzyme substrate can be lauroyl choline. A change in fluorescence between the exposing step (i) and the introducing an enzyme step (ii) can indicate the presence of a chemical agent that does interact with the enzyme.

Sensor for Detecting the Presence of a Chemical Agent

In various embodiments, a sensor for detecting the presence of a chemical agent is described herein. The sensor including a sensor composition including a complex including a p-phenylene ethynylene compound and an enzyme substrate.

In various embodiments, the the p-phenylene ethynylene compound can be a cationic p-phenylene ethynylene compound. In various embodiments, the cationic p-phenylene ethynylene compound can have the structure:

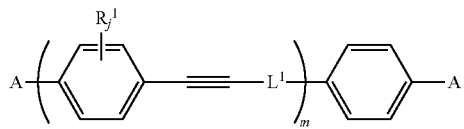

The variable $R^1$ can have the structure:

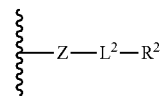

The variable Z, at each occurrence, can be independently chosen from —$CH_2$—, —O—, —S—, and —NH—. The variable $L^2$, at each occurrence, can be independently chosen from ($C_1$-$C_{50}$)hydrocarbylene interrupted by 0, 1, 2, 3, 4, 5, 6, 7, 8, 9, or 10 groups independently chosen from —O—, —S—, and —NH—. The variable $R^2$, at each occurrence, can be independently chosen from —H, ($C_1$-$C_5$)alkyl, —$SO_3^-$, —$CO_2^-$, —$H_2PO_4^-$, $HPO_4^{2-}$, $PO_4^{3-}$, phenolate, —$N^+(R^A)_3$, ($C_1$-$C_{10}$)alkyl-(1,4-substituted 1,4-diazabicyclo[2.2.2]octane-1,4-diium)-, and 3-methylimidazolium. The variable $R^A$, at each occurrence, can be independently ($C_1$-$C_5$)alkyl. Further, at least one $R^2$ can be independently chosen from $N^+(R^A)_3$, ($C_1$-$C_{10}$)alkyl-(1,4-substituted 1,4-diazabicyclo[2.2.2]octane-1,4-diium)-, and 3-methylimidazolium such that the cationic p-phenylene ethynylene compound has a net positive charge. The variable j can be about 0 to about 4, about 1 to about 2, or 0, 1, 2, 3, or 4. The variable $L^1$, at each occurrence, can be independently chosen from a bond and

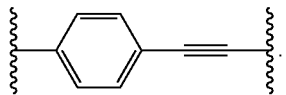

The variable A, at each occurrence, can be independently chosen from —H, substituted or unsubstituted —C(O)O—($C_1$-$C_{10}$)hydrocarbyl, and —C(O)NH—($C_1$-$C_{10}$)hydrocarbyl. The variable m can be about 1 to about 10, about 1 to about 7 about 1 to about 5, about 1 to about 3 or about 1, 2, 3, 4, 5, 6, 7, 8, 9, or about 10 or greater.

In various embodiments, the cationic p-phenylene ethynylene compound can have the structure:

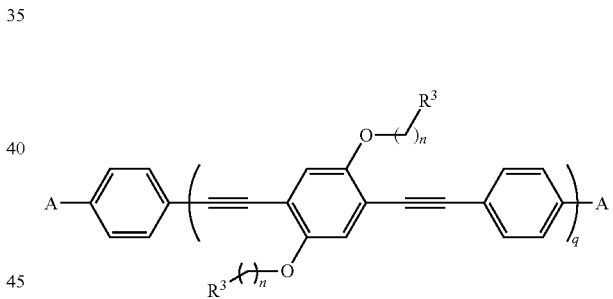

The variable $R^3$, at each occurrence, can be independently chosen from —$N^+(CH_3)_3$,

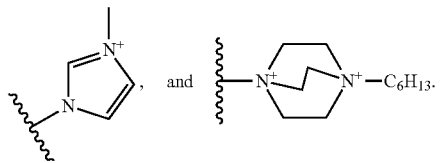

The variable n can be about 2 to about 4, or about 2, 3, or about 4 or greater. The variable A, at each occurrence, can be independently chosen from —H and —C(O)O—($C_1$-$C_5$)alkyl. The variable q can be about 1 to about 5, about 1 to about 3, or about 1, 2, 3, 4, or about 5 or greater.

In various embodiments, the cationic p-phenylene ethynylene compound can have the structure:

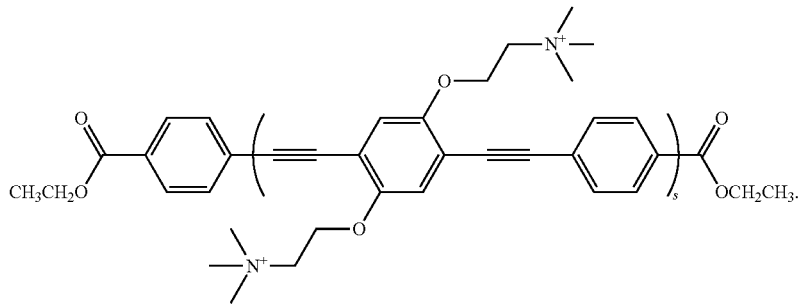

The variable s can be about 1 to about 3, or about 1, 2 or about 3 or greater.

In various embodiments, the enzyme substrate can be an anionic enzyme substrate. For example, the anionic enzyme substrate can be 1,2-dilauroyl-sn-glycero-phospho-(1'-rac-glycerol).

In various embodiments, the p-phenylene ethynylene compound can be an anionic p-phenylene ethynylene compound. In various embodiments, the anionic p-phenylene ethynylene compound can have the structure:

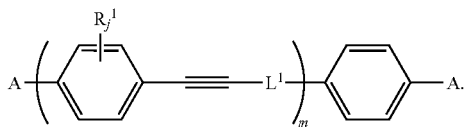

The variable $R^1$ can have the structure:

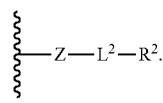

The variable Z, at each occurrence, can be independently chosen from —$CH_2$—, —O—, —S—, and —NH—. The variable $L^2$, at each occurrence, can be independently chosen from ($C_1$-$C_{50}$)hydrocarbylene interrupted by 0, 1, 2, 3, 4, 5, 6, 7, 8, 9, or 10 groups independently chosen from —O—, —S—, and —NH—. The variable $R^2$, at each occurrence, can be independently chosen from —H, ($C_1$-$C_5$)alkyl, —$SO_3^-$, —$CO_2^-$, —$H_2PO_4^-$, $HPO_4^{2-}$, $PO_4^{3-}$, and phenolate. Further, at least one $R^2$ can be an anionic group such as —$SO_3^-$, —$CO_2^-$, —$H_2PO_4^-$, $HPO_4^{2-}$, $PO_4^{3-}$, or phenolate, such that the anionic p-phenylene ethynylene compound can have a net negative charge. The variable j can be about 0 to about 4, about 1 to about 2, or 0, 1, 2, 3, or 4. The variable $L^1$, at each occurrence, can be independently chosen from a bond and

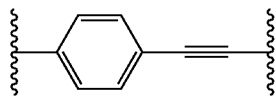

The variable A, at each occurrence, can be independently chosen from —H, substituted or unsubstituted —C(O)O—($C_1$-$C_{10}$)hydrocarbyl, and —C(O)NH—($C_1$-$C_{10}$)hydrocarbyl. The variable m can be about 1 to about 10, about 1 to about 7 about 1 to about 5, about 1 to about 3 or about 1, 2, 3, 4, 5, 6, 7, 8, 9, or about 10 or greater.

In various embodiments, the anionic p-phenylene ethynylene compound can have the structure:

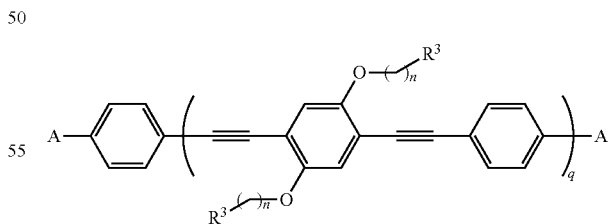

The variable $R^3$, at each occurrence, can be independently chosen from —$SO_3^-$, —$CO_2^-$, —$H_2PO_4^-$, $HPO_4^{2-}$, $PO_4^{3-}$, and phenolate. The variable $R^3$ can be —$SO_3^-$. The variable n can be about 2 to about 4, or about 2, 3, or about 4 or greater. The variable A, at each occurrence, can be independently chosen from —H and —C(O)O—($C_1$-$C_5$)alkyl. The variable q can be about 1 to about 5, about 1 to about 3, or about 1, 2, 3, 4, or about 5 or greater.

In various embodiments, the anionic p-phenylene ethynylene compound can have the structure:

$$\text{CH}_3\text{CH}_2\text{O}-\underset{O}{\overset{O}{\parallel}}-\text{C}-\text{C}_6\text{H}_4-\left(-\text{C}\equiv\text{C}-\text{C}_6\text{H}_2(\text{OCH}_2\text{CH}_2\text{SO}_3^-)_2-\text{C}\equiv\text{C}-\text{C}_6\text{H}_4-\right)_s-\text{C}(\text{O})-\text{OCH}_2\text{CH}_3$$

The variable s can be about 1 to about 3 or about 1, 2 or about 3 or greater.

In various embodiments, the enzyme substrate can be a cationic enzyme substrate. The cationic enzyme substrate can be a substituted or unsubstituted $(C_1\text{-}C_{25})$hydrocarbyl-$C(O)O\text{—}(C_1\text{-}C_{10})$alkyl-$N^+((C_1\text{-}C_5)$alkyl$)_3$. The cationic enzyme substrate can be a substituted or unsubstituted $(C_1\text{-}C_{25})$alkyl-$C(O)O\text{—}(C_1\text{-}C_4)$alkyl-$N^+(CH_3)_3$. In various embodiments the cationic enzyme substrate can be chosen from lauroyl choline and acetylcholine. The cationic enzyme substrate can be lauroyl choline.

In various embodiments, the sensor includes a sensor composition including a complex including a p-phenylene ethynylene compound and an enzyme substrate. The p-phenylene ethynylene compound can have the structure:

$$\text{CH}_3\text{CH}_2\text{O}-\underset{O}{\overset{O}{\parallel}}-\text{C}-\text{C}_6\text{H}_4-\left(-\text{C}\equiv\text{C}-\text{C}_6\text{H}_2(\text{OCH}_2\text{CH}_2\text{SO}_3^-)_2-\text{C}\equiv\text{C}-\text{C}_6\text{H}_4-\right)_s-\text{C}(\text{O})-\text{OCH}_2\text{CH}_3$$

The variable s can be 1. The enzyme substrate can be lauroyl choline.

EXAMPLES

Various embodiments of the present invention can be better understood by reference to the following Examples which are offered by way of illustration. The present invention is not limited to the Examples given herein.

Example 1

Example 1.1

Growth and Preparation of *Bacillus atrophaeus* Spores.

*Bacillus atrophaeus* (ATCC #9372) spores were obtained from 20% glycerol-suspended spore stock stored at −70° C. A working batch of *B. atrophaeus* spores was obtained by induced germination and subsequent sporulation on sporulation agar. Using a sterile inoculation loop, spore colonies were scraped off the sporulation agar, suspended in sterile DI water, and filtered through glass wool. Spores were then washed three times via centrifugation (15 minutes, 4.4 k RPM), with the pellet being resuspended in 50% ethanol, and stored at 4° C. for 12 hours to provide time for vegetative cell death. Spores were then washed another three times via centrifugation and resuspension in sterile DI water. Spores were then aliquoted into glass vials and stored at 4° C. until use. The concentration of spores in these aliquots was determined with a hemocytometer.

Example 1.2

Growth and Preparation of *Bacillus atrophaeus* Vegetative Cells.

*Bacillus atrophaeus* vegetative cells were obtained by adding 1 mL of prepared spore aliquot to 50 mL Bacto tryptic soy broth (TSB; Beckton Dickinson), which was then incubated for 18 hours at 30° C. with shaking (250 RPM). Vegetative cells were prepared for analysis by a triple-wash step consisting of three centrifugations of 4.4 k RPM for 15 minutes each; with pellets resuspended in 0.85% NaCl (physiological saline solution). The resulting cell concentrations were determined with a hemocytometer.

Example 1.3

*Bacillus atrophaeus* Viability Testing.

Viability testing was carried out at concentrations of $10^7$ bacteria/mL in 0.85% NaCl, p-Phenylene ethynylene compound ("PE") concentrations of 10 μg/mL and 20 μg/mL were used to target *B. atrophaeus* vegetative cells and spores, respectively. Samples were prepared at volumes of 1 mL in 0.5-dram glass vials (VWR; Radnor, PA), and exposed to light or dark conditions for varying time periods. Light experiments were carried out in a 10-lamp LZC-ORG photoreactor (Luzchem Research; Ontario, Canada) fitted with UVA lamps (Hitachi FL8BL-B) exhibiting a power density of 0.975 mW/cm², over a wavelength range of 316-400 nm (centered at 350 nm). Samples were loaded into a rotating carousel in the center of the photoreactor to ensure uniform light exposure. Following light exposure, samples were stained with a membrane-permeable stain, SYTO 21 (Life Technologies; Carlsbad, CA), and a membrane-impermeable stain, propidium iodide (PI; Life Technologies).

Membrane-permeable nucleic acid dyes such as SYTO 21 stain nucleic acids throughout a bacterium, independent of membrane damage. On the other hand, membrane-impermeable stains such as propidium iodide selectively stain nucleic acids in bacteria with compromised membranes. Vegetative cell samples were permitted 15 minutes to stain at room temperature (in the dark), while spores were allowed 45 minutes to stain at room temperature (also in the dark). Staining of spores with hydrophilic nucleic acid stains, such as propidium iodide, takes longer than that of vegetative cells due to the fact that a spore's DNA is supercoiled within the inner membrane, which is inherently impermeable to hydrophilic molecules.

Stained samples were then evaluated with an Accuri C6 (Becton Dickinson) flow cytometer equipped with a 488 nm, 50 mW laser. SYTO 21 fluorescence was quantified with the FL1 detector at 530±15 nm; PI fluorescence was quantified with the FL3 detector at wavelengths exceeding 670 nm.

Two thresholds were used in viability analysis; the first was a forward scatter (FSC) threshold that ensured that only events exceeding 50.000 FSC units were included in the data sets. Lowering the forward scatter threshold to 50,000 helps ensure that small Bacillus spores aren't omitted as events. The second threshold was specific to the FL1 detector, and ensured that only events exhibiting some degree of SYTO 21 uptake (at least 250 fluorescence units) were included as data points. Bacteria were analyzed at a nominal flow rate of 14 µL/min, with a stream core diameter of 10 µm. All samples were evaluated until at least 10,000 events had been recorded. Using B. atrophaeus vegetative cells, the live gate was based on untreated negative controls, while the dead gate was based on positive controls exposed to 70% ethanol for 60 minutes. An additional gate was obtained to denote the fluorescence regions of viable, untreated spores.

Example 1.4

SEM of *Bacillus atrophaeus* Vegetative Cells and Spores.

Spores exposed to EO-PE (Th,C2), or simply 0.85% NaCl as a negative control, were examined by scanning electron spectroscopy (SEM) (Quanta 250 FEG SEM; FEI; Hillsboro, OR). Samples were fixed in 2.5% glutaraldehyde overnight at room temperature, rinsed in phosphate-buffered saline (PBS), and subsequently dehydrated in ethanol. Dehydrated samples were sputercoated in approximately 12 nm of gold and palladium under vacuum and subsequently analyzed by SEM.

Example 1.5

Growth and Preparation of *Bacillus Anthracis* Sterne.

BSL2 agent *B. anthracis* Sterne was not permitted for use in flow cytometry facilities and thus was prepared and evaluated differently from the aforementioned *B. atrophaeus*. *B. anthracis* Sterne spore stocks were prepared as previously described. Briefly, spores were prepared in phage assay broth; sporulation was subsequently confirmed with phase-contrast microscopy, and any remaining vegetative cells were killed with a 40 minute, 68° C. heat treatment. Bacteria were then washed and resuspended in Dulbecco's phosphate-buffered saline (DPBS; Gibco), tittered, aliquoted, and stored at −80° C. Colony growth of aliquots was evaluated before and after heat treatment (40 minutes at 68° C.) to ensure the absence of vegetative cells.

*B. anthracis* Sterne vegetative cells were prepared exclusively for the experiments described herein. *B. anthracis* Sterne spores were removed from frozen storage and thawed at room temperature before 20 µL of suspension was streaked onto a tryptic soy agar (TSA) plate. TSA plates were incubated for 16 hours at 37° C. A sterile inoculation loop was then used to transfer 2 colonies from the TSA plate into 40 mL of brain heart infusion (BHI), along with 200 µL of glycerol. The flask was then aerobically incubated for 16 hours at 37° C. with 250 RPM shaking. To ensure sterility of BHI a second flask was aerobically incubated with 10 mL BHI. Following verification of sterility, 200 µL of the inoculated BHI was added to 800 µL sterile BHI, vortexed, and subsequently transferred to a disposable cuvette. The absorbance of the cuvette was measured at 600 nm relative to sterile BHI. A subculture was then prepared at an OD of 0.1 and aerobically incubated at 37° C. with shaking until the subculture's OD reached 1.0—indicating a vegetative cell concentration of $2 \times 10^7$ CFU/mL (confirmed by colony growth on TSA).

Saline-washed *B. anthracis* Sterne vegetative cells were exposed to 10 µg/mL EO-PE (Th,C2) in light and dark conditions for varying time durations, diluted, and streaked onto TSA plates. TSA plates were incubated at 37° C. for 18 hours and the colonies counted to estimate viability. *B. anthracis* Sterne spores were evaluated by a similar technique, albeit with the implementation of heat treatment. In this case, samples were diluted, plated, and subsequently heat-treated to kill vegetative cells. Heat treatment is applied via a 68° C. water bath for 30 minutes, such that *B. atrophaeus* vegetative cells are killed; presumably, any resulting colony growth would result from spores and not vegetative cells. Heat-treated samples were also diluted and plated—the difference of colony growth between the heat-treated and non-heat treated samples was used to gauge the percentage of sample which was vegetative cells. Negative controls contained no PE, while heat treatment consisted of submersion in a 68° C. water bath for 30 minutes. Equations 1.1, 1.2, and 1.3 were used to infer sample populations based on colony growth:

$$\% \text{ of } CFUs \text{ that are Viable Vegetative} \tag{1.1}$$
$$\text{Cells} = 100 \times \frac{CFU - CFU_{HT}}{CFU}$$

$$\% \text{ of } CFUs \text{ that are Viable Spores} = 100 \times \frac{CFU_{HT}}{CFU} \tag{1.2}$$

$$\% \text{ of } CFUs \text{ that are nonviable relativeve} \tag{1.3}$$
$$\text{to negative control } 100 \times \frac{CFU_{NC} - CFU}{CFU_{NC}}$$

As used herein, "CFUs" and "CFU" refer to the number of colony forming units on TSA prior to Heat Treatment, $CFU_{HT}$ is the number of colony forming units on TSA after Heat Treatment, and $CFU_{NC}$ is the number of colony forming units on TSA in the negative control (no heat treatment). These equations are implemented in FIG. 5 as a means to monitor viability and germination, under the assumption that heat treated vegetative cells lose their ability to form colonies. All *B. anthracis* Sterne experiments (those shown in FIGS. 4 and 5) were conducted in triplicate.

Example 1.5

Results.

PE-induced cell death was inferred using a complementary set of nucleic acid stains such that bacteria with intact cell membranes exhibit uptake of SYTO 21, while only cells with compromised membranes exhibit uptake of PI. In these studies, flow cytometry was utilized to gauge cell viability by rapid interrogation of dual-stain fluorescence. FIGS. 1A-D illustrate flow cytometry-reported viability of 10,000 *B. atrophaeus* vegetative cells determined by changes in PI (X-axis) and SYTO 21 (Y-axis) fluorescence; the L Gate represents the live vegetative cells and the D gate represents the dead vegetative cells; *B. atrophaeus* vegetative were cells suspended in physiological saline solution for 1 hr; A: negative control (0 μg/mL PE); B: 10 μg/mL PE in the dark; C: negative control (0 μg/mL) in UVA light; D: 10 μg/mL PE in UVA light.

Figure 1B:
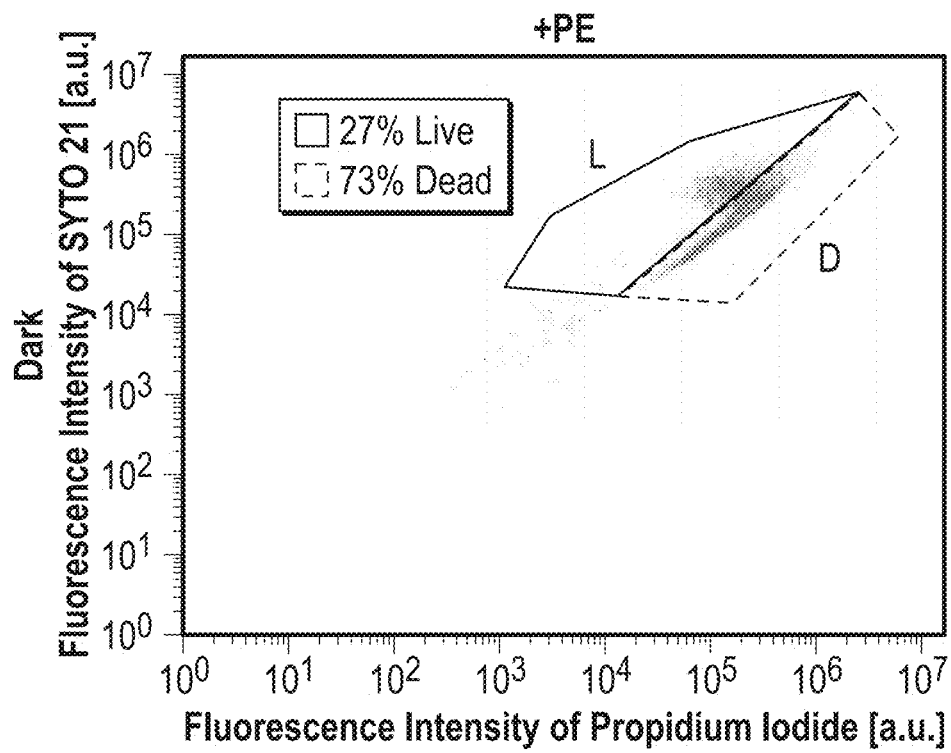
Figure 1C:
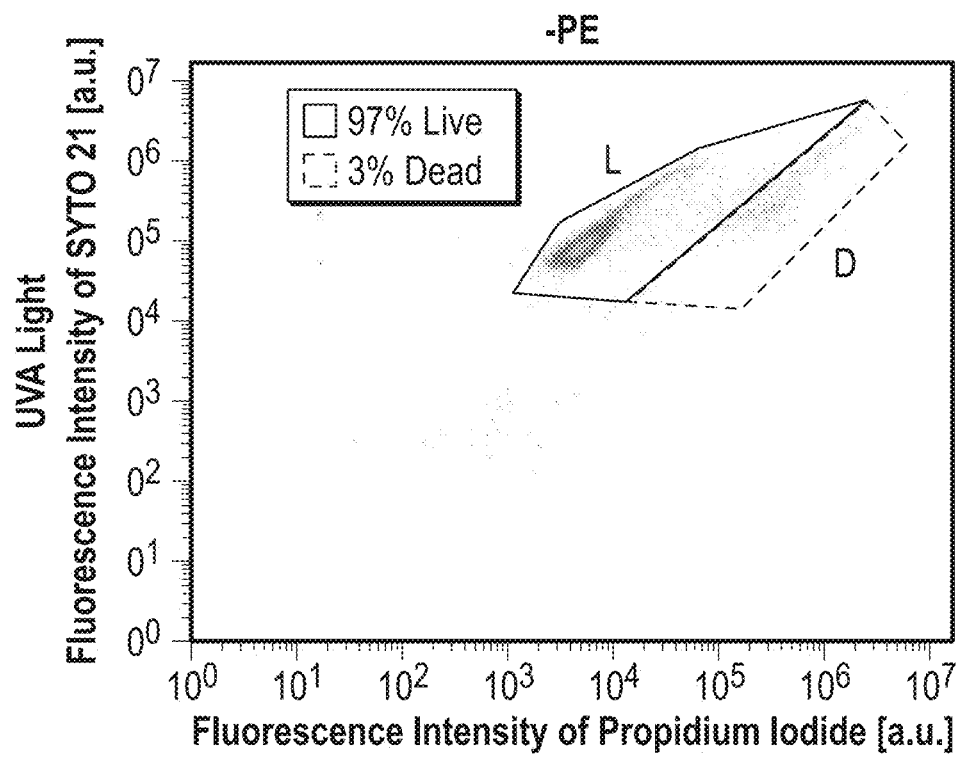
Figure 1D:
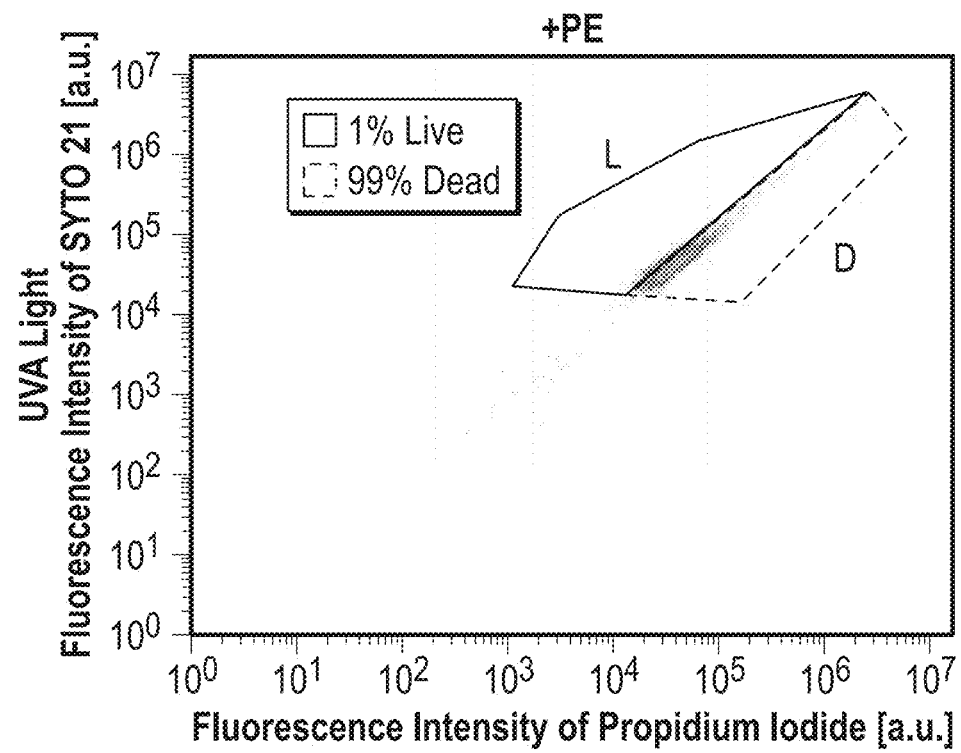
Figure 2A:
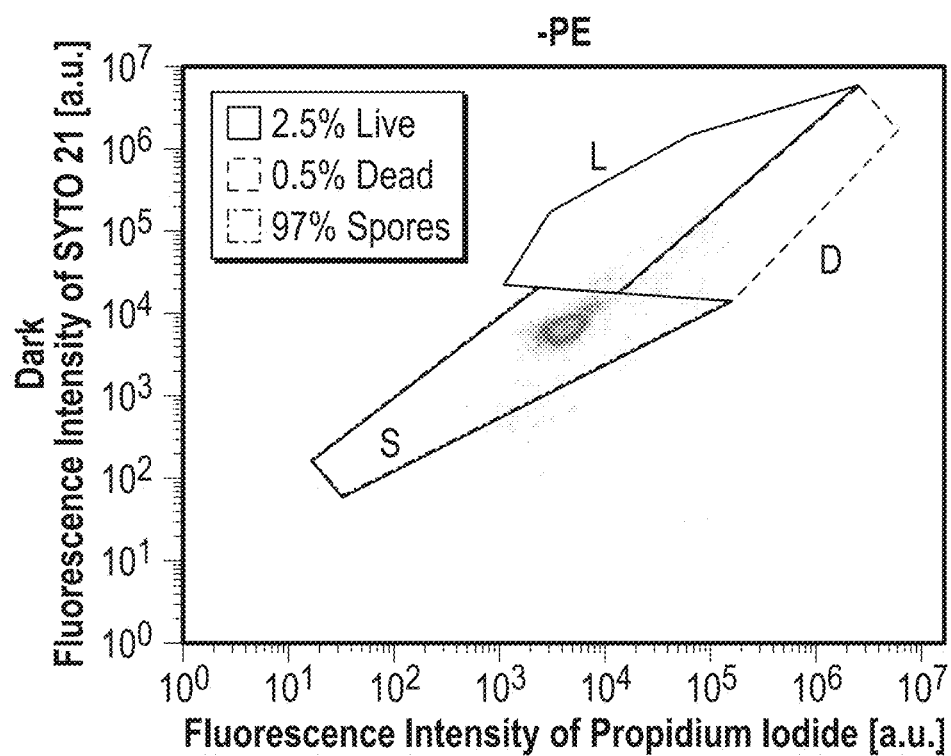
FIGS. 2A-D illustrate flow cytometry-reported germination of *B. atrophaeus* spores under various treatment conditions, in accordance with various embodiments.
Figure 2B:
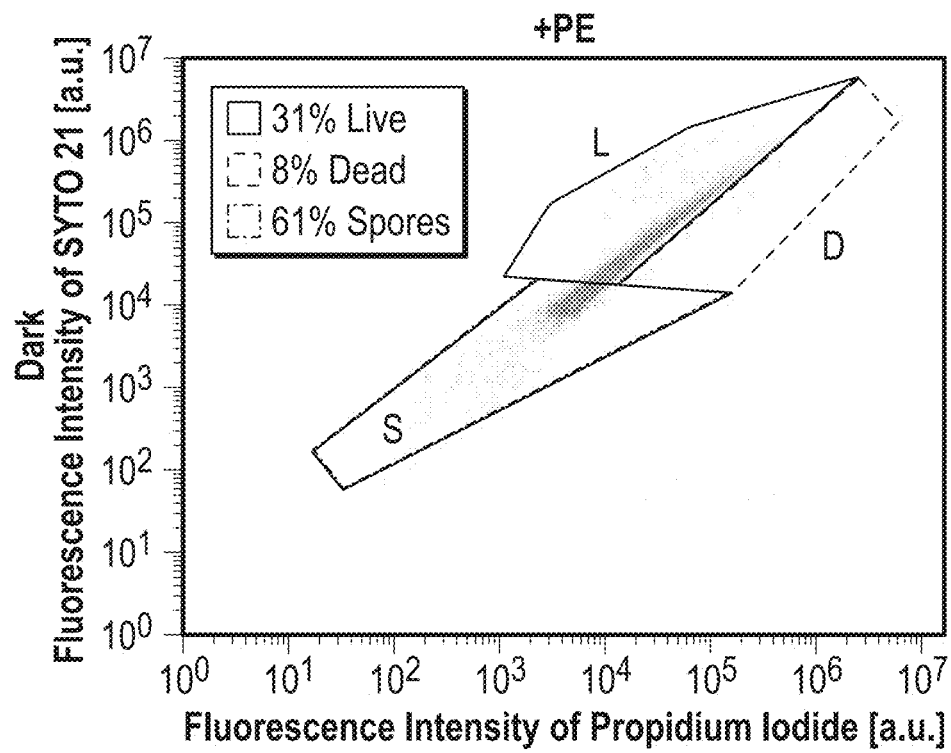

FIG. 1A illustrates fluorescence emitted from untreated *B. atrophaeus* vegetative cells: 1 hr in physiological saline solution at a temperature of 28.5 OC. Under these conditions, 100% of untreated *B. atrophaeus* vegetative cells retained their ability to form colonies and exhibit greater uptake of SYTO 21 (~10 arbitrary fluorescence units) than PI (~$10^4$ arbitrary fluorescence units). In this case, cellular membranes remained intact, limiting propidium iodide uptake. The addition of a known membrane-disrupting agent, such as EO-PE (Th,C2), results in a noticeable fluorescence shift (FIG. 1B). The structure of EO-PE (Th, C2) is depicted below in Scheme 1. Following an hour's exposure to this PE at a concentration of 10 μg/mL, *B. atrophaeus* cells exhibit uptake of SYTO 21 with the same propensity as untreated cells (FIG. 1A); however, the uptake of PI has increased tenfold, demonstrating that PEs induce moderate membrane damage to the extent that 73% of cells are killed in the absence of light. FIG. 1C shows that *B. atrophaeus* vegetative cells are somewhat vulnerable to UVA irradiation, with 3% of bacilli killed in an hour. Significant killing of *B. atrophaeus* vegetative cells was only achieved upon exposure to light-activated PE; an exposure duration of 1 hour causes 99% cell death (FIG. 1D). It is important to note that membrane damage to vegetative bacilli rarely results in non-specific uptake of both stains; that is, the uptake of one stain appears to occur independently of the other.

negative control (0 μg/mL PE) in UVA light; D: 20 μg/mL PE in UVA light. Despite a prolonged staining period, the untreated *B. atrophaeus* spores depicted in FIG. 2A exhibit decreased uptake of both stains relative to the untreated vegetative cells shown in FIG. 1A. Decreased nucleic acid staining in *Bacillus* spores is attributed to their low water content, relatively small volume, and limited access of stains to centralized supercoiled DNA resulting from an intact inner spore membrane. The S gate is therefore included in FIGS. 2A-D to indicate regions of fluorescence characteristic of untreated *B. atrophaeus* spores. As can be seen in FIG. 2B, the addition of EO-PE (Th,$C_2$) affects spores' stain uptake in a different manner than was observed with *B. atrophaeus* vegetative cells in FIG. 1B. While exposure to PEs in the dark selectively enhanced uptake of PI in vegetative cells, the uptake of SYTO 21 is also significantly enhanced in spores following PE exposure in the dark. This non-specific fluorescent enhancement is characteristic of *Bacillus* spore germination: within 10 minutes of induced germination, spore coat porosity rapidly increases, leading to a water influx event, and thus, increased cell volume and increased uptake of stains.

This method of interrogation suggests that the water influx event sufficiently progressed in 39% of spores to the point where the magnitude of stain uptake matched that of *B. atrophaeus* vegetative cells. FIG. 2B shows that 61% of spores still fluoresce in a manner characteristic of that of untreated spores (the S gate), which suggests these spores either underwent delayed germination or were not induced to germinate at all. In the absence of light, PE-exposed spores were found to germinate into viable vegetative cells-meaning they were capable of forming colonies on TSA, while also exhibiting fluorescence characteristic of late-log-phase vegetative cells.

Figure 2C:
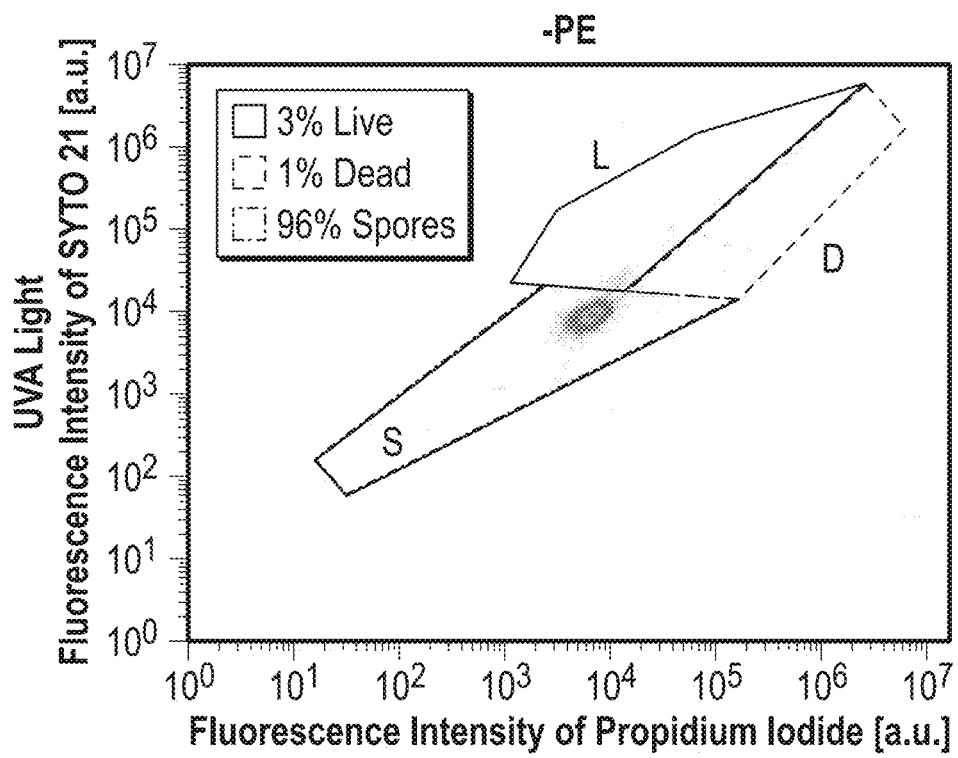
Figure 2D:
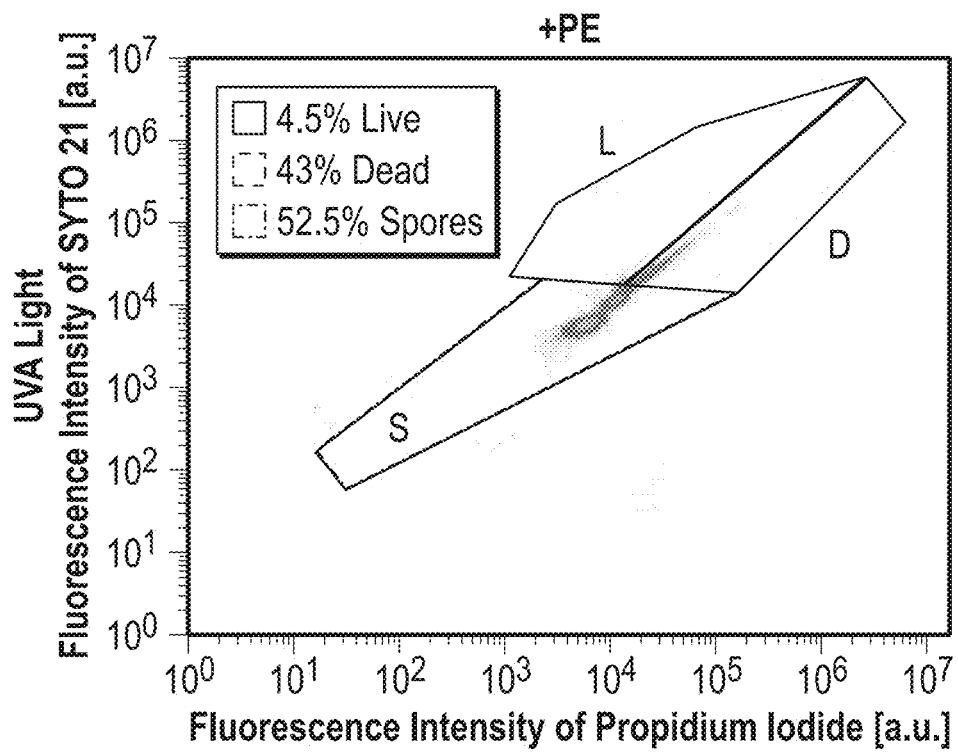

Irradiating *B. atrophaeus* spores with UVA light, alone, does not affect stain uptake, as is shown in FIG. 2C. FIG. 2D shows that exposing spores to light-activated PE also results in non-specific stain uptake; however, in this case, the Scheme 1.

EO-PE (Th, C2)

Having defined regions of fluorescence characteristic of viable and non-viable *B. atrophaeus* vegetative cells, flow cytometry was then utilized to determine the extent by which EO-PE (Th,$C_2$) inflicts damage on *B. atrophaeus* spores. Spores were treated under the same conditions as the aforementioned vegetative cells (depicted in FIGS. 1A-D); however, spores were stained with SYTO 21 and PI for 45 minutes, whereas vegetative cells needed just 15 minutes to stain.

FIGS. 2A-D illustrate flow cytometry-reported germination of 10,000 *B. atrophaeus* spores determined by changes in PI (X-axis) and SYTO 21 (Y-axis) fluorescence; the S gate represents spores, the L Gate represents viable germinating spores, and the D gate represents cells that have died during germination; *B. atrophaeus* spores were suspended in physiological saline solution for 1 hr; A: negative control (0 μg/mL PE) in the dark; B: 20 μg/mL PE in the dark; C:

uptake ratio of membrane impermeable stain (PI) to membrane permeable stain (SYTO 21) is increased, resulting in failed germination and inability to form colonies. Therefore, light-activated PE promptly kills most germinating spores— not surprising, given the susceptibility of *Bacillus* vegetative cells to light-activated PE (FIG. 1D). Increasing the PE concentration to 50 or 100 μg/mL was found to have no increased effect on the death or germination of *B. atrophaeus* spores, presumably to the inner filter effect.

The presence of UVA light is significant in achieving significant biocidal activity with cationic PEs, as light-induced inactivation of *B. anthracis* Steme is believed to involve three steps. First, the PE is excited from the ground state, $S_0$, to its excited singlet state, $S_1$. Second, via inter-system crossing, $S_1$ decays to a longer-lived, albeit lower energy, triplet state, $S_3$; in turn, $S_3$ transfers its energy to molecular triplet oxygen, subsequently generating singlet oxygen ($^1O_2$) and ROS via a type I and type II photoreactions, respectively. Thirdly, ROS and $^1O_2$ can locally oxidize lipids, proteins, and nucleic acids. It is evident that the additional level of PE-inflicted damage conferred by the presence of UVA light plays a major role in viability of germinating B. atrophaeus spores. The additional damage inflicted by light activation of PE (as opposed to PE in the dark) may stunt germination by limiting the progression of one or both water influx events, as both fluorescence magnitudes (FIG. 2D) and forward scatter values are mitigated in this scenario.

Figure 3A:
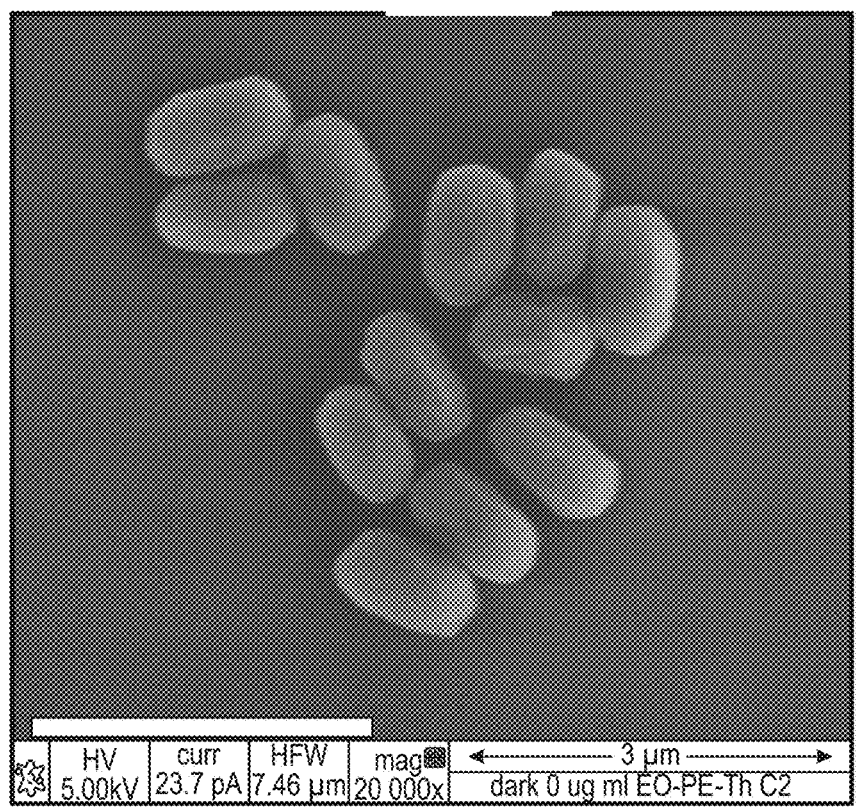
FIGS. 3A-E illustrate scanning electron microscope images of *B. atrophaeus* spores and vegetative cells, in accordance with various embodiments.
Figure 3B:
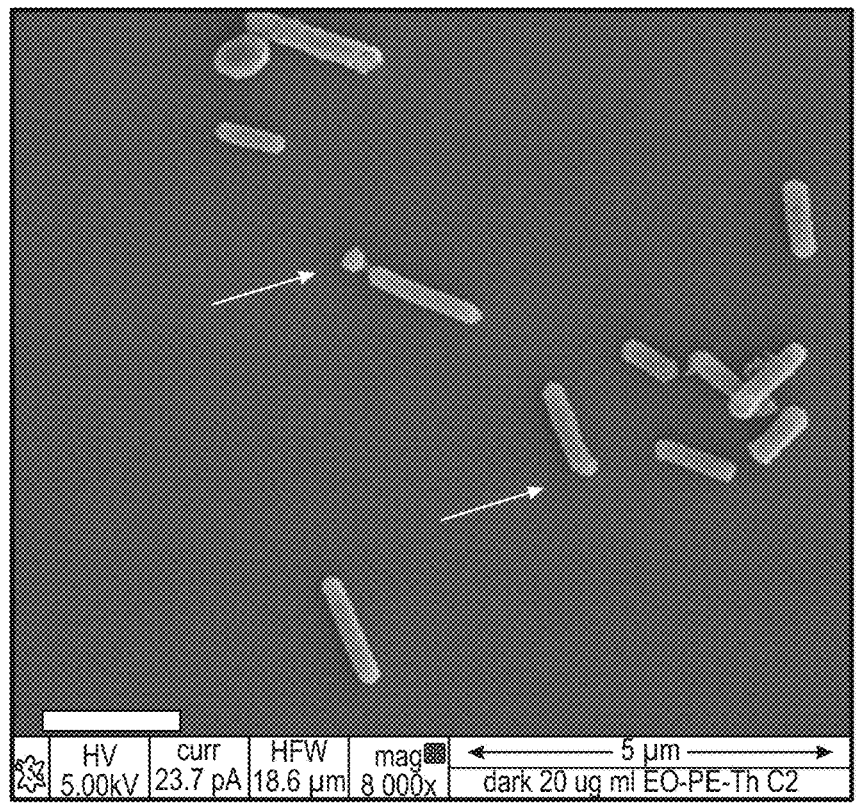
Figure 3C:
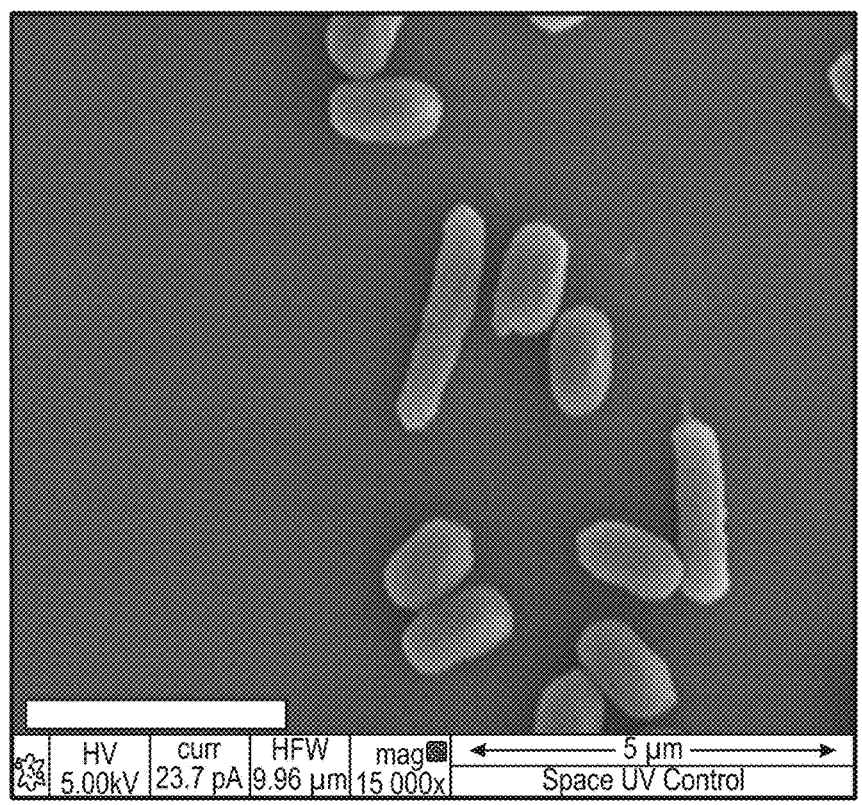
Figure 3D:
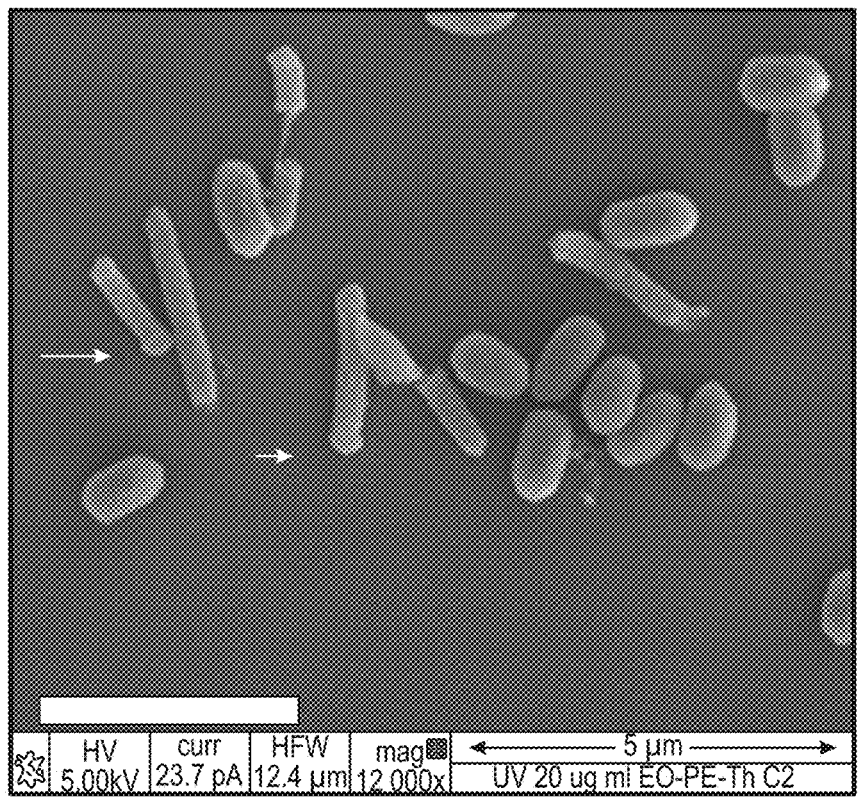
Figure 3E:
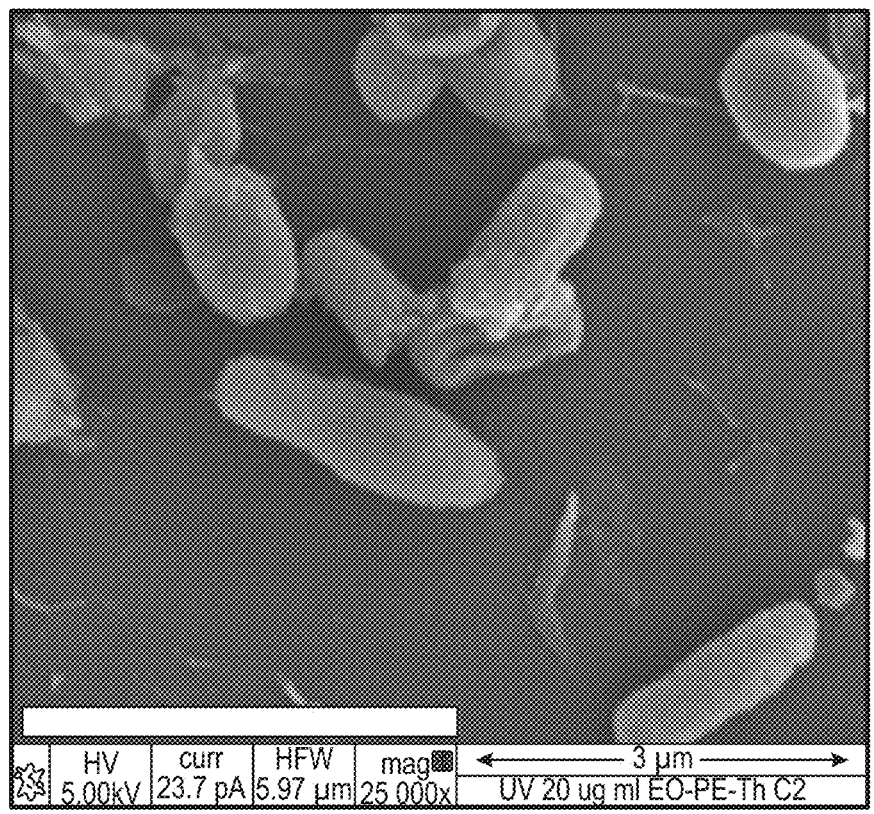

The ability of PEs to induce germination of B. atrophaeus spores was confirmed with scanning electron microscopy (SEM). FIGS. 3A-E illustrate scanning electron microscope images of B. atrophaeus spores (with vegetative cells that arose from PE-induced spore germination also visible); A: spores suspended in physiological saline solution for 5 hrs in the dark; B: spores exposed to 20 µg/mL PE for 5 hrs in the dark; C: spores suspended in physiological saline solution for 5 hrs in UVA light; D and E: spores exposed to 20 µg/mL PE for 5 hrs in UVA light. Scale bars spanning 3 µm are included. Arrows indicate spore coat remnants. As shown in FIGS. 3A-E, SEM imaging illustrates an increased quantity of germinating cells following their exposure to PE in the dark, as evidenced by their increased volume, rod-like morphology, and spore coat remnants. Vegetative cells were present in the negative control, although they were far outnumbered by spores (the gating scheme used in FIG. 2A indicates that spores represent 3% of all bacteria, in this instance). The observed dimensions of the rod-like vegetative cells (diameter: 0.8 µm; length: 2-3 µm) and spores (width: 0.7 µm; length: 1.8 µm) both match previously reported records. Arrows are included (FIGS. 3B and 3D) to highlight the presence of spore coat remnants—the presence of which generally coincides with one of the last stages of spore germination. In the case of many bacilli, however, there is no sign of a spore coat remnant, signifying that there is a large degree of disparity concerning germination progress across the sample population-corroborating the heterogeneous fluorescence exhibited by germinating B. atrophaeus spores seen via flow cytometry. While germination is still observed in the presence of light-activated PE, the majority of cells exhibit significant morphological damage that is too severe for the bacterium to overcome (FIGS. 3D and 3E).

Figure 4:
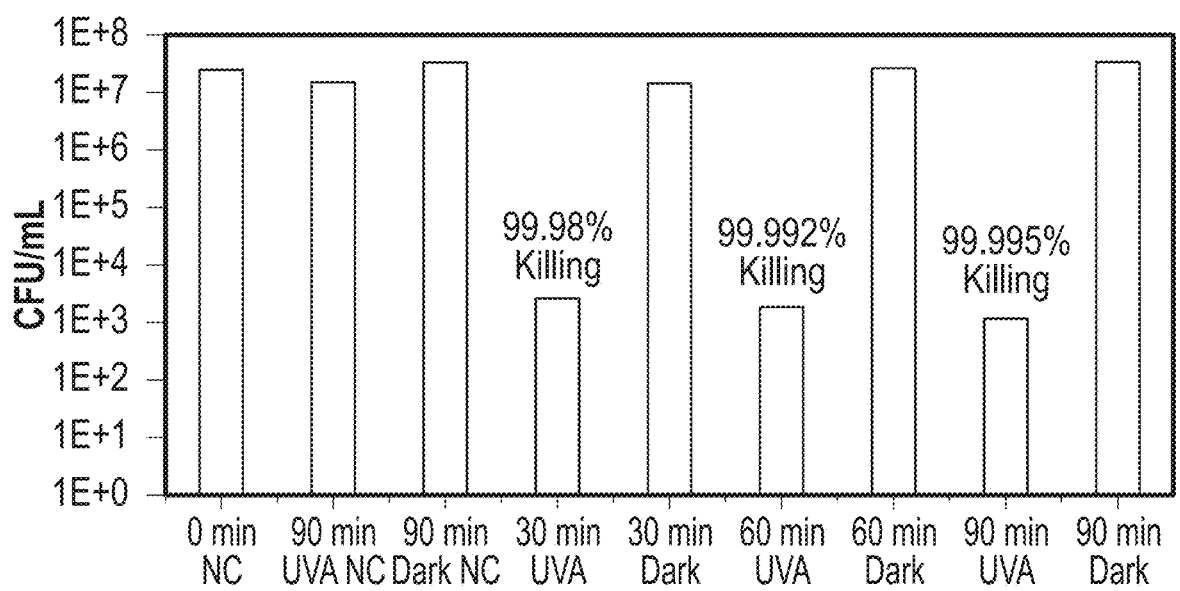
FIG. 4 illustrates *B. anthracis* Sterne vegetative cell viability with and without exposure to a PE, in accordance with various embodiments.
Figure 5:
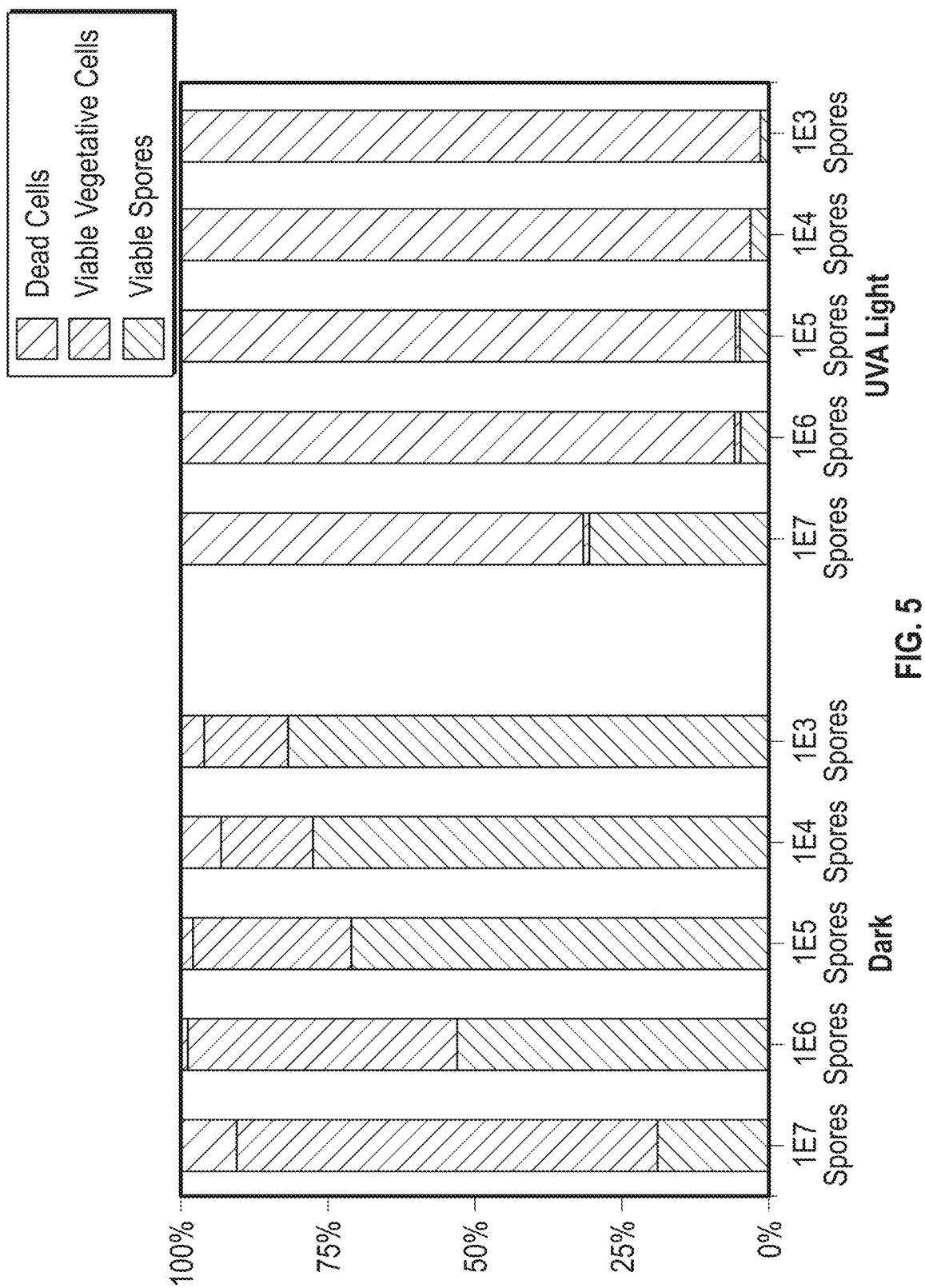
FIG. 5 illustrates *B. anthracis* Sterne spore and germinated vegetative cell viability as a function of starting concentration, in accordance with various embodiments.
Figure 6A:
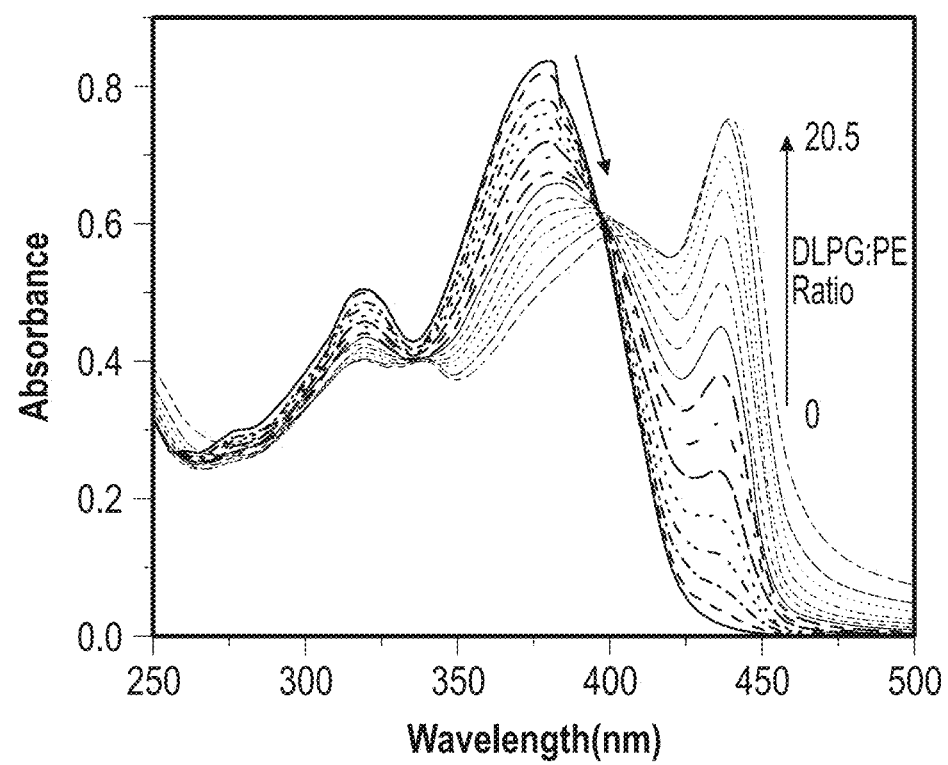
FIGS. 6A-D illustrate absorbance and fluorescence of various p-phenylene ethynylene compounds (PEs) versus wavelength in the presence of varying amounts of 1,2-dilauroyl-sn-glycero-3-phospho-(1'-rac-glycerol) (DLPG) or lauroyl choline (LaCh), in accordance with various embodiments.
Figure 6B:
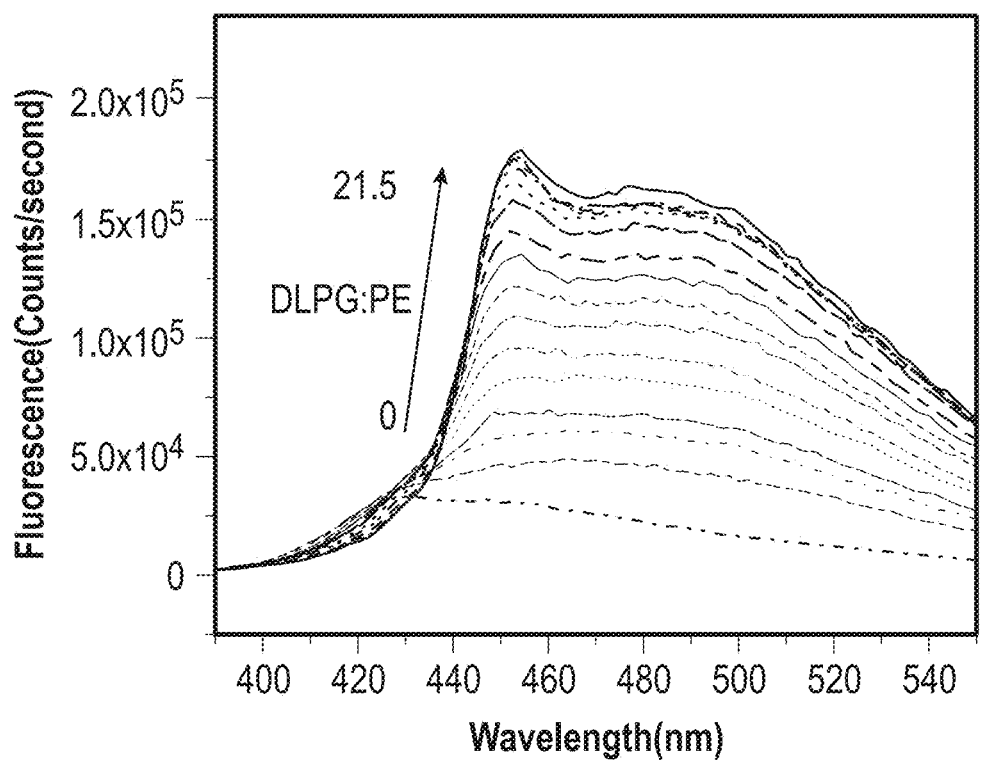
Figure 6C:
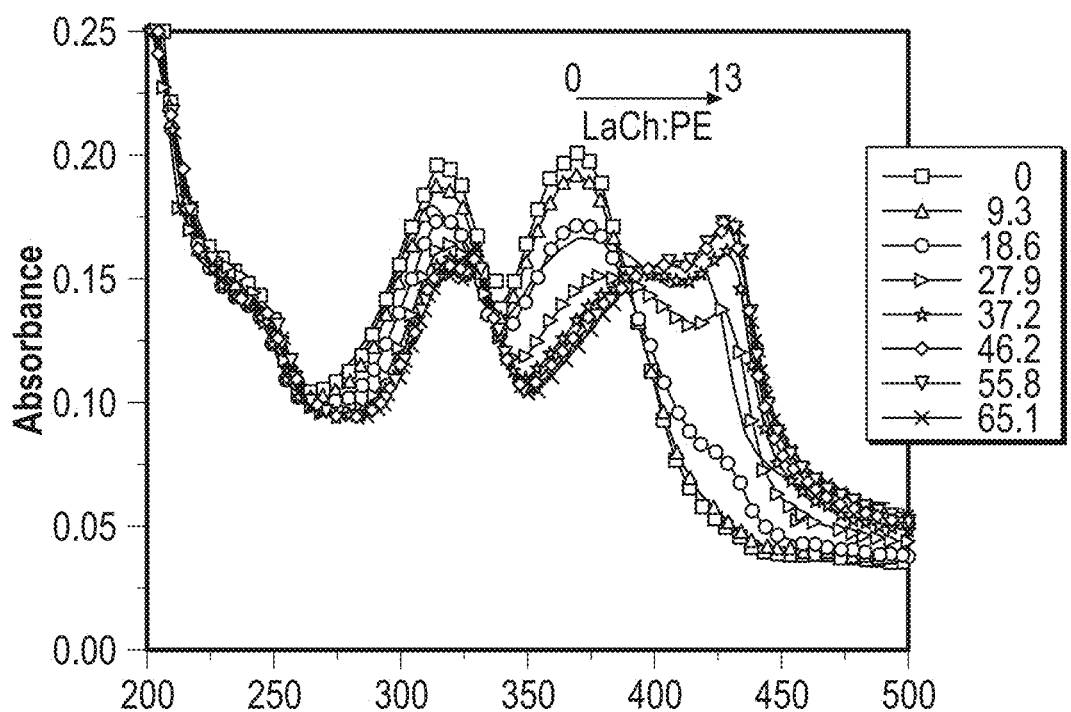
Figure 6D:
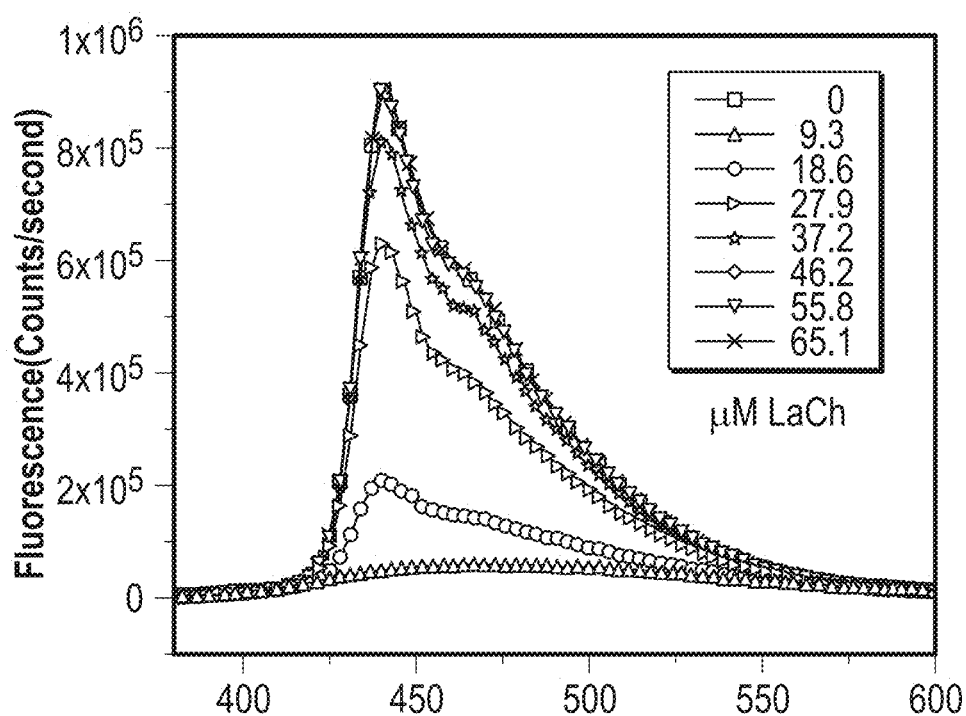

In order to accurately determine the viability of Bacillus spores and subsequently germinated vegetative cells with accuracy, Bacillus anthracis Sterne was evaluated by standard plating techniques. FIG. 4 illustrates B. anthracis Sterne vegetative cell viability following exposure to 10 µg/mL PE. NC denotes Negative Controls, where PE was not used. FIG. 5 illustrates B. anthracis Sterne spore and germinated vegetative cell viability as a function of starting concentration. PE exposed to varying spore concentrations for 90-min durations in the absence (A) and presence (B) of UVA light. Viability was inferred based on the spore's capacity to grow colonies on TSA before and after heat treatment, as described by Equations 1.1-1.3. FIG. 4 illustrates the profound killing of B. anthracis Sterne vegetative cells in the presence of light-activated PE, thereby corroborating the rapid death of germinating spores observed in FIG. 5. Once again, standard plating techniques are implemented, with colony growth being used as the determining factor in viability. Nearly 4 log reduction of B. anthracis Sterne vegetative cells is observed within 30 minutes; within 90 minutes, 5 log reduction is observed.

FIG. 5 illustrates that, within 90 minutes, 81% of spores were induced to germinate, even though the large majority (72% of all spores) are not killed and thus achieve successful germination into a viable, colony-forming vegetative cell. The percentage of spores able to germinate into viable vegetative cells actually decreased when the starting concentration of spores was lessened. Germination still occurs in the presence of UVA light, however, the resulting viability of germinated vegetative cells is severely compromised in this case, 90 minutes is a sufficient amount of time for light-activated PEs to induce germination in B. anthracis Steme spores and subsequently damage resulting vegetative cells to the point where they are incapable of colony growth. Exposing B. anthracis Steme spores at a relatively high PE-to-spore ratio (20 ng PE/spore) resulted in 99% killing within just 90 minutes.

FCS Express (De Novo Software) was used to quantify the fraction of all spores that germinate upon exposure to UVA light and/or oligomer, according to the florescence gates defined in FIGS. 1A-D and 2A-D. Even though exposure of B. atrophaeus spores to PE in the dark facilitates germination within 30 minutes, longer exposure times only marginally increased the percentage of spores that are induced to germinate. Increasing the exposure time beyond 90 minutes did not increase the percentage of spores that were induced to germinate—presumably due to PE photodegradation and loss of biocidal efficacy. In the presence of light-activated PE, just 15% of spores will successfully germinate. Furthermore, in the case of both B. atrophaeus and B. anthracis Steme spores, 20 µg/mL PE was insufficient to induce complete germination. In an effort to induce complete spore germination, the starting concentration of spores was diminished, with the PE concentration held constant at 20 g/mL.

Example 2

Example 2.1

Materials.

−1C was synthesized as previously described. +2C was synthesized as previously reported. Both PEs are light yellow solids, and readily dissolve in aqueous solution. Lauroyl choline chloride (Tokyo Chemical Industry Co.: Tokyo, Japan) was obtained as a solid powder and the container was stored under vacuum over dessicant, 1,2-dilauroyl-sn-glycero-3-phospho-(1'-rac-glycerol) (DLPG) (Avanti Polar Lipids, Alabaster, AL) was obtained as a lyophilized solid powder, and was dissolved in methanol and stored at −21° C. prior to use. Phospholipase $A_1$ (PLA1) from Thermomyces lanuginosus was obtained (Sigma-Aldrich, St. Louis, MO) as a liquid solution with a concentration of 10,000 Units/g. Phospholipase $A_2$ (PLA2) from Crotalus adamanteus venom was obtained as a lyophilized power with buffer salts at an activity of 320 U/mg (Worthington Biochemical, Lakewood, NJ). Acetylcholinesterase (AChE) from human erythrocytes was obtained as a pH 8.0 buffered solution with an activity of >500 U/mg (Sigma-Aldrich, St. Louis, MO). A "unit (U) of PLA2 activity," as referred to herein, is measured as the amount of enzyme needed to release one micromole of titratable fatty acid per minute at pH 8.9 and 25° C. from lecithin emulsion. A "unit of activity for PLA1," as referred to herein, is defined the same, except at a pH of 7.5 AChE activity units are defined similarly, with one micromole of acetylthiocholine iodide hydrolyzed per minute at pH 7.4 and 37° C. The AChE inhibitors Meptazinol HCl (3-(3-ethylhexahydro-1-methyl- 1H-azepin-3-yl)-phenol hydrochloride), Itopride HCl (N-[[4-[2-(Dimethylamino)ethoxy]phenyl]methyl]-3,4-dimethoxy benzamidehydrochloride), and TAE-1 (2,2',2'-[1,3,5-Triazine-2,4,6-triyltris(oxy-4,1-phenylenecarbonyloxy)]tris [N,N,N-trimethyl-ethanaminium tri-iodide) were obtained as solids (Sigma-Aldrich, St. Louis, MO). All solutions were prepared using filtered water with a resistivity of >18.2 MΩ*cm (EMD Millipore, Billerica, MA), with a pH of 7.5. The PEs tested were as shown below in Scheme 2.

Scheme 2.

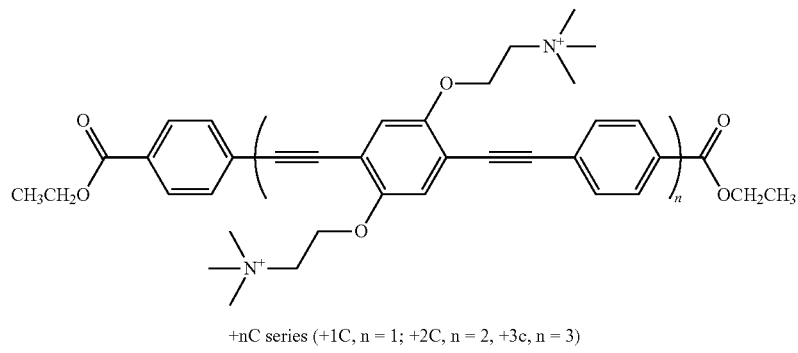

+nC series (+1C, n = 1; +2C, n = 2, +3c, n = 3)

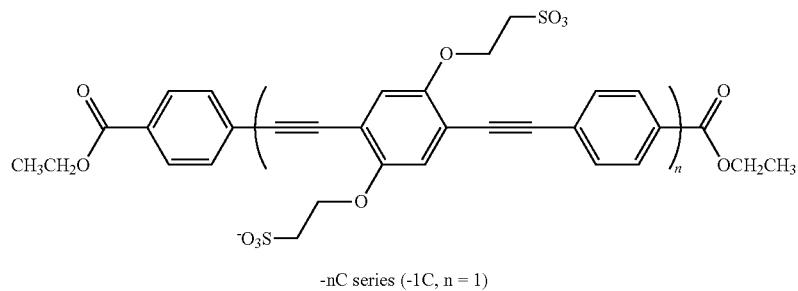

-nC series (-1C, n = 1)

Example 2.2

Sample Preparation.

A typical preparation of a −1C/lauroyl choline("LaCh") sensor is given. In a quartz cuvette with stirring, 20 μL of 500 mM −1C is added to 1970 μL of water. After 15-30 seconds of mixing, 10 μL of a 2 mg/mL solution of LaCh is added and allowed to mix for several minutes. A similar procedure is followed for the preparation of the +2C/DLPG sensor. Typical sensors used in experiments with +2C/DLPG had concentrations of 1.4 μM PE and DLPG concentrations of 16 μM. For the AChE sensor, 5 μM of −1C was used, and LaCh used for enzyme studies was 32 μM. Enzyme concentrations in the range of 50 to 0.5 mU were tested for PLA1 and PLA2, and 15 the range for AChE was 0.1 to 0.8 U.

Example 2.3

Absorbance and Fluorescence Spectroscopy.

UV-visible absorption spectra were obtained using a Lambda-35 UV-VIS Spectrometer fitted with a temperature-controlled cell with magnetic stirring (Perkin Elmer, Waltham, MA). Fluorescence spectra were obtained using a Photon Technology International fluorescence spectrometer equipped with a 75 W xenon arc lamp housed in an elliptical reflector (Photon Technology International, Birmingham, NJ). Fluorescence quantum yields were calculated using the comparative method relative to the previously reported value for +2C. Least-squares linear regressions for substrate concentration calibration and fluorescence quantum yield determinations were performed using the software Origin 9.

Example 2.4

Detection of Enzyme Activity.

The monitoring of the sensor was performed using the absorbance wavelength of 430 nm and the fluorescence wavelength of 440 nm (excitation of 370 nm for −1C, 375 nm for +2C). For both absorbance and fluorescence measurements of the sensor upon addition of enzyme, the sensor was prepared as described above in a quartz cuvette with constant stirring at room temperature (25° C.). The lid of the instrument was quickly lifted and enzyme injected, resulting in a ~0.5 second delay in the initial change registered. Enzyme kinetics were determined for PLA1 and PLA2 by converting the intensity of fluorescence or absorbance of the aggregate to substrate (DLPG) concentration, as given in equation (2.1), below.

$$[S]_t = [S]_0 \frac{\left(\frac{I_t}{I_b}\right) - 1}{\left(\frac{I_0}{I_b}\right) - 1} \quad (2.1)$$

Where: $[S]_t$ denotes substrate concentration at time t, $[S]_0$ is initial substrate concentration, $I_t$ is fluorescence intensity at time t. $I_0$ is initial fluorescence intensity, $I_b$ is background fluorescence intensity. Once the fluorescence at 440 nm or absorbance at 430 nm is converted to substrate concentration, standard Michaelis-Menten kinetics can be used. Non-linear fitting to a velocity vs substrate concentration plot was performed using the Hill equation using Origin 9, with the formula given in equation (2.2). The Michaelis-Menten equation serves as a special example of the Hill equation, and when n=1 the Hill equation is equivalent to the Michaelis-Menten equation commonly used for enzyme kinetics.

$$y = \frac{V_{max} \cdot x^n}{(k_m^n + x^n)} \quad (2.2)$$

Where n=cooperativity, $V_{max}$ is the max velocity in μMol/min*mg or μM/min, and $k_m$, which is the substrate concentration at half of $V_{max}$.

Example 2.5

Computational Methods.

PEs were parametrized to the generalized Amber forcefield (GAFF) framework using the antechamber program in AmberTools12. The Lipid14 parameters for Amber were used for the lipid 1,2-dioleoyl-sn-glycero-3-phosphospho-1'-rac-glycerol (DOPG). The Gaussian09 software package was used for all quantum-level calculations for residue parametrization, with geometry optimized at the B3LYP/6-31 g level and electrostatic potentials used for residue parametrization derived with Hartree-Fock and a 6-31 g basis set. GAFF atomtypes were used to assign Van der Waals parameters and bonding force constants. The assigned partial charges of the PE from the quantum-level calculations were fitted using the RESP charge fitting method. The initial system configurations were prepared using the program Packmol. Systems were solvated with water and neutralized with sodium and chloride ions, and the TIP3 water model was used. Simulations used full PME electrostatics and cubic periodic boundary conditions. The system was first minimized using the steepest descent method for 2500 steps, followed by a 250 step gradient minimization. Heating was carried out from 0 K to 100 K in 500 ps, and then from 100 K to 303.15 K in 500 ps using the NVT ensemble. Simulations were performed for 100-250 ns using the NPT ensemble with the Langevin barostat and thermostat with a time constant of 1/ps. The Amber12-GPU software package was used with SPFP precision. Radial distribution functions were measured over the simulation trajectory using the center of masses of the individual PEs using the cpptraj program in AmberTools. In order to sort out the most likely aggregated form of an PE dimer, cpptraj was used to cluster interacting pairs of PEs with the hierarchical agglomerative approach. The distance between frames was calculated using best-fit RMSD of the coordinates, and clustering analysis was carried out for PEs within 5 Å apart. UCSF Chimera version 1.10 was used for rendering snapshots of the trajectories and further clustering of the trajectories of the top clustered results from cpptraj, based on pairwise best-fit root-mean-square deviations between separate PEs, to distinguish common aggregate structures and provide a graphical representation of the clusters over time.

Example 2.6

Photophysical Effects of Complex Formation.

The fluorescence detection of enzyme activity on lipids or lauroyl choline was enabled by the strong photophysical changes which occurred upon aggregation of the PEs. The changes in absorbance and fluorescence spectra of +2C with DLPG and −1C with LaCh are shown in FIGS. 6A-D. FIGS. 6A-D illustrate absorbance and fluorescence Spectra of (A) absorbance and (B) fluorescence (Ex: 375 nm) of 1.4 μM +2C with DLPG; (C) absorbance and (D) fluorescence (Ex: 370 nm) of 5 μM −1C with LaCh; all spectra indicate the varying DLPG/LaCh concentration or ratio of substrate to PE.

As can be seen in FIGS. 6A-D, there are significant changes in the fluorescence and absorbance of aggregates of both anionic and cationic PEs. Interestingly, the changes resulting from aggregation are very similar for the +2C/DLPG and −1C/LaCh complexes. The absorbance spectrum is strongly red-shifted, with the major transition moving from 375 to 440 nm. The minor band at ~320 nm forms a bimodal shape with a second peak at 330 nm for −1C and 340 nm for +2C upon aggregation. In a solution of 0.5 OD or higher, the aggregates give a transparent yellow solution with a slight bluish haze. In addition to the strong changes to absorbance, the fluorescence is significantly altered upon aggregation with the substrate molecules. The most significant effect which can be utilized for sensing is a strong enhancement of fluorescence from a broadened, weak fluorescence to a very strong, structured emission centered at 450 nm for +2C and 442 nm for −1C.

The spectra in FIGS. 6A-D also show that the aggregates result in structured bands in both the absorbance and fluorescence spectra which are within 10 nm apart. This suggests that a very highly-efficient fluorescence is occurring, resulting in very little energy loss and a very active sensor. This contrasts significantly with the non-fluorescent, uncolored compound before complexation. The red-shifted absorbance and enhanced fluorescence is typical of a "J-aggregate", which leads to the prediction that the molecular structure that results in these enhanced electronic properties allows these rigid molecules to align. Comparing FIG. 6B with FIG. 6D, it is clear that the −1C/LaCh aggregate has a more dominant structured band at ~440 nm than the +2C/DLPG aggregate. This suggests that the structure of the −1C/LaCh aggregate is that of a well-defined J-dimer, where the +2C/DLPG aggregate likely is also a J-dimer but with more conformational freedom. This result of fluorescence enhancement suggests that the fluorescence quantum yields would be useful for describing the enhancement by the aggregation.

Figure 7A:
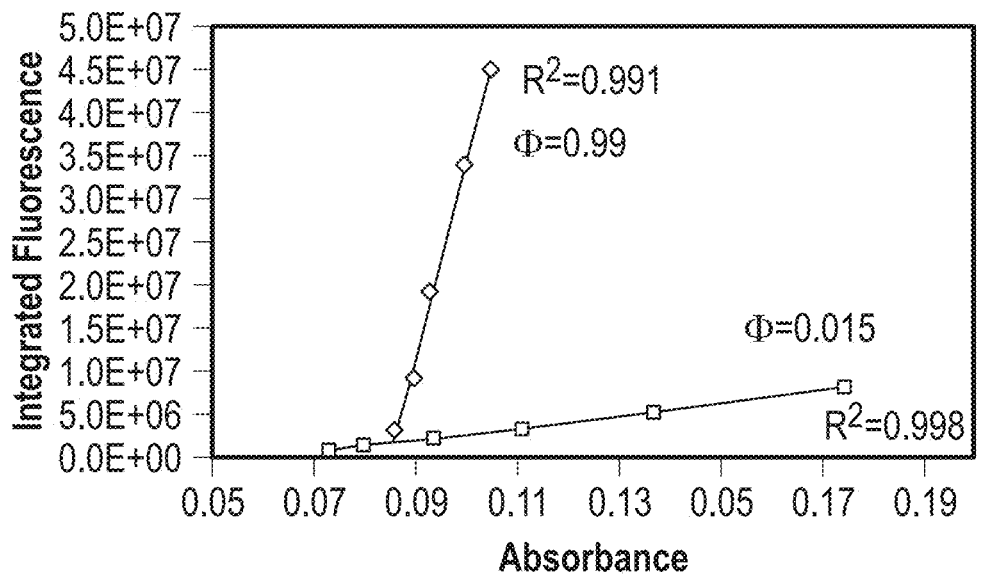
FIGS. 7A-B illustrate integrated fluorescence versus absorbance for various PEs, in accordance with various embodiments.
Figure 7B:
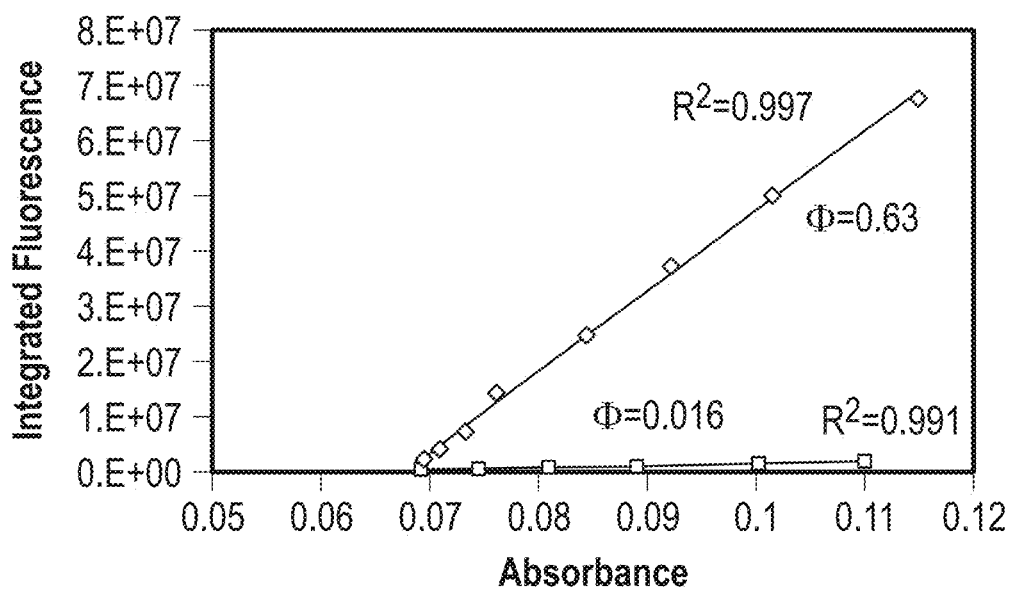

FIGS. 7A-B illustrates integrated fluorescence versus absorbance for (A) 5 uM −1C (squares) and 5 uM −1C with 32 uM LaCh (diamonds), and (B) 1.4 uM +2C (squares) and 1.4 uM +2C with 16 uM DLPG (diamonds). This data was used to calculate the fluorescence quantum yields by the comparative method, and the new values for the quantum yields that were corrected from a previous study are given next to the line. Excitation was 370 nm for A and 375 nm for B, with fluorescence excitation wavelengths from 390 to 600 nm. Fluorescence quantum yields were determined using the comparative method as discussed above, and the least-squares linear regressions of the results are given in FIGS. 7A-B. FIGS. 7A-B demonstrate that the quantum yields of the PEs are greatly enhanced by the aggregation induced by the substrates DLPG or LaCh. Calculation of the fluorescence yield by the comparative method using the reported value of 0.039 for +2C leads to vastly overstated quantum yields of fluorescence of both AChE and PLA sensors in excess of unity. While it is understandable that the previous value of +2C was difficult to pinpoint due to the very low fluorescence of +2C in water, the results of fluorescence quantum yield measurements performed in this study suggest that the quantum yield for +2C is no larger than 0.016 rather than 0.039. This value would assume a quantum yield for the –1C/LaCh complex of near unity, and while the aggregation-induced fluorescence is extremely efficient, the quantum yield is more likely between 90 and 100 percent. The aggregation of +2C with DLPG results in a fluorescence enhancement 39 times at 440 nm, which correlates to an increase of fluorescence quantum yield from 0.016 to 0.63. The aggregation of –1C with LaCh results in a considerable enhancement of fluorescence quantum yield, which is 66 times higher for the –1C/LaCh complex than –1C alone. This correlates with an enhancement from 0.015 to 0.991, following the correction of the quantum yield of fluorescence of +2C from 0.039 to 0.016.

In addition to the strong changes in absorbance and fluorescence of the PEs, the formation of a complex can be confirmed through circular dichroism (CD) spectroscopy. Circular dichroism spectra of 1.4 uM +2C with and without 16 uM DLPG added were acquired, and illustrated that +2C strongly absorbs circularly polarized light with a strong negative band at 445 nm. Since DLPG is chiral, it is reasonable that an aggregate formed on a DLPG template would be optically active. The photophysical changes observed upon complexation allow for a variety of strategies for indication of the presence of a substrate. While the magnitude of the fluorescence enhancement is much greater than that of the absorbance change, the ability to use colorimetric means for determinations allows for cheaper and more flexible detection strategies than are accessible by fluorescence measurements. The aggregation with surfactants and substrates is useful, and the introduction of substrates which are degradable by enzymes allows use of PEs as fluorescence-quenching enzyme sensors. The use of PEs for sensing of enzyme activity is powerful, as their strong fluorescence quenching and dequenching allows for highly sensitive detection.

The aggregate formed between –1C and lauroyl choline gives rise to evidence of a structured aggregate with "J-type" character. In order to further investigate the structure of the aggregate that is formed, a set of large-scale molecular simulations was carried out.

Example 2.7

Molecular Aggregates for Monitoring Enzyme Activity—Phospholipases A1, A2 and C.

The use of lipids such as DLPG to induce aggregation allows for the creation of a sensor which can be affected by phospholipases. Phospholipases are a class of phosphodiesterases that can cleave the acyl chains or phosphate groups of the lipids, depending on the class. Phospholipases A1 and A2 ("PLA1," "PLA2") cleave the SN-1 and SN-2 acyl chains respectively, while Phospholipase C ("PLC") cleaves before the phosphate, forming diacylglycerol and a phosphate-containing headgroup. Observation of the effects of these three different enzymes on the photophysical properties of the +2C/DLPG complex allow for assessment of the ability of the enzymatic products to maintain aggregation of the PEs. The changes in absorbance and fluorescence of the +2C/DLPG complexes were monitored after addition of either PLA1, PLA2, or PLC to the solution as described in the methods section. In addition to varying enzyme concentration, a study varying the concentration of DLPG was also carried out to determine changes in the response rate of the sensor when excess lipid is present.

The effects of enzymatic activity on the +2C/DLPG sensor are shown for PLA1 and PLA2 in FIGS. 8A-D. FIGS. 8A-D illustrate fluorescence versus time for PE with various concentrations of DLPG and PLA1 or PLA2; (A) fluorescence of the +2C/DLPG aggregates over the course of PLA1 activity with 1.4 µM PE and a DLPG concentration of 7.27 µM, with enzyme added ranging from 0.5 to 5 mU of PLA1; (B) 1.4 µM of +2C with DLPG at a series of concentrations from 10.6 to 35.6 µM (7.5-25.4 DLPG: PE ratio), followed by addition of 4 mU of PLA1; (C) fluorescence of the +2C/DLPG aggregates over the course of PLA2 activity with 1.4 µM PE and a DLPG concentration of 7.27 µM, with enzyme added ranging from 0.5 to 5 mU of PLA2; (D) 1.4 µM of +2C with DLPG at a series of concentrations from 2.37 to 17.8 JAM (1.7-12.7 DLPG:PE ratio), followed by addition of 40 mU of PLA1. t=–1 s is the time of enzyme addition.

Figure 8A:
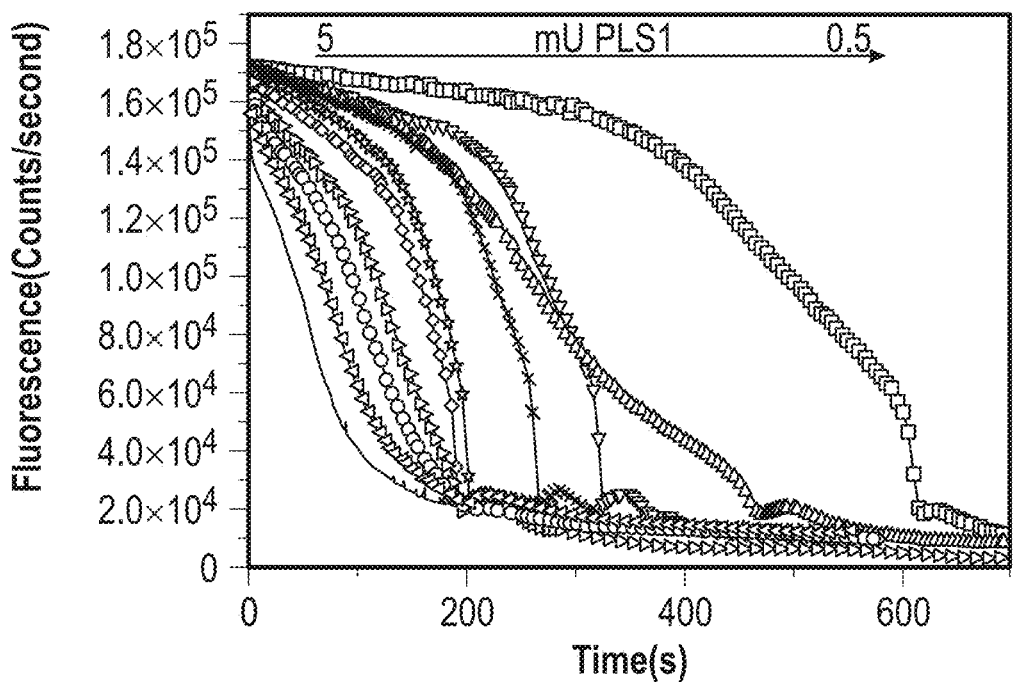
FIGS. 8A-D illustrate fluorescence versus time for PE with various concentrations of DLPG and PLA1 or PLA2, in accordance with various embodiments.
Figure 8B:
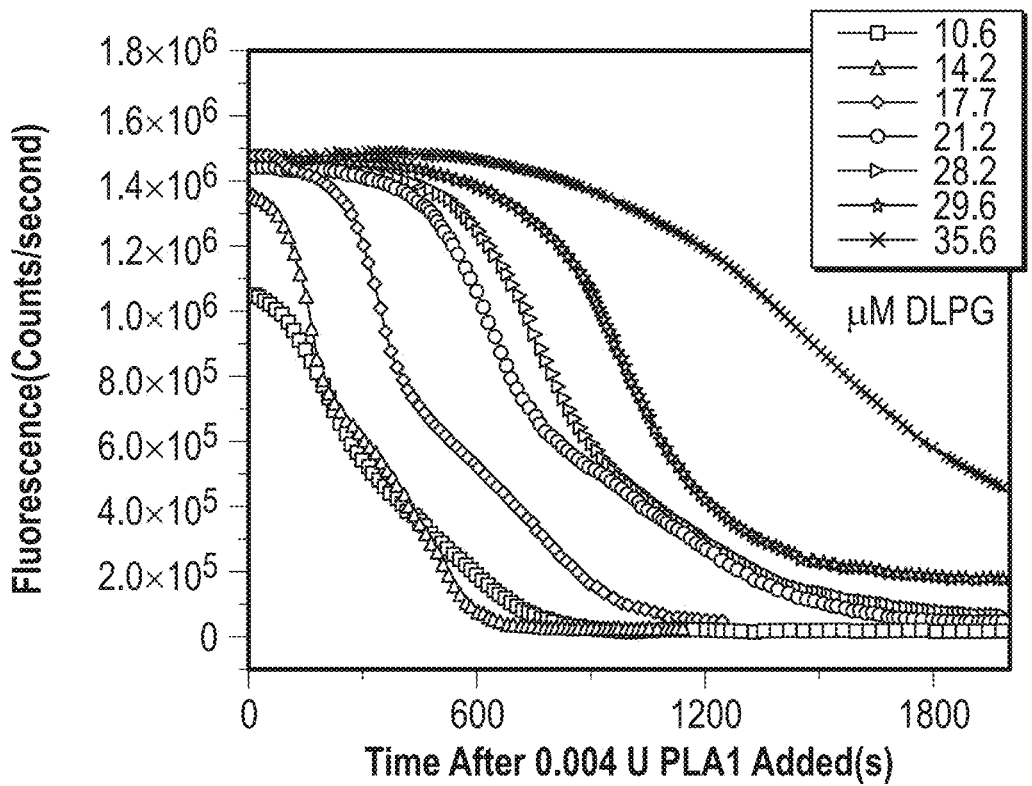
Figure 8C:
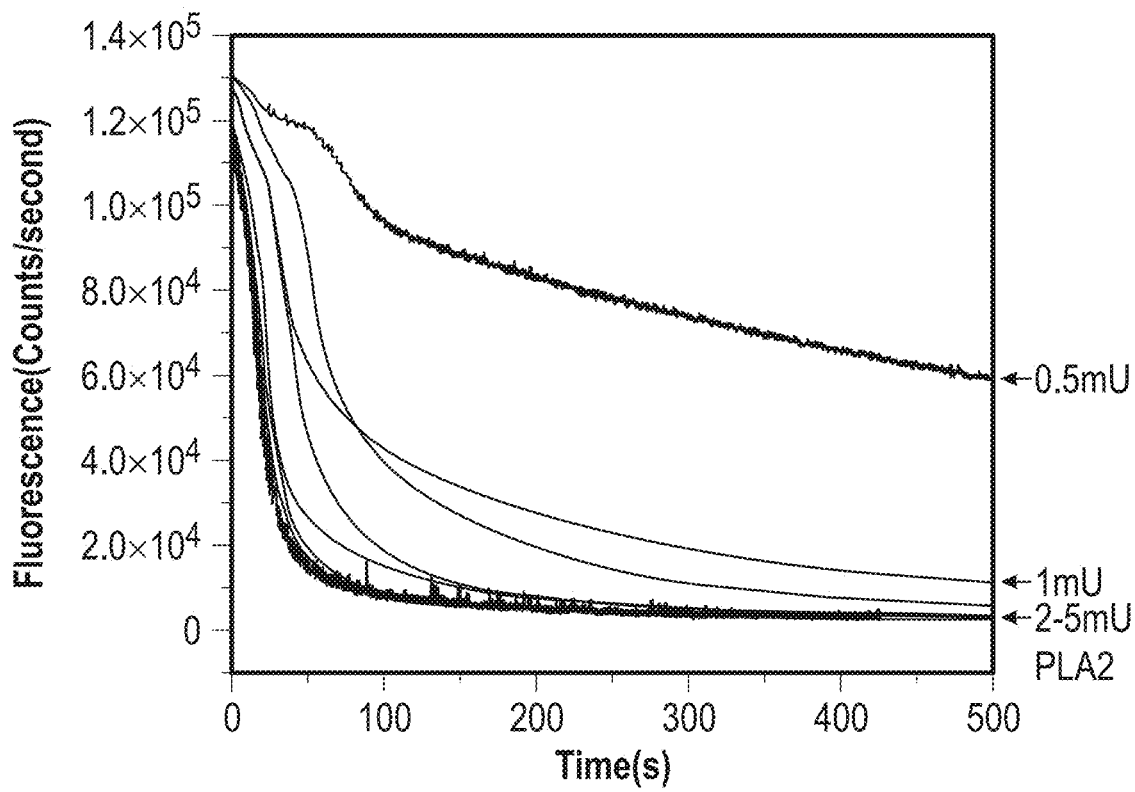
Figure 8D:
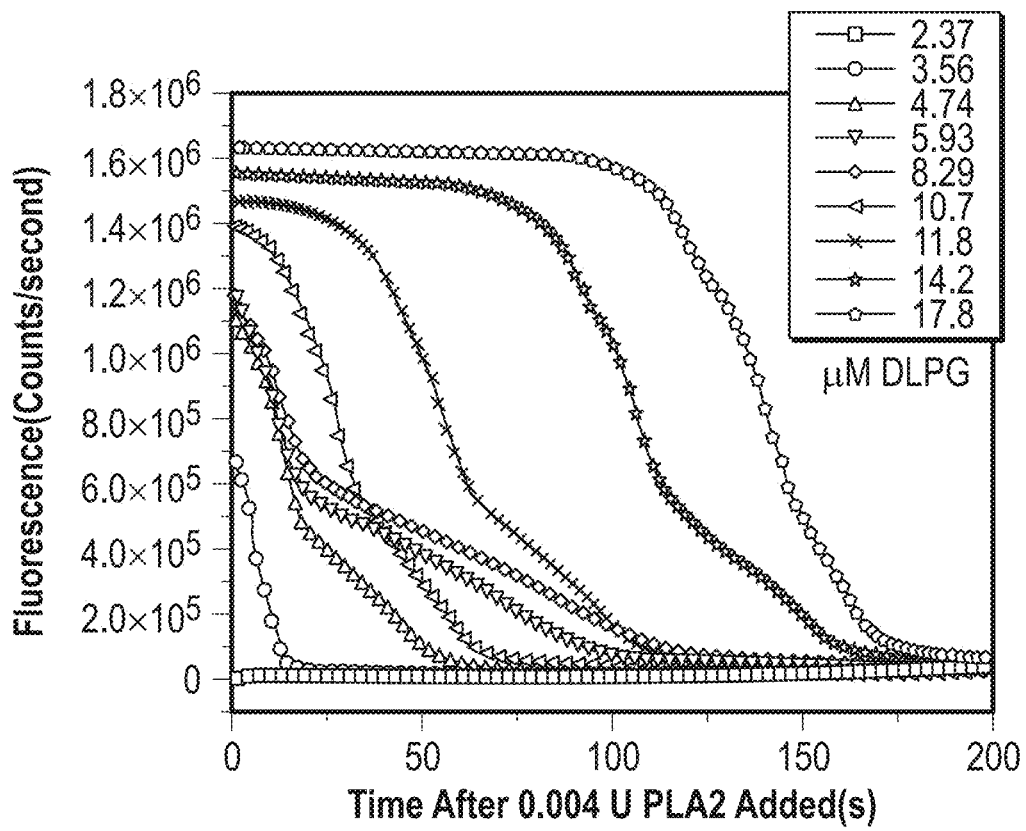

As can be seen in FIGS. 8A-D, decomposition of the DLPG lipids by PLA1 and PLA2 results in swift quenching of the fluorescence and increased transmittance at 440 nm. While monitoring either absorbance or fluorescence can allow one to determine enzyme activity, enhanced fluorescence quenching and dequenching allows for a more sensitive sensor to be achieved through fluorescence monitoring. In FIGS. 8B and D, the effects of varying lipid concentration on the rate of enzymatic degradation was tested. In samples which had a lipid concentration higher than the saturation point of ~1:16 PE:lipid ratio, a lag period was observed after the addition of the enzyme. This lag period is tied to the amount of excess, "free" lipid in solution, as it increases with increasing lipid and constant PE concentration. It is likely that there is a population of lipids which are circulating in solution without being involved in an aggregate with a PE, and these lipids can act as a sort of "reserve," which can become involved in an aggregate, if needed. The enzymes will also be acting on these free lipids, halting the degradation of the PE-Lipid sensor. Once this population of excess lipids is enzymatically cleaved by PLA1 or PLA2, the lipids making up the sensor are then disassembled and the fluorescence quenching occurs. FIGS. 8A and C demonstrate the high sensitivity of the phospholipase sensor, as enzymatic cleavage is observed with both PLA1 and PLA2 at enzyme concentrations below 5 mU/mL. Since the weight of PLA1 from *T. lanuginosus* is not known, and the enzyme is obtained with concentration listed in terms of units of activity, it is difficult to compare PLA1 limits of detection on a molar basis. The concentration of PLA2 that corresponds with 0.5 mU/mL at 320 U/mg protein is 500 fM, marking at least a 10-fold increase in sensitivity over the previously reported PLC sensor.

Interestingly, the activity of PLC does not result in a strong change to the sensors aggregated state. The changes resulting from addition of PLC were studied, and it was clear that not only is there no rapid fluorescence quenching or absorbance change observed with PLC as was seen with PLA1 and PLA2, but there is even a slight fluorescence enhancement. This behavior suggests that one or both of the products of PLC degradation, diacyl glycerol and 1-lauroyl-sn-glycerol 3-phosphate, also result in aggregation of the PE which allows retention of the enhanced fluorescence.

Example 2.8

Monitoring Enzyme Kinetics-PLA Sensing.

The difference between the aggregation of PLA and AChE sensors is further shown by examining the kinetics of complex formation at different concentrations. The ability to quantify substrate concentration is afforded by these sensors when substrate concentration can be effectively calculated from the fluorescence or absorbance of the aggregate. It is visible when comparing FIGS. 6A and B with FIGS. 6C and D that the increase of the absorbance (430 nm) or fluorescence peaks (440 nm) representing the aggregate changes with a different concentration dependence for the two sensors. This is better shown via calibration curves to fit fluorescence or absorbance to substrate (DLPG or LaCh) concentration.

Figure 9A:
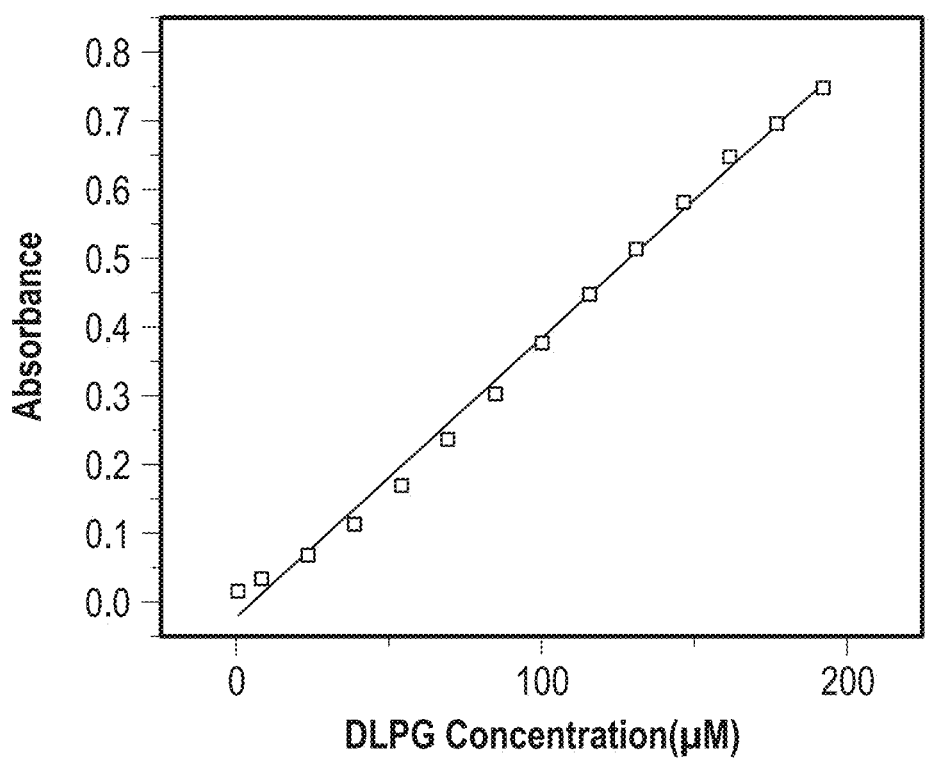
FIGS. 9A-C illustrate absorbance or fluorescence versus substrate concentration for various sensors, in accordance with various embodiments.
Figure 9B:
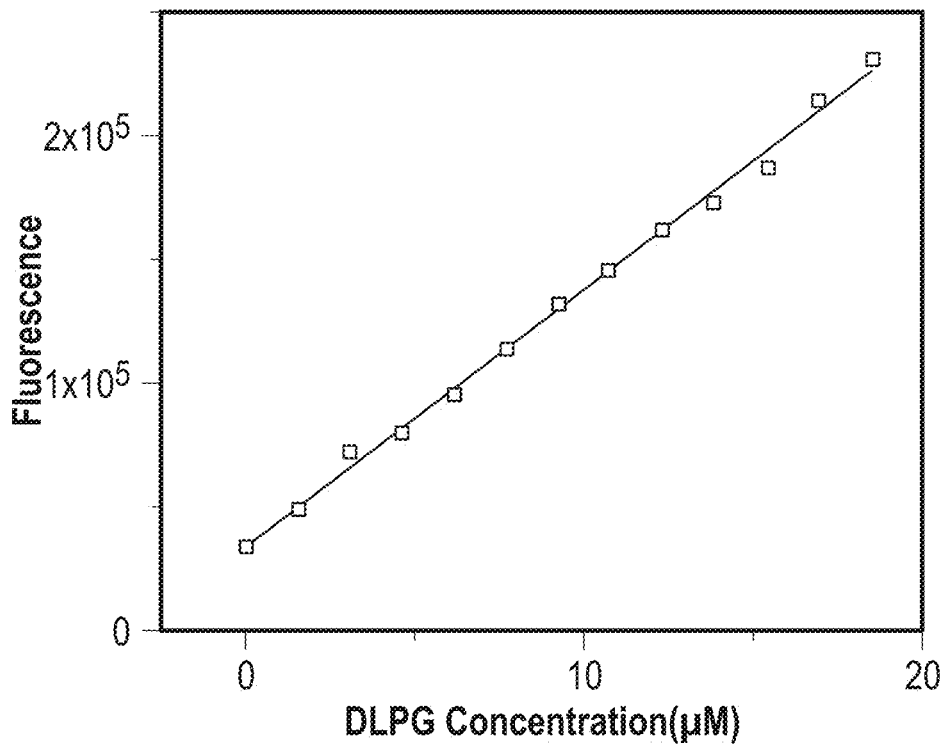
Figure 9C:
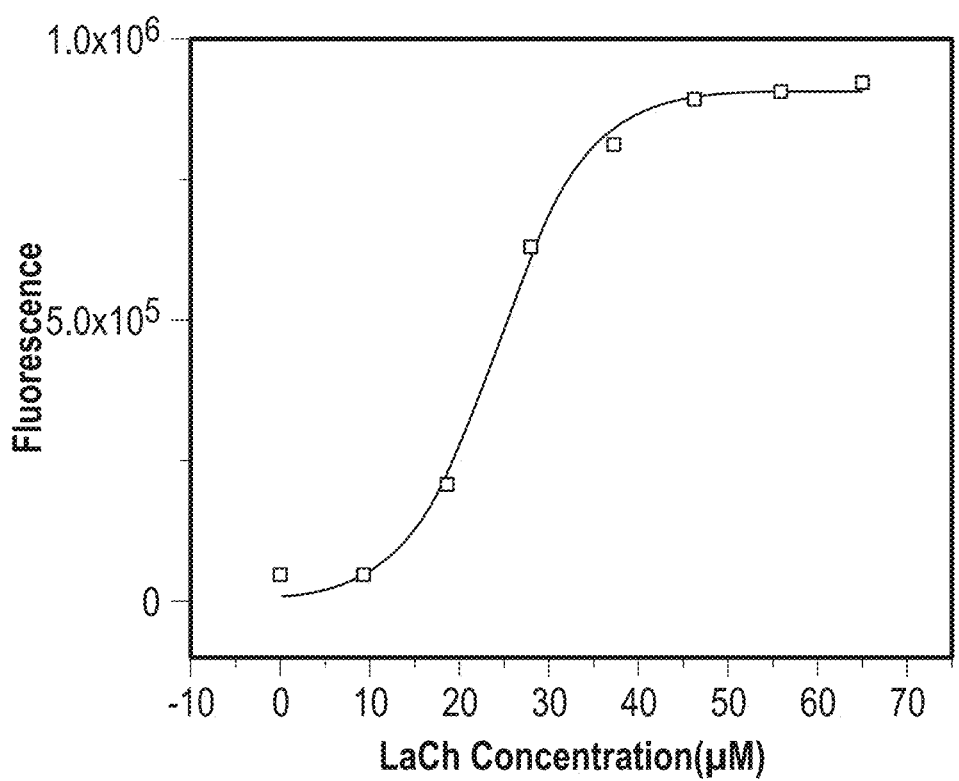
Figure 10A:
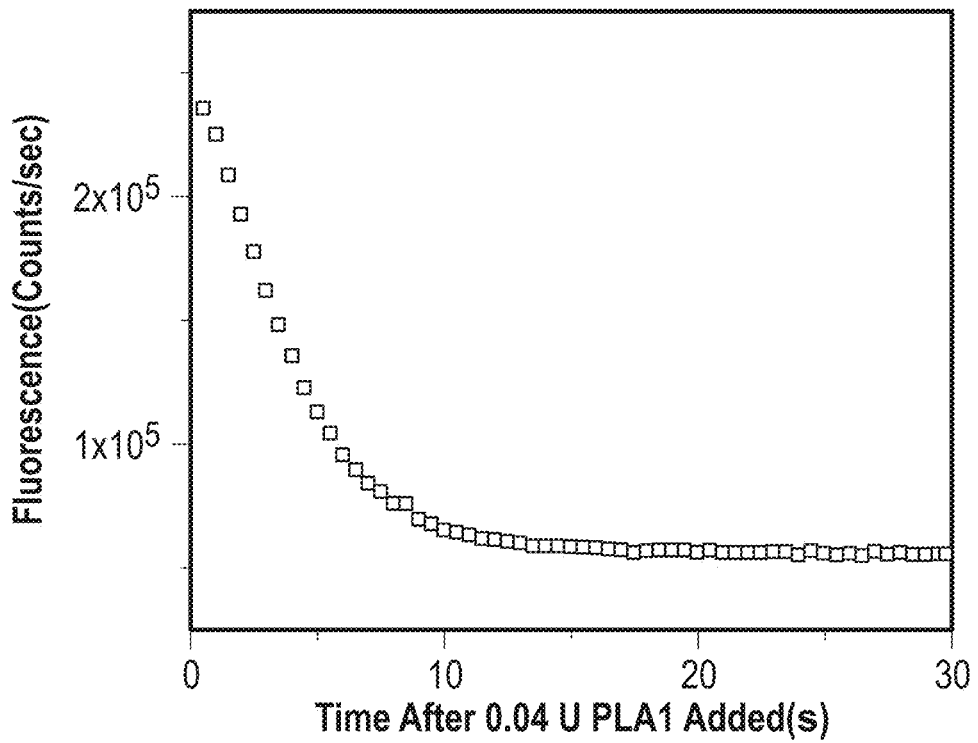
FIGS. 10A-B illustrate loss of fluorescence over time and velocity versus substrate concentration, in accordance with various embodiments.
Figure 10B:
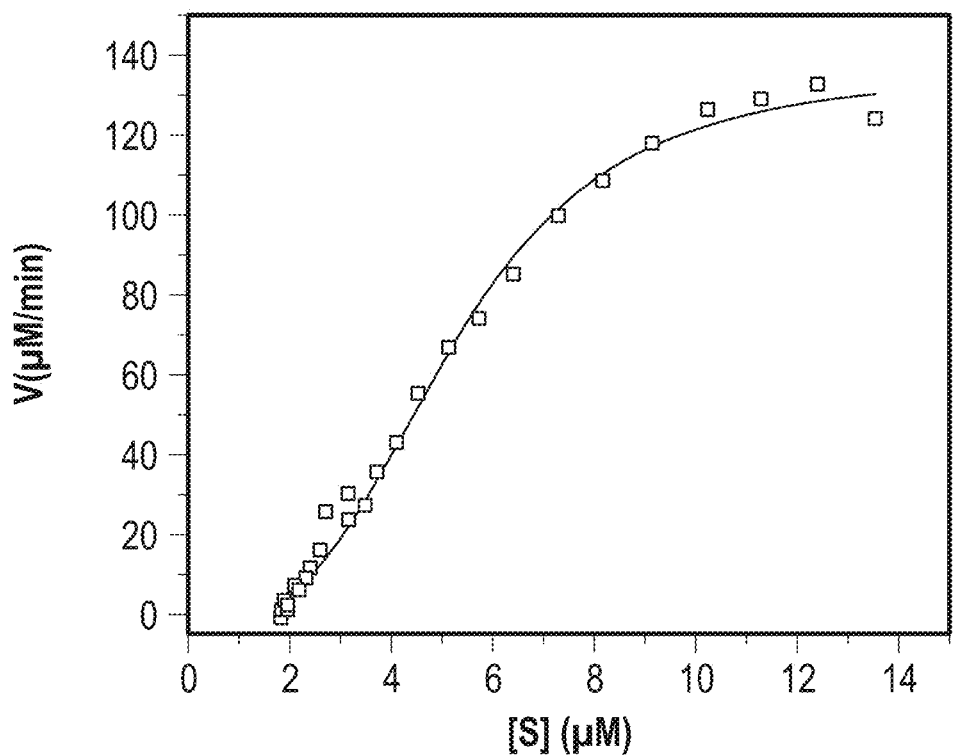

The linear correlation between fluorescence at 440 nm and substrate concentration is given for both PLA and AChE sensors in FIGS. 9A-C, showing linear regression of (A) absorbance of 10 µM PE-2+; (B) fluorescence of 1.4 M PE-2+ (Ex: 375 nm, Em: 440 nm), with increasing DLPG concentration. (C) fluorescence of PE-1– with increasing LaCh concentration (Ex:370 nm. Em: 440 nm). The curves shown in FIGS. 9A-C illustrate a difference in the concentration dependence for formation of the PLA and AChE sensor. +2C shows a linear increase in fluorescence with increasing DLPG concentration, but –1C shows a sharp change with a typical sinusoidal shape between 20 and 30 µM of LaCh. The linear response of the PLA sensor is ideal for quantification of kinetic parameters, as the concentration of lipid can be calculated from the linear regression. The sinusoidal response of the AChE sensor does provide a linear fluorescence signal to LaCh concentration. This suggests that despite the similarities between the aggregates, the formation of the aggregates follows different kinetics. The kinetics of the degradation of the +2C/DLPG sensor by PLA1 and PLA2 were followed by conversion of the fluorescence or absorbance to concentration, as discussed above. An example of the result is given in FIGS. 10A-B, where the loss of fluorescence over time is converted into velocity vs substrate concentration for calculating enzyme kinetics. FIGS. 10A-B illustrate (A) fluorescence of PLA sensor (Ex. 375 nm; Em. 440 nm) composed of 1.4 µM +2C and 16 µM DLPG following addition of 0.04 U of PLA1; (B) velocity versus substrate plot after conversion of data in (A) to velocity and substrate following the equations given in the methods section.

The activity of PLA1 and PLA2 were determined by nonlinear fitting of fluorescence or absorbance of the aggregated PEs in the sensor by the Hill fit. PLA1 from *T. lanuginosus* was found to have a $V_{max}$ of 141.7+/–6.8 µM/min. and a $k_m$ of 5.41+/–0.28. PLA2 from *C. adamanteus* venom had a $V_{max}$ of 37.4+/–1.84 µM/min and a $k_m$ of 6.39+/–0.29. The specific activity of PLA2 was calculated using 0.05 U/mL of 320 U/mg PLA2 to be 1295 µMol·min$^{-1}$ mg$^{-1}$, nearly 1000-fold greater than the 14 µMol·min$^{-1}$ mg$^{-1}$ obtained from a previous study of PLA2 from *C. atrox* venom. For these sensors the $k_m$ is tied to the PE concentration, and in cases with PLA1 where the PE concentration is 10 µM instead of 1.4 µM, the kM is 97 µM rather than 5.4. A strong correlation is observed between increased substrate concentration and enzyme activity due to a cooperative effect. This is expressed as n in equation 2, which was fit to the results to determine kinetic parameters. In a case of no cooperativity, n is equal to one, but for both PLA1 and PLA2 it is fit to be 3. The cooperative effect is visible in FIG. 10B, where there is a decreased slope of vi[S] in regions of low substrate. This is reasonable, as PLA1 and PLA2 have been previously shown to be membrane-associated proteins which have activity that is highly dependent on the local lipid environment.

Example 2.9

Figure 11A:
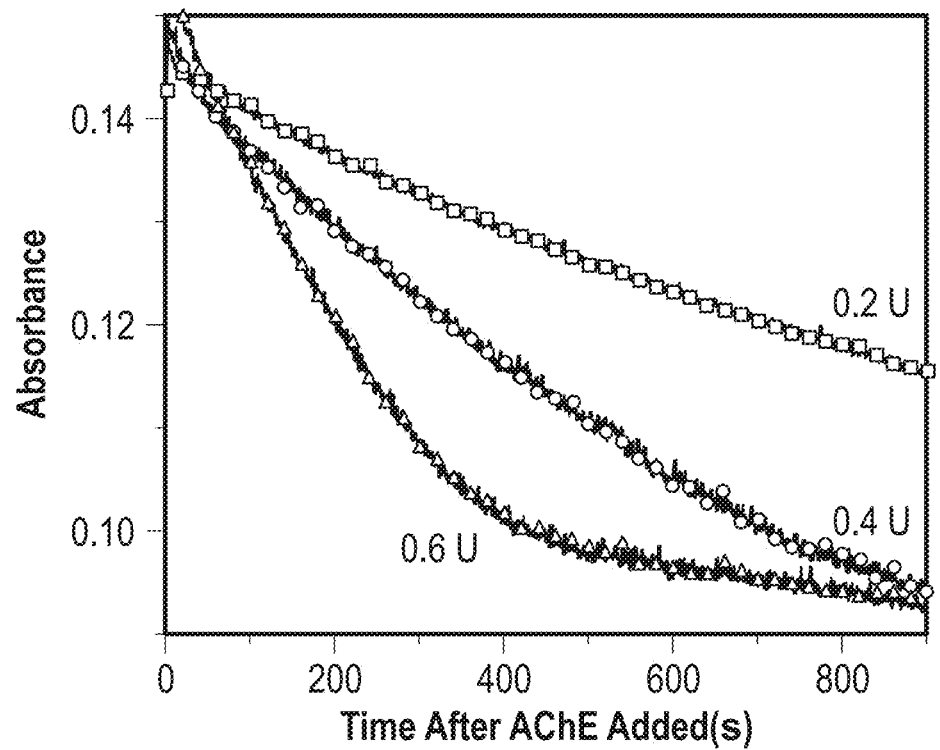
FIGS. 11A-B illustrate absorbance and fluorescence versus time after addition of various concentrations of substrate, in accordance with various embodiments.
Figure 11B:
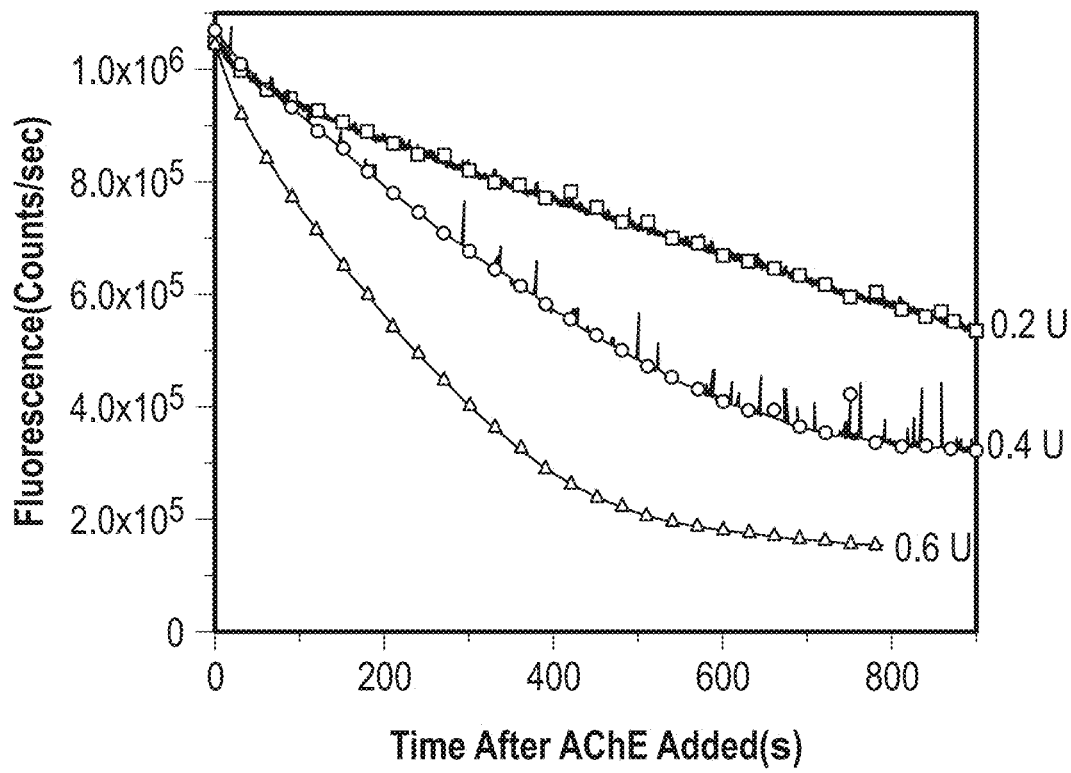

Monitoring Enzyme Activity—Acetylcholinesterase. Acetylcholinesterase ("AChE") is an important enzyme which is responsible for terminating synaptic transmission by hydrolyzing the neurotransmitter acetylcholine. In addition to the absorbance and fluorescence spectra in FIGS. 6A-D, the quantum yields were calculated to be near unity upon formation of aggregates between –1C and lauroyl choline. This highly-sensitive fluorescence response in particular makes this an ideal sensor for detection of AChE. The detection of AChE by fluorescence and absorbance using the –1C/LaCh sensor is shown in FIGS. 11A-B, showing (A) absorbance at 430 nm and (B) fluorescence (Ex:370 nm. Em:440 nm) of –lC and LaCh at 0.2, 0.4, and 0.6 U of AChE.

As shown in FIGS. 11A-B, there is clear detection of AChE activity through the loss of the characteristic absorbance at 430 nm and fluorescence at 440 nm over time. There was a clear difference in the rate of enzymatic degradation of the complex which correlated with amount of enzyme added. There is a slightly different profile to the change in absorbance versus fluorescence over time. In the absorbance spectrum, there is a quick drop from 0.16 OD, and for the 0.4 and 0.2 Unit additions of AChE this rate progressively decreases, leading to a curve with a more gradual slope. The slope of the 430 nm absorbance loss after adding 0.6 Units of enzyme is fairly constant until 0.1 OD approaches, indicating that the aggregate has been dissociated. Monitoring the enzyme activity through fluorescence gives similar results as absorbance, except that the magnitude of change is greater. In FIG. 11B, the fluorescence drops an order of magnitude from 1E6 to 1E5 photons/second, compared with a change from 0.16 to 0.1 OD for the change in absorbance at the same concentration. The fluorescence spectra in FIG. 11B are similar to the absorbance spectra in FIG. 11A, and the changes occur on the same timeframe. These results show that the –1C/LaCh sensor is effective at detection of AChE activity both through colorimetric means (absorbance) and through fluorescence assays.

Figure 12A:
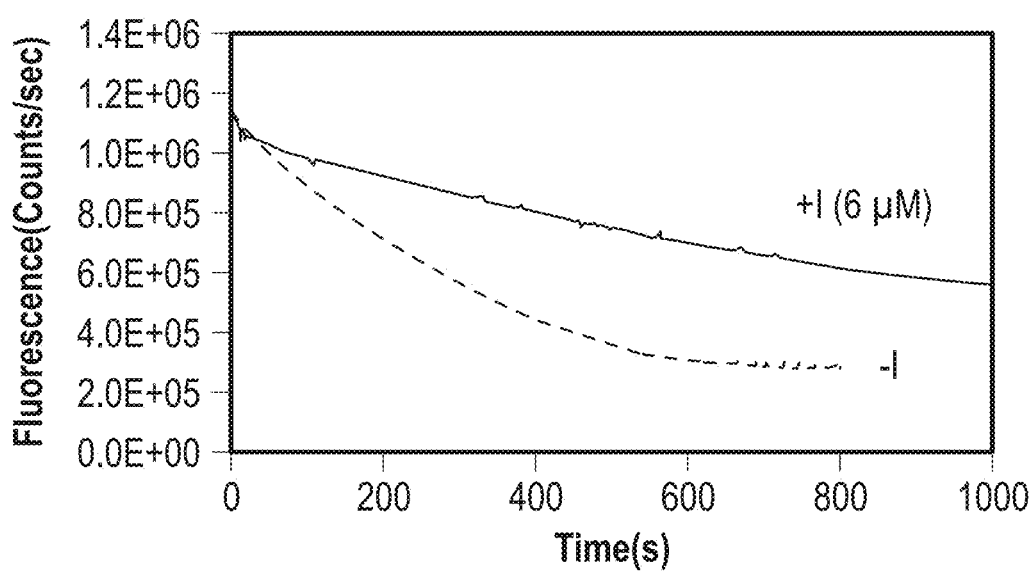
FIGS. 12A-C illustrate fluorescence versus time for a PE/LaCh sensor over time with and without inhibitor, in accordance with various embodiments.
Figure 12B:
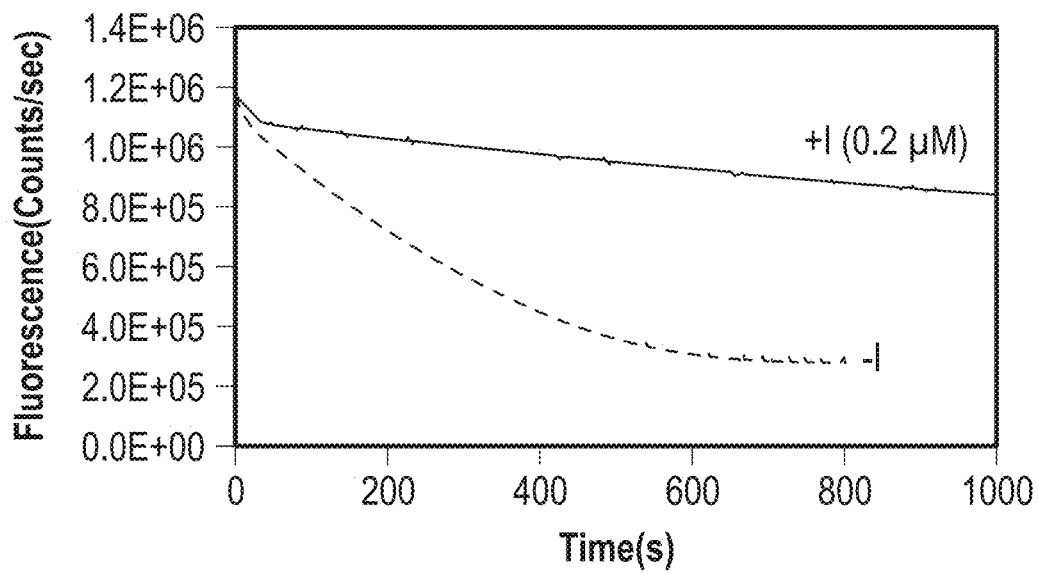
Figure 12C:
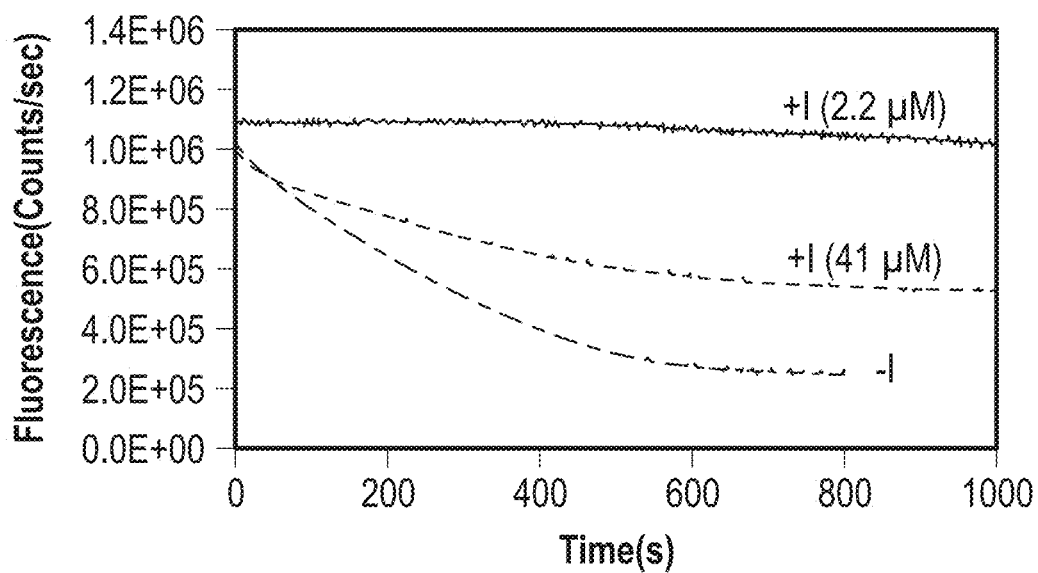

As stated above, AChE is responsible for termination of nerve signals. This causes many inhibitors of AChE to be highly neurotoxic, and many pesticides and nerve agents are strong AChE inhibitors. In order to determine whether the AChE sensor based on the –1C/LaCh complex could be used for detection of AChE inhibitors such as nerve agents and pesticides, the sensor was added to a solution of one of three different AChE inhibitors prior to addition of AChE. While the compounds; TAE-1, Itopride, and Meptazinol, all have been shown to be AChE inhibitors, these compounds are less volatile and toxic than the nerve agents and pesticides that are of primary interest for AChE inhibition detection. The inhibition of AChE by these three inhibitors using the −1C/LaCh sensor was carried out as described above, and the fluorescence of the sensor over time with and without inhibitor is given in FIGS. 12A-C, illustrating a −1C/LaCh complex (5 μM PE, 32 μM LaCh) showing fluorescence change after addition of 0.6 U of AChE in the presence of AChE inhibitor (A) itopride HCl; (B) meptazinol HCl; and (C) TAE-1; traces with inhibitor are denoted with +1 and the inhibitor concentration, and −I indicates no inhibitor.

Figure 13A:
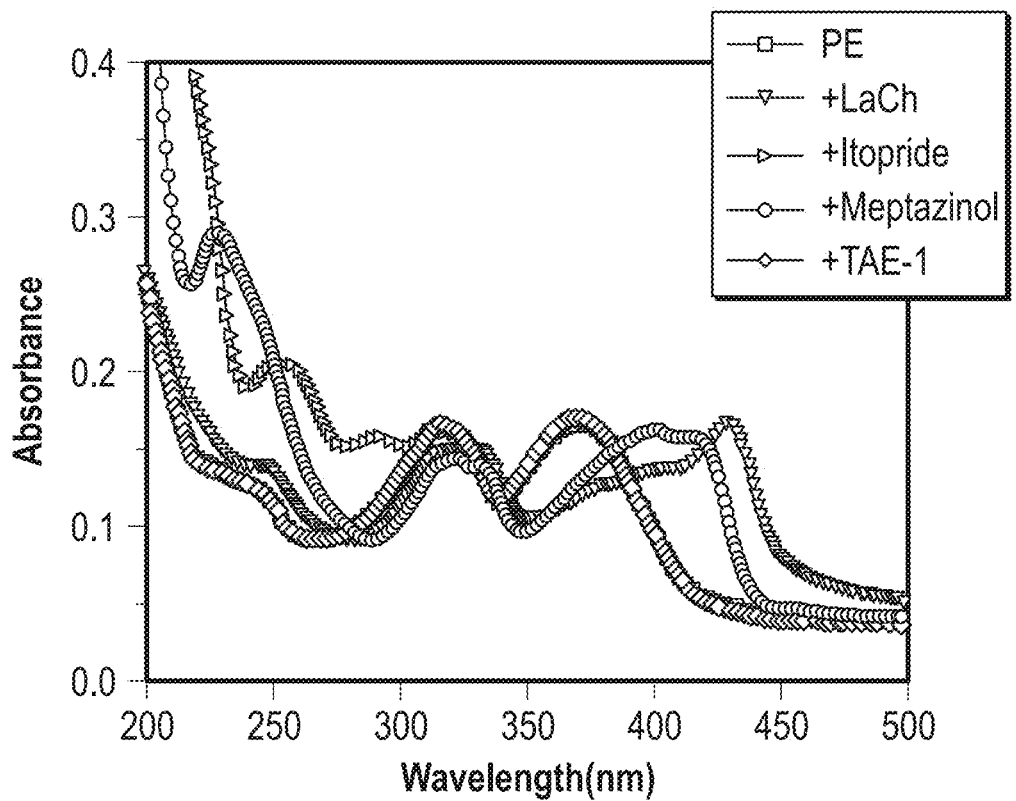
FIGS. 13A-B illustrate absorbance and fluorescence versus wavelength for a PE alone, with LaCh, and with various inhibitors, in accordance with various embodiments.
Figure 13B:
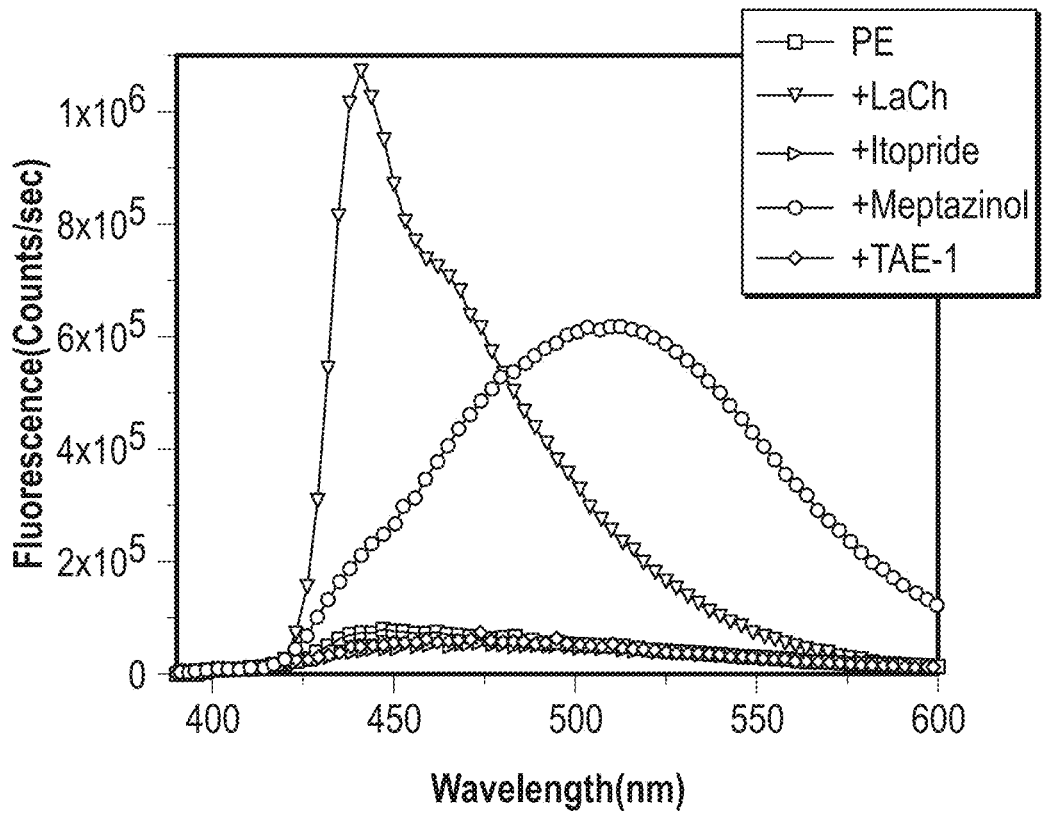

As shown in FIGS. 12A-C, it is clear that inhibition of AChE by several different inhibitors is apparent in the attenuated loss of fluorescence compared with the reference solution, with no inhibitor. In order to confirm that this result is not due to aggregation between the PE and the inhibitors, the absorbance and fluorescence spectra of the PE and inhibitor without LaCh were obtained. FIGS. 13A-B illustrate (A) absorbance and (B) fluorescence (Ex: 370 nm) of 5 uM −1C with 5 ug/mL of either LaCh or one of the three AChE Inhibitors used in this study. As shown in FIGS. 13A-B, there is no significant aggregation induced by Itopride or Meptazinol. TAE-1 however, does result in a red-shifted absorbance and a strongly red-shifted and broadened green fluorescence. Further, there is little overlap between the fluorescence of the TAE-1/IPE complex and that of the PE/LaCh complex.

Example 2.10

Prediction of Aggregate Structure by Molecular Simulations.

Figure 14A:
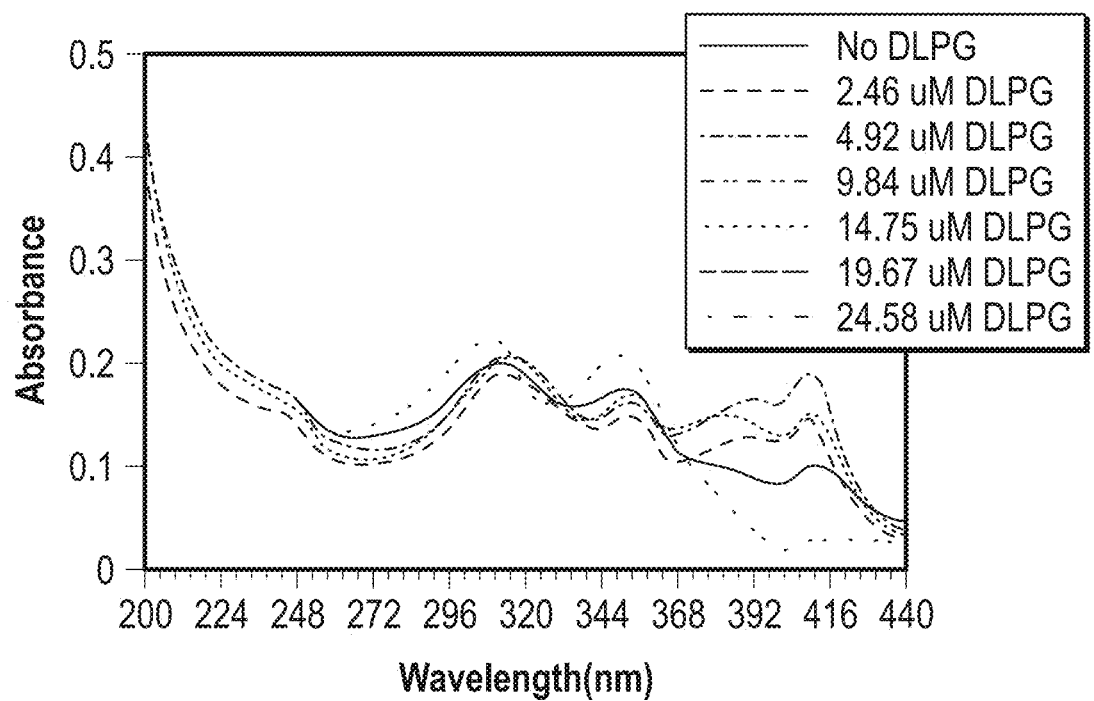
FIGS. 14A-B illustrate absorbance and fluorescence of a PE with various concentrations of DLPG, in accordance with various embodiments.
Figure 14B:
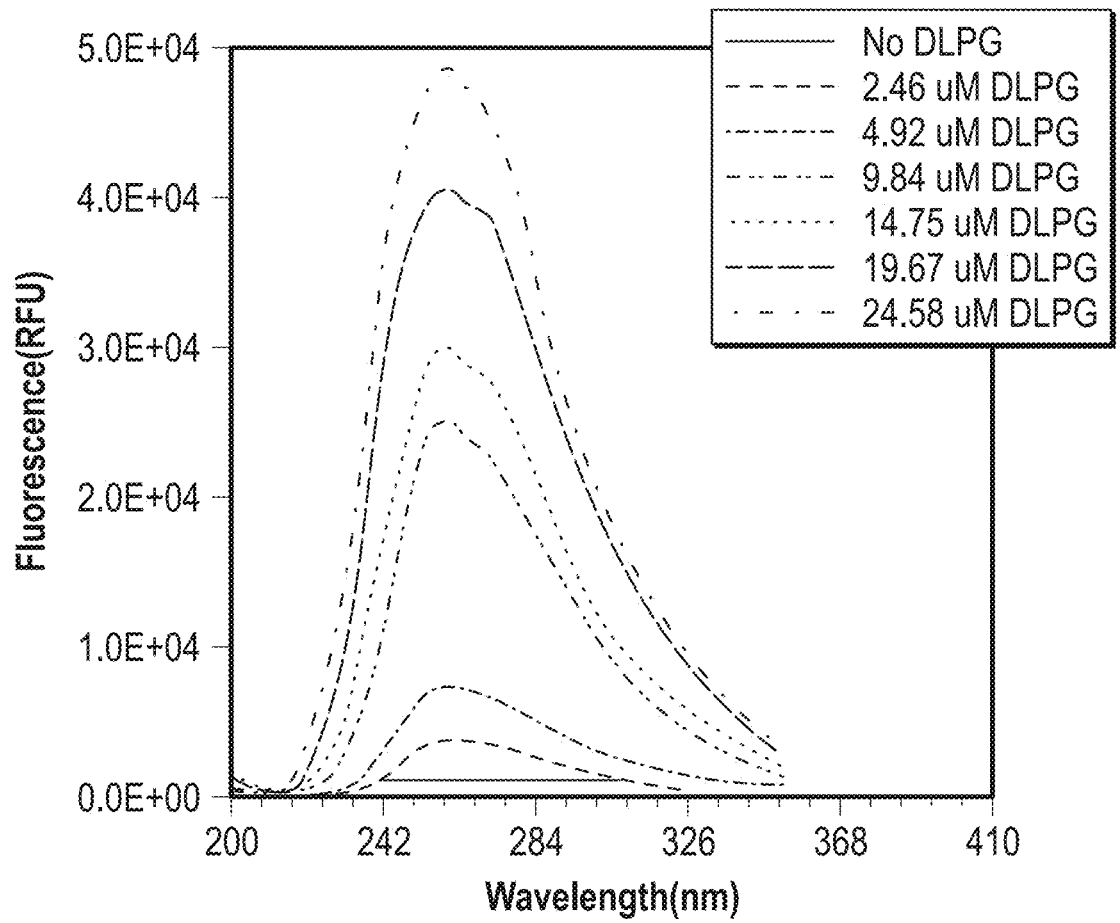

To study the structure of the aggregate formed between cationic PEs and anionic phospholipids, simulations with +1C and DOPG near the experimentally-observed ratio of lipid:PE were performed using all-atom molecular dynamics. While +2C was used primarily in this study, +1C was shown to form an aggregate resulting in similar photophysical changes (FIGS. 14A-B, illustrating (A) absorbance and (B) fluorescence of 4.3 uM+1C with various concentrations of DLPG). In order to reduce computational time, +1C was used in the simulations rather than +2C. It should be noted that the simulations where only 2 PEs were used did not result in the formation of an aggregate within the 150 ns simulation time, as the two PEs in the simulation never came close enough to interact with one another in this time. This was observed at both simulation box sizes used (8 nm or 10 nm side length), and with a PE lipid ratio of 1:3 and 1:10. Timelines of the three simulations in which a Example 3

Example 3.1: Overview

Four PEs (Scheme 3) were synthesized for evaluation against native hen egg white lysozyme (HEWL) amyloids. The PEs used, designated for brevity PEn+ and PE1−, all have ethyl ester terminal moieties on the PE backbone and side-pendant charged groups; the cationic compounds have n=1, 2 and 3 repeat units and the anionic compound has one repeat unit. The compounds are amphiphilic and water soluble due to the hydrophobic backbone and charged side groups. These ester-terminated compounds were selected for the effective sensing modality of fluorescence yield increase from reduced quenching by water when bound to a hydrophobic surface.

Scheme 3.

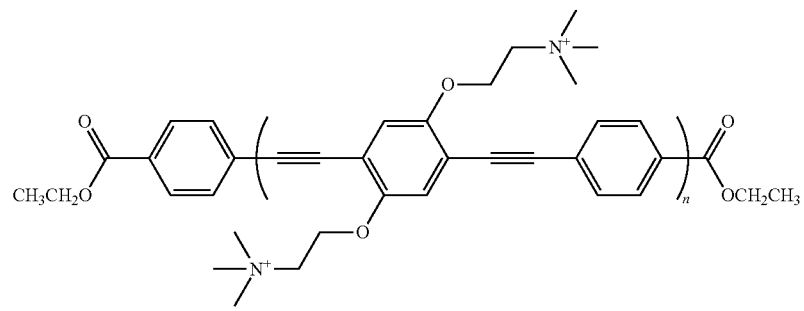

PEn+ series (PE1+, n = 1; PE1+, n = 2; PE1+, n = 3)

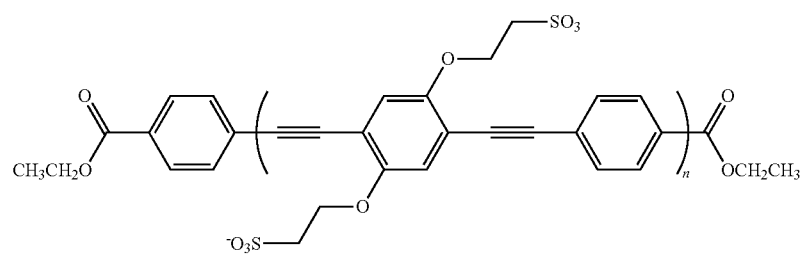

PEn- series (PE-1, n = 1)

Example 3.2

Formation and Characterization of HEWL Amyloids.

Figure 15:
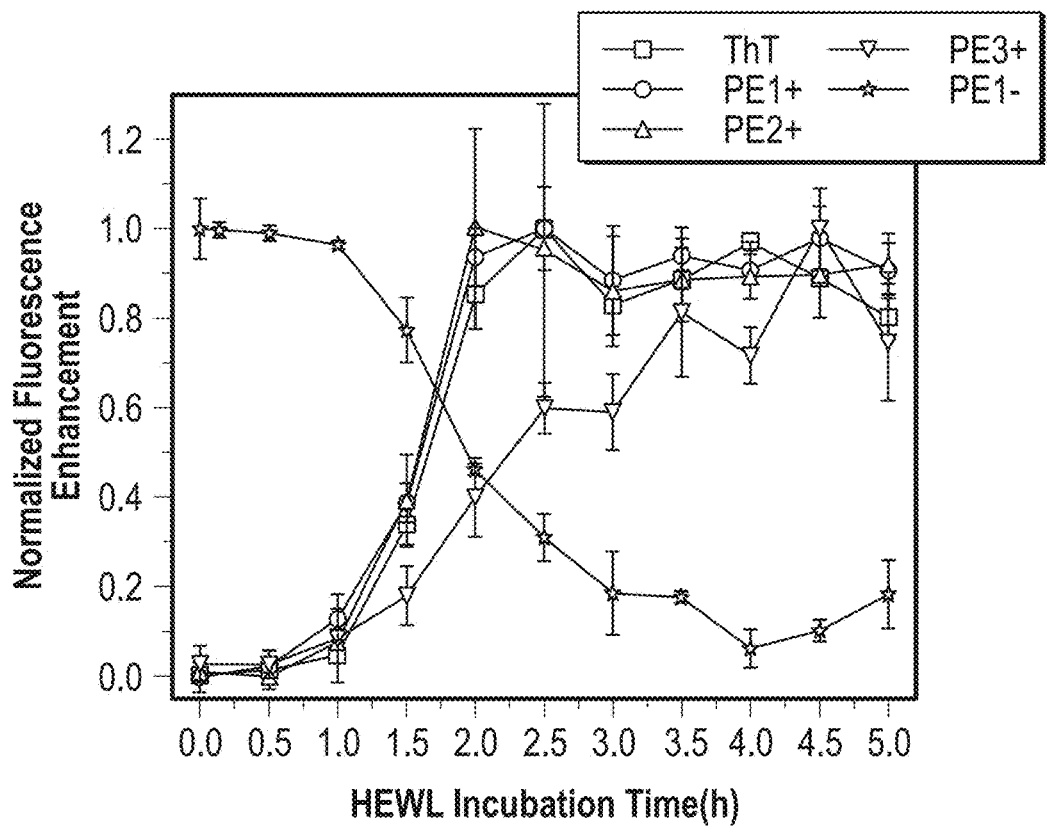
FIG. 15 illustrates fluorescence enhancement versus hen egg white lysozyme (HEWL) incubation time, in accordance with various embodiments.
Figure 16:
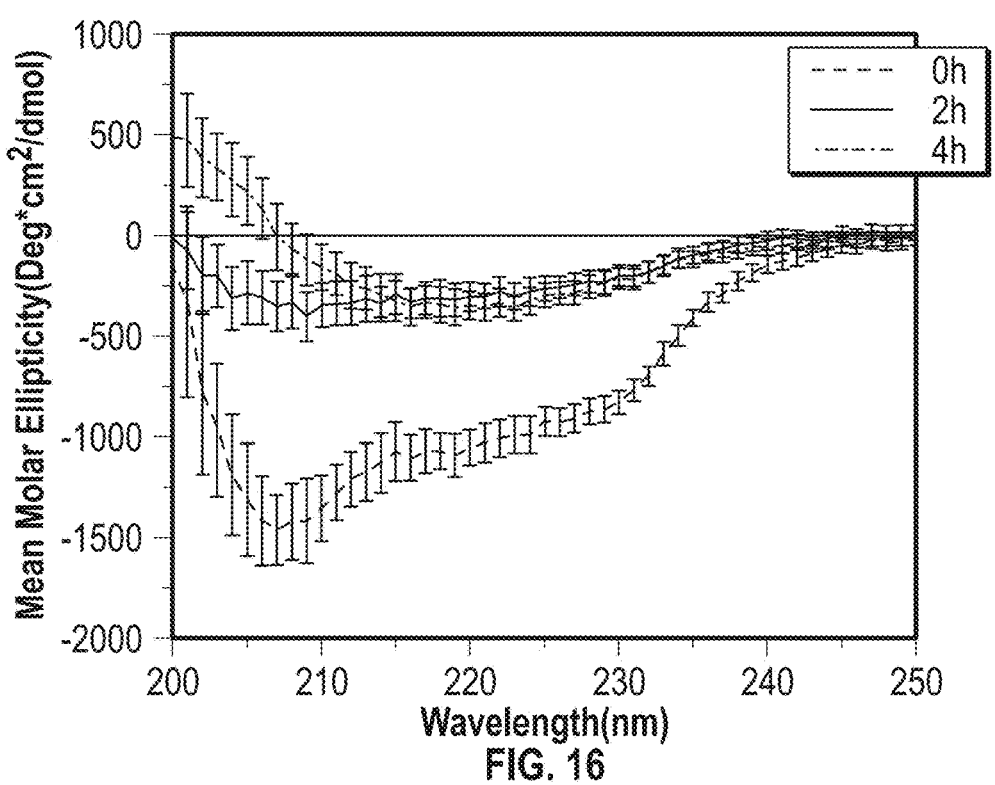
FIG. 16 illustrates mean molar ellipticity versus wavelength for HEWL incubated for various times, in accordance with various embodiments.
Figure 17:
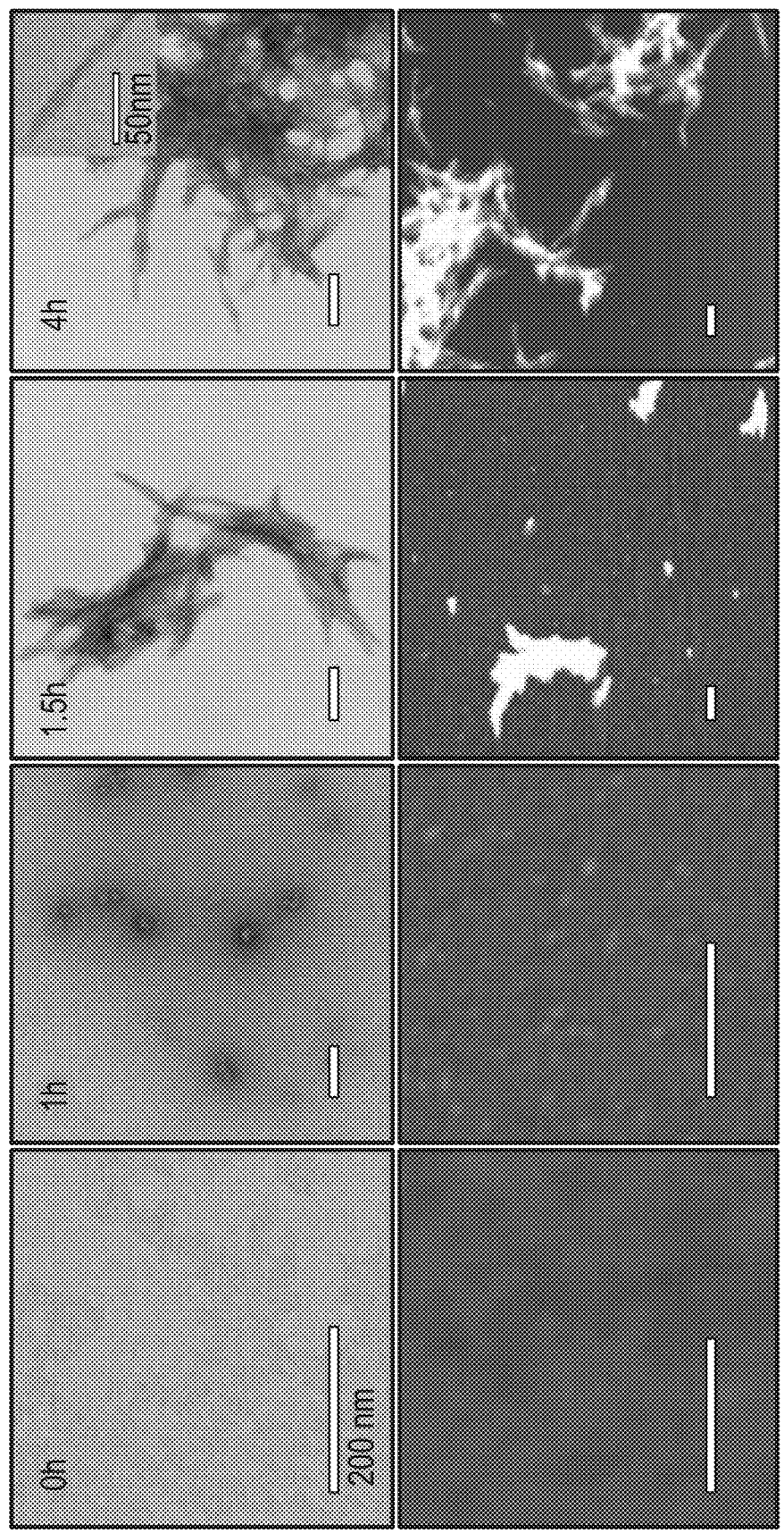
FIG. 17 illustrates transmission electron spectroscopy and atomic force microscopy images of HEWL incubated for various times, in accordance with various embodiments.
Figure 18A:
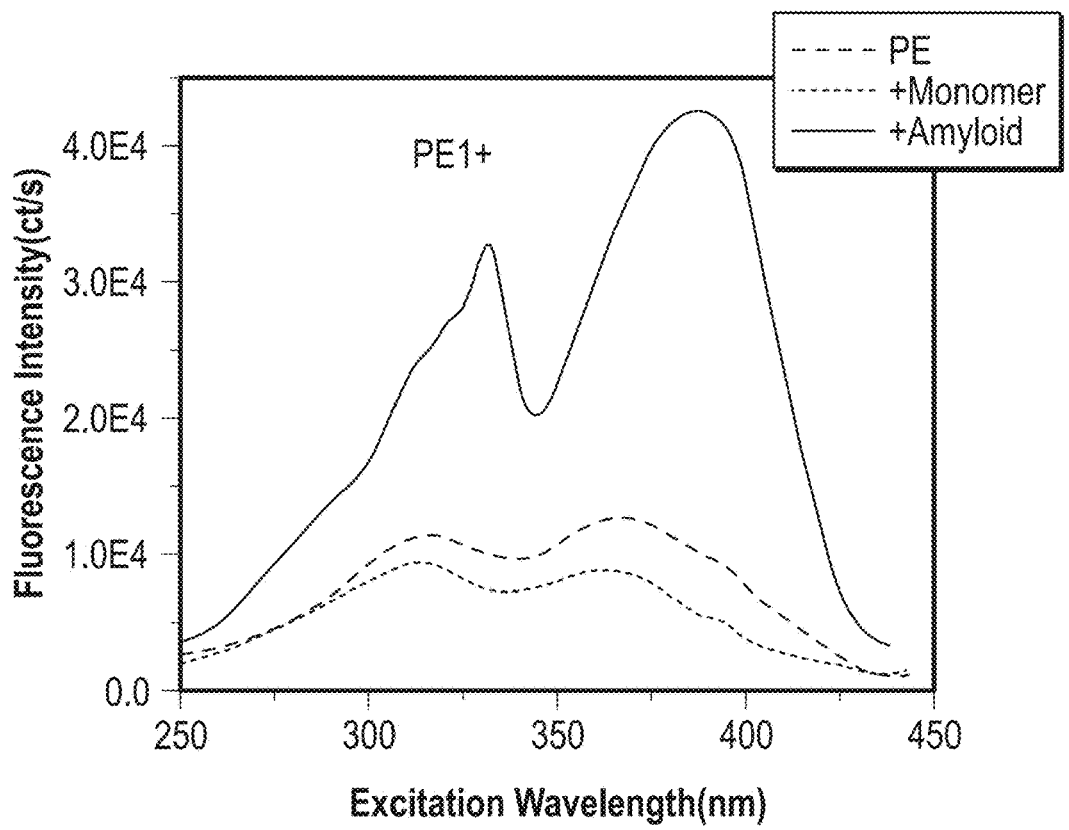
FIGS. 18A-H illustrate fluorescence versus wavelength for various PEs, in accordance with various embodiments.
Figure 18B:
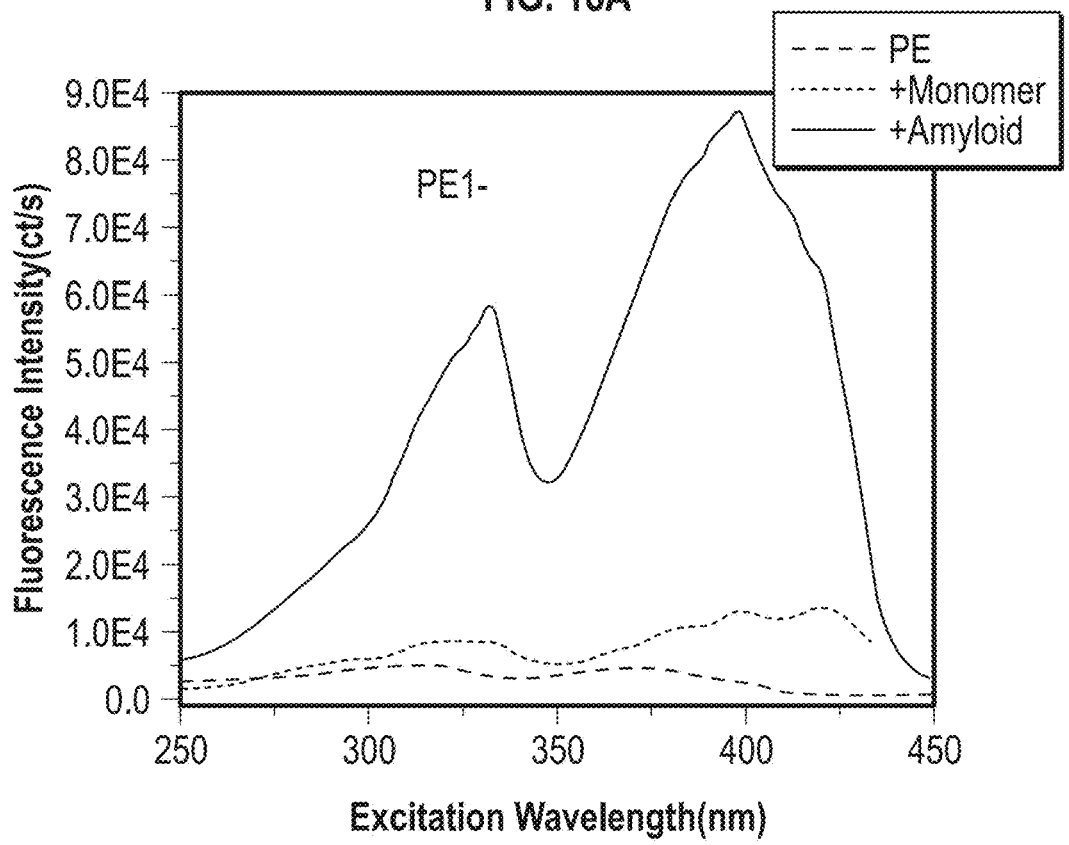
Figure 18C:
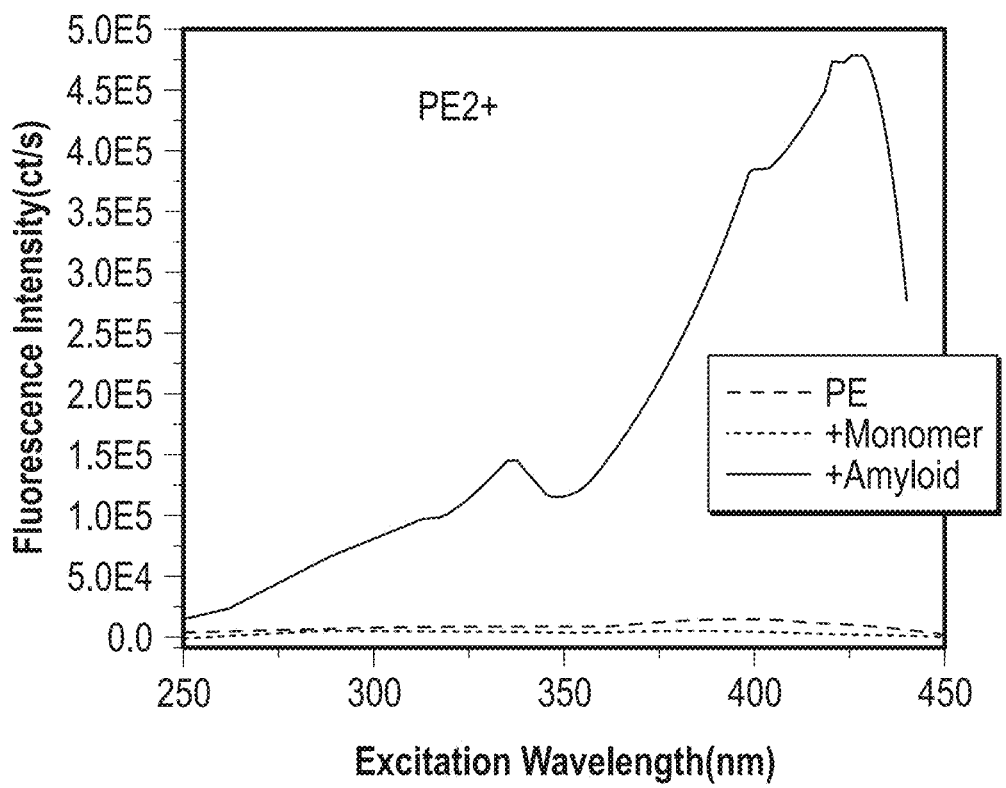
Figure 18D:
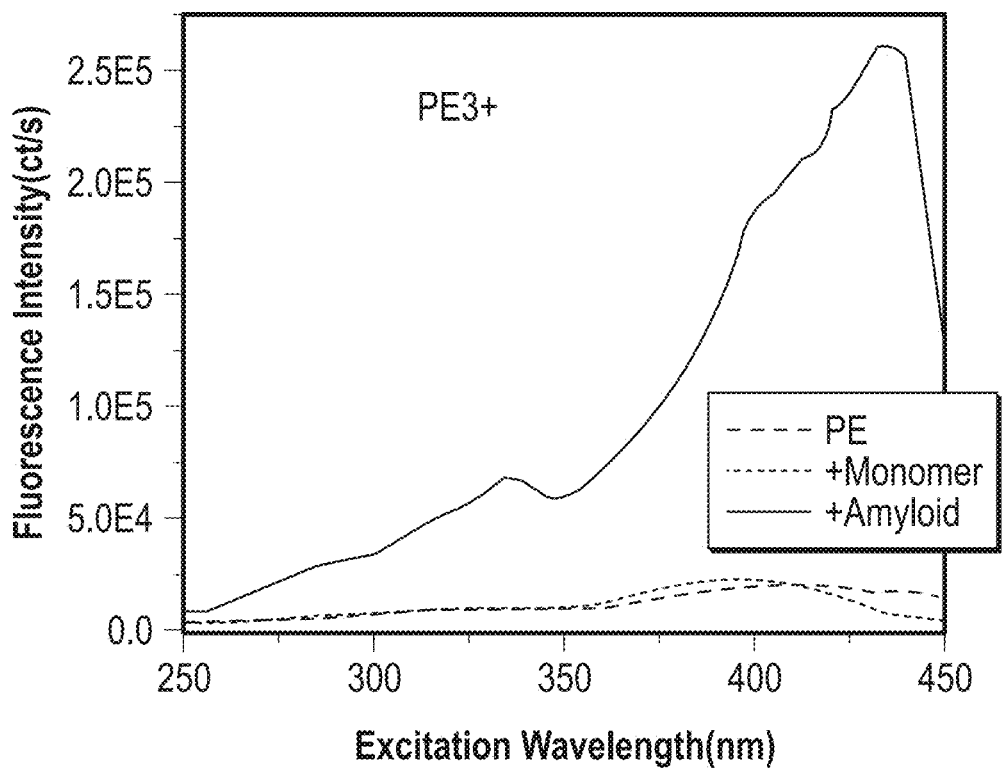
Figure 18E:
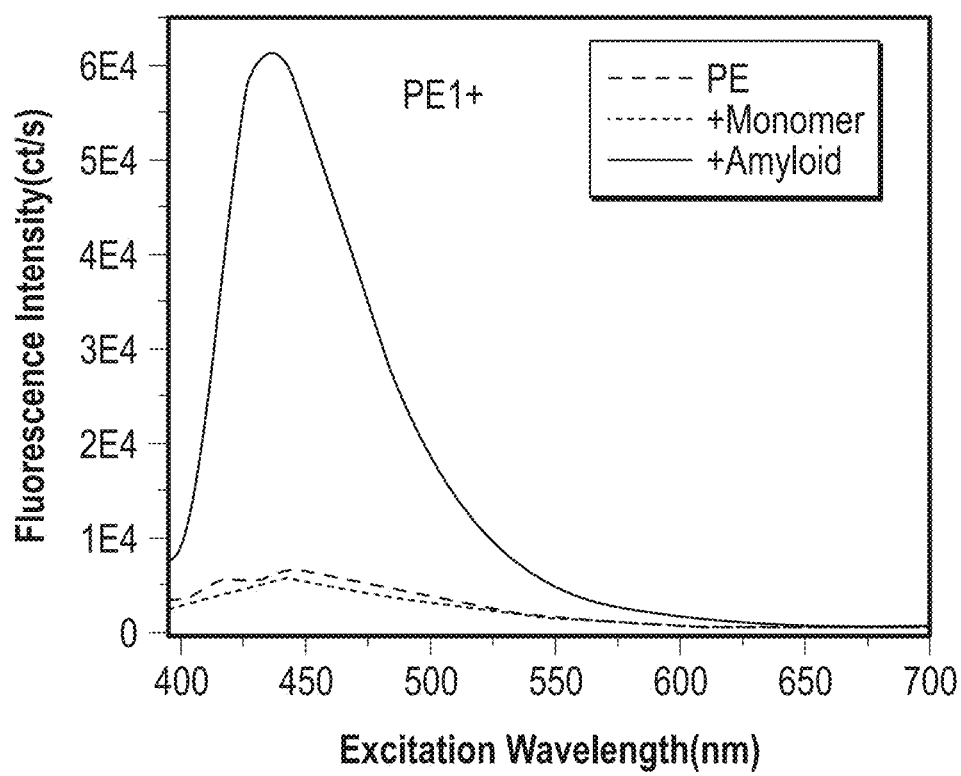
Figure 18F:
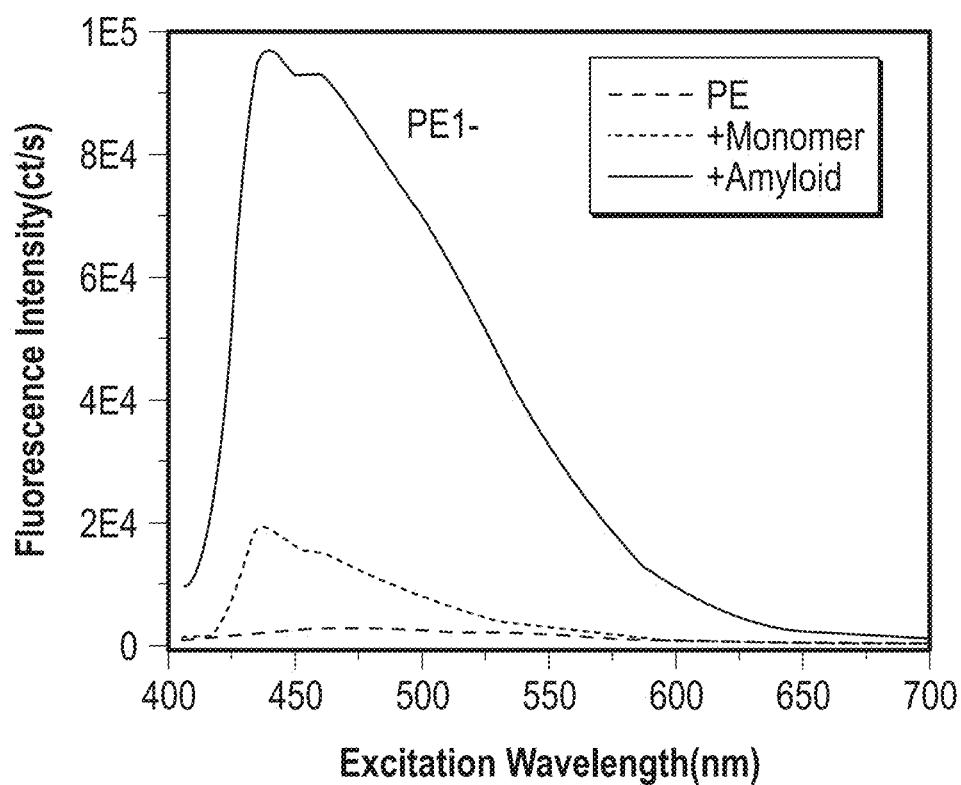
Figure 18G:
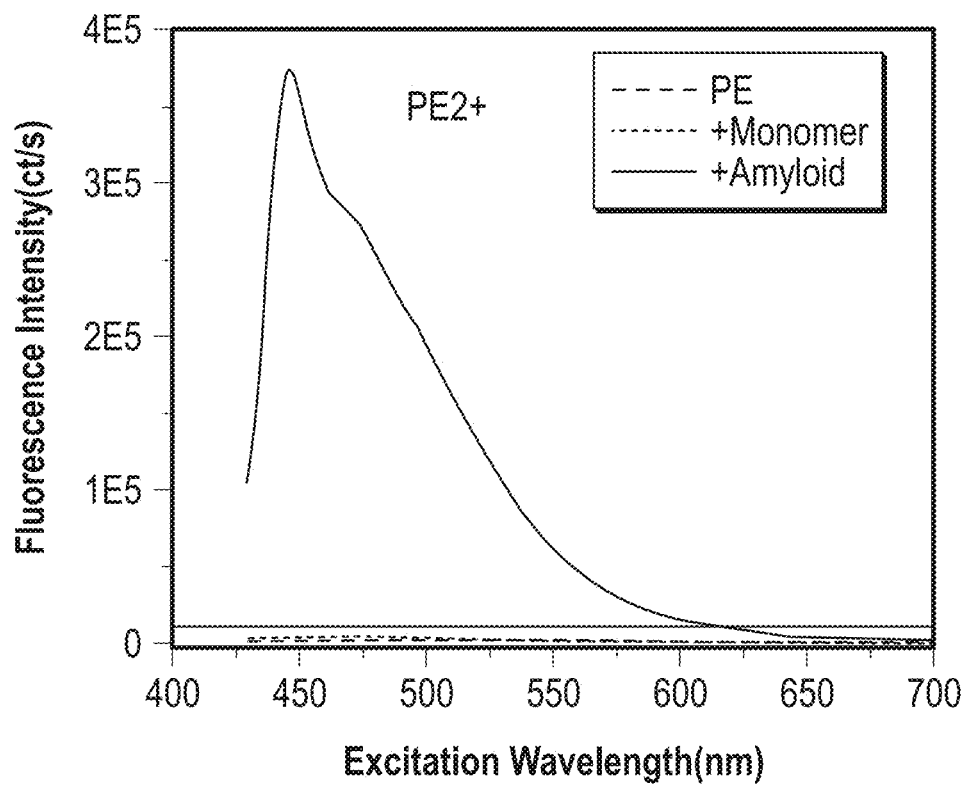
Figure 18H:
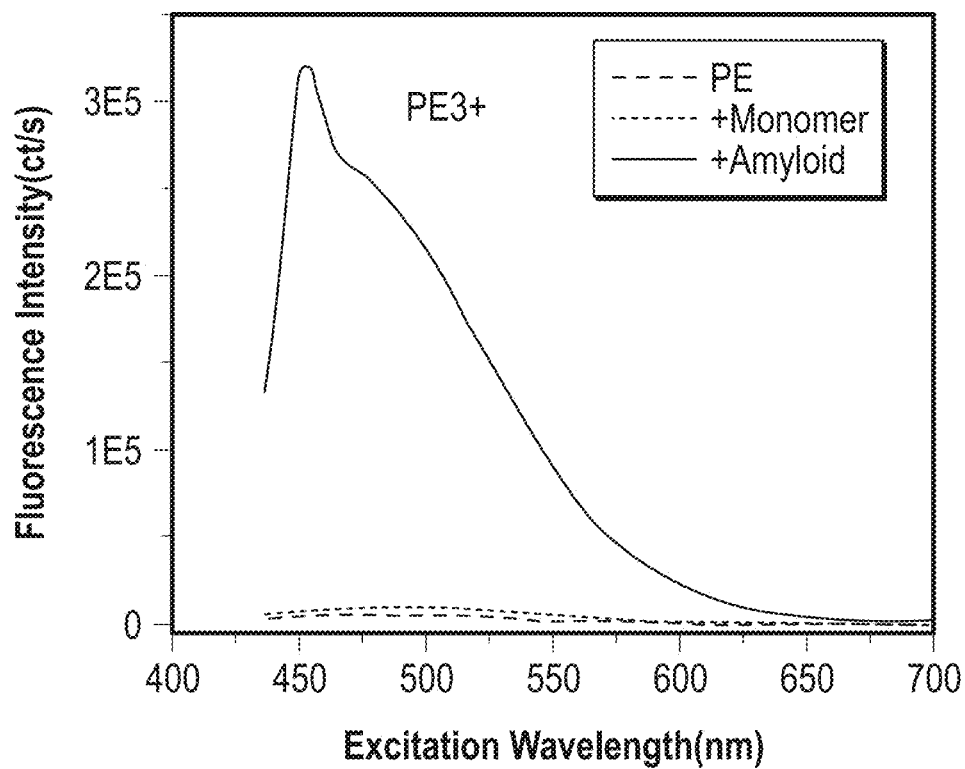

Hen egg white lysozyme (HEWL) was used to form fibrillary amyloid aggregates for use in this study. Lysozyme has been suggested as a useful model protein for amyloid studies, due to its low cost and the relative ease with which it can be induced to form amyloid aggregates. Lysozyme amyloid oligomers and fibrils have also been shown to exhibit cytotoxicity towards human neuroblastoma cells, indicating that the amyloid-aggregate conformer of lysozyme recapitulates most of the relevant properties of known disease-associated proteins. For these experiments. HEWL (Sigma-Aldrich) was incubated at 70'C and a concentration of 350 µM in pH 3 sodium citrate buffer (10 mM) with 100 mM NaCl. Visible precipitates of aggregated lysozyme were observed to accumulate over the time of incubation, and the formation of amyloid fibrils was determined by Thioflavin T (ThT) fluorescence assay (FIG. 15, illustrating a plot of PE and Thioflavin T (10 µM) fluorescence enhancement with variously incubated HEWL (10 µM monomer basis, 0.5 mg/mL), with unbound dye fluorescence normalized to 0 and maximum dye fluorescence normalized to 1), far-UV circular dichroism (CD) spectroscopy (FIG. 16, illustrating far-UV circular dichroism spectra of 0 h, 2 h and 4 h incubated HEWL (0.14 mg/mL) in pH 3 citrate buffer (10 mM)), and atomic force microscopy (AFM) and transmission electron microscopy (TEM) (FIG. 17, illustrating TEM (top) and AFM (bottom) images of 0 h, 1 h, 1.5 h and 4 h incubated HEWL; scale bars=200 nm; 4 h, inset: view of a single isolated fibril, showing twisted morphology; AFM image Z-height: 0 h, 25 nm; 1 h, 25 nm; 1.5 h, 15 nm 4 h, 100 nm).

ThT-positive aggregates were detected by the second hour of incubation (FIG. 15), and the profile of ThT fluorescence enhancement over incubation time had the sigmoidal shape consistent with the nucleation-dependent mechanism that is well accepted for amyloid formation. Far-UV circular dichroism measurements (FIG. 16) showed conversion of primarily α-helix structure of monomeric lysozyme (0 h), as indicated by the negative bands at 222 and 208 nm, into primarily β-sheet structure in the mature aggregates (2 h and 4 h), as indicated by the single negative band at 218 nm and the positive band just visible at the 200 nm edge of the spectrum.

Fibrillar morphology of HEWL aggregates was confirmed by direct visualization by AFM and TEM. AFM on dry mica and TEM (FIG. 17) on non-glow discharged carbon grids showed that unincubated HEWL formed a homogeneous film without large features. One hour of incubation caused the HEWL to form distinguishable bumps, hypothesized to be pre-thioflavinophilic oligomers. By 1.5 hours of incubation when amyloid formation was just reaching plateau phase as indicated by ThT fluorescence, small linear aggregates were observed, which lengthened by the fourth hour into short, bundled fibrils 20-30 nm wide and 60-200 nm long. No fibrils significantly longer than these were observed, even for longer incubated samples. These fibrillary, β-sheet enriched, ThT-positive HEWL amyloid aggregates were then used to evaluate the binding activity and photophysical changes of PEs against amyloid.

Example 3.3

Spectrophotometry of PE-HEWL Interactions.

Excitation and emission spectra of PEs in phosphate buffer alone, with monomeric HEWL and with HEWL amyloids (8 h incubated) are shown in FIGS. 18A-H, and relevant photophysical properties are summarized in Table 1. FIGS. 18A-H illustrate excitation (A, B, C, D) and emission (right; E, F, G. H) spectra of PEs (A, E: PE1+; B, F: PE1−; C, G: PE2+; D, H: PE3+) in phosphate buffer (PB, pH 7.4, 10 mM) alone (long dashed line) with HEWL monomers (short dashed line) and with HEWL amyloids (solid line); PE concentration: 500 nM, protein concentration: 5 µM monomer basis/0.25 mg/mL; emission and excitation wavelengths, respectively, were chosen as shown in Table 1 for each sample. A 10:1 molar ratio of protein to PE was used for these experiments. Absorbance spectra were taken, but background light scattering from insoluble amyloid aggregates made them difficult to interpret, so "fluorescence detected absorbance" in the form of excitation spectra was used instead. Normalized excitation and emission spectra, in which peak shifts and lineshape changes of spectra were somewhat easier to visualize, were used. All four PEs exhibited significant fluorescence enhancement in solution with HEWL amyloids (FIGS. 18E, F, G, H), and no fluorescence change with HEWL monomers except for PE1−. The fluorescence enhancement over baseline was most significant for the longer PE2+ and PE3+(FIGS. 18G and H), which also had notably sharpened fluorescence spectra with small (~10 nm) blueshifting of the maximum. PE1− had a similarly sharpened and blueshifted emission spectrum (FIG. 18F) with both HEWL monomers and amyloid, with the addition of a shoulder at 465 nm with amyloid. PE1+ (FIG. 18E) had no change in wavelength or lineshape of emission spectrum, just a large increase in intensity when mixed with amyloids. The excitation spectra (FIGS. 18A, B, C, D) show a notable bathochromic shift for each PE in solution mixed with amyloid, of 23, 27, 35 and 29 nm for PE1+, PE2+, PE3+ and PE1−, respectively, observing only the low-energy band. The high-energy band, less relevant for imaging purposes, was also bathochromically shifted. The cationic PEs, as before, did not appear to interact with HEWL monomer in such a way as to produce a fluorescence change. PE1− had similar excitation spectrum (FIG. 18B) with monomer and amyloid, except for a large intensity difference.

A plot of normalized fluorescence enhancement for all four PEs and Thioflavin T with HEWL fibrils incubated for different lengths of time is shown in FIG. 15. PE1+ and PE2+ track amyloid formation in roughly the same way as ThT, showing a sigmoidal curve with onset of a logarithmic growth phase occurring at the same time, around 1 hour of incubation. The plateau phase, as monitored by fluorescence of any of those three PEs or ThT, appeared at 2 hours incubation. PE3+ fluorescence enhancement shows a similar length lag phase but a slower growth phase, taking up to 3.5 hours to reach its plateau phase. PE1− has greater fluorescence enhancement when mixed with monomeric species than with amyloid at the equimolar concentrations used for this assay.

Example 3.4

Determination of PE/Amyloid Binding Constants.

Figure 19:
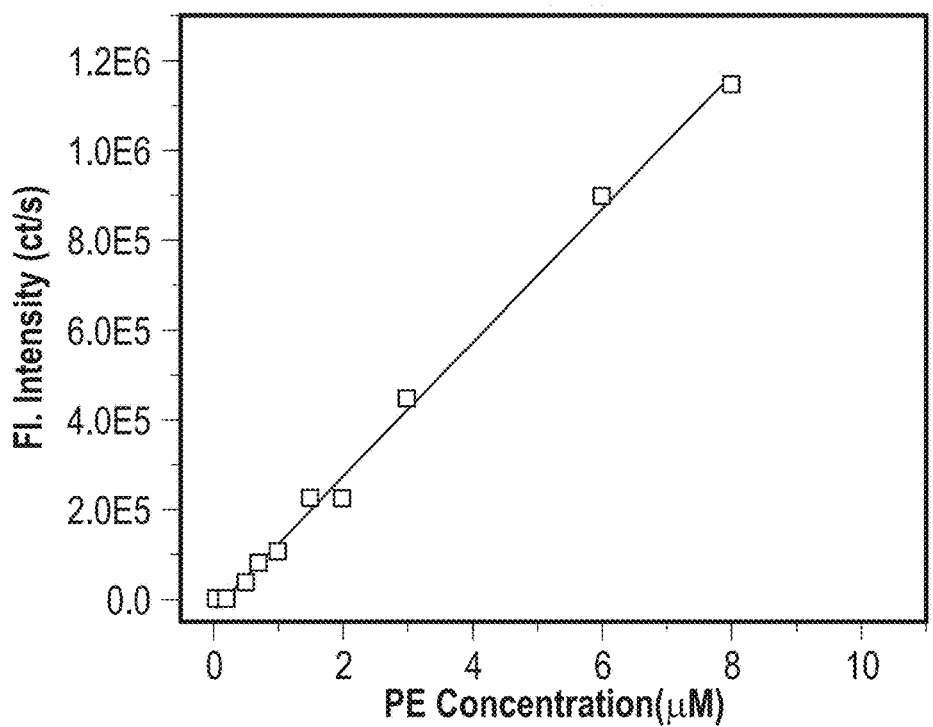
FIG. 19 illustrates fluorescence versus PE concentration in the presence of HEWL monomers, in accordance with various embodiments.

Next, binding saturation assays were conducted to quantify the affinity of PE-amyloid binding; data and fitted curves were produced and the fitted parameters are summarized in the last two columns of Table 1. Since the linear fibril binding sites could fit many PEs, fits to binding curves were performed to the Hill equation to capture possible binding cooperativity:

$$y = \frac{F_{max}x^n}{K^n + x^n}$$

where x is PE concentration (with protein concentration fixed), y is PE fluorescence intensity. $F_{max}$ is PE fluorescence intensity at saturation, k is the equilibrium dissociation constant and the exponential term n is the Hill parameter which describes cooperativity of binding, n=1 indicates non-cooperative, independent binding, n>1 indicates that binding of one ligand increases affinity of the binding of a second, and n<1 indicated that binding of one ligand decreases affinity of the binding of a second. Fits to the data for the three cationic PEs produced $F_{max}$ values close to the observed saturation value, and the other two parameters are reported as calculated. The fits indicated that PE1+, PE2+ and OPE3+ bound to HEWL amyloid with low micromolar affinity dependent on PE length, with the calculated dissociation constant decreasing from 2.6 µM for PE1+ to 1.15 µM for PE2+, and still further to 858 nM for PE3+. Furthermore, the cooperativity of PE binding increased from almost no cooperativity for PE1+, to some positive cooperativity for PE2+, to still more positive cooperativity for PE3+. The quantitative physical meaning of the Hill parameter is not quite clear except in special cases, but in a general way it is possible to conclude that for the cationic PEs, the shortest PE has non-cooperative binding to HEWL amyloid (Michaelis-Menten binding), and the two longer PEs have increasingly positively cooperative binding. The binding of PE1− to HEWL monomers appeared to be linear and non-saturable at reasonable concentrations (see, FIG. 19, illustrating linear (non-saturable) binding of PE1− to HEWL monomers (5 µM/0.25 mg/mL); linear fit shown for clarity; this experiment was performed once), indicating a low-affinity binding to a very large number of sites. The effect of PE1− non-specific binding to HEWL monomers precluded accurate determination of a binding constant for PE1−/amyloid interactions such that a quantitative comparison of binding between the cationic and anionic compounds could not be made.

had optical activity by itself in phosphate buffer solution and none of the PEs had any CD with HEWL monomer, including PE1−. PE1+ did not have optical activity with HEWL amyloid, but the other three PEs did. PE1−, PE2+ and PE3+ all had strong induced CD with a negative Cotton effect when bound to HEWL amyloid fibrils. PE2+ and PE3+ gave rise to similar CD spectra, with more intense bands in the spectrum for PE3+. The induced CD spectrum for PE1− had a pronounced two-band structure, reflecting the more intense high-energy band for the anionic PE when bound to HEWL amyloid.

Example 3.6

Protein→PE Energy Transfer in PE-Amyloid Complexes.

Figure 20:
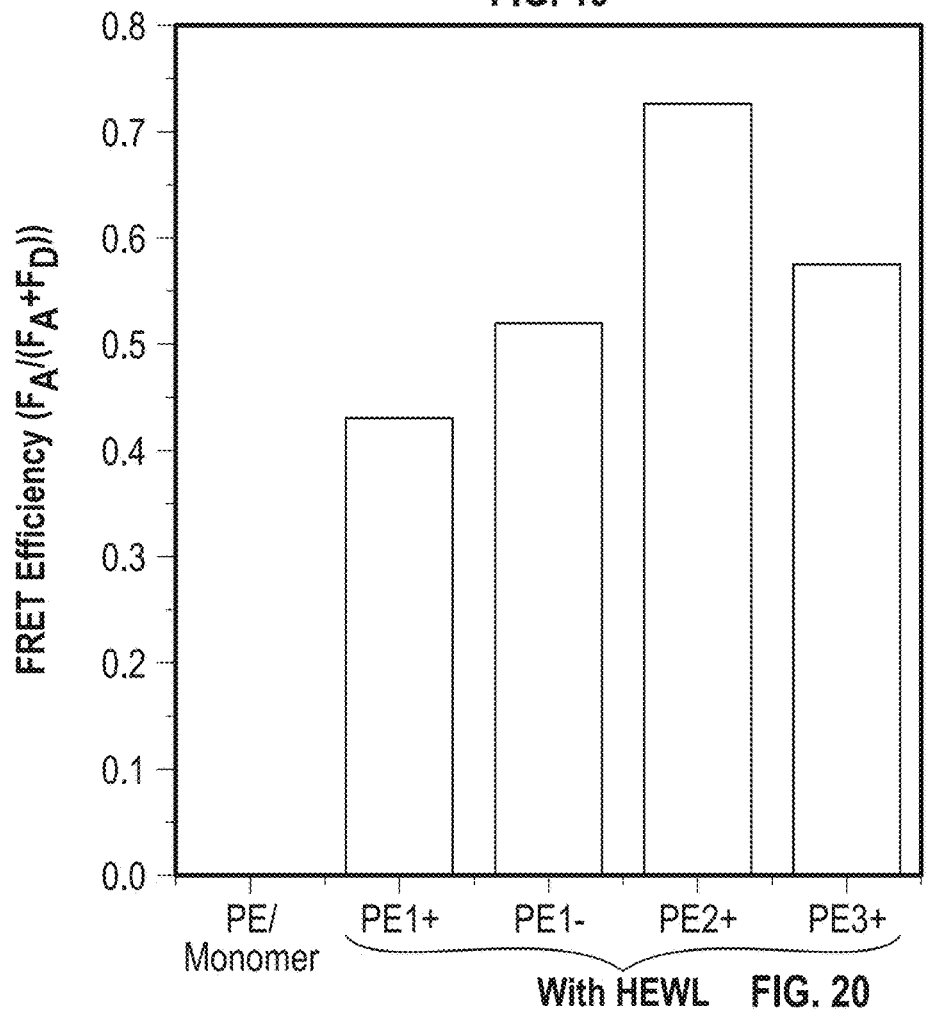
FIG. 20 illustrates HEWL/PE Förster resonance energy transfer (FRET) efficiencies for various PEs calculated from spectral data, in accordance with various embodiments.

Since lysozyme is an intrinsically fluorescent protein whose emission spectrum overlaps significantly with the excitation spectra of PEs, we chose to investigate the possibility of Förster resonance energy transfer (FRET) from the protein chromophore to PEs by a simple spectroscopic method. Emission spectra of solutions containing PEs and HEWL amyloids or monomers were obtained using the excitation wavelength of HEWL (280 nm) and PE emission was observed only from PE/amyloid samples, indicating that HEWL→PE energy transfer was occurring only with PEs bound to amyloid fibrils. The results are summarized as FRET efficiencies in FIG. 20, illustrating HEWL→PE FRET efficiencies calculated from spectral data by the equation $E=F_A/(F_D+F_A)$ where $F_D$ is the integrated area under the donor emission peak, and $F_A$ is the integrated area under the acceptor emission peak. This simple expression is valid for this case since the PEs are nonfluorescent when excited at the donor excitation wavelength, eliminating crosstalk. Thus, $F_A$ is the total number of energy transfer events, and $(F_A+F_D)$ is the total number of excitation events. Theoretically, the efficiencies should be convertible into distances by

TABLE 1

Relevant photophysical properties of PEs alone and bound to HEWL amyloid, and apparent binding constants and Hill coefficients of PE binding to HEWL amyloid.

| Comp. | $\varphi_{fl}$ (H$_2$O) | $\varphi_{fl}$ (MeOH) | $\lambda_{ex}$ (PB) (nm) | $\lambda_{ex}$ (PB w/HEWL) (nm) | $\lambda_{em}$ (H$_2$O) (nm) | $\lambda_{em}$ (PB) (nm) | $\lambda_{em}$ (PB w/HEWL) (nm) | $K_d$ (µM) | Hill coeffi. |
|---|---|---|---|---|---|---|---|---|---|
| PE1+ | 0.023 | 0.75 | 314, 362 | 332, 385 | 454 | 454 | 454 | 2.63 ± 0.58 | 1.04 |
| PE2+ | 0.039 | 0.71 | 330, 399 | 337, 426 | 448 | 460 | 445 | 1.15 ± 0.26 | 1.15 |
| PE3+ | 0.069 | 0.70 | 340, 399 | 335, 434 | 440 | 464 | 453 | 0.858 ± 0.058 | 1.89 |
| PE1− | — | — | 314, 370 | 327, 399 | 454 | 454 | 439 | — | — |

Example 3.5

Induced Circular Dichroism of PE-Amyloid Complexes.

Circular dichroism measurements were performed to determine if the intrinsic chirality of the HEWL fibrils was transferred to the PE chromophore by a chiral backbone twist or an "excitonic" chiral supramolecular aggregate. CD spectroscopy (CPEs in PB with HEWL monomer and with HEWL amyloid; performed for (a): PE1+; (b): PE1−; (c): PE2+; (d): PE3+; PEs 10 µM, HEWL 10 µM monomer basis/0.5 mg/mL) indicated induced circular dichroism of PEs when bound to HEWL amyloids. As expected, no PE $$E = \frac{1}{1+\left(\frac{r}{R_0}\right)^6},$$

but $PE_S$ and HEWL amyloids are not a well-characterized FRET pair with a defined Förster radius $R_0$. Qualitatively, some determinations based on the relative measured efficiencies for the different PEs can be made. The measured FRET efficiency will be affected by multiple independent factors averaged over all the PE-HEWL pairs in solution, such as the number of bound PE molecules, the bound PE-HEWL chromophore distance, and the spectral overlap integral $J(\lambda)$, all of which will vary by PE. The highest efficiency observed for PE2+ is probably the result of its higher binding constant than PE1− or PE1+ combined with its greater overlap integral than PE2+.

Example 3.7

Explicating the Mode of PE-Amyloid Binding.

Figure 21:
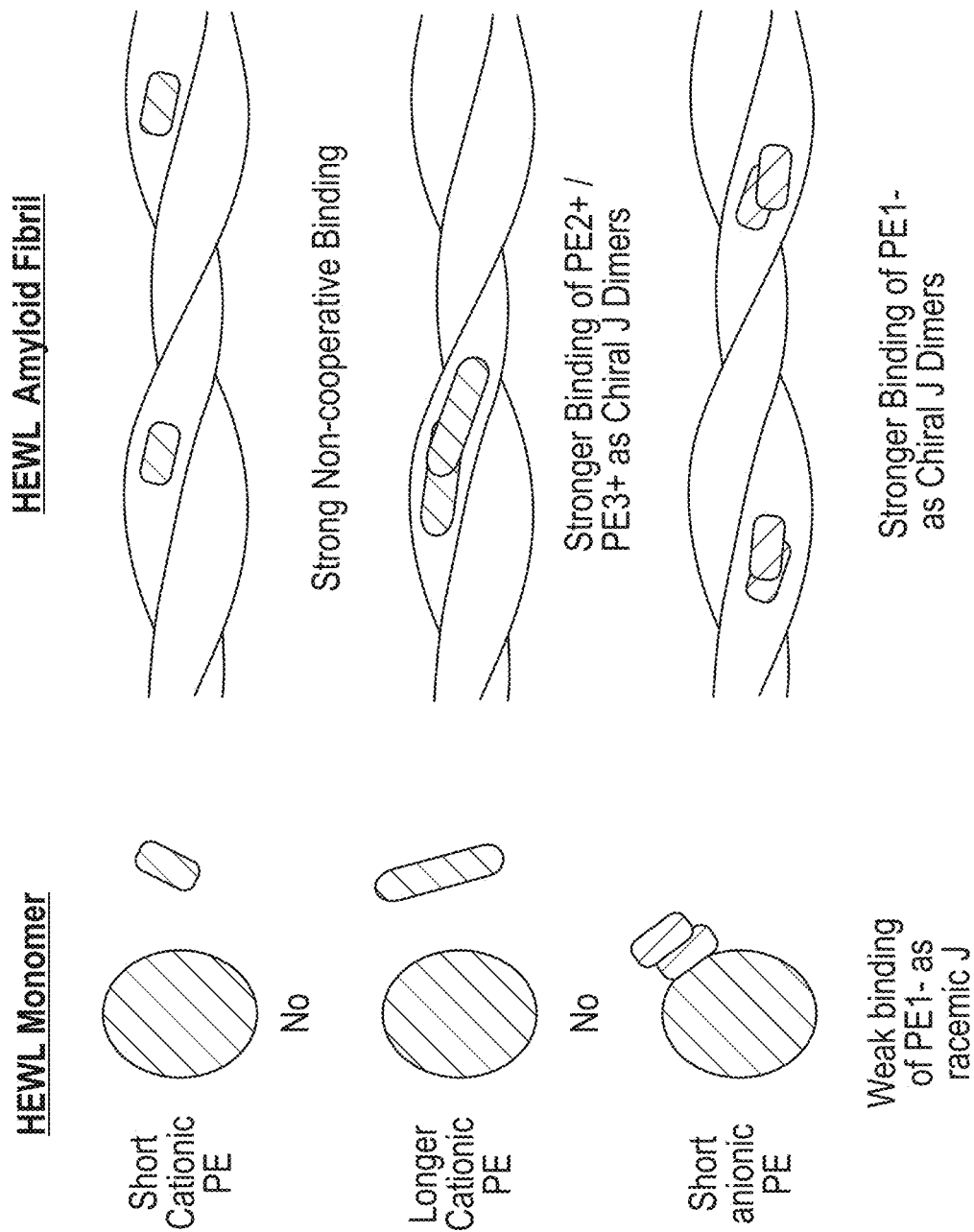
FIG. 21 illustrates modes of interaction between PEs and HEWL monomers and amyloids, in accordance with various embodiments.

The results of these experiments indicate modes of interaction between PEs and HEWL monomers and amyloids, as summarized in cartoon form in FIG. 21. All four PEs tested were observed to bind to HEWL amyloid, with good affinity, but with different properties depending on chain length and charge. Generally, the PEs either do not interact with protein, bind as single molecules, or bind as J dimers which are either racemic or chirally biased. Overall, it has become clear that J-type aggregation is a naturally favorable mode of PE-PE interaction for PEs with side chain charged groups when the Coulombic repulsion between the charged groups is reduced.

The spectral changes of PE2+. PE3+, and PE1− in complex with HEWL amyloids, and of PE1− in complex with HEWL monomers, are highly indicative of J aggregation: redshifted absorbance, sharpening of fluorescence band, and narrowed Stokes shift. The enhancement of fluorescence intensity is attributable all or in part to the reduced quenching of the PE by water when bound to the hydrophobic surface of the protein; this solvent-access effect is in play for all four PEs. The current study indicates that the longer cationic PEs, PE2+ and PE3+, form J dimers (or possibly larger aggregates) on the HEWL amyloid fibril surface, and PE1− forms J dimers on both HEWL monomers and HEWL amyloid fibrils. The aggregates formed on amyloid have a chiral bias to the PE-PE offset angle, producing a chiral supramolecular chromophore, or an excitonic optical activity, responsible for the circular dichroism seen experimentally. The exact source of this bias is hard to pin down; it could be a result of the helically twisted fibril axis or more specific to a binding site. Notably, the aggregates formed by PE1− must be racemic, indicating that the PEs are not interacting with a specific site but simply sticking to oppositely charged areas of the lysozyme surface. PE1+ has some small redshifting of excitation spectrum, but its emission spectrum does not shift at all and it acquires no optical activity, indicating that this compound binds to HEWL fibrils as single molecules rather than as a structured aggregate. The small excitation redshift could be due to minor backbone planarization, and the increase of fluorescence intensity to reduced solvent access.

The results of binding saturation assays support these conclusions for the cationic PEs. PE2+ and PE3+ show positive cooperativity, meaning that the binding of one PE increases the affinity of the next binding event. The formation of J aggregates on the fibril surface satisfies this condition: a single PE might bind to a favorable site, and a second finds it and forms an even more favorable J aggregate due to n-n and hydrophobic interactions. It is also possible that PEs could form J dimers in solution that subsequently find the fibril surface, but this seems unlikely due to charge repulsion. Furthermore, the curve for PE3+ shows a larger cooperative effect than that for PE2+, and the induced CD bands for PE3+ are also more intense; the increased length of PE3+ increases the available area for aggregate formation, forming more or larger chiral aggregates. The PE1+/HEWL amyloid binding assay indicated no cooperative binding effect, which is consistent with independent, single-molecule binding.

One notable result of this study is the large differences between PE1+ and PE1− in their interactions with HEWL monomers and amyloid. The two single-repeat PEs tested differ by the charge on the side-pendant solubilizing groups, and their interactions with HEWL monomer and amyloids were highly different. PE1+ exhibited non-cooperative and saturable binding to amyloid without induced optical activity or large shifts in absorption or emission bands, and when bound, its emission was the least enhanced over free PE. Its anionic counterpart, PE1−, proved quite different both in its nonspecific binding to HEWL monomer and in its interaction with HEWL amyloid. This interaction was seen to be fairly weak, as indicated by the non-saturable binding, but it overwhelms the PE1−/amyloid interaction at high PE concentrations, after all the amyloid binding sites are occupied. In vitro, without interfering effects from other cellular/tissue components, such an effect could prove useful for monitoring the disappearance of similarly charged monomers. The differences in the PE1+ and PE1− binding to amyloid-PE1+ binds singly and PE1− as chiral J aggregates-could be due to charge or H-bonding interactions specific to sites on the lysozyme fibril surface. The specificity of these possible charge effects is notable, since the arrangement of charged residues on the fibril surface is controlled by the protein's primary, secondary and tertiary structure. This effect may provide useful means of differentiating amyloids formed from different monomers.

The absence of FRET in any monomer/PE solution reconfirms the weak and non-specific nature of PE1−/monomer binding, since the PE is not held within range of the fluorescing residues. Aromatic residues may also only be surface exposed, and within range of transfer to PEs, in the amyloid state; HEWL intrinsic fluorescence is found to decrease over the course of incubation, which implies that fluorescing residues are increasingly exposed to solvent as more amyloid forms. The large differences between PE1+ and PE1−'s interactions with monomeric and amyloid HEWL, likely influenced by specific charged residues in the HEWL primary sequence, may be employed for differentiation of amyloids with different monomers, a useful effect, for example, in the study of the intermediate disorder called dementia with Lewy bodies, in which Lewy bodies (formed of alpha-synuclein and normally characteristic of Parkinson's disease) and amyloid plaques are comorbid.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Example 3.8

PE Synthesis and Chemical Reagents.
Except PEs, all reagents were obtained commercially and used without further purification. Synthesis of PEs has been reported previously, except for PE1−, which was synthesized analogously to PE1+. Hen egg white lysozyme and Thioflavin T were obtained from Sigma-Aldrich Chemical Company (St. Louis, MO). Suspensions of protein aggregates were gently vortexed to distribute aggregates before use in experiments.

Preparation of Lysozyme Amyloid Fibrils.

Lyophilized HEWL was dissolved at 10 mg/mL in 10 mM pH 3 sodium citrate buffer with 0.1 M NaCl. The solution was incubated in a 70C oil bath and magnetically stirred at 250 rpm for 12 h, and aliquots were withdrawn at half-hour intervals. The initially clear solution was observed to form cloudy aggregates by 1 h incubation. Half of each aliquot was immediately diluted into pH 7.4 phosphate buffer to prevent further influence of acidic conditions and stored at 4C. The samples were observed to undergo no noticeable degradation over the course of one month, and these neutralized aliquots were used for all following experiments except for measurements of protein circular dichroism.

Spectrophotometry of PE/ThT-protein Complexes.

For studies of fluorescence enhancement vs. protein incubation time, dyes were mixed with protein sample in phosphate buffer (10 mM, pH 7.4) at equal monomer concentration of 10 μM in the wells of a standard 96-well plate. Emission spectra were obtained using top read with a SpectraMax M2e plate-reading spectrophotometer (Molecular Devices, Sunnyvale, CA). Experiments were performed in duplicate and errors are reported as standard deviation. For analysis of bound PE excitation and emission spectra and protein-PE energy transfer, PEs (500 nM) were mixed with protein sample (5 μM, monomer basis) in phosphate buffer and the solution transferred to a quartz, fluorometry cuvette. Spectra were obtained on a PTI QuantaMaster 40 steady state spectrofluorometer (HORIBA Scientific, Edison, NJ).

Circular Dichroism Spectroscopy.

PEs and protein samples were diluted in phosphate buffer, gently vortexed, and read in a 1 mm pathlength quartz CD cuvette using an Aviv 410 CD spectrometer (Aviv Biomedical, Lakewood, NJ), 15 s averaging time. A blank spectrum (PB only) was subtracted from each sample to remove background activity. Error bars are standard deviation over multiple reads of a single sample as reported by the instrument.

Determination of Binding Constant.

For determination of binding constant of PEs to amyloid aggregates, PEs were mixed with HEWL amyloid in phosphate buffer at a final concentration of 100 nM-5 μM for PEs and 5 μM (monomer basis) for protein. The solutions were then transferred to a quartz fluorometry cuvette and emission measured at the pertinent wavelength. Experiments were performed in duplicate and errors reported as standard deviation. Hill function fits to PE binding curves were calculated in OriginPro 9.

AFM Imaging.

For AFM, a droplet of each protein sample at 5 mg/mL was pipetted onto freshly cleaved mica substrate and allowed to physisorb for 20 min, followed by a single rinse with HPLC-grade water and gentle drying under a stream of $N_2$. Imaging was performed with a Nanoscope IIIa AFM (Veeco, Plainview, NY) in tapping mode under a constant stream of dry $N_2$ gas using a rectangular silicon cantilever with a spring constant of 40 N/m (Veeco model RTESPA-W). Veeco Nanoscope software was used to capture and analyze the images. 0 h and 1 h images are cropped from 1 μm width images subjected to a first-order x,y plane fit and flattened. 1.5 h image is cropped from a 5 m width image subjected to a third-order x,y plane fit and flattened. 4 h image is cropped from a 5 μm width image subjected to a first-order x,y plane fit.

TEM Imaging.

For TEM imaging, incubated HEWL solutions at a concentration of 350 μM were diluted 1:5 in water and aliquoted onto carbon-coated grids, allowed to adsorb, washed with deionized water and stained with 2% uranyl acetate solution. Excess liquid was removed and the samples allowed to dry in air. Samples were imaged on a Hitatchi H7500 transmission electron microscope (Hitachi High Technologies Corp., Tokyo, Japan) with tungsten filament illumination, operating with an AMT X60 bottom mount CCD camera detector.

Additional Embodiments

The following exemplary embodiments are provided, the numbering of which is not to be construed as designating levels of importance:

Embodiment 1 provides a method of inducing germination of microbial spores comprising contacting the microbial spores with a p-phenylene ethynylene compound.

Embodiment 2 provides the method of Embodiment 1, wherein the microbial spore is at least one of a *Bacillus anthracis*, a *Bacillus atrophaeus*, a *Bacillus cereus*, and a *Bacillus subtilis*.

Embodiment 3 provides the method of any one of Embodiments 1-2, wherein the p-phenylene ethynylene compound comprises a repeating unit having the structure:

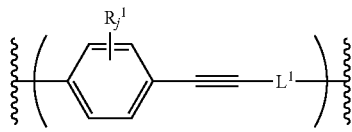

wherein
R$^1$ has the structure:

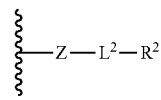

wherein
at each occurrence Z is independently chosen from —CH$_2$—, —O—, —S—, and —NH—;
at each occurrence L$^2$ is independently chosen from (C$_1$-C$_{50}$)hydrocarbylene interrupted by 0, 1, 2, 3, 4, 5, 6, 7, 8, 9, or 10 groups independently chosen from —O—, —S—, and —NH—;
at each occurrence R$^2$ is independently chosen from —H, (C$_1$-C$_5$)alkyl, —SO$_3^-$, —CO$_2^-$, —H$_2$PO$_4^-$, HPO$_4^{2-}$, PO$_4^{3-}$, phenolate, (C$_1$-C$_{10}$)alkyl-(1,4-substituted 1,4-diazabicyclo[2.2.2]octane-1,4-diium)-, and 3-methylimidazolium, and —N$^+$(R$^A$)$_3$ wherein at each occurrence R$^A$ is independently (C$_1$-C$_5$)alkyl;

at each occurrence L¹ is independently chosen from a bond and

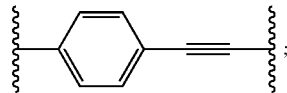

and j is about 0 to about 4.

Embodiment 4 provides the method of any one of Embodiments 1-3, wherein the p-phenylene ethynylene compound comprising a repeating unit having the structure:

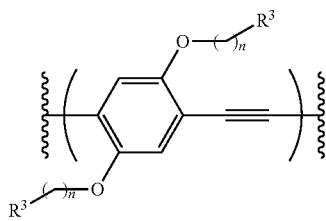

wherein at each occurrence R³ is independently chosen from —N⁺(CH₃)₃,

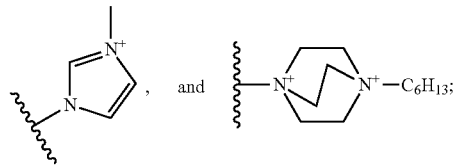

n is about 2 to about 4.

Embodiment 5 provides the method of any one of Embodiments 1-4, wherein the p-phenylene ethynylene compound has the structure:

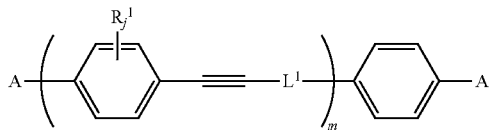

wherein

R¹ has the structure:

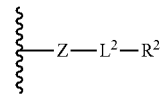

wherein at each occurrence Z is independently chosen from —CH₂—, —O—, —S—, and —NH—;

at each occurrence L² is independently chosen from (C₁-C₅₀)hydrocarbylene interrupted by 0, 1, 2, 3, 4, 5, 6, 7, 8, 9, or 10 groups independently chosen from —O—, —S—, and —NH—;

at each occurrence R² is independently chosen from —H, (C₁-C₅)alkyl, —SO₃⁻, —CO₂⁻, —H₂PO₄⁻, HPO₄²⁻, PO₄³⁻, phenolate, (C₁-C₁₀)alkyl-(1,4-substituted 1,4-diazabicyclo[2.2.2]octane-1,4-diium)-, and 3-methylimidazolium, and —N⁺(R^A)₃ wherein at each occurrence R^A is independently (C₁-C₅)alkyl;

j is about 0 to about 4;

at each occurrence L¹ is independently chosen from a bond and

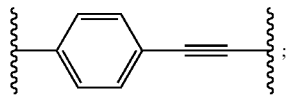 [SMILES: *C#Cc1ccc(*)cc1]

at each occurrence A is independently chosen from —H, substituted or unsubstituted —C(O)O—(C₁-C₁₀)hydrocarbyl, —C(O)NH—(C₁-C₁₀)hydrocarbyl, and C(O)OH; and m is about 1 to about 1,000.

Embodiment 6 provides the method of Embodiment 5, wherein the p-phenylene ethynylene compound has the structure:

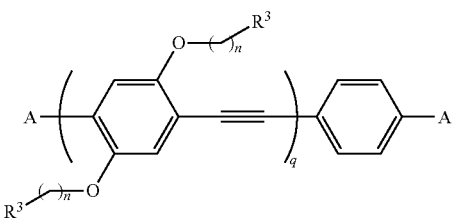

wherein at each occurrence R³ is independently chosen from —N⁺(CH₃)₃,

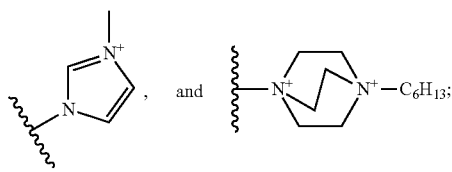

n is about 2 to about 4;

at each occurrence A is independently chosen from —H and —C(O)O—(C₁-C₅)alkyl; and q is about 1 to about 50.

Embodiment 7 provides the method of Embodiment 6, wherein A is —C(O)OCH₂CH₃.

Embodiment 8 provides the method of any one of Embodiments 1-7, wherein the p-phenylene ethynylene compound has the structure:

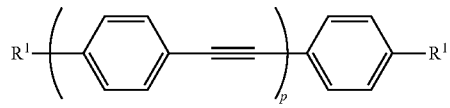

wherein
R¹ has the structure:

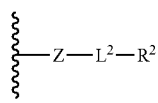

wherein
at each occurrence Z is independently chosen from —CH₂—, —O—, —S—, and —NH—;
at each occurrence L² is independently (C₁-C₅₀) hydrocarbylene interrupted by 0, 1, 2, 3, 4, 5, 6, 7, 8, 9, or 10 groups independently chosen from —O—, —S—, and —NH—;
at each occurrence R² is independently chosen from —H, (C₁-C₅)alkyl, —SO₃⁻, —CO₂⁻, —H₂PO₄⁻, HPO₄²⁻, PO₄³⁻, phenolate, (C₁-C₁₀)alkyl-(1,4-substituted 1,4-diazabicyclo[2.2.2]octane-1,4-diium)-, and 3-methylimidazolium, and —N⁺(R^A)₃ wherein at each occurrence R^A is independently (C₁-C₅)alkyl; and
p is about 1 to about 10.

Embodiment 9 provides the method of Embodiment 8, wherein at each occurrence Z is —O—;
at each occurrence L² is independently (C₁-C₅)alkyl;
at each occurrence R² is independently chosen from —N⁺(CH³)₃,

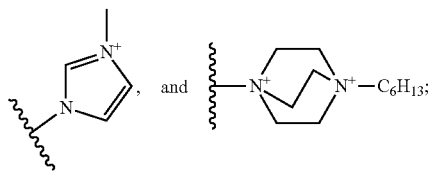

and
p is about 1 to about 5.

Embodiment 10 provides the method of any one of Embodiments 8-9, wherein the p-phenylene ethynylene compound has the structure:

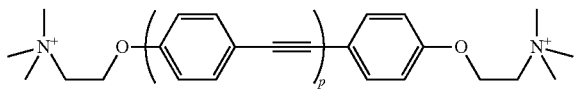

wherein p is about 2.

Embodiment 11 provides a method for detecting an enzyme, the method comprising (i) introducing an enzyme to a composition comprising a p-phenylene ethynylene compound and an enzyme substrate; and (ii) analyzing the change in fluorescence of the p-phenylene ethynylene compound following introduction of the enzyme.

Embodiment 12 provides the method of Embodiment 11, wherein the p-phenylene ethynylene compound and the enzyme substrate form a complex.

Embodiment 13 provides the method of any one of Embodiments 11-12, wherein the introduction step (i) and the analyzing step (ii) occur in an aqueous environment.

Embodiment 14 provides the method of Embodiment 12, wherein the fluorescence of the p-phenylene ethynylene compound decreases following the introduction of the enzyme.

Embodiment 15 provides the method of Embodiment 14, wherein the fluorescence decreases due to a molecular transformation of the enzyme substrate to an entity or entities that do not complex with the p-phenylene ethynylene compound.

Embodiment 16 provides the method of any one of Embodiments 11-15, wherein the p-phenylene ethynylene compound is a cationic p-phenylene ethynylene compound.

Embodiment 17 provides the method of Embodiment 16, wherein the cationic p-phenylene ethynylene compound has the structure:

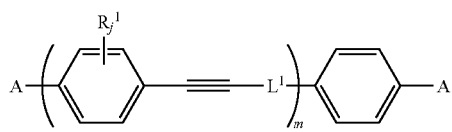

wherein
R¹ has the structure:

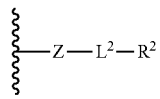

wherein
at each occurrence Z is independently chosen from —CH₂—, —O—, —S—, and —NH—;
at each occurrence L² is independently chosen from (C₁-C₅₀)hydrocarbylene interrupted by 0, 1, 2, 3, 4, 5, 6, 7, 8, 9, or 10 groups independently chosen from —O—, —S—, and —NH—;
at each occurrence R² is independently chosen from —H, (C₁-C₅)alkyl, —SO₃⁻, —CO₂⁻, —H₂PO₄⁻, HPO₄²⁻, PO₄³⁻, phenolate, (C₁-C₁₀)alkyl-(1,4-substituted 1,4-diazabicyclo[2.2.2]octane-1,4-diium)-, and 3-methylimidazolium, and —N⁺(R^A)₃ wherein at each occurrence R^A is independently (C₁-C₅)alkyl;
j is about 0 to about 4;
at each occurrence L¹ is independently chosen from a bond and

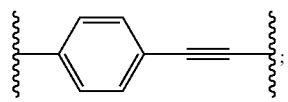

at each occurrence A is independently chosen from —H, substituted or unsubstituted —C(O)O—(C₁-C₁₀)hydrocarbyl, and —C(O)NH—(C₁-C₁₀)hydrocarbyl, and
m is about 1 to about 10.

Embodiment 18 provides the method of any one of Embodiments 16-17, wherein the cationic p-phenylene ethynylene compound has the structure:

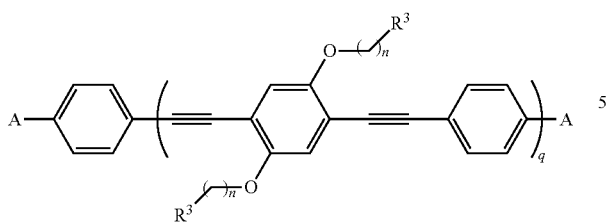

wherein
at each occurrence $R^3$ is independently chosen from $—N^+(CH_3)_3$,

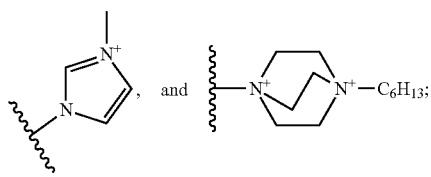
and n is about 2 to about 4;
at each occurrence A is independently chosen from —H and $—C(O)O—(C_1-C_5)$alkyl, and
q is about 1 to about 5.

Embodiment 19 provides the method of any one of Embodiments 16-18, wherein the cationic p-phenylene ethynylene compound has the structure:

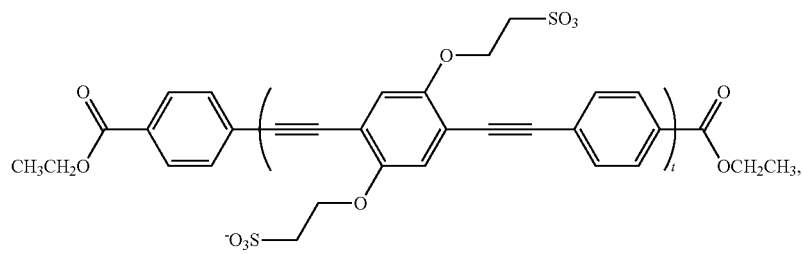

wherein t is about 1 to about 3.

Embodiment 20 provides the method of any one of Embodiments 16-19, wherein the enzyme substrate is an anionic enzyme substrate.

Embodiment 21 provides the method of Embodiment 20, wherein the anionic enzyme substrate is 1,2-dilauroyl-sn-glycero-phospho-(1'-rac-glycerol).

Embodiment 22 provides the method of any one of Embodiments 11-21, wherein the p-phenylene ethynylene compound is an anionic p-phenylene ethynylene compound.

Embodiment 23 provides the method of Embodiment 22, wherein the anionic p-phenylene ethynylene compound has the structure:

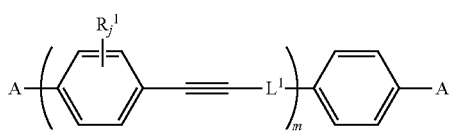

wherein
$R^1$ has the structure:

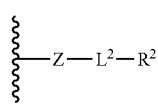

wherein
at each occurrence Z is independently chosen from $—CH_2—$, $—O—$, $—S—$, and $—NH—$:
at each occurrence $L^2$ is independently chosen from $(C_1-C_{50})$hydrocarbylene interrupted by 0, 1, 2, 3, 4, 5, 6, 7, 8, 9, or 10 groups independently chosen from $—O—$, $—S—$, and $—NH—$;
at each occurrence $R^2$ is independently chosen from —H, $(C_1-C_5)$alkyl, $—SO_3^-$, $—CO_2^-$, $—H_2PO_4^-$, $HPO_4^{2-}$, $PO_4^{3-}$, and phenolate:
j is about 0 to about 4;
at each occurrence $L^1$ is independently chosen from a bond and

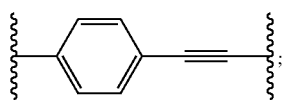

at each occurrence A is independently chosen from —H, substituted or unsubstituted $—C(O)O—(C_1-C_{10})$hydrocarbyl, and $—C(O)NH—(C_1-C_{10})$hydrocarbyl,
m is about 1 to about 10.

Embodiment 24 provides the method of any one of Embodiments 22-23, wherein the anionic p-phenylene ethynylene compound has the structure:

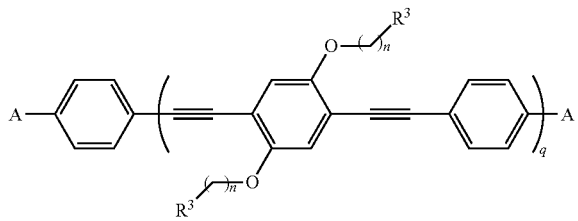

wherein
at each occurrence $R^3$ is independently chosen from $—SO_3^-$, $—CO_2^-$, $—H_2PO_4^-$, $HPO_4^{2-}$, $PO_4^{3-}$, and phenolate;

n is about 2 to about 4;
at each occurrence A is independently chosen from —H and —C(O)O—(C₁-C₅)alkyl; and
q is about 1 to about 5.

Embodiment 25 provides the method of any one of Embodiments 22-24, wherein the anionic p-phenylene ethynylene compound has the structure:

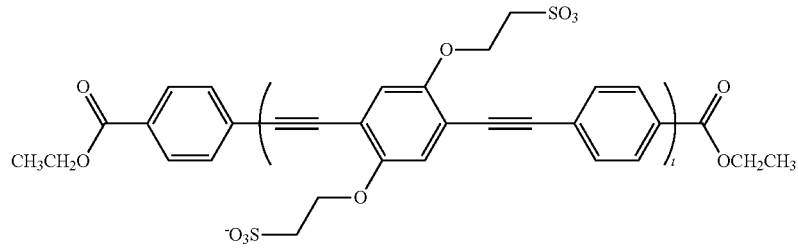

wherein t is about 1 to about 3.

Embodiment 26 provides the method of any one of Embodiments 22-25, wherein the enzyme substrate is a cationic enzyme substrate.

Embodiment 27 provides the method of Embodiment 26, wherein the cationic enzyme substrate is a substituted or unsubstituted (C₁-C₂₅)hydrocarbyl-C(O)O—(C₁-C₁₀)alkyl-N⁺((C₁-C₅)alkyl)₃.

Embodiment 28 provides the method of any one of Embodiments 26-27, wherein the cationic enzyme substrate is a substituted or unsubstituted (C₁-C₂₅)alkyl-C(O)O—(C₁-C₄)alkyl-N⁺(CH₃)₃.

Embodiment 29 provides the method of any one of Embodiments 26-28, wherein the cationic enzyme substrate is chosen from lauroyl choline and acetylcholine.

Embodiment 30 provides the method of any one of Embodiments 26-29, wherein the cationic enzyme substrate is lauroyl choline.

Embodiment 31 provides the method of any one of Embodiments 11-30, wherein the enzyme is chosen from phospholipase A1, phospholipase A2, phospholipase C, and acetyl cholinesterase.

Embodiment 32 provides a method for detecting an enzyme, the method comprising (i) introducing an enzyme to a composition comprising a p-phenylene ethynylene compound and an enzyme substrate; and (ii) analyzing the change in fluorescence of the p-phenylene ethynylene compound following introduction of the enzyme;
wherein
the p-phenylene ethynylene compound has the structure:

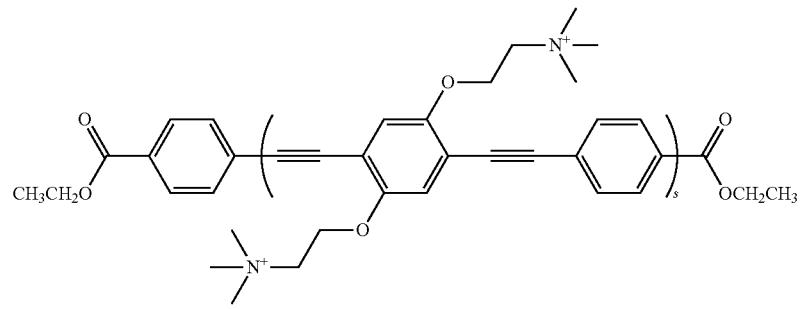

wherein s is about 1 to about 3;
the enzyme substrate is 1,2-dilauroyl-sn-glycero-phospho-(1'-rac-glycerol); and
the enzyme is at least one of phospholipase A1, phospholipase A2, and phospholipase C.

Embodiment 33 provides a method for detecting an enzyme, the method comprising (i) introducing an enzyme to a composition comprising a p-phenylene ethynylene compound and an enzyme substrate; and (ii) analyzing the change in fluorescence of the p-phenylene ethynylene compound following introduction of the enzyme;

wherein
the p-phenylene ethynylene compound has the structure:

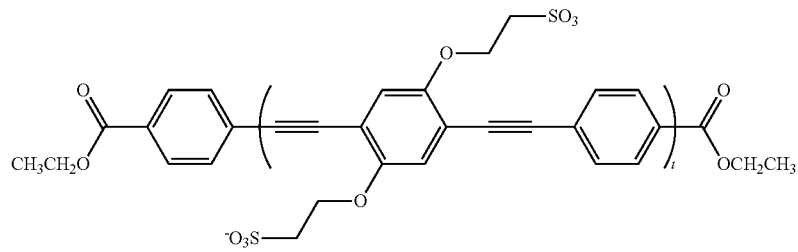

wherein t is about 1 to about 3;
the enzyme substrate is lauroyl choline; and
the enzyme is acetylcholinesterase.

Embodiment 34 provides a sensor, the sensor comprising a p-phenylene ethynylene compound and an enzyme substrate.

Embodiment 35 provides the sensor of Embodiment 34, wherein the p-phenylene ethynylene compound is a charged p-phenylene ethynylene compound and the enzyme substrate is an oppositely charged enzyme substrate.

Embodiment 36 provides the sensor of any one of Embodiments 34-35, wherein the p-phenylene ethynylene compound is a cationic p-phenylene ethynylene compound.

Embodiment 37 provides the sensor of Embodiment 36, wherein the cationic p-phenylene ethynylene compound has the structure:

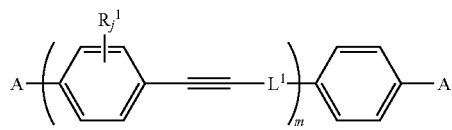

wherein
$R^1$ has the structure:

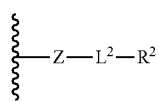

wherein
at each occurrence Z is independently chosen from —$CH_2$—, —O—, —S—, and —NH—;
at each occurrence $L^2$ is independently chosen from ($C_1$-$C_{50}$)hydrocarbylene interrupted by 0, 1, 2, 3, 4, 5, 6, 7, 8, 9, or 10 groups independently chosen from —O—, —S—, and —NH—;
at each occurrence $R^2$ is independently chosen from —H, ($C_1$-$C_5$)alkyl, —$SO_3^-$, —$CO_2^-$, —$H_2PO_4^-$, $HPO_4^{2-}$, $PO_4^{3-}$, phenolate, ($C_1$-$C_{10}$)alkyl-(1,4-substituted 1,4-diazabicyclo[2.2.2]octane-1,4-diium)-, and 3-methylimidazolium, and —$N^+$($R^4$)$_3$ wherein at each occurrence $R^4$ is independently ($C_1$-$C_5$)alkyl;
j is about 0 to about 4;
at each occurrence $L^1$ is independently chosen from a bond and

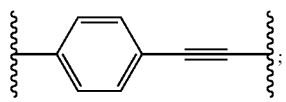

at each occurrence A is independently chosen from —H, substituted or unsubstituted —C(O)O—($C_1$-$C_{10}$)hydrocarbyl, and —C(O)NH—($C_1$-$C_{10}$)hydrocarbyl; and
m is about 1 to about 10.

Embodiment 38 provides the sensor of any one of Embodiments 36-37, wherein the cationic p-phenylene ethynylene compound has the structure:
wherein

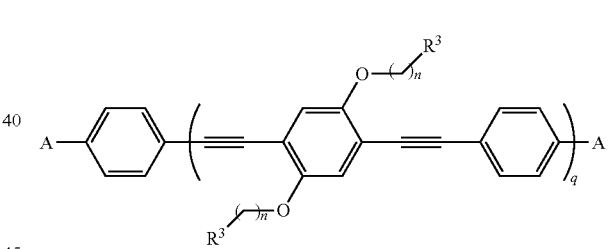

at each occurrence $R^3$ is independently chosen from —$N^+$($CH_3$)$_3$,

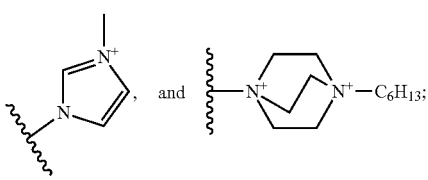

n is about 2 to about 4;
at each occurrence A is independently chosen from —H and —C(O)O—($C_1$-$C_5$)alkyl; and
q is about 1 to about 5.

Embodiment 39 provides the sensor of any one of Embodiments 36-38, wherein the cationic p-phenylene ethynylene compound has the structure:

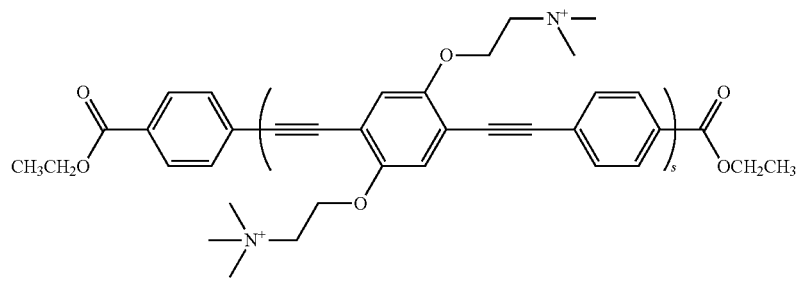

wherein s is about 1 to about 3.

Embodiment 40 provides the sensor of any one of Embodiments 36-39, wherein the enzyme substrate is an anionic enzyme substrate.

Embodiment 41 provides the sensor of Embodiment 40, wherein the anionic enzyme substrate is 1,2-dilauroyl-sn-glycero-phospho-(1'-rac-glycerol).

Embodiment 42 provides the sensor of any one of Embodiments 34-41, wherein the p-phenylene ethynylene compound is an anionic p-phenylene ethynylene compound.

Embodiment 43 provides the sensor of Embodiment 42, wherein the anionic p-phenylene ethynylene compound has the structure:

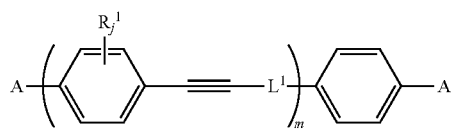

wherein
R$^1$ has the structure:

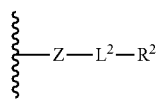

wherein
at each occurrence Z is independently chosen from —CH$_2$—, —O—, —S—, and —NH—;
at each occurrence L$^2$ is independently chosen from (C$_1$-C$_{50}$)hydrocarbylene interrupted by 0, 1, 2, 3, 4, 5, 6, 7, 8, 9, or 10 groups independently chosen from —O—, —S—, and —NH—;
at each occurrence R$^2$ is independently chosen from —H, (C$_1$-C$_5$)alkyl, —SO$_3^-$, —CO$_2^-$, —H$_2$PO$_4^-$, HPO$_4^{2-}$, PO$_4^{3-}$, and phenolate;

j is about 0 to about 4;
at each occurrence L$^1$ is independently chosen from a bond and

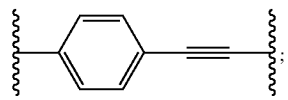

at each occurrence A is independently chosen from —H, substituted or unsubstituted —C(O)O—(C$_1$-C$_{10}$)hydrocarbyl, and —C(O)NH—(C$_1$-C$_{10}$)hydrocarbyl,
m is about 1 to about 10.

Embodiment 44 provides the sensor of any one of Embodiments 42-43, wherein the anionic p-phenylene ethynylene compound has the structure:

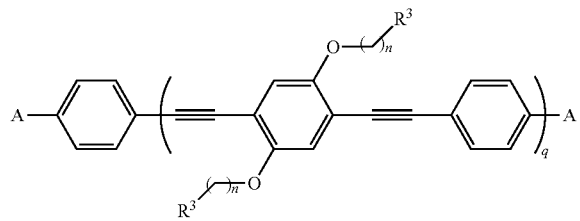

wherein
at each occurrence R$^3$ is independently chosen from —SO$_3^-$, —CO$_2^-$, —H$_2$PO$_4^-$, HPO$_4^{2-}$, PO$_4^{3-}$, and phenolate;
n is about 2 to about 4;
at each occurrence A is independently chosen from —H and —C(O)O—(C$_1$-C$_5$)alkyl; and
q is about 1 to about 5.

Embodiment 45 provides the sensor of any one of Embodiments 42-44, wherein the anionic p-phenylene ethynylene compound has the structure:

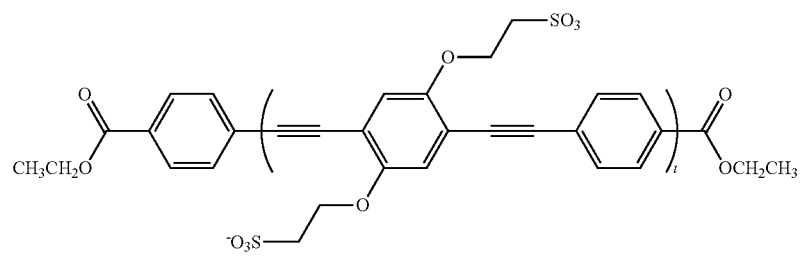

wherein t is about 1 to about 3.

Embodiment 46 provides the sensor of any one of Embodiments 42-45, wherein the enzyme substrate is a cationic enzyme substrate.

Embodiment 47 provides the sensor of Embodiment 46, wherein the cationic enzyme substrate is a substituted or unsubstituted $(C_1-C_{25})$hydrocarbyl-C(O)O—$(C_1-C_{10})$alkyl-N$((C_1-C_5)$alkyl$)_3$.

Embodiment 48 provides the sensor of any one of Embodiments 46-47, wherein the cationic enzyme substrate is a substituted or unsubstituted $(C_1-C_{25})$alkyl-C(O)O—$(C_1-C_4)$alkyl-N$^+$(CH$_3$)$_3$.

Embodiment 49 provides the sensor of any one of Embodiments 46-48, wherein the cationic enzyme substrate is chosen from lauroyl choline and acetylcholine.

Embodiment 50 provides the sensor of any one of Embodiments 46-49, wherein the cationic enzyme substrate is lauroyl choline.

Embodiment 51 provides the sensor of any one of Embodiments 34-50, wherein the enzyme is chosen from phospholipase A1, phospholipase A2, phospholipase C, and acetyl cholinesterase.

Embodiment 52 provides a sensor, the sensor comprising a cationic p-phenylene ethynylene compound and an anionic enzyme substrate;
wherein
the p-phenylene ethynylene compound has the structure:

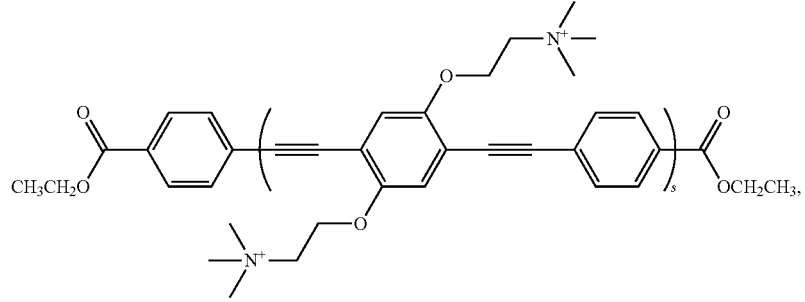

wherein s is about 1 to about 3; and
the anionic enzyme substrate is 1,2-dilauroyl-sn-glycero-phospho-(1'-rac-glycerol).

Embodiment 53 provides a sensor, the sensor comprising a p-phenylene ethynylene compound and an enzyme substrate:
wherein
the p-phenylene ethynylene compound has the structure:

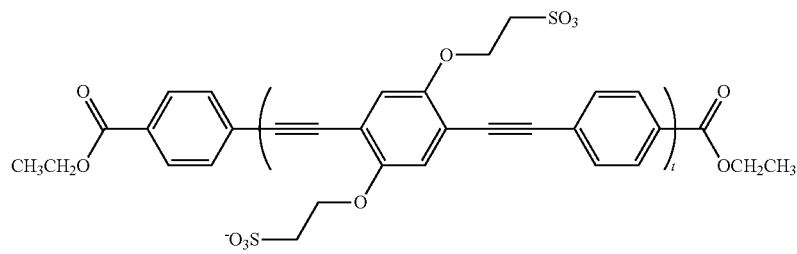

wherein t is about 1 to about 3; and
the enzyme substrate is lauroyl choline.

Embodiment 54 provides a method for protein analysis, the method comprising (i) introducing a p-phenylene ethynylene compound to a biological sample comprising at least one protein and (ii) analyzing the fluorescence of the p-phenylene ethynylene compound in the presence of the biological sample comprising the at least one protein.

Embodiment 55 provides the method of Embodiment 54, wherein the fluorescence of the p-phenylene ethynylene compound is analyzed prior to being introduced to the biological sample comprising the at least one protein.

Embodiment 56 provides the method of any one of Embodiments 54-55, wherein analyzing the fluorescence of the p-phenylene ethynylene compound in the presence of the biological sample comprising the at least one protein comprises analyzing the spectral changes between the fluorescence of the p-phenylene ethynylene compound of step (i) and the fluorescence of the p-phenylene ethynylene compound in the presence of the biological sample comprising the at least one protein of step (ii).

Embodiment 57 provides the method of any one of Embodiments 54-56, wherein the morphology of the protein in the biological sample is determined by analyzing spectral changes between the fluorescence of the p-phenylene ethynylene compound of step (i) and the fluorescence of the p-phenylene ethynylene compound in the presence of the biological sample comprising the at least one protein of step (ii).

Embodiment 58 provides the method of Embodiment 57, wherein the spectral changes in the fluorescence of the p-phenylene ethynylene compound between step (i) and step (ii) are induced by changes in the conformational freedom of the p-phenylene ethynylene compound between step (i) and step (ii).

Embodiment 59 provides the method of any one of Embodiments 54-58, wherein the p-phenylene ethynylene compound has the structure:

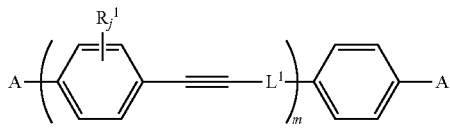

wherein
$R^1$ has the structure:

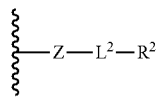

wherein
at each occurrence Z is independently chosen from —$CH_2$—, —O—, —S—, and —NH—;
at each occurrence $L^2$ is independently chosen from ($C_1$-$C_{10}$)hydrocarbylene interrupted by 0, 1, 2, 3, 4, 5, 6, 7, 8, 9, or 10 groups independently chosen from —O—, —S—, and —NH—; at each occurrence $R^2$ is independently chosen from —H, ($C_1$-$C_5$)alkyl, —$SO_3^-$, —$CO_2^-$, —$H_2PO_4^-$, $HPO_4^{2-}$, $PO_4^{3-}$, phenolate, ($C_1$-$C_{10}$)alkyl-(1,4-substituted 1,4-diazabicyclo[2.2.2]octane-1,4-diium)-, and 3-methylimidazolium, and —$N^+(R^4)_3$ wherein at each occurrence $R^4$ is independently ($C_1$-$C_5$)alkyl;
j is about 0 to about 4;
at each occurrence $L^1$ is independently chosen from a bond and

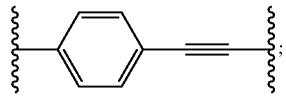

at each occurrence A is independently chosen from —H, substituted or unsubstituted —C(O)O—($C_1$-$C_{10}$)hydrocarbyl, and —C(O)NH—($C_1$-$C_{10}$)hydrocarbyl; and
m is about 1 to about 10.

Embodiment 60 provides the method of any one of Embodiments 54-59, wherein the p-phenylene ethynylene compound has the structure:
wherein

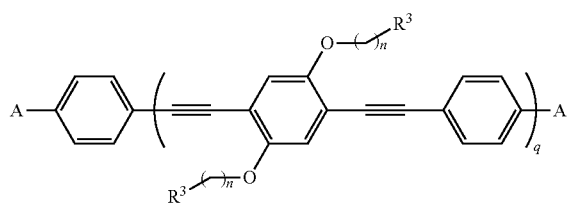

at each occurrence $R^3$ is independently chosen from —$N^+(CH_3)_3$,

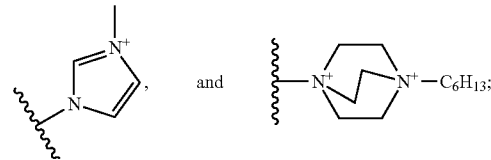

n is about 2 to about 4;
at each occurrence A is independently chosen from —H and —C(O)O—($C_1$-$C_5$)alkyl; and
q is about 1 to about 5.

Embodiment 61 provides the method of any one of Embodiments 54-60, wherein the p-phenylene ethynylene compound has the structure:

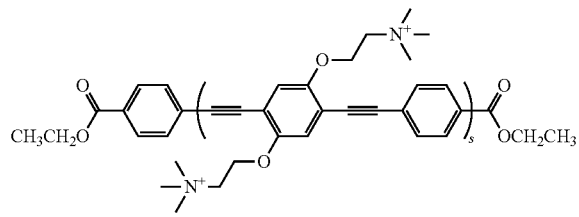

wherein s is about 1 to about 3.

Embodiment 62 provides the method of any one of Embodiments 54-61, wherein the protein is at least one of an amyloid beta protein, Aβ-40, Aβ-42, tau, and α-synuclein, islet amyloid precursor protein, Huntingtin, prion, lysozyme, TDP-43 (transactive response DNA-binding protein 43), FUS (fused in sarcoma) and insulin.

Embodiment 63 provides a method for protein analysis, the method comprising (i) analyzing the fluorescence of a p-phenylene ethynylene compound; (ii) introducing the p-phenylene ethynylene compound to a biological sample comprising at least one protein; (iii) analyzing the fluorescence of the p-phenylene ethynylene compound in the presence of the biological sample comprising the at least one protein; and (iv) determining the morphology of the at least one protein in the biological sample by analyzing spectral changes between the fluorescence of the p-phenylene ethynylene compound of step (i) and the fluorescence of the p-phenylene ethynylene compound in the presence of the biological sample comprising the at least one protein of step (iii);

wherein
the p-phenylene ethynylene compound has the structure:

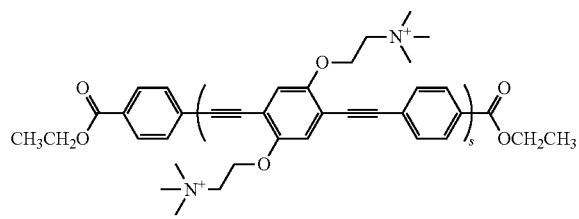

wherein s is 1; and the protein is at least one of an amyloid beta protein, Aβ-40, Aβ-42, tau, and α-synuclein, islet amyloid precursor protein, Huntingtin, prion, lysozyme, TDP-43 (transactive response DNA-binding protein 43). FUS (fused in sarcoma) and insulin.

Embodiment 64 provides a method for detecting a chemical agent, the method comprising (i) exposing a sensor composition comprising a complex comprising a p-phenylene ethynylene compound and an enzyme substrate to a sample; (ii) introducing an enzyme to the sensor composition of step (i); and (iii) analyzing the change in fluorescence of the p-phenylene ethynylene compound between the exposing step (i) and the introducing an enzyme step (ii).

Embodiment 65 provides the method of Embodiment 64, wherein a change in fluorescence between the exposing step (i) and the introducing an enzyme step (ii) indicates the presence of a chemical agent that does interact with the enzyme.

Embodiment 66 provides the method of any one of Embodiments 64-65, wherein a minimal change in fluorescence between the exposing step (i) and the introducing an enzyme step (ii) indicates the presence of a chemical agent that does interact with the enzyme.

Embodiment 67 provides the method of any one of Embodiments 64-66, wherein the p-phenylene ethynylene compound is a cationic p-phenylene ethynylene compound.

Embodiment 68 provides the method of Embodiment 67, wherein the cationic p-phenylene ethynylene compound has the structure:

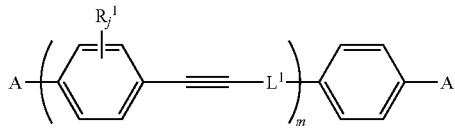

wherein
R$^1$ has the structure:

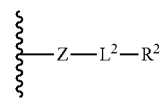

wherein
at each occurrence Z is independently chosen from —CH$_2$—, —O—, —S—, and —NH—;
at each occurrence L$^2$ is independently chosen from (C$_1$-C$_{50}$)hydrocarbylene interrupted by 0, 1, 2, 3, 4, 5, 6, 7, 8, 9, or 10 groups independently chosen from —O—, —S—, and —NH—;
at each occurrence R$^2$ is independently chosen from —H, (C$_1$-C$_5$)alkyl, —SO$_3^-$, —CO$_2^-$, —H$_2$PO$_4^-$, HPO$_4^{2-}$, PO$_4^{3-}$—, phenolate, (C$_1$-C$_{10}$)alkyl-(1,4-substituted 1,4-diazabicyclo[2.2.2]octane-1,4-diium)-, and 3-methylimidazolium, and —N$^+$(R$^A$)$_3$ wherein at each occurrence R$^A$ is independently (C$_1$-C$_5$)alkyl;
j is about 0 to about 4;
at each occurrence L$^1$ is independently chosen from a bond and

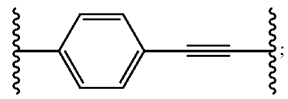

at each occurrence A is independently chosen from —H, substituted or unsubstituted —C(O)O—(C$_1$-C$_{10}$)hydrocarbyl, and —C(O)NH—(C$_1$-C$_{10}$)hydrocarbyl; and
m is about 1 to about 10.

Embodiment 69 provides the method of any one of Embodiments 67-68, wherein the cationic p-phenylene ethynylene compound has the structure:

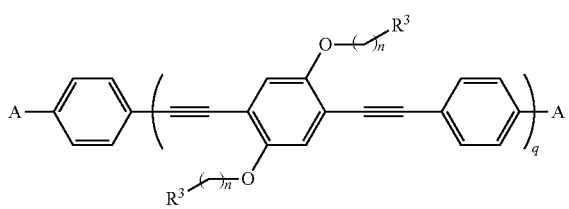

wherein
at each occurrence R$^3$ is independently chosen from —N$^+$(CH$_3$)$_3$,

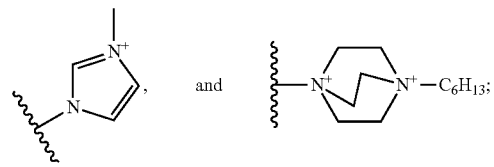

n is about 2 to about 4;
at each occurrence A is independently chosen from —H and —C(O)O—(C$_1$-C$_5$)alkyl; and
q is about 1 to about 5.

Embodiment 70 provides the method of any one of Embodiments 67-69, wherein the cationic p-phenylene ethynylene compound has the structure:

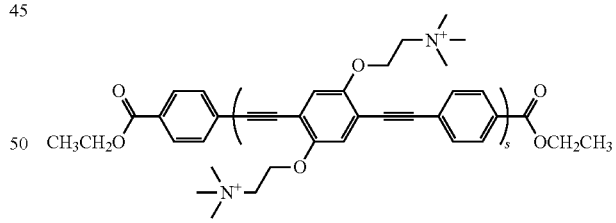

wherein s is about 1 to about 3.

Embodiment 71 provides the method of any one of Embodiments 67-70, wherein the enzyme is chosen from phospholipase A1, phospholipase A2, and phospholipase C.

Embodiment 72 provides the method of any one of Embodiments 67-71, wherein the enzyme substrate is an anionic enzyme substrate.

Embodiment 73 provides the method of Embodiment 72, wherein the anionic enzyme substrate is 1,2-dilauroyl-sn-glycero-phospho-(1-rac-glycerol).

Embodiment 74 provides the method of any one of Embodiments 64-73, wherein the p-phenylene ethynylene compound is an anionic p-phenylene ethynylene compound.

Embodiment 75 provides the method of Embodiment 74, wherein the anionic p-phenylene ethynylene compound has the structure:

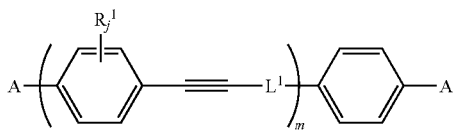

wherein
R¹ has the structure:

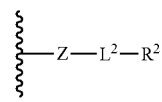

wherein
at each occurrence Z is independently chosen from —$CH_2$—, —O—, —S—, and —NH—;
at each occurrence $L^2$ is independently chosen from ($C_1$-$C_{50}$)hydrocarbylene interrupted by 0, 1, 2, 3, 4, 5, 6, 7, 8, 9, or 10 groups independently chosen from —O—, —S—, and —NH—;
at each occurrence $R^2$ is independently chosen from —H, ($C_1$-$C_5$)alkyl, —$SO_3^-$, —$CO_2$, —$H_2PO_4^-$, $HPO_4^{2-}$, $PO_4^{3-}$, and phenolate:
j is about 0 to about 4;
at each occurrence $L^1$ is independently chosen from a bond and

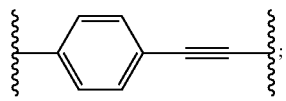

at each occurrence A is independently chosen from —H, substituted or unsubstituted —C(O)O—($C_1$-$C_{10}$)hydrocarbyl, and —C(O)NH—($C_1$-$C_{10}$)hydrocarbyl,
m is about 1 to about 10.

Embodiment 76 provides the method of any one of Embodiments 74-75, wherein the anionic p-phenylene ethynylene compound has the structure:

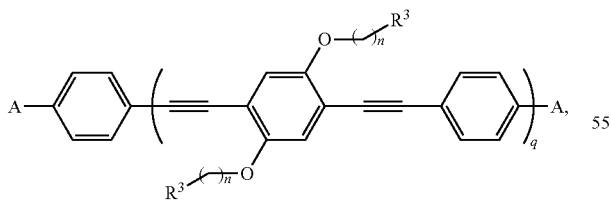

wherein
at each occurrence $R^3$ is independently selected from —$SO_3^-$, —$CO_2^-$, —$H_2PO_4^-$, $HPO_4^{2-}$, $PO_4^{3-}$, and phenolate;
n is about 2 to about 4;
at each occurrence A is independently chosen from —H and —C(O)O—($C_1$-$C_5$)alkyl; and
q is about 1 to about 5.

Embodiment 77 provides the method of any one of Embodiments 74-76, wherein the anionic p-phenylene ethynylene compound has the structure:

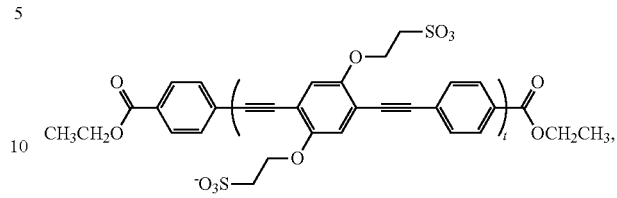

wherein t is about 1 to about 3.

Embodiment 78 provides the method of any one of Embodiments 74-77, wherein the enzyme substrate is a cationic enzyme substrate.

Embodiment 79 provides the method of Embodiment 78, wherein the cationic enzyme substrate is a substituted or unsubstituted ($C_1$-$C_{25}$)hydrocarbyl-C(O)O—($C_1$-$C_{10}$)alkyl-$N^+$(($C_1$-$C_5$)alkyl)$_3$.

Embodiment 80 provides the method of any one of Embodiments 78-79, wherein the cationic enzyme substrate is a substituted or unsubstituted ($C_1$-$C_{25}$)alkyl-C(O)O—($C_1$-$C_4$)alkyl-$N^+$($CH_3$)$_3$.

Embodiment 81 provides the method of any one of Embodiments 78-80, wherein the cationic enzyme substrate is chosen from lauroyl choline and acetylcholine.

Embodiment 82 provides the method of any one of Embodiments 78-81, wherein the cationic enzyme substrate is lauroyl choline.

Embodiment 83 provides the method of any one of Embodiments 78-82, wherein the enzyme is acetylcholinesterase.

Embodiment 84 provides a method for detecting a chemical agent, the method comprising (i) exposing a sensor composition comprising a complex comprising a p-phenylene ethynylene compound and an enzyme substrate to a sample; (ii) introducing an enzyme to the sensor composition of step (i); and (iii) analyzing the change in fluorescence of the p-phenylene ethynylene compound between the exposing step (i) and the introducing an enzyme step (ii):
wherein
the p-phenylene ethynylene compound has the structure:

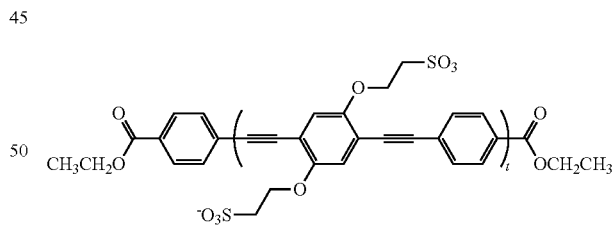

wherein t is about 1 to about 3: and
the enzyme substrate is lauroyl choline; and
a change in fluorescence between the exposing step (i) and the introducing an enzyme step (ii) indicates the presence of a chemical agent that does interact with the enzyme.

Embodiment 85 provides a sensor for detecting the presence of a chemical agent, the sensor comprising a sensor composition comprising a complex comprising a p-phenylene ethynylene compound and an enzyme substrate.

Embodiment 86 provides the sensor of Embodiment 85, wherein the p-phenylene ethynylene compound is a cationic p-phenylene ethynylene compound.

Embodiment 87 provides the sensor of Embodiment 86, wherein the cationic p-phenylene ethynylene compound has the structure:

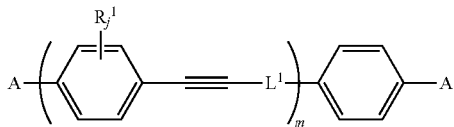

wherein
R¹ has the structure:

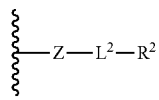

wherein
at each occurrence Z is independently chosen from —CH₂—, —O—, —S—, and —NH—;
at each occurrence L² is independently chosen from (C₁-C₅₀)hydrocarbylene interrupted by 0, 1, 2, 3, 4, 5, 6, 7, 8, 9, or 10 groups independently chosen from —O—, —S—, and —NH—; at each occurrence R² is independently chosen from —H, (C₁-C₅)alkyl, —SO₃⁻, —CO₂⁻, —H₂PO₄⁻, HPO₄²⁻, PO₄³⁻, phenolate, (C₁-C₁₀)alkyl-(1,4-substituted 1,4-diazabicyclo[2.2.2]octane-1,4-diium)-, and 3-methylimidazolium, and —N⁺(R^A)₃ wherein at each occurrence R^A is independently (C₁-C₅)alkyl;
j is about 0 to about 4;
at each occurrence L¹ is independently chosen from a bond and

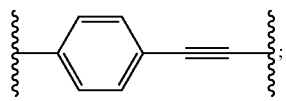

at each occurrence A is independently chosen from —H, substituted or unsubstituted —C(O)O—(C₁-C₁₀)hydrocarbyl, and —C(O)NH—(C₁-C₁₀)hydrocarbyl; and
m is about 1 to about 10.

Embodiment 88 provides the sensor of any one of Embodiments 86-87, wherein the cationic p-phenylene ethynylene compound has the structure:

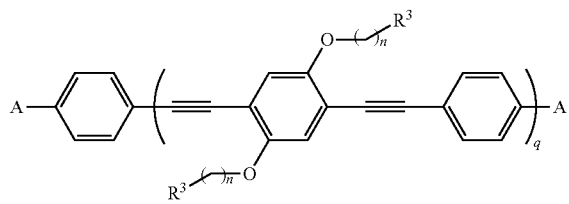

wherein
at each occurrence R³ is independently chosen from —N⁺(CH₃)₃,

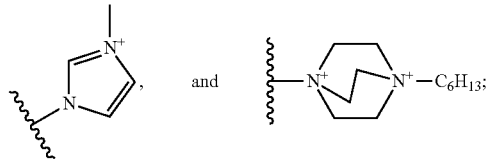

n is about 2 to about 4;
at each occurrence A is independently chosen from —H and —C(O)O—(C₁-C₅)alkyl; and
q is about 1 to about 5.

Embodiment 89 provides the sensor of any one of Embodiments 86-88, wherein the cationic p-phenylene ethynylene compound has the structure:

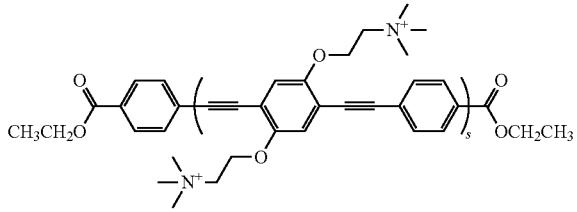

wherein s is about 1 to about 3.

Embodiment 90 provides the sensor of any one of Embodiments 86-89, wherein the enzyme substrate is an anionic enzyme substrate.

Embodiment 91 provides the sensor of Embodiment 90, wherein the anionic enzyme substrate is 1,2-dilauroyl-sn-glycero-phospho-(1'-rac-glycerol).

Embodiment 92 provides the sensor of any one of Embodiments 85-91, wherein the p-phenylene ethynylene compound is an anionic p-phenylene ethynylene compound.

Embodiment 93 provides the sensor of Embodiment 92, wherein the anionic p-phenylene ethynylene compound has the structure:

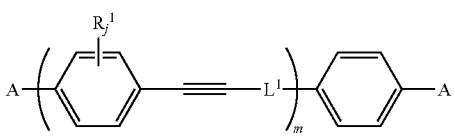

wherein
R¹ has the structure:

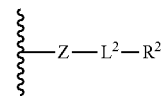

wherein
at each occurrence Z is independently chosen from —CH₂—, —O—, —S—, and —NH—;
at each occurrence L² is independently chosen from (C₁-C₅₀)hydrocarbylene interrupted by 0, 1, 2, 3, 4, 5, 6, 7, 8, 9, or 10 groups independently chosen from —O—, —S—, and —NH—;
at each occurrence R² is independently chosen from —H, (C₁-C₅)alkyl, —SO₃⁻, —CO₂⁻, —H₂PO₄⁻, HPO₄²⁻, PO₄³⁻, and phenolate;

j is about 0 to about 4;
at each occurrence $L^1$ is independently chosen from a bond and

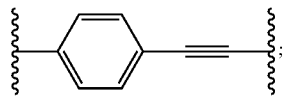

at each occurrence A is independently chosen from —H, substituted or unsubstituted —C(O)O—($C_1$-$C_{10}$)hydrocarbyl, and —C(O)NH—($C_1$-$C_{10}$)hydrocarbyl,
m is about 1 to about 10.

Embodiment 94 provides the sensor of any one of Embodiments 92-93, wherein the anionic p-phenylene ethynylene compound has the structure:

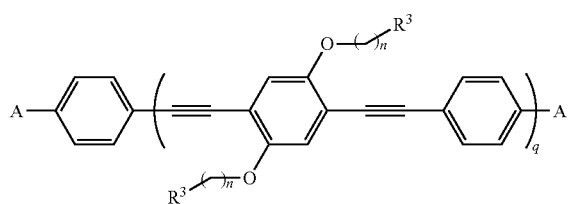

wherein
at each occurrence $R^3$ is independently chosen from —$SO_3^-$, —$CO_2^-$, —$H_2PO_4^-$, $HPO_4^{2-}$, $PO_4^{3-}$, and phenolate;
n is about 2 to about 4;
at each occurrence A is independently chosen from —H and —C(O)O—($C_1$-$C_5$)alkyl; and
q is about 1 to about 5.

Embodiment 95 provides the sensor of any one of Embodiments 92-94, wherein the anionic p-phenylene ethynylene compound has the structure:

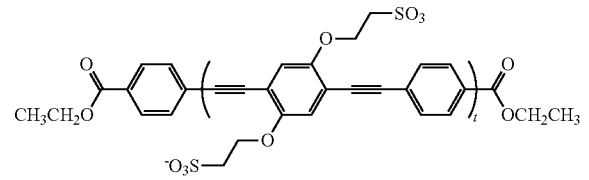

wherein t is about 1 to about 3.

Embodiment 96 provides the sensor of any one of Embodiments 92-95, wherein the enzyme substrate is a cationic enzyme substrate.

Embodiment 97 provides the sensor of any one of Embodiments 92-96, wherein the cationic enzyme substrate is a substituted or unsubstituted ($C_1$-$C_{25}$)hydrocarbyl-C(O)O—($C_1$-$C_{10}$)alkyl-$N^+$(($C_1$-$C_5$)alkyl)$_3$.

Embodiment 98 provides the sensor of any one of Embodiments 92-97, wherein the cationic enzyme substrate is a substituted or unsubstituted ($C_1$-$C_{25}$)alkyl-C(O)O—($C_1$-$C_4$)alkyl-N($CH_3$)$_3$.

Embodiment 99 provides the sensor of any one of Embodiments 92-98, wherein the cationic enzyme substrate is chosen from lauroyl choline and acetylcholine.

Embodiment 100 provides the sensor of any one of Embodiments 92-99, wherein the cationic enzyme substrate is lauroyl choline.

Embodiment 101 provides a sensor for detecting the presence of a chemical agent, the sensor comprising a sensor composition comprising a complex comprising a p-phenylene ethynylene compound and an enzyme substrate:
wherein
the p-phenylene ethynylene compound has the structure:

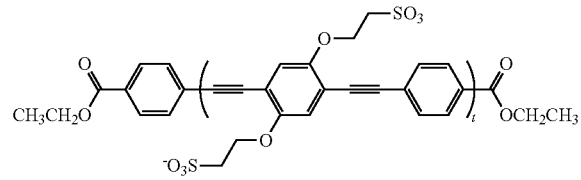

wherein t is about 1 to about 3; and
enzyme substrate is lauroyl choline.

Embodiment 102 provides the method or sensor of any one or any combination of Embodiments 1-101 optionally configured such that all elements or options recited are available to use or select from.

What is claimed is:
1. A sensor comprising a p-phenylene ethynylene compound and an enzyme substrate, wherein the p-phenylene ethynylene compound has the structure:

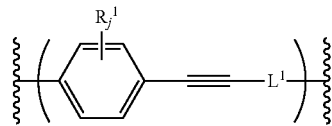

wherein
$R^1$ has the structure:

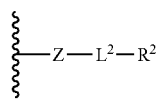

at each occurrence Z is independently chosen from —$CH_2$—, —O—, —S—, and —NH—;
at each occurrence $L^2$ is independently chosen from ($C_1$-$C_{50}$) hydrocarbylene interrupted by 0, 1, 2, 3, 4, 5, 6, 7, 8, 9, or 10 groups independently chosen from —O—, —S—, and —NH—;
at each occurrence $R^2$ is independently chosen from —H, ($C_1$-$C_5$) alkyl, —$SO_3$, —$CO_2$, —$H_2PO_4^-$, $HPO_4^{2-}$, $PO_4^{3-}$, phenolate, ($C_1$-$C_{10}$) alkyl-(1,4-substituted 1,4-diazabicyclo [2.2.2]octane-1,4-diium)-, and 3-methylimidazolium, and —$N^+$ ($R^A$)$_3$, wherein at each occurrence $R^A$ is independently ($C_1$-$C_5$) alkyl;
j is about 0 to about 4;
at each occurrence $L^1$ is independently chosen from a bond and

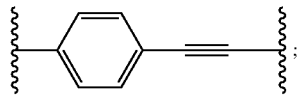

at each occurrence A is independently chosen from a substituted or unsubstituted —C(O)O—($C_1$-$C_{10}$) hydrocarbyl and a substituted or unsubstituted —C(O)NH—($C_1$-$C_{10}$) hydrocarbyl; and m is about 1 to about 10.

2. The sensor of claim 1, wherein the p-phenylene ethynylene compound is a cationic compound.

3. The sensor of claim 1, wherein the p-phenylene ethynylene compound is an anionic compound.

4. The sensor of claim 1, wherein the p-phenylene ethynylene compound comprises a cationic repeating unit having the structure:

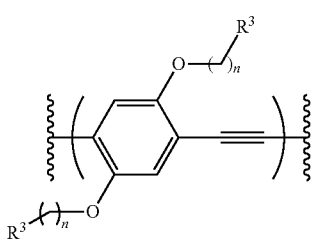

wherein
at each occurrence $R^3$ is independently chosen from —$N^+(CH_3)_3$,

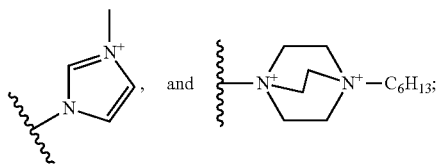

and
n is about 2 to about 4.

5. The sensor of claim 1, wherein the p-phenylene ethynylene compound is a cationic p-phenylene ethynylene compound and has the structure:

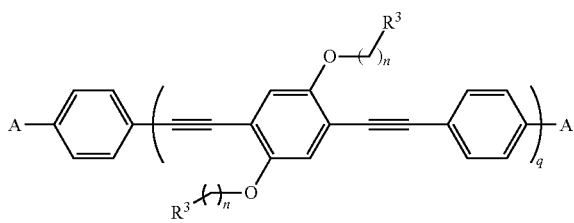

wherein
at each occurrence $R^3$ is independently chosen from —$N^+(CH_3)_3$,

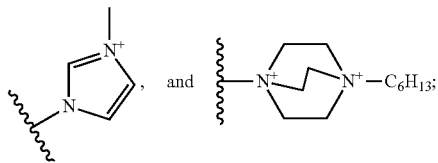

n is about 2 to about 4;
at each occurrence A is independently —C(O)O—($C_1$-$C_5$) alkyl; and
q is about 1 to about 5.

6. The sensor of claim 1, wherein the p-phenylene ethynylene compound is an anionic p-phenylene ethynylene compound, wherein the anionic p-phenylene ethynylene compound has the structure:

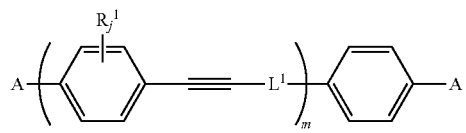

wherein
$R^1$ has the structure:

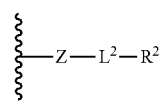

at each occurrence Z is independently chosen from —$CH_2$—, —O—, —S—, and —NH—;
at each occurrence $L^2$ is independently chosen from ($C_1$-$C_{50}$) hydrocarbylene interrupted by 0, 1, 2, 3, 4, 5, 6, 7, 8, 9, or 10 groups independently chosen from —O—, —S—, and —NH—;
at each occurrence $R^2$ is independently chosen from —H, ($C_1$-$C_5$) alkyl, —$SO_3^-$, —$CO_2^-$, —$H_2PO_4^-$, $HPO_4^{2-}$, $PO_4^{3-}$, and phenolate;
j is about 0 to about 4;
at each occurrence $L^1$ is independently chosen from a bond and

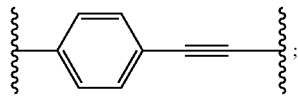

at each occurrence A is independently chosen from a substituted or unsubstituted —C(O)O—($C_1$-$C_{10}$) hydrocarbyl and a substituted or unsubstituted —C(O)NH—($C_1$-$C_{10}$) hydrocarbyl; and
m is about 1 to about 10.

7. The sensor of claim 1, wherein the p-phenylene ethynylene compound is an anionic p-phenylene ethynylene compound, wherein the anionic p-phenylene ethynylene compound has the structure:

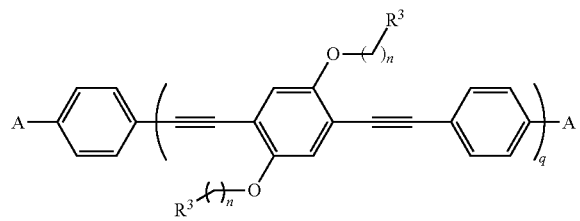

wherein
at each occurrence $R^3$ is independently chosen from —$SO_3^-$, —$CO_2^-$, —$H_2PO_4^-$, $HPO_4^{2-}$, $PO_4^{3-}$, and phenolate;

n is about 2 to about 4;

at each occurrence A is independently —C(O)O—($C_1$-$C_5$) alkyl; and q is about 1 to about 5.

8. The sensor of claim 1, wherein the p-phenylene ethynylene compound is an anionic p-phenylene ethynylene compound, wherein the anionic p-phenylene ethynylene compound has the structure:

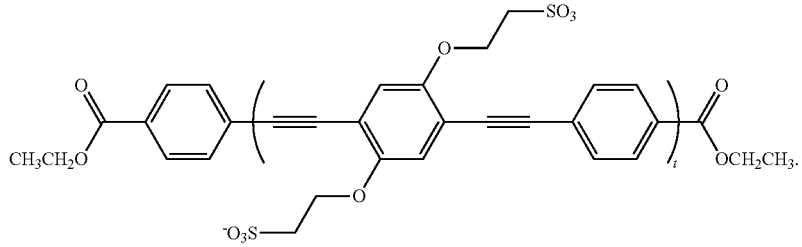

wherein t is about 1 to about 3.

9. The sensor of claim 1, wherein the enzyme substrate is a cationic enzyme substrate chosen from lauroyl choline and acetylcholine.

10. The sensor of claim 1, wherein the enzyme substrate is a substrate of phospholipase A1, phospholipase A2, phospholipase C, and acetyl cholinesterase.

11. The sensor of claim 1, wherein the enzyme substrate is an anionic enzyme substrate that is 1,2-dilauroyl-sn-glycero-phospho-(1'-rac-glycerol).

12. The sensor of claim 1, wherein the p-phenylene ethynylene compound is an anionic p-phenylene ethynylene compound and the enzyme substrate is a cationic enzyme substrate, or the p-phenylene ethynylene compound is a cationic p-phenylene ethynylene compound and the enzyme substrate is an anionic enzyme substrate.

13. The sensor of claim 1, wherein the cationic enzyme substrate is a substituted or unsubstituted ($C_1$-$C_{25}$) hydrocarbyl—C(O)O—($C_1$-$C_{10}$) alkyl-$N^+$(($C_1$-$C_5$) alkyl)$_3$.

14. The sensor of claim 1, wherein the p-phenylene ethynylene compound is complexed with the enzyme substrate.

15. A composition for protein characterization, the composition comprising:

the sensor of claim 1; and at least one protein.

16. The composition of claim 15, wherein the protein comprises at least one of an amyloid beta protein, Aβ-40, Aβ-42, tau, and α-synuclein, islet amyloid precursor protein, Huntingtin, prion, lysozyme, TDP-43 (transactive response DNA-binding protein 43), FUS (fused in sarcoma) and insulin.

17. A composition for evaluating chemical agent exposure, the composition comprising:

the sensor of claim 1, an enzyme, and at least one chemical agent.

18. The composition of claim 17, wherein the chemical agent comprises at least one of anorganophosphate nerve agent, a G-type nerve agent, or an organophosphate pesticide or insecticide.

19. A sensor comprising a p-phenylene ethynylene compound and an enzyme substrate, wherein the p-phenylene ethynylene compound has the structure:

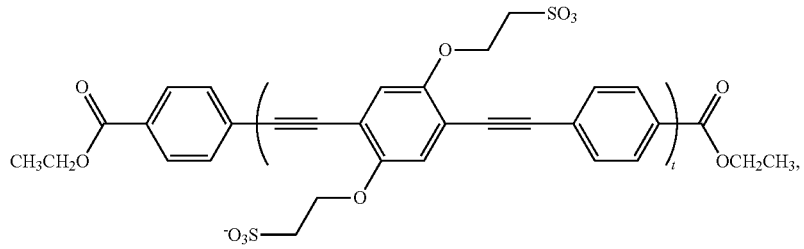

wherein t is about 1 to about 3.

* * * * *

UNITED STATES PATENT AND TRADEMARK OFFICE
CERTIFICATE OF CORRECTION

PATENT NO. : 12,163,953 B2
APPLICATION NO. : 16/707501
DATED : December 10, 2024
INVENTOR(S) : Whitten et al.

Page 1 of 3

It is certified that error appears in the above-identified patent and that said Letters Patent is hereby corrected as shown below:

On the Title Page

Item (57), in "Abstract", in Column 2, Line 9, delete "ethylylene" and insert --ethynylene-- therefor On page 3, in Column 1, Item (56) under "Other Publications", Line 12, delete "Actino" and insert --Action-- therefor On page 4, in Column 1, Item (56) under "Other Publications", Line 33, delete "Feb. 2025, 09"," and insert --Feb. 25, 2009",-- therefor On page 5, in Column 1, Item (56) under "Other Publications", Line 16, delete "fillaments"," and insert --filaments",-- therefor On page 5, in Column 2, Item (56) under "Other Publications", Line 33, delete "tTeatment" and insert --Treatments-- therefor On page 6, in Column 1, Item (56) under "Other Publications", Lines 62-63, delete "seggregation" and insert --segregation-- therefor On page 6, in Column 2, Item (56) under "Other Publications", Line 30, delete "anibiotics"," and insert --antibiotics",-- therefor On page 7, in Column 1, Item (56) under "Other Publications", Line 31, delete "Abilitty" and insert --Ability-- therefor On page 7, in Column 1, Item (56) under "Other Publications", Line 59, delete "Lomitation" and insert --Limitation-- therefor On page 7, in Column 2, Item (56) under "Other Publications", Line 2, delete "aprotio" and insert --aprotic-- therefor Signed and Sealed this
Twenty-first Day of October, 2025

John A. Squires
*Director of the United States Patent and Trademark Office*

CERTIFICATE OF CORRECTION (continued)

On page 7, in Column 2, Item (56) under "Other Publications", Line 17, delete "*Staphylococcusaureus*" and insert --*Staphylococcus aureus*-- therefor On page 7, in Column 2, Item (56) under "Other Publications", Line 46, delete "Bio?lm" and insert --Biofilm-- therefor On page 8, in Column 1, Item (56) under "Other Publications", Line 21, delete "electronc" and insert --electron-- therefor In the Claims In Column 90, Lines 30-35, in Claim 1, delete " 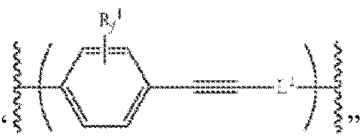 " and insert

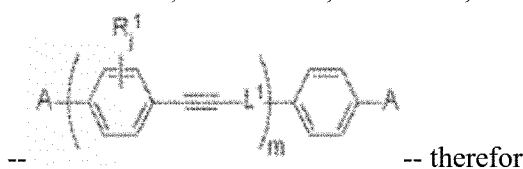 -- therefor

In Column 90, Line 49, in Claim 1, delete "$(C_1-C_{50})$ hydrocarbylene" and insert --$(C_1-C_{50})$hydrocarbylene-- therefor In Column 90, Lines 52-53, in Claim 1, delete "—H, $(C_1-C_5)$ alkyl, —$SO_3$, —$CO_2$,—$H_2PO_4^-$," and insert -- —H, $(C_1-C_5)$alkyl, —$SO_3^-$, —$CO_2^-$, —$H_2PO_4^-$,-- therefor In Column 90, Lines 54-55, in Claim 1, delete "$(C_1-C_{10})$ alkyl-(1,4-substituted 1,4-diazabicyclo[2.2.2]octane-1,4-diium)-," and insert --$(C_1-C_{10})$alkyl-(1,4-substituted 1,4-diazabicyclo[2.2.2]octane-1,4-diium)-,-- therefor In Column 90, Line 56, in Claim 1, delete "—$N^+$ $(R^4)_3$," and insert -- —$N^+(R^4)_3$,-- therefor In Column 90, Line 57, in Claim 1, delete "$(C_1-C_5)$ alkyl;" and insert --$(C_1-C_5)$alkyl;-- therefor In Column 91, Lines 2-3, in Claim 1, delete "unsubstituted—C(O)O—$(C_1-C_{10})$ hydrocarbyl" and insert --unsubstituted —C(O)O—$(C_1-C_{10})$hydrocarbyl-- therefor In Column 91, Lines 3-4, in Claim 1, delete "—C(O)NH—$(C_1-C_{10})$ hydrocarbyl;" and insert -- —C(O)NH—$(C_1-C_{10})$hydrocarbyl;-- therefor In Column 91, Line 27, in Claim 4, delete "—$N^+(CH_3)_3$," and insert -- —$N^+(CH_3)_3$,-- therefor In Column 91, Line 57, in Claim 5, delete "—$N^+(CH_3)_3$," and insert -- —$N^+(CH_3)_3$,-- therefor In Column 92, Lines 2-3, in Claim 5, delete "—C(O)O—$(C_1-C_5)$ alkyl;" and insert -- —C(O)O—$(C_1-C_5)$alkyl;-- therefor

CERTIFICATE OF CORRECTION (continued)
U.S. Pat. No. 12,163,953 B2

In Column 92, Line 28, in Claim 6, delete "($C_1$-$C_{50}$) hydrocarbylene" and insert --($C_1$-$C_{50}$)hydrocarbylene-- therefor In Column 92, Line 32, in Claim 6, delete "($C_1$-$C_5$) alkyl," and insert --($C_1$-$C_5$)alkyl,-- therefor In Column 92, Line 32, in Claim 6, delete "—$CO_2^-$,—$H_2PO_4^-$," and insert -- —$CO_2^-$, —$H_2PO_4^-$,-- therefor In Column 92, Lines 45-46, in Claim 6, delete "—C(O)O—($C_1$-$C_{10}$) hydrocarbyl" and insert -- —C(O)O—($C_1$-$C_{10}$)hydrocarbyl-- therefor In Column 92, Lines 46-47, in Claim 6, delete "—C(O)NH—($C_1$-$C_{10}$) hydrocarbyl;" and insert -- —C(O)NH—($C_1$-$C_{10}$)hydrocarbyl;-- therefor In Column 92, Line 66, in Claim 7, delete "—$SO_3^-$,—$CO_2^-$," and insert -- —$SO_3^-$, —$CO_2^-$,-- therefor In Column 93, Lines 2-3, in Claim 7, delete "—C(O)O—($C_1$-$C_5$) alkyl;" and insert -- —C(O)O—($C_1$-$C_5$)alkyl;-- therefor In Column 93, Line 22, in Claim 8, delete "tis" and insert --t is-- therefor In Column 93, Lines 39-40, in Claim 13, delete "($C_1$-$C_{25}$) hydrocarbyl—C(O)O—($C_1$-$C_{10}$) alkyl-$N^+$(($C_1$-$C_5$) alkyl)$_3$." and insert --($C_1$-$C_{25}$)hydrocarbyl—C(O)O—($C_1$-$C_{10}$)alkyl-$N^+$(($C_1$-$C_5$)alkyl)$_3$.-- therefor In Column 94, Line 38, in Claim 18, delete "anorganophosphate" and insert --an organophosphate-- therefor